US009133425B2

(12) United States Patent
Cascao-Pereira et al.

(10) Patent No.: US 9,133,425 B2
(45) Date of Patent: Sep. 15, 2015

(54) METHODS FOR IMPROVING MULTIPLE PROTEIN PROPERTIES

(75) Inventors: Luis G. Cascao-Pereira, Redwood City, CA (US); David A. Estell, San Francisco, CA (US); James T. Kellis, Woodside, CA (US); Ayrookaran J. Poulose, Belmont, CA (US)

(73) Assignee: Danisco US Inc., Palo Alto, CA (US)

( * ) Notice: Subject to any disclaimer, the term of this patent is extended or adjusted under 35 U.S.C. 154(b) by 533 days.

(21) Appl. No.: 12/602,991

(22) PCT Filed: Jun. 6, 2008

(86) PCT No.: PCT/US2008/007103

§ 371 (c)(1), (2), (4) Date: May 12, 2010

(87) PCT Pub. No.: WO2008/153925

PCT Pub. Date: Dec. 18, 2008

(65) Prior Publication Data

US 2010/0216682 A1 Aug. 26, 2010

Related U.S. Application Data

(60) Provisional application No. 60/933,312, filed on Jun. 6, 2007, provisional application No. 60/933,307, filed on Jun. 6, 2007, provisional application No. 60/933,331, filed on Jun. 6, 2007.

(51) Int. Cl.

| | |
|---|---|
| ***C40B 30/10*** | (2006.01) |
| ***C11D 3/02*** | (2006.01) |
| ***C11D 3/37*** | (2006.01) |
| ***C07K 1/00*** | (2006.01) |
| ***C07H 21/04*** | (2006.01) |
| ***C12N 9/14*** | (2006.01) |
| ***C12N 9/16*** | (2006.01) |
| ***C12N 9/24*** | (2006.01) |
| ***C12N 9/26*** | (2006.01) |
| ***C11D 3/386*** | (2006.01) |
| ***C12N 9/28*** | (2006.01) |
| ***C12N 9/54*** | (2006.01) |
| ***C12N 15/10*** | (2006.01) |

(52) U.S. Cl.

CPC ............ *C11D 3/38681* (2013.01); *C11D 3/386* (2013.01); *C12N 9/2411* (2013.01); *C12N 9/2417* (2013.01); *C12N 9/54* (2013.01); *C12N 15/1034* (2013.01); *C12Y 302/01001* (2013.01); *C12Y 304/21062* (2013.01)

(58) Field of Classification Search

CPC .. C11D 3/386; C11D 3/38681; C12N 9/2411; C12N 9/54; C12N 15/1034; C12N 9/2417; C12Y 304/21062; C12Y 302/01001

USPC ......... 506/12, 7; 510/218, 276; 530/402, 350; 536/23.2; 435/195, 196, 200, 201

See application file for complete search history.

(56) References Cited

U.S. PATENT DOCUMENTS

| | | | | |
|---|---|---|---|---|
| 4,683,195 | A | 7/1987 | Mullis et al. | |
| 4,683,202 | A | 7/1987 | Mullis | |
| 4,965,188 | A | 10/1990 | Mullis et al. | |
| 5,322,770 | A | 6/1994 | Gelfand | |
| 5,324,653 | A | 6/1994 | Van Eekelen et al. | |
| 5,336,611 | A | 8/1994 | van Eekelen et al. | |
| 5,453,372 | A | 9/1995 | Vetter et al. | |
| 6,103,512 | A | 8/2000 | Venema et al. | |
| 6,197,567 | B1 | 3/2001 | Aaslyng et al. | |
| 6,211,134 | B1 | 4/2001 | Caldwell et al. | |
| 6,376,450 | B1 | 4/2002 | Ghosh et al. | |
| 6,582,914 | B1 | 6/2003 | Caldwell et al. | |
| 6,673,590 | B1 | 1/2004 | Poulose et al. | |
| 7,306,937 | B2 | 12/2007 | Poulose et al. | |
| 7,354,752 | B2 | 4/2008 | Dunn-Coleman et al. | |
| 7,413,877 | B2 | 8/2008 | Collier et al. | |
| 7,666,648 | B2 | 2/2010 | Foreman et al. | |
| 8,008,056 | B2 | 8/2011 | Aehle et al. | |
| 2005/0084937 | A1 * | 4/2005 | Borchert et al. | 435/69.1 |
| 2005/0221461 | A1 | 10/2005 | Poulose et al. | |
| 2008/0145353 | A1 | 6/2008 | Amin et al. | |
| 2008/0293610 | A1 | 11/2008 | Shaw et al. | |
| 2010/0233780 | A1 | 9/2010 | Aehle et al. | |
| 2010/0297727 | A1 | 11/2010 | Aehle et al. | |

FOREIGN PATENT DOCUMENTS

| | | | |
|---|---|---|---|
| EP | 0 945 502 | A | 9/1999 |
| EP | 0 995 801 | A1 | 4/2000 |
| EP | 0 479 870 | B1 | 10/2000 |

(Continued)

OTHER PUBLICATIONS

Chica et al., Semi-rational approaches to engineering enzyme activity: combining the benefits of directed evolution and rational design. Curr. Opin. Biotechnol., 2005, vol. 16: 378-384.*

Chirumamilla et al., Improving the quality of industrially important enzymes by directed evolution. Mol. Cell. Biochem., 2001, vol. 224: 159-168.*

Deere et al., Mechanistic and structural features of protein adsorption onto mesoporous silicates. J. Phys. Chem., B 2002, vol. 106: 7340-7347.*

Faber et al., Study of solubility of a modified *Bacillus licheniformis* a-amylase around the isoelectric point. J. Chem. Eng. Data., 2007, vol. 52: 707-713.*

Sabate et al., Interaction of a-amylase with n-alkylammonium bromides. Int. J. Biol. Macromol., 2001, vol. 28: 151-156.*

(Continued)

*Primary Examiner* — Ganapathirama Raghu

(74) *Attorney, Agent, or Firm* — Danisco US Inc.

(57) ABSTRACT

The present invention provides efficient methods for obtaining a protein with one or more beneficial attributes in industrial, consumer or pharmaceutical applications. In some preferred embodiments, the present invention provides methods for producing superior enzymes for a given application through screening an abbreviated set of candidate enzymes.

14 Claims, 22 Drawing Sheets

(56) References Cited

FOREIGN PATENT DOCUMENTS

| | | | | |
|---|---|---|---|---|
| EP | 1 553 174 | A2 | 7/2005 | |
| EP | 1612271 | | 1/2006 | |
| WO | WO-91/00345 | A1 | 1/1991 | |
| WO | WO-95/07991 | A2 | 3/1995 | |
| WO | WO95/09909 | | 4/1995 | |
| WO | WO99/20771 | | 4/1999 | |
| WO | WO99/23211 | | 5/1999 | |
| WO | WO-99/34011 | A2 | 7/1999 | |
| WO | WO00/24924 | | 5/2000 | |
| WO | WO-02/14490 | A2 | 2/2002 | |
| WO | WO-03/062380 | A2 | 7/2003 | |
| WO | WO03/062381 | | 7/2003 | |
| WO | WO03/076580 | | 9/2003 | |
| WO | WO2004/63318 | | 7/2004 | |
| WO | WO-2005/001036 | A2 | 1/2005 | |
| WO | WO-2005/005654 | A1 | 1/2005 | |
| WO | WO-2005/052146 | A2 | 6/2005 | |
| WO | WO 2005/052161 | A2 * | 6/2005 | ............ C12N 15/53 |
| WO | WO-2006/023635 | A2 | 3/2006 | |
| WO | WO-2007/044993 | A2 | 4/2007 | |
| WO | WO-2008/153925 | A9 | 12/2008 | |
| WO | WO-2008/153935 | A2 | 12/2008 | |

OTHER PUBLICATIONS

Aboderin, A.A. "An empirical hydrophobicity scale for alpha-amino-acids and some of its applications." *International Journal of Biochemistry* 2(11):537-544, 1971.

Abraham, D.J. et al. "Extension of the fragment method to calculate amino acid zwitterion and side chain partition coefficients." *Proteins: Structure, Function, and Genetics* 2(2):130-152, 1987.

Altschul, S.F. et al. "Local alignment statistics." *Methods Enzymol* 266:460-80, 1996.

Altschul, S.F. et al. "Basic local alignment search tool." *J. Mol. Biol* 215(3):403-410, 1990.

Baker, J.O. et al. "Hydrolysis of cellulose using ternary mixtures of purified celluloses." *Applied Biochemistry and Biotechnology* 70-72 (1):395-403, 1998.

Berlin, A. et al. "Weak lignin-binding enzymes." *Applied Biochemistry and Biotechnology* 121(1):163-170, 2005.

Black, S.D. et al. "Development of hydrophobicity parameters to analyze proteins which bear post- or cotranslational modifications." *Analytical Biochemistry* 193(1):72-82, 1991.

Bolivar, F. et al. "Construction and characterization of new cloning vehicles. II. A multipurpose cloning system." *Gene* 2(2):95-113, 1977.

Bornscheuer, U.T. et al. "Optimizing lipases and related enzymes for efficient application." *Trends in Biotechnology* 20 (10):433-437, 2002.

Bowen, W.R. et al. "The relevance of particle size and zeta-potential in protein processing." *Nature Biotechnology* 16(8):785-787, 1998.

Bull, H.B. et al. "Surface tension of amino acid solutions: a hydrophobicity scale of the amino acid residues." *Archives of Biochemistry and Biophysics* 161(2):665-670, 1974.

Cedrone, F. et al. "Tailoring new enzyme functions by rational redesign." *Current Opinion in Structural Biology* 10(4):405-410, 2000.

Cha, J. et al. "Lowering the pH optimum of D-xylose isomerase: the effect of mutations of the negatively charged residues." *Molecules and Cells* 8(4):374-382, 1998.

Chamberlin, M. et al. "New RNA polymerase from *Escherichia coli* infected with bacteriophage T7." *Nature* 228(5268):227-231, 1970.

Cherry, J.R. et al. "Directed evolution of a fungal peroxidase." *Nature Biotechnology* 17(4):379-384, 1999.

Chirumamilla, R. R. et al. "Improving the quality of industrially important enzymes by directed evolution." *Molecular and Cellular Biochemistry* 224(1):159-168, 2001.

Chothia, C. "The nature of the accessible and buried surfaces in proteins." *Journal of Molecular Biology* 105(1):1-12, 1976.

Cohen, N. et al. "In vitro enzyme evolution: the screening challenge of isolating the one in a million." *Trends in Biotechnology* 19 (12):507-510, 2001.

Cowan, R. et al. "Hydrophobicity indices at ph 3.4 determined by HPLC." *Peptide Res.* 3:75-80, 1990.

DelMar, E.G. et al. "A sensitive new substrate for chymotrypsin." *Analytical Biochemistry* 99(2):316-320, 1979.

Devereux, P. et al. "A comprehensive set of sequence analysis programs for the VAX." *Nucl. Acids Res* 12:387-395, 1984.

Dynan, W.S. et al. "Control of eukaryotic messenger RNA synthesis by sequence-specific DNA-binding proteins." *Nature* 316(6031):774-778, 1985.

Eisenberg, D. et al. "Analysis of membrane and surface protein sequences with the hydrophobic moment plot." *Journal of Molecular Biology* 179 (1 ):125-142, 1984.

Estell, D.A. et al. "Engineering an enzyme by site-directed mutagenesis to be resistant to chemical oxidation." *J. Biol. Chem.* 260(11):6518-6521, 1985.

Fauchere, J.L. et al. "Hydrophobic parameters of amino acid side chains from the partitioning of N-acetyl-amino acid amides." *Eur. J. Med. Chem.-Chim. Ther.* 18:369-375, 1983.

Feng, D.F. et al. "Progressive sequence alignment as a prerequisite to correct phylogenetic trees." *J. Mol. Evol* 25(4):351-360, 1987.

Ferrari, E. et al. "Genetics." In *Bacillus*, Biotechnology Handbooks, No. 2, ed. C.R. Harwood. New York: Plenum Press, pp. 57-72, 1989.

George, A. et al. "Predicting protein crystallization from a dilute solution property." *Acta Crystallographica Section D Biological Crystallography* 50 (4):361-365, 1994.

Gryczan, T.J. et al. "Characterization of *Staphylococcus aureus* plasmids introduced by transformation into *Bacillus subtilis*.." *J. Bacteriol.* 134(1):318-329, 1978.

Guérout-Fleury, A.-M. et al. "Antibiotic-resistance cassettes for *Bacillus subtilis*." *Gene* 167(1-2):335-336, 1995.

Guy, H.R. "Amino acid side-chain partition energies and distribution of residues in soluble proteins." *Biophysical Journal* 47(1):61-70, 1985.

Heinz, D.W. et al. "Changing the inhibitory specificity and function of the proteinase inhibitor eglin c by site-directed mutagenesis: functional and structural investigation." *Biochemistry* 31(37):8755-8766, 1992.

Higgins, D.G. et al. "Fast and sensitive multiple alignment sequence on a microcomputer." *CABIOS* 5:151-153, 1989.

Horinouchi, S. et al. "Nucleotide sequence and functional map of pC194, a plasmid that specifies inducible chloramphenicol resistance.." *J. Bacteriol.* 150(2):815-825, 1982.

Janin, J. "Surface and inside volumes in globular proteins." *Nature* 277(5696):491-492, 1979.

Kacian, D.L. et al. "A Replicating RNA Molecule Suitable for a Detailed Analysis of Extracellular Evolution and Replication." *Proc. Natl. Acad. Sci. USA* 69(10):3038-3042, 1972.

Kalisz, H.M. "Microbial proteinases." *Advances in Biochemical Engineering/Biotechnology* 36:1-65, 1988.

Karlin, S. et al. "Applications and statistics for multiple high-scoring segments in molecular sequences." *Proc. Natl. Acad. Sci. USA* 90(12):5873-7, 1993.

Kuchner, O. et al. "Directed evolution of enzyme catalysts." *Trends in Biotechnology* 15(12):523-530, 1997.

Kyte, J. et al. "A simple method for displaying the hydropathic character of a protein." *Journal of Molecular Biology* 157(1):105-132, 1982.

Manavalan, P. et al. "Hydrophobic character of amino acid residues in globular proteins." *Nature* 275(5681):673-674, 1978.

McKenzie, T. et al. "The nucleotide sequence of pUB110: some salient features in relation to replication and its regulation." *Plasmid* 15(2):93-103, 1986.

Miyazawa, S. et al. "Estimation of effective interresidue contact energies from protein crystal structures: quasi-chemical approximation." *Macromolecules* 18:534-552, 1985.

Mohana Rao, J.K. et al. "A conformational preference parameter to predict helices in integral membrane proteins." *Biochimica et Biophysica Acta (BBA)—Protein Structure and Molecular Enzymology* 869 (2):197-214, 1986.

Needleman, S.B. et al. "A general method applicable to the search for similarities in the amino acid sequence of two proteins." *J. Mol. Biol* 48(3):443-53, 1970.

Neidhardt, F.C. et al. "Culture Medium for Enterobacteria." *J. Bacteriol.* 119(3):736-747, 1974.

(56) References Cited

OTHER PUBLICATIONS

Neves-Petersen, M.T. et al. "Engineering the pH-optimum of a triglyceride lipase: from predictions based on electrostatic computations to experimental results." *Journal of Biotechnology* 87(3):225-254, 2001.
Palmeros, B. et al. "A family of removable cassettes designed to obtain antibiotic-resistance-free genomic modifications of *Escherichia coli* and other bacteria." *Gene* 247(1-2):255-264, 2000.
Parker, J.M. et al. "New hydrophilicity scale derived from high-performance liquid chromatography peptide retention data: correlation of predicted surface residues with antigenicity and X-ray-derived accessible sites." *Biochemistry* 25(19):5425-5432, 1986.
Pearson, W.R. et al. "Improved Tools for Biological Sequence Comparison." *Proc. Natl. Acad. Sci. USA* 85(8):2444-2448, 1988.
Petrounia, I.P. et al. "Designed evolution of enzymatic properties." *Current Opinion in Biotechnology* 11 (4):325-330, 2000.
Rezwan, K. et al. "Bovine Serum Albumin Adsorption onto Colloidal A12O3 Particles: A New Model Based on Zeta Potential and UV-VIS Measurements." *Langmuir* 20(23)10055-10061, 2004.
Rose, G.D. et al. "Hydrophobicity of amino acid residues in globular proteins." *Science* 229(4716):834-838, 1985.
Roseman, M.A. "Hydrophilicity of polar amino acid side-chains is markedly reduced by flanking peptide bonds." *Journal of Molecular Biology* 200(3):513-522, 1988.
Rubingh, D.N. "Protein engineering from a bioindustrial point of view." *Current Opinion in Biotechnology* 8(4) :417-422, 1997.
Russell, A.J., and A R Fersht. "Rational modification of enzyme catalysis by engineering surface charge." *Nature* 328(6130):496-500, 1987.
Russell, A.J., P G Thomas, et al. "Electrostatic effects on modification of charged groups in the active site cleft of subtilisin by protein engineering." *Journal of Molecular Biology* 193(4):803-813, 1987.
Schell, D. et al. "Dilute-sulfuric acid pretreatment of corn stover in pilot-scale reactor." *Applied Biochemistry and Biotechnology* 105(1):69-85, 2003.
Smith, T.F. et al. "Comparison of biosequences." *Adv. Appl. Math* 2:482-489, 1981.
Solingen, P. et al. "Cloning and expression of an endocellulase gene from a novel streptomycete isolated from an East African soda lake." *Extremophiles* 5(5):333-341, 2001.
Soumillion, P. et al. "Novel concepts for selection of catalytic activity." *Current Opinion in Biotechnology* 12(4):387-394, 2001.
Sparks, D.L. et al. "Quantitative measurement of lipoprotein surface charge by agarose gel electrophoresis." *J. Lipid Res.* 33(1):123-130, 1992.
Trieu-Cuot, P. et al. "Nucleotide sequence of the *Streptococcus faecalis* plasmid gene encoding the 3'5"-aminoglycoside phosphotransferase type III." *Gene* 23(3):331-41, 1983.
Wu, D.Y. et al. "The ligation amplification reaction (LAR)—amplification of specific DNA sequences using sequential rounds of template-dependent ligation." *Genomics* 4(4):560-9, 1989.
Bommarius, A.S. et al. "High-throughput screening for enhanced protein stability." *Current Opinion in Biotechnology* 17(6):606-610, 2006.
Bolt, R. et al. "The role of high-resolution structural studies in the development of commercial enzymes." *Current Opinion in Biotechnology* 10(4):391-397, 1999.
Chica, R.A. et al. "Semi-rational approaches to engineering enzyme activity: combining the benefits of directed evolution and rational design." *Current Opinion in Biotechnology* 16(4):378-384, 2005.
van Ee, J.H. et al. "Protein-Engineering of the High Alkaline Detergent Protease Maxacal." *Communicaciones Presentadas a las Jornadas de Comite Espagnolde la Detergencia* 19:257-266, 1988.
Guo et al. "Protein Tolerance to Random Amino Acid Change," PNAS USA 101:9205-9210 (2004).
Gupta, R. et al. "Bacterial alkaline proteases: molecular approaches and industrial applications." *Applied Microbiology and Biotechnology* 59(1):15-32, 2002.
Hill et al. "Functional Analysis of Conserved Histidines in ADP-Glucose Pyrophosphorylase from *Eschericia coli,*" Biochem Biophys Res Comm 244:573-577 (1998).
International Search Report mailed Dec. 10, 2008 for PCT/US2008/007113, 4 pp.
International Search Report mailed Dec. 19, 2008 for PCT/US2008/007114, 5 pp.
International Search Report mailed Jan. 28, 2009 for PCT/US2008/007103, 4 pp.
Kirk, O. et al. "Industrial enzyme applications." Current Opinion in Biotechnology 13(4):345-351, 2002.
Lazar et al. "Transforming Growth Factor α: Mutation of Aspartic Acid 47 and Leucine 48 Reults in Different Biologcal Activity," Mol Cell Biol 8:1247-1252 (1988).
Mansfeld, J. et al. "The stability of engineered thermostable neutral proteases from Bacillus stearothermophilus in organic solvents and detergents." *Biotechnology and Bioengineering* 97(4):672-679, 2007.
Morley, K.L. et al. "Improving enzyme properties: when are closer mutations better?." *Trends in Biotechnology* 23(5):231-237, 2005.
Mulder et al. "Altered Flexibility in the Substrate-Binding Site of Related Native and Engineered High-Alkaline *Bacillus subtilisins,*" Journal of Molecular Biology 292:111-123 (1999).
Moran, L.A. "Mutation Rates," accessed at http://sandwalk.blogspot.com/2007/07/mutation-rates.html on May 30, 2012, 28 pp. (2007).
Patrick, W.M. et al. "Strategies and computational tools for improving randomized protein libraries." *Biomolecular Engineering* 22(4):105-112, 2005.
Reetz, M.T. et al. "Iterative saturation mutagenesis (ISM) for rapid directed evolution of functional enzymes." *Nat. Protocols* 2(4):891-903, 2007.
Sellami-Kamoun, A. et al. "Stability of thermostable alkaline protease from *Bacillus licheniformis* RP1 in commercial solid laundry detergent formulations." *Microbiological Research* 163(3):299-306, 2008.
Strausberg, S.L. et al. "Directed coevolution of stability and catalytic activity in calcium-free subtilisin." *Biochemistry* 44(9):3272-3279, 2005.
Tindbaek et al. "Engineering a Substrate-Specific Cold-Adapted Subtilisin," Protein Engineering Design and Selection, 17:149-156 (2004).
von der Osten et al. "Protein Engineering of Subtilisins to Improve Stability in Detergent Formulations," *Journal of Biotechnology* 28:55-68 (1993).
Wacey et al. "Disentangling the Perturbational Effects of Amino Acid Substitutions in the DNA-Binding Domain of p53," Hum. Genet. 104:15-22 (1999).
Branden, C., et al., "The Building Blocks." In *Introduction to Protein Structure,* 2nd Edition, Garland Science, pp. 3-12, 1999.
Gudiksen, K., et al., "Increasing the Net Charge and Decreasing the Hydrophobicity of Bovine Carbonic Anhydrase Decreases the Rate of Denaturation with Sodium Dodecyl Sulfate." *Biophys. J.* 91: 298-310, 2006.
Hamamatsu N. et al., "Directed evolution by accumulating tailored mutations: thermostabilization of lactate oxidase with less trade-off with catalytic activity." *Protein Eng. Des. Sel.* 19(11): 483-489, 2006.
de Kreij, A., et al., "The Effects of Modifying the Surface Charge on the Catalytic Activity of a Thermolysin-like Protease." *J. Biol. Chem.* 277(18):15432-15438, 2002.
Mildvan, A.S., et al., "Quantitative interpretations of double mutations of enzymes." *Arch. Biochem. Biophys.* 294: 327-340, 1992.
Pakula, A.A., et al., "Genetic analysis of protein stability and function." *Annu. Rev. Genet.* 23: 289-310, 1989.
Shoichet B.K. et al., A relationship between protein stability and protein function // Proc. Natl. Acad. Sci. USA, 1995, vol. 92, pp. 452-456.
Strickler, S.S., et al., "Protein stability and surface electrostatics: a charged relationship." *Biochem* 45:2761-2776, 2006.
Zhang, W., et al., "Improving the activity and stability of GL-7-ACA Acylase CA130 by site-directed mutagenesis." *Appl. Environ. Microbiol.* 71(9): 5290-5296, 2005.

* cited by examiner

Matrix of Charge Change at pH 8.6 by Amino Acid Substitution

| Amino Acid | A | C | D | E | F | G | H | I | K | L | M | N | P | Q | R | S | T | V | W | Y |
|---|---|---|---|---|---|---|---|---|---|---|---|---|---|---|---|---|---|---|---|---|
| A | 0 | 0 | -1 | -1 | 0 | 0 | 0 | 0 | 1 | 0 | 0 | 0 | 0 | 0 | 1 | 0 | 0 | 0 | 0 | 0 |
| C | 0 | 0 | -1 | -1 | 0 | 0 | 0 | 0 | 1 | 0 | 0 | 0 | 0 | 0 | 1 | 0 | 0 | 0 | 0 | 0 |
| D | 1 | 1 | 0 | 0 | 1 | 1 | 1 | 1 | 2 | 1 | 1 | 1 | 1 | 1 | 2 | 1 | 1 | 1 | 1 | 1 |
| E | 1 | 1 | 0 | 0 | 1 | 1 | 1 | 1 | 2 | 1 | 1 | 1 | 1 | 1 | 2 | 1 | 1 | 1 | 1 | 1 |
| F | 0 | 0 | -1 | -1 | 0 | 0 | 0 | 0 | 1 | 0 | 0 | 0 | 0 | 0 | 1 | 0 | 0 | 0 | 0 | 0 |
| G | 0 | 0 | -1 | -1 | 0 | 0 | 0 | 0 | 1 | 0 | 0 | 0 | 0 | 0 | 1 | 0 | 0 | 0 | 0 | 0 |
| H | 0 | 0 | -1 | -1 | 0 | 0 | 0 | 0 | 1 | 0 | 0 | 0 | 0 | 0 | 1 | 0 | 0 | 0 | 0 | 0 |
| I | 0 | 0 | -1 | -1 | 0 | 0 | 0 | 0 | 1 | 0 | 0 | 0 | 0 | 0 | 1 | 0 | 0 | 0 | 0 | 0 |
| K | -1 | -1 | -2 | -2 | -1 | -1 | -1 | -1 | 0 | -1 | -1 | -1 | -1 | -1 | 0 | -1 | -1 | -1 | -1 | -1 |
| L | 0 | 0 | -1 | -1 | 0 | 0 | 0 | 0 | 1 | 0 | 0 | 0 | 0 | 0 | 1 | 0 | 0 | 0 | 0 | 0 |
| M | 0 | 0 | -1 | -1 | 0 | 0 | 0 | 0 | 1 | 0 | 0 | 0 | 0 | 0 | 1 | 0 | 0 | 0 | 0 | 0 |
| N | 0 | 0 | -1 | -1 | 0 | 0 | 0 | 0 | 1 | 0 | 0 | 0 | 0 | 0 | 1 | 0 | 0 | 0 | 0 | 0 |
| P | 0 | 0 | -1 | -1 | 0 | 0 | 0 | 0 | 1 | 0 | 0 | 0 | 0 | 0 | 1 | 0 | 0 | 0 | 0 | 0 |
| Q | 0 | 0 | -1 | -1 | 0 | 0 | 0 | 0 | 1 | 0 | 0 | 0 | 0 | 0 | 1 | 0 | 0 | 0 | 0 | 0 |
| R | -1 | -1 | -2 | -2 | -1 | -1 | -1 | -1 | 0 | -1 | -1 | -1 | -1 | -1 | 0 | -1 | -1 | -1 | -1 | -1 |
| S | 0 | 0 | -1 | -1 | 0 | 0 | 0 | 0 | 1 | 0 | 0 | 0 | 0 | 0 | 1 | 0 | 0 | 0 | 0 | 0 |
| T | 0 | 0 | -1 | -1 | 0 | 0 | 0 | 0 | 1 | 0 | 0 | 0 | 0 | 0 | 1 | 0 | 0 | 0 | 0 | 0 |
| V | 0 | 0 | -1 | -1 | 0 | 0 | 0 | 0 | 1 | 0 | 0 | 0 | 0 | 0 | 1 | 0 | 0 | 0 | 0 | 0 |
| W | 0 | 0 | -1 | -1 | 0 | 0 | 0 | 0 | 1 | 0 | 0 | 0 | 0 | 0 | 1 | 0 | 0 | 0 | 0 | 0 |
| Y | 0 | 0 | -1 | -1 | 0 | 0 | 0 | 0 | 1 | 0 | 0 | 0 | 0 | 0 | 1 | 0 | 0 | 0 | 0 | 0 |

*FIG. 27*

Matrix of Hydrogen-Bonding Changes by Amino Acid Substitution

| Amino Acid | A | C | D | E | F | G | H | I | K | L | M | N | P | Q | R | S | T | V | W | Y |
|---|---|---|---|---|---|---|---|---|---|---|---|---|---|---|---|---|---|---|---|---|
| A | 0 | 1 | 3 | 3 | 0 | 0 | 2 | 0 | 3 | 0 | 0 | 2 | 0 | 2 | 3 | 1 | 1 | 0 | 0 | 1 |
| C | -1 | 0 | 2 | 2 | -1 | -1 | 1 | -1 | 2 | -1 | -1 | 1 | -1 | 1 | 2 | 0 | 0 | -1 | -1 | 0 |
| D | -3 | -2 | 0 | 0 | -3 | -3 | -1 | -3 | 0 | -3 | -3 | -1 | -3 | -1 | 0 | -2 | -2 | -3 | -3 | -2 |
| E | -3 | -2 | 0 | 0 | -3 | -3 | -1 | -3 | 0 | -3 | -3 | -1 | -3 | -1 | 0 | -2 | -2 | -3 | -3 | -2 |
| F | 0 | 1 | 3 | 3 | 0 | 0 | 2 | 0 | 3 | 0 | 0 | 2 | 0 | 2 | 3 | 1 | 1 | 0 | 0 | 1 |
| G | 0 | 1 | 3 | 3 | 0 | 0 | 2 | 0 | 3 | 0 | 0 | 2 | 0 | 2 | 3 | 1 | 1 | 0 | 0 | 1 |
| H | -2 | -1 | 1 | 1 | -2 | -2 | 0 | -2 | 1 | -2 | -2 | 0 | -2 | 0 | 1 | -1 | -1 | -2 | -2 | -1 |
| I | 0 | 1 | 3 | 3 | 0 | 0 | 2 | 0 | 3 | 0 | 0 | 2 | 0 | 2 | 3 | 1 | 1 | 0 | 0 | 1 |
| K | -3 | -2 | 0 | 0 | -3 | -3 | -1 | -3 | 0 | -3 | -3 | -1 | -3 | -1 | 0 | -2 | -2 | -3 | -3 | -2 |
| L | 0 | 1 | 3 | 3 | 0 | 0 | 2 | 0 | 3 | 0 | 0 | 2 | 0 | 2 | 3 | 1 | 1 | 0 | 0 | 1 |
| M | 0 | 1 | 3 | 3 | 0 | 0 | 2 | 0 | 3 | 0 | 0 | 2 | 0 | 2 | 3 | 1 | 1 | 0 | 0 | 1 |
| N | -2 | -1 | 1 | 1 | -2 | -2 | 0 | -2 | 1 | -2 | -2 | 0 | -2 | 0 | 1 | -1 | -1 | -2 | -2 | -1 |
| P | 0 | 1 | 3 | 3 | 0 | 0 | 2 | 0 | 3 | 0 | 0 | 2 | 0 | 2 | 3 | 1 | 1 | 0 | 0 | 1 |
| Q | -2 | -1 | 1 | 1 | -2 | -2 | 0 | -2 | 1 | -2 | -2 | 0 | -2 | 0 | 1 | -1 | -1 | -2 | -2 | -1 |
| R | -3 | -2 | 0 | 0 | -3 | -3 | -1 | -3 | 0 | -3 | -3 | -1 | -3 | -1 | 0 | -2 | -2 | -3 | -3 | -2 |
| S | -1 | 0 | 2 | 2 | -1 | -1 | 1 | -1 | 2 | -1 | -1 | 1 | -1 | 1 | 2 | 0 | 0 | -1 | -1 | 0 |
| T | -1 | 0 | 2 | 2 | -1 | -1 | 1 | -1 | 2 | -1 | -1 | 1 | -1 | 1 | 2 | 0 | 0 | -1 | -1 | 0 |
| V | 0 | 1 | 3 | 3 | 0 | 0 | 2 | 0 | 3 | 0 | 0 | 2 | 0 | 2 | 3 | 1 | 1 | 0 | 0 | 1 |
| W | 0 | 1 | 3 | 3 | 0 | 0 | 2 | 0 | 3 | 0 | 0 | 2 | 0 | 2 | 3 | 1 | 1 | 0 | 0 | 1 |
| Y | -1 | 0 | 2 | 2 | -1 | -1 | 1 | -1 | 2 | -1 | -1 | 1 | -1 | 1 | 2 | 0 | 0 | -1 | -1 | 0 |

*FIG. 28*

Matrix of Hydropathicity Changes by Amino Acid Substitution (Kyte-Doolittle)

| Amino Acid | A | C | D | E | F | G | H | I | K | L | M | N | P | Q | R | S | T | V | W | Y |
|---|---|---|---|---|---|---|---|---|---|---|---|---|---|---|---|---|---|---|---|---|
| A | 0.0 | 0.7 | -5.3 | -5.3 | 1.0 | -2.2 | -5.0 | 2.7 | -5.7 | 2.0 | 0.1 | -5.3 | -3.4 | -5.3 | -6.3 | -2.6 | -2.5 | 2.4 | -2.7 | -3.1 |
| C | -0.7 | 0.0 | -6.0 | -6.0 | 0.3 | -2.9 | -5.7 | 2.0 | -6.4 | 1.3 | -0.6 | -6.0 | -4.1 | -6.0 | -7.0 | -3.3 | -3.2 | 1.7 | -3.4 | -3.8 |
| D | 5.3 | 6.0 | 0.0 | 0.0 | 6.3 | 3.1 | 0.3 | 8.0 | -0.4 | 7.3 | 5.4 | 0.0 | 1.9 | 0.0 | -1.0 | 2.7 | 2.8 | 7.7 | 2.6 | 2.2 |
| E | 5.3 | 6.0 | 0.0 | 0.0 | 6.3 | 3.1 | 0.3 | 8.0 | -0.4 | 7.3 | 5.4 | 0.0 | 1.9 | 0.0 | -1.0 | 2.7 | 2.8 | 7.7 | 2.6 | 2.2 |
| F | -1.0 | -0.3 | -6.3 | -6.3 | 0.0 | -3.2 | -6.0 | 1.7 | -6.7 | 1.0 | -0.9 | -6.3 | -4.4 | -6.3 | -7.3 | -3.6 | -3.5 | 1.4 | -3.7 | -4.1 |
| G | 2.2 | 2.9 | -3.1 | -3.1 | 3.2 | 0.0 | -2.8 | 4.9 | -3.5 | 4.2 | 2.3 | -3.1 | -1.2 | -3.1 | -4.1 | -0.4 | -0.3 | 4.6 | -0.5 | -0.9 |
| H | 5.0 | 5.7 | -0.3 | -0.3 | 6.0 | 2.8 | 0.0 | 7.7 | -0.7 | 7.0 | 5.1 | -0.3 | 1.6 | -0.3 | -1.3 | 2.4 | 2.5 | 7.4 | 2.3 | 1.9 |
| I | -2.7 | -2.0 | -8.0 | -8.0 | -1.7 | -4.9 | -7.7 | 0.0 | -8.4 | -0.7 | -2.6 | -8.0 | -6.1 | -8.0 | -9.0 | -5.3 | -5.2 | -0.3 | -5.4 | -5.8 |
| K | 5.7 | 6.4 | 0.4 | 0.4 | 6.7 | 3.5 | 0.7 | 8.4 | 0.0 | 7.7 | 5.8 | 0.4 | 2.3 | 0.4 | -0.6 | 3.1 | 3.2 | 8.1 | 3.0 | 2.6 |
| L | -2.0 | -1.3 | -7.3 | -7.3 | -1.0 | -4.2 | -7.0 | 0.7 | -7.7 | 0.0 | -1.9 | -7.3 | -5.4 | -7.3 | -8.3 | -4.6 | -4.5 | 0.4 | -4.7 | -5.1 |
| M | -0.1 | 0.6 | -5.4 | -5.4 | 0.9 | -2.3 | -5.1 | 2.6 | -5.8 | 1.9 | 0.0 | -5.4 | -3.5 | -5.4 | -6.4 | -2.7 | -2.6 | 2.3 | -2.8 | -3.2 |
| N | 5.3 | 6.0 | 0.0 | 0.0 | 6.3 | 3.1 | 0.3 | 8.0 | -0.4 | 7.3 | 5.4 | 0.0 | 1.9 | 0.0 | -1.0 | 2.7 | 2.8 | 7.7 | 2.6 | 2.2 |
| P | 3.4 | 4.1 | -1.9 | -1.9 | 4.4 | 1.2 | -1.6 | 6.1 | -2.3 | 5.4 | 3.5 | -1.9 | 0.0 | -1.9 | -2.9 | 0.8 | 0.9 | 5.8 | 0.7 | 0.3 |
| Q | 5.3 | 6.0 | 0.0 | 0.0 | 6.3 | 3.1 | 0.3 | 8.0 | -0.4 | 7.3 | 5.4 | 0.0 | 1.9 | 0.0 | -1.0 | 2.7 | 2.8 | 7.7 | 2.6 | 2.2 |
| R | 6.3 | 7.0 | 1.0 | 1.0 | 7.3 | 4.1 | 1.3 | 9.0 | 0.6 | 8.3 | 6.4 | 1.0 | 2.9 | 1.0 | 0.0 | 3.7 | 3.8 | 8.7 | 3.6 | 3.2 |
| S | 2.6 | 3.3 | -2.7 | -2.7 | 3.6 | 0.4 | -2.4 | 5.3 | -3.1 | 4.6 | 2.7 | -2.7 | -0.8 | -2.7 | -3.7 | 0.0 | 0.1 | 5.0 | -0.1 | -0.5 |
| T | 2.5 | 3.2 | -2.8 | -2.8 | 3.5 | 0.3 | -2.5 | 5.2 | -3.2 | 4.5 | 2.6 | -2.8 | -0.9 | -2.8 | -3.8 | -0.1 | 0.0 | 4.9 | -0.2 | -0.6 |
| V | -2.4 | -1.7 | -7.7 | -7.7 | -1.4 | -4.6 | -7.4 | 0.3 | -8.1 | -0.4 | -2.3 | -7.7 | -5.8 | -7.7 | -8.7 | -5.0 | -4.9 | 0.0 | -5.1 | -5.5 |
| W | 2.7 | 3.4 | -2.6 | -2.6 | 3.7 | 0.5 | -2.3 | 5.4 | -3.0 | 4.7 | 2.8 | -2.6 | -0.7 | -2.6 | -3.6 | 0.1 | 0.2 | 5.1 | 0.0 | -0.4 |
| Y | 3.1 | 3.8 | -2.2 | -2.2 | 4.1 | 0.9 | -1.9 | 5.8 | -2.6 | 5.1 | 3.2 | -2.2 | -0.3 | -2.2 | -3.2 | 0.5 | 0.6 | 5.5 | 0.4 | 0.0 |

*FIG. 29*

Matrix of Hydrophobicity Changes by Amino Acid Substitution (Eisenberg)

| Amino Acid | A | C | D | E | F | G | H | I | K | L | M | N | P | Q | R | S | T | V | W | Y |
|---|---|---|---|---|---|---|---|---|---|---|---|---|---|---|---|---|---|---|---|---|
| A | 0.0 | -0.3 | -1.5 | -1.4 | 0.6 | -0.1 | -1.0 | 0.8 | -2.1 | 0.4 | 0.0 | -1.4 | -0.5 | -1.5 | -3.2 | -0.8 | -0.7 | 0.5 | 0.2 | -0.4 |
| C | 0.3 | 0.0 | -1.2 | -1.0 | 0.9 | 0.2 | -0.7 | 1.1 | -1.8 | 0.8 | 0.4 | -1.1 | -0.2 | -1.1 | -2.8 | -0.5 | -0.3 | 0.8 | 0.5 | 0.0 |
| D | 1.5 | 1.2 | 0.0 | 0.2 | 2.1 | 1.4 | 0.5 | 2.3 | -0.6 | 2.0 | 1.5 | 0.1 | 1.0 | 0.1 | -1.6 | 0.7 | 0.9 | 2.0 | 1.7 | 1.2 |
| E | 1.4 | 1.0 | -0.2 | 0.0 | 1.9 | 1.2 | 0.3 | 2.1 | -0.8 | 1.8 | 1.4 | 0.0 | 0.9 | -0.1 | -1.8 | 0.6 | 0.7 | 1.8 | 1.6 | 1.0 |
| F | -0.6 | -0.9 | -2.1 | -1.9 | 0.0 | -0.7 | -1.6 | 0.2 | -2.7 | -0.1 | -0.6 | -2.0 | -1.1 | -2.0 | -3.7 | -1.4 | -1.2 | -0.1 | -0.4 | -0.9 |
| G | 0.1 | -0.2 | -1.4 | -1.2 | 0.7 | 0.0 | -0.9 | 0.9 | -2.0 | 0.6 | 0.2 | -1.3 | -0.4 | -1.3 | -3.0 | -0.7 | -0.5 | 0.6 | 0.3 | -0.2 |
| H | 1.0 | 0.7 | -0.5 | -0.3 | 1.6 | 0.9 | 0.0 | 1.8 | -1.1 | 1.5 | 1.0 | -0.4 | 0.5 | -0.5 | -2.1 | 0.2 | 0.4 | 1.5 | 1.2 | 0.7 |
| I | -0.8 | -1.1 | -2.3 | -2.1 | -0.2 | -0.9 | -1.8 | 0.0 | -2.9 | -0.3 | -0.7 | -2.2 | -1.3 | -2.2 | -3.9 | -1.6 | -1.4 | -0.3 | -0.6 | -1.1 |
| K | 2.1 | 1.8 | 0.6 | 0.8 | 2.7 | 2.0 | 1.1 | 2.9 | 0.0 | 2.6 | 2.1 | 0.7 | 1.6 | 0.7 | -1.0 | 1.3 | 1.5 | 2.6 | 2.3 | 1.8 |
| L | -0.4 | -0.8 | -2.0 | -1.8 | 0.1 | -0.6 | -1.5 | 0.3 | -2.6 | 0.0 | -0.4 | -1.8 | -0.9 | -1.9 | -3.6 | -1.2 | -1.1 | 0.0 | -0.3 | -0.8 |
| M | 0.0 | -0.4 | -1.5 | -1.4 | 0.6 | -0.2 | -1.0 | 0.7 | -2.1 | 0.4 | 0.0 | -1.4 | -0.5 | -1.5 | -3.2 | -0.8 | -0.7 | 0.4 | 0.2 | -0.4 |
| N | 1.4 | 1.1 | -0.1 | 0.0 | 2.0 | 1.3 | 0.4 | 2.2 | -0.7 | 1.8 | 1.4 | 0.0 | 0.9 | -0.1 | -1.8 | 0.6 | 0.7 | 1.9 | 1.6 | 1.0 |
| P | 0.5 | 0.2 | -1.0 | -0.9 | 1.1 | 0.4 | -0.5 | 1.3 | -1.6 | 0.9 | 0.5 | -0.9 | 0.0 | -1.0 | -2.7 | -0.3 | -0.2 | 1.0 | 0.7 | 0.1 |
| Q | 1.5 | 1.1 | -0.1 | 0.1 | 2.0 | 1.3 | 0.5 | 2.2 | -0.7 | 1.9 | 1.5 | 0.1 | 1.0 | 0.0 | -1.7 | 0.7 | 0.8 | 1.9 | 1.7 | 1.1 |
| R | 3.2 | 2.8 | 1.6 | 1.8 | 3.7 | 3.0 | 2.1 | 3.9 | 1.0 | 3.6 | 3.2 | 1.8 | 2.7 | 1.7 | 0.0 | 2.4 | 2.5 | 3.6 | 3.3 | 2.8 |
| S | 0.8 | 0.5 | -0.7 | -0.6 | 1.4 | 0.7 | -0.2 | 1.6 | -1.3 | 1.2 | 0.8 | -0.6 | 0.3 | -0.7 | -2.4 | 0.0 | 0.1 | 1.3 | 1.0 | 0.4 |
| T | 0.7 | 0.3 | -0.9 | -0.7 | 1.2 | 0.5 | -0.4 | 1.4 | -1.5 | 1.1 | 0.7 | -0.7 | 0.2 | -0.8 | -2.5 | -0.1 | 0.0 | 1.1 | 0.9 | 0.3 |
| V | -0.5 | -0.8 | -2.0 | -1.8 | 0.1 | -0.6 | -1.5 | 0.3 | -2.6 | 0.0 | -0.4 | -1.9 | -1.0 | -1.9 | -3.6 | -1.3 | -1.1 | 0.0 | -0.3 | -0.8 |
| W | -0.2 | -0.5 | -1.7 | -1.6 | 0.4 | -0.3 | -1.2 | 0.6 | -2.3 | 0.3 | -0.2 | -1.6 | -0.7 | -1.7 | -3.3 | -1.0 | -0.9 | 0.3 | 0.0 | -0.6 |
| Y | 0.4 | 0.0 | -1.2 | -1.0 | 0.9 | 0.2 | -0.7 | 1.1 | -1.8 | 0.8 | 0.4 | -1.0 | -0.1 | -1.1 | -2.8 | -0.4 | -0.3 | 0.8 | 0.6 | 0.0 |

*FIG. 30*

METHODS FOR IMPROVING MULTIPLE PROTEIN PROPERTIES

CROSS REFERENCE TO RELATED APPLICATIONS

The present application claims priority to U.S. Provisional Patent Application Nos. 60/933,307, 60/933,331, and 60/933,312, filed on Jun. 6, 2007, hereby incorporated by reference in their entirety.

SEQUENCE LISTING

The sequence listing submitted via EFS, in compliance with 37 C.F.R. §1.52(e), is incorporated herein by reference. The sequence listing text file submitted via EFS contains the file "30974US-SEQLIST.txt" created on Jun. 3, 2015, which is 69,632 bytes in size.

FIELD OF THE INVENTION

The present invention provides efficient methods for obtaining a protein with one or more beneficial attributes in industrial, consumer or pharmaceutical applications. In some preferred embodiments, the present invention provides methods for producing superior enzymes for a given application through screening an abbreviated set of candidate enzymes.

BACKGROUND OF THE INVENTION

The properties of proteins functioning outside their natural milieu are often suboptimal. For instance, enzymes (e.g., proteases, lipases, amylases, cellulases, etc.) are frequently used for cleaning stains from fabric in laundry detergents, which typically include a complex combination of active ingredients. In fact, most cleaning products include a surfactant system, bleaching agents, builders, suds suppressors, soil-suspending agents, soil-release agents, optical brighteners, softening agents, dispersants, dye transfer inhibition compounds, abrasives, bactericides, and perfumes, as well as enzymes for cleaning. Thus despite the complexity of current detergents, there are many stains that are difficult to completely remove, due in part to suboptimal enzyme performance. Despite much research in enzyme development, there remains a need in the art for methods to engineer proteins for particular uses and conditions. Indeed, there remains a need in the art for methods to rapidly and systematically tailor electrostatic properties of other to optimize their performance in commercial applications. In particular, there remains a need in the art for methods to engineer industrially useful enzymes, including but not limited to lipases, amylases, cutinases, mannanases, oxidoreductases, cellulases, pectinases, proteases, and other enzymes, in order to provide improved activity, stability, and solubility in cleaning solutions. In addition, there remains a need in the art for methods to engineer recombinant enzymes that can be expressed at high levels from transformed host cells.

SUMMARY OF THE INVENTION

The present invention provides efficient methods for obtaining a protein with one or more beneficial attributes in industrial, consumer or pharmaceutical applications. In some preferred embodiments, the present invention provides methods for producing superior enzymes for a given application through screening an abbreviated set of candidate enzymes.

The present invention provides methods of providing a library of protein variants, comprising: testing multiple protein variants spanning a range of a property of interest (e.g., a physical property) in a test of interest; identifying an optimum within the range of the property of interest that is associated with a favorable outcome in the test of interest; and providing a plurality of protein variants within the optimum of the range of the property of interest, thereby providing a library of protein variants enriched in members having the favorable outcome in the test of interest. In some preferred embodiments, the favorable outcome corresponds to a value of greater than about 50%, about 60%, about 70%, about 80%, about 90%, or about 95% of a maximal value observed in the test of interest. In additional embodiments, the methods further comprise the step of testing the plurality of protein variants and a wild type protein, in the test of interest. In yet further embodiments, the methods comprise the step of identifying the protein variants as having an improved outcome, wherein the wild type protein achieves a value of 1.0 in the test of interest and the protein variants having an improved outcome achieve a value greater than 1.0. In some preferred embodiments, the performance index=test performance/wild type performance. In some particularly preferred embodiments, the protein is an enzyme. In some additional preferred embodiments, the enzyme is a protease, amylase, cellulase, polyesterse, esterase, lipase, cutinase, pectinase or oxidase. In some further embodiments, the protein is an antibody, or a hormone or cytokine (e.g., a growth factor). In some preferred embodiments, the protease is a neutral metalloprotease. In some particularly preferred embodiments, the parent protease is a wild type mature form of the neutral metalloprotease. In yet additional preferred embodiments, the variant is derived from a neutral metalloprotease of the family Bacillaceae. In still other embodiments, the variant is derived from a neutral metalloprotease of the genus *Bacillus*. In some other embodiments, the protease is a serine protease. In some particularly preferred embodiments, the parent protease is a wild type mature form of the serine protease. In yet additional preferred embodiments, the variant is derived from a serine protease of the suborder Micrococcineae. In further embodiments, the variant is derived from a serine protease of the genus *Cellulomonas*. In yet additional embodiments, the property of interest is charge relative to the wild type enzyme. In some particularly preferred embodiments, the property of interest is zeta potential. In some additional preferred embodiments, the test of interest comprises wash performance. In some particularly preferred embodiments, the wash performance comprises blood milk ink (BMI) wash performance in detergent. In some embodiments, wash performance is tested in a detergent composition formulated into a powdered or liquid detergent having a pH of between 5 and 12.0. In yet additional embodiments, wash performance is tested in a cold water liquid detergent having a basic pH. In some alternative embodiments, the test of interest comprises measuring substrate binding, and/or measuring enzyme inhibition, and/or measuring expression levels, and/or measuring detergent stability, and/or measuring thermal stability; and/or measuring reaction rate; and/or measuring extent of reaction; and/or measuring thermal activity.

The present invention also provides methods for producing an improved variant of a test protein fold, comprising: assaying multiple variants of a probe protein fold spanning a range of a property of interest in an assay of interest; identifying an optimum within the range of the property of interest that is associated with a favorable outcome in the assay of interest; assaying a parent protein of the test protein fold in the assay of interest; and producing an improved variant of the test protein fold by introducing an amino acid substitution is the parent protein such that the improved variant is within the optimum of the range of the property of interest. In some embodiments, the test protein fold and the probe protein fold are different. In some additional embodiments, the test protein fold is a serine protease and the probe protein fold is a neutral metalloprotease.

The present invention also provides methods for producing a substrate stain-specific enzyme variant, comprising: determining zeta potential of a substrate stain in a reference buffer; determining zeta potential of a parent enzyme in the reference buffer; and producing a substrate stain-specific enzyme variant by introducing an amino acid substitution in the parent enzyme such that zeta potential of the variant enzyme is closer to the zeta potential of the substrate stain than to the zeta potential of the parent enzyme.

The present invention further provides methods for producing a composition for cleaning multiple stains comprising: determining zeta potential of each of the multiple stains in a reference buffer; selecting a cleaning enzyme having a zeta potential in the reference buffer essentially equal to the zeta potential of one of the multiple stains, wherein the selecting continues until each of the multiple stains is paired with at least one cleaning enzyme; and preparing a composition for cleaning multiple stains by inclusion of the cleaning enzymes of step b in a detergent solution with a pH and conductivity essentially equal to that of the reference buffer.

The present invention provides methods of providing a library of protein variants, comprising: a) testing multiple protein variants spanning a range of at least one property of interest in at least one test of interest; b) identifying an optimum within the range of the property of interest that is associated with a favorable outcome in at least one test of interest; and c) providing a plurality of protein variants within the optimum of the range of the property of interest, such that a library of protein variants enriched in members having the favorable outcome in at least one test of interest is provided. In some embodiments, the property of interest is a physical property. In some further embodiments, the favorable outcome corresponds to a value of greater than at least about 50%, of a maximal value observed in the test of interest. In some additional embodiments, the favorable outcome corresponds to a value of greater than at least about 60%, about 70%, about 80%, about 90%, or about 95% of a maximal value observed in the test of interest. In some further embodiments, the methods further comprise the step of: d) testing the plurality of protein variants and at least one wild type protein, in at least one test of interest. In some additional embodiments, the methods further comprise the step of identifying the protein variants as having an improved outcome, wherein the wild type protein achieves a performance index value of 1.0 in at least one test of interest and the protein variants having an improved outcome achieve a value greater than 1.0. In some embodiments, the protein is an antibody, hormone, or cytokine. In some preferred embodiments, the protein is an enzyme. In some particularly preferred embodiments, the enzyme is a protease, amylase, cellulase, polyesterse, esterase, lipase, cutinase, pectinase, oxidase, or a transferase. In some more particularly preferred embodiments, the protease is a neutral metalloprotease or serine protease. In some additional preferred embodiments, the serine protease is a subtilisin. In some alternative preferred embodiments, the neutral metalloprotease is obtained from a member of the family Bacillaceae. In some yet further embodiments, the serine protease is obtained from a member of the genus *Cellulomonas*. In some additional embodiments, the enzyme is a cellulase, while in other embodiments, the enzyme is an amylase. In some further embodiments, the property of interest is charge. In some additional embodiments, the charge of the protein variants and the wild type enzyme are determined and compared. In some further embodiments, the property of interest is zeta potential. In some yet further embodiments, the zeta potential of the protein variants and the wild type enzyme are determined and compared. In some preferred embodiments, the zeta potential of the protein variant is between about −40 mV and about +40 mV, while in other embodiments, the zeta potential of the protein variant is between about −20 mV and about +20 mVm, and in still additional embodiments, the zeta potential of the protein variant is between about −10 mV and about +10 mV. In some further embodiments, the test of interest comprises wash performance. In some preferred embodiments, the wash performance comprises blood milk ink wash performance. In some further embodiments, the protein variants and wild-type protein are tested in a detergent composition. In some preferred embodiments, the detergent composition is formulated into a powdered or liquid detergent having a pH of between about 5 and about 12.0. In some further preferred embodiments, the wash performance is tested in a cold water liquid detergent having a basic pH. In some alternative embodiments, the wash performance is tested in a hot water detergent. In some preferred embodiments, the at least one test of interest comprises measuring substrate binding, enzyme inhibition, expression levels, detergent stability, thermal stability, reaction rate, extent of reaction, thermal activity, starch liquefaction, biomass degradation, and/or saccharification.

The present invention also provides methods for producing at least one improved variant of a test protein fold, comprising: a) assaying multiple variants of a probe protein fold spanning a range of at least one property of interest in at least one assay of interest; b) identifying an optimum within the range of the at least one property of interest that is associated with a favorable outcome in the at least one assay of interest; c) assaying a parent protein of the test protein fold in the at least one assay of interest; and d) producing at least one improved variant of the test protein fold by introducing an amino acid modification in the parent protein such that the at least one improved variant is within the optimum range of the at least one property of interest. In some further embodiments, the modification comprises at least one amino acid substitution. In some yet additional embodiments, the test protein fold and the probe protein fold are different. In some embodiments, the property of interest is zeta potential. In some still further embodiments, the test protein fold comprises at least one serine protease and the probe protein fold comprises at least one neutral metalloprotease.

The present invention also provides methods for producing a substrate stain-specific enzyme variant, comprising: a) determining the zeta potential of a substrate stain in a reference buffer; b) determining the zeta potential of a parent enzyme in the reference buffer; and c) producing a substrate stain-specific enzyme variant by introducing at least one amino acid modification in the parent enzyme, such that the zeta potential of the substrate stain-specific enzyme variant is closer to the zeta potential of the substrate stain than to the zeta potential of the parent enzyme. In some embodiments, the modification comprises at least one amino acid substitution, deletion and/or insertion. In some alternative embodiments, the modification comprises chemical modification of the parent enzyme. In some further embodiments, the substrate stain-specific enzyme variant is positively charged and endothermic, and the substrate stain is negatively charged. In some alternative embodiments, the stain-specific enzyme variant is negatively charged and exothermic, and the substrate stain is negatively charged. In some further embodiments, the stain-specific enzyme variant is positively charged and exothermic, and the substrate stain is positively charged. In still further embodiments, the stain-specific enzyme variant is negatively charged and endothermic, and the substrate stain is positively charged.

The present invention also provides methods for producing a composition for cleaning multiple stains comprising: a) determining the zeta potential of each of the multiple stains in a reference buffer; b) selecting a cleaning enzyme having a zeta potential in the reference buffer that is essentially equal to the zeta potential of at least one of the multiple stains; and c) producing a composition for cleaning multiple stains, wherein the composition comprises at least one cleaning enzyme selected in step b). In some further embodiments, the composition comprises a detergent solution with a pH and conductivity that is essentially equal to that of the reference buffer. In some further embodiments, the selecting step identifies more than one cleaning enzyme. In still some additional embodiments, the composition comprises at least two cleaning enzymes and wherein the at least two cleaning enzymes have zeta potentials that correspond to the zeta potentials of at least two of the multiple stains.

The present invention also provides compositions for cleaning multiple stains produced using the methods set forth herein. In some preferred embodiments, the compositions comprise at least one cleaning enzyme. In some alternative embodiments, the at least one cleaning enzyme is a variant protein. In some further embodiments, the variant protein is more negatively charged than the wild-type precursor protein used to produce the variant protein, while in some alternative embodiments, the variant protein is more positively charged than the wild-type precursor protein used to produce the variant protein. In some additional embodiments, the variant protein is more negatively charged than the wild-type precursor protein used to produce the variant protein for enhanced stability in detergents containing anionic surfactants.

BRIEF DESCRIPTION OF THE DRAWINGS

FIG. 27 provides a charge change matrix indicating the charge change for amino acid residue substitutions at pH 8.6. From this matrix the net charge change of a variant enzyme as compared to a parent enzyme can be easily determined.

FIG. 28 provides a hydrogen-bonding capability change matrix indicating the hydrogen-bonding capability change for amino acid residue substitutions. From this matrix the net hydrogen-bonding capability change of a variant enzyme as compared to a parent enzyme can be easily determined.

FIG. 29 provides a Kyte-Doolittle hydropathicity change matrix indicating the hydropathicity change for amino acid residue substitutions. From this matrix the net hydropathicity change of a variant enzyme as compared to a parent enzyme can be easily determined.

FIG. 30 provides an Eisenberg hydrophobicity change matrix indicating the hydrophobicity change for amino acid residue substitutions. From this matrix the net hydrophobicity change of a variant enzyme as compared to a parent enzyme can be easily determined.

GENERAL DESCRIPTION OF THE INVENTION

Figure 2:
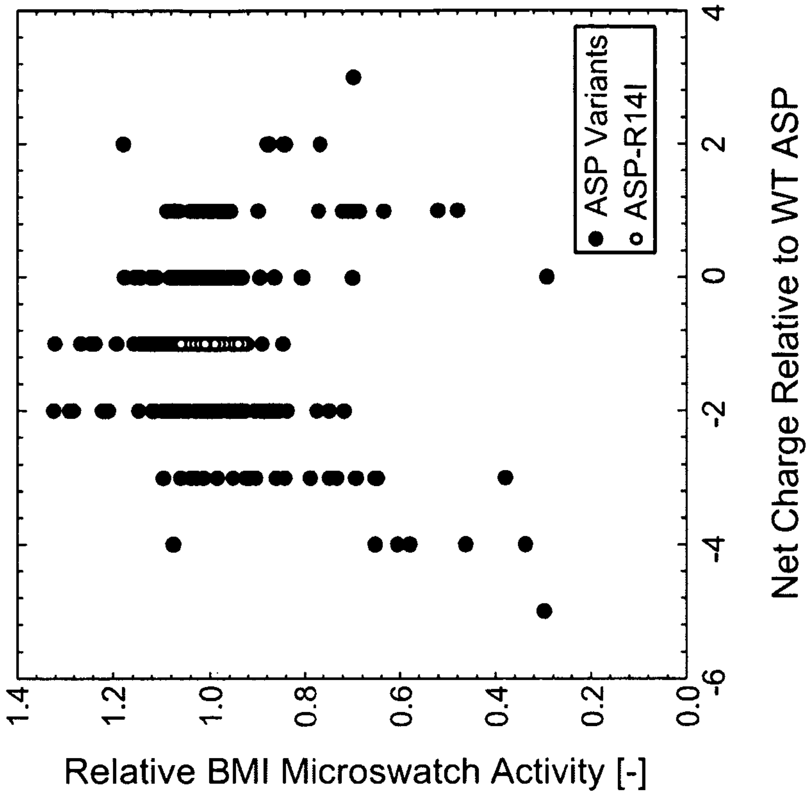
FIG. 2 depicts relative blood, milk, ink (BMI) microswatch activity (normalized with respect to best performer) of ASP charge combinatorial library as a function of net charge change relative to wild type ASP as measured in AATCC liquid detergent (filled triangles).

The present invention provides efficient methods for obtaining a protein with one or more beneficial attributes in industrial, consumer or pharmaceutical applications. In some preferred embodiments, the present invention provides methods for producing superior enzymes for a given application through screening an abbreviated set of candidate enzymes.

The protease subtilisin is a major enzyme used in laundry detergents and perhaps the most widely used enzyme in the world. Almost twenty years ago, it was noted that surface electrostatic effects could modulate the catalytic activity of subtilisin (See e.g., Russell and Fersht, Nature 328:496-500 [1987]). More recently, mutations that involved changing the net charge of subtilisin were observed to have a dramatic effect on wash performance in detergents (See e.g., EP Patent No. 0 479 870 B1, incorporated herein by reference). This beneficial effect was believed to be a result of shifting the pI (isoelectric point) of subtilisin toward the pH of the wash liquor. However, later work demonstrated that this conclusion is not always applicable (See e.g., U.S. Pat. No. 6,673,590 B1, incorporated herein by reference). As indicated in this patent, the effect of charge mutations in subtilisin depend dramatically on detergent concentrations, with mutations lowering the pI of the parent subtilisin providing an enzyme that is more effective at low detergent concentration and mutations raising the pI providing an enzyme that is more effective at high detergent concentration. This is of great utility because detergent concentration in the wash liquors varies greatly across the globe. Thus, it has become apparent to those of skill in the art that there is an optimal pI for wash performance of subtilisin, which depends on the pH and detergent concentration in the wash liquor. Further efforts to improve the activity of subtilisin in laundry detergents have been described (See, US Pat. Publication No. 2005/0221461, incorporated herein by reference). Surprisingly, subtilisin variants having the same net electrostatic charge as the parent subtilisin were found to have increased wash performance under both high and low detergent concentration wash conditions. Thus, electrostatic properties of proteins (e.g., enzymes) have major effects on their function.

Previously, efforts to develop superior proteins focused upon minimizing enzyme binding to surfaces. For example, some methods involved altering the subtilisin sequence to obtain variant enzymes with decreased adsorption to insoluble substrates (See e.g., WO 95/07991). In another approach, the pI of subtilisin was altered in order to obtain variant enzymes with a net charge of zero at a defined pH (See e.g., WO 91/00345). However, as determined during development of the present invention, these approaches are not always successful. As described herein, surface properties of enzymes, including binding properties, generally have optima, instead of continually varying, as a function of change in surface charge or hydrophobicity. Even for enzymes that are normally quite active, surface properties can cause the overall reaction to be much slower under some conditions and with some substrates than under other conditions and/or with other substrates. In some embodiments of the present invention, the surface properties of an enzyme are modified by changing the nature of one or more amino acids on the enzyme surface. When these changes are made at sites on the surface that do not interact with any other amino acids and are not necessary for enzyme function, the properties of the protein are predicted using the methods of the present invention, based on the properties of the amino acids substituted at those positions. In some embodiments, these sites are readily identified from structure data, while in other embodiments homologous sequence alignments, site evaluation library data and/or any combination thereof find use. In further embodiments, amino acid scoring matrices find use in guiding amino acid substitution(s) and to identify those physical properties of the protein that correlate with the properties of the substituted amino acids.

The present invention provides efficient methods for obtaining a protein with one or more beneficial attributes in industrial, consumer or pharmaceutical applications. In particular the present invention provides methods for producing superior enzymes for a given application through screening an abbreviated set of candidate enzymes. Although described herein in regard to an exemplary serine protease (e.g., ASP) and an exemplary metalloprotease (e.g., NprE), the compositions and methods of the present invention are not limited to proteases. Indeed, the present invention finds use in improving the performance of various classes of enzymes as well as proteases (e.g., amylases, cellulases, oxidases, oxidoreductases, cutinases, mannanases, pectinases, amylases, lipases. etc). Indeed, it is not intended that the present invention be limited to any particular enzyme nor class of enzyme. In addition, the present invention finds use in the optimization of non-enzymatic protein properties and the production of superior proteins as desired.

Unless otherwise indicated, the practice of the present invention involves conventional techniques commonly used in molecular biology, microbiology, and recombinant DNA, which are within the skill of the art. Such techniques are known to those of skill in the art and are described in numerous texts and reference works well known to those skilled in the art. All patents, patent applications, articles and publications mentioned herein, both supra and infra, are hereby expressly incorporated herein by reference.

Unless defined otherwise herein, all technical and scientific terms used herein have the same meaning as commonly understood by one of ordinary skill in the art to which this invention pertains. Although any methods and materials similar or equivalent to those described herein find use in the practice of the present invention, some of the preferred methods and materials are described herein. Accordingly, the terms defined immediately below are more fully described by reference to the Specification as a whole.

Also, as used herein, the singular "a," "an," and "the" include the plural reference unless the context clearly indicates otherwise. Numeric ranges are inclusive of the numbers defining the range. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Furthermore, the headings provided herein are not limitations of the various aspects or embodiments of the invention, which can be had by reference to the specification as a whole. Accordingly, the terms defined immediately below are more fully defined by reference to the specification as a whole. Nonetheless, in order to facilitate understanding of the invention, a number of terms are defined below.

DEFINITIONS

As used herein, the terms "protease," and "proteolytic activity" refer to a protein or peptide exhibiting the ability to hydrolyze peptides or substrates having peptide linkages. Many well known procedures exist for measuring proteolytic activity (See e.g., Kalisz, "Microbial Proteinases," In: Fiechter (ed.), *Advances in Biochemical Engineering/Biotechnology, [*1988]). For example, proteolytic activity may be ascertained by comparative assays, which analyze the respective protease's ability to hydrolyze a commercial substrate. Exemplary substrates useful in the such analysis of protease or proteolytic activity, include, but are not limited to dimethyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO 99/34011; and U.S. Pat. No. 6,376,450, both of which are incorporated herein by reference). The pNA assay (See e.g., Del Mar et al., Anal Biochem, 99:316-320 [1979]) also finds use in determining the active enzyme concentration for fractions collected during gradient elution. This assay measures the rate at which p-nitroaniline is released as the enzyme hydrolyzes the soluble synthetic substrate, succinyl-alanine-alanine-proline-phenylalanine-p-nitroanilide (sAAPF-pNA). The rate of production of yellow color from the hydrolysis reaction is measured at 410 nm on a spectrophotometer and is proportional to the active enzyme concentration. In addition, absorbance measurements at 280 nm can be used to determine the total protein concentration. The active enzyme/total-protein ratio gives the enzyme purity.

As used herein, the terms "ASP protease," "Asp protease," and "Asp," refer to the serine proteases described herein and described in U.S. patent application Ser. No. 10/576,331, incorporated herein by reference). In some preferred embodiments, the Asp protease is the protease designed herein as 69B4 protease obtained from *Cellulomonas* strain 69B4. Thus, in preferred embodiments, the term "69B4 protease" refers to a naturally occurring mature protease derived from *Cellulomonas* strain 69B4 (DSM 16035) having a substantially identical amino acid sequence as provided in SEQ ID NO:8. In alternative embodiments, the present invention provides portions of the ASP protease.

The term "*Cellulomonas* protease homologues" refers to naturally occurring proteases having substantially identical amino acid sequences to the mature protease derived from *Cellulomonas* strain 69B4 or polynucleotide sequences which encode for such naturally occurring proteases, and which proteases retain the functional characteristics of a serine protease encoded by such nucleic acids. In some embodiments, these protease homologues are referred to as "cellulomonadins."

As used herein, the terms "ASP variant," "ASP protease variant," and "69B protease variant" are used in reference to proteases that are similar to the wild-type ASP, particularly in their function, but have mutations in their amino acid sequence that make them different in sequence from the wild-type protease.

As used herein, "*Cellulomonas* 'ssp." refers to all of the species within the genus "*Cellulomonas*," which are Gram-positive bacteria classified as members of the Family Cellulomonadaceae, Suborder Micrococcineae, Order Actinomycetales, Class Actinobacteria. It is recognized that the genus *Cellulomonas* continues to undergo taxonomical reorganization. Thus, it is intended that the genus include species that have been reclassified.

As used herein, "*Streptomyces* ssp." refers to all of the species within the genus "*Streptomyces*," which are Gram-positive bacteria classified as members of the Family Streptomycetaceae, Suborder Streptomycineae, Order Actinomycetales, class Actinobacteria. It is recognized that the genus *Streptomyces* continues to undergo taxonomical reorganization. Thus, it is intended that the genus include species that have been reclassified As used herein, "the genus *Bacillus*" includes all species within the genus "*Bacillus*," as known to those of skill in the art, including but not limited to *B. subtilis, B. lichenifonnis, B. lentus, B. brevis, B. stearothermophilus, B. alkalophilus, B.*

*amyloliquefaciens, B. clausii, B. halodurans, B. megaterium, B. coagulans, B. circulans, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*.

The terms "polynucleotide" and "nucleic acid", used interchangeably herein, refer to a polymeric form of nucleotides of any length, either ribonucleotides or deoxyribonucleotides. These terms include, but are not limited to, a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The following are non-limiting examples of polynucleotides: genes, gene fragments, chromosomal fragments, ESTs, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. In some embodiments, polynucleotides comprise modified nucleotides, such as methylated nucleotides and nucleotide analogs, uracil, other sugars and linking groups such as fluororibose and thioate, and nucleotide branches. In alternative embodiments, the sequence of nucleotides is interrupted by non-nucleotide components.

As used herein, the terms "DNA construct" and "transforming DNA" are used interchangeably to refer to DNA used to introduce sequences into a host cell or organism. The DNA may be generated in vitro by PCR or any other suitable technique(s) known to those in the art. In particularly preferred embodiments, the DNA construct comprises a sequence of interest (e.g., as an incoming sequence). In some embodiments, the sequence is operably linked to additional elements such as control elements (e.g., promoters, etc.). The DNA construct may further comprise a selectable marker. It may further comprise an incoming sequence flanked by homology boxes. In a further embodiment, the transforming DNA comprises other non-homologous sequences, added to the ends (e.g., stuffer sequences or flanks). In some embodiments, the ends of the incoming sequence are closed such that the transforming DNA forms a closed circle. The transforming sequences may be wild-type, mutant or modified. In some embodiments, the DNA construct comprises sequences homologous to the host cell chromosome. In other embodiments, the DNA construct comprises non-homologous sequences. Once the DNA construct is assembled in vitro it may be used to: 1) insert heterologous sequences into a desired target sequence of a host cell; and/or 2) mutagenize a region of the host cell chromosome (i.e., replace an endogenous sequence with a heterologous sequence), and/or 3) delete target genes; and/or introduce a replicating plasmid into the host.

As used herein, the terms "expression cassette" and "expression vector" refer to nucleic acid constructs generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In preferred embodiments, expression vectors have the ability to incorporate and express heterologous DNA fragments in a host cell. Many prokaryotic and eukaryotic expression vectors are commercially available. Selection of appropriate expression vectors is within the knowledge of those of skill in the art. The term "expression cassette" is used interchangeably herein with "DNA construct," and their grammatical equivalents. Selection of appropriate expression vectors is within the knowledge of those of skill in the art.

As used herein, the term "vector" refers to a polynucleotide construct designed to introduce nucleic acids into one or more cell types. Vectors include cloning vectors, expression vectors, shuttle vectors, plasmids, cassettes and the like. In some embodiments, the polynucleotide construct comprises a DNA sequence encoding the protease (e.g., precursor or mature protease) that is operably linked to a suitable prosequence (e.g., secretory, etc.) capable of effecting the expression of the DNA in a suitable host.

As used herein, the term "plasmid" refers to a circular double-stranded (ds) DNA construct used as a cloning vector, and which forms an extrachromosomal self-replicating genetic element in some eukaryotes or prokaryotes, or integrates into the host chromosome.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, and transduction (See e.g., Ferrari et al., "*Genetics*," in Hardwood et al., (eds.), *Bacillus*, Plenum Publishing Corp., pages 57-72 [1989]).

As used herein, the terms "transformed" and "stably transformed" refer to a cell that has a non-native (heterologous) polynucleotide sequence integrated into its genome or as an episomal plasmid that is maintained for at least two generations.

As used herein, the term "selectable marker-encoding nucleotide sequence" refers to a nucleotide sequence, which is capable of expression in host cells and where expression of the selectable marker confers to cells containing the expressed gene the ability to grow in the presence of a corresponding selective agent or lack of an essential nutrient.

As used herein, the terms "selectable marker" and "selective marker" refer to a nucleic acid (e.g., a gene) capable of expression in host cell which allows for ease of selection of those hosts containing the vector. Examples of such selectable markers include but are not limited to antimicrobials. Thus, the term "selectable marker" refers to genes that provide an indication that a host cell has taken up an incoming DNA of interest or some other reaction has occurred. Typically, selectable markers are genes that confer antimicrobial resistance or a metabolic advantage on the host cell to allow cells containing the exogenous DNA to be distinguished from cells that have not received any exogenous sequence during the transformation. A "residing selectable marker" is one that is located on the chromosome of the microorganism to be transformed. A residing selectable marker encodes a gene that is different from the selectable marker on the transforming DNA construct. Selective markers are well known to those of skill in the art. As indicated above, preferably the marker is an antimicrobial resistant marker (e.g., $amp^R$; $phleo^R$; $spec^R$; $kan^R$; $ery^R$; $tet^R$; $cmp^R$; and $neo^R$ (See e.g., Guerot-Fleury, Gene, 167:335-337 [1995]; Palmeros et al., Gene 247:255-

264 [2000]; and Trieu-Cuot et al., *Gene,* 23:331-341, [1983]). Other markers useful in accordance with the invention include, but are not limited to auxotrophic markers, such as tryptophan; and detection markers, such as β-galactosidase.

As used herein, the term "promoter" refers to a nucleic acid sequence that functions to direct transcription of a downstream gene. In preferred embodiments, the promoter is appropriate to the host cell in which the target gene is being expressed. The promoter, together with other transcriptional and translational regulatory nucleic acid sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

A nucleic acid is "operably linked" when it is placed into a functional relationship with another nucleic acid sequence. For example, DNA encoding a secretory leader (i.e., a signal peptide), is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein the term "gene" refers to a polynucleotide (e.g., a DNA segment) that encodes a polypeptide and includes regions preceding and following the coding regions as well as intervening sequences (introns) between individual coding segments (exons).

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, "ortholog" and "orthologous genes" refer to genes in different species that have evolved from a common ancestral gene (i.e., a homologous gene) by speciation. Typically, orthologs retain the same function during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

As used herein, "homology" refers to sequence similarity or identity, with identity being preferred. This homology is determined using standard techniques known in the art (See e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA, 85:2444 [1988]; programs such as GAP, BESTFIT, FASTA, and TFASTA in the Wisconsin Genetics Software Package, Genetics Computer Group, Madison, Wis.; and Devereux et al., Nucl. Acid Res., 12:387-395 [1984]).

As used herein, an "analogous sequence" is one wherein the function of the gene is essentially the same as the gene based on a parent gene (e.g., the *Cellulomonas* strain 69B4 protease). Additionally, analogous genes include at least about 45%, about 50%, about 55%, about 60%, about 65%, about 70%, about 75%, about 80%, about 85%, about 90%, about 95%, about 97%, about 98%, about 99%, or about 100% sequence identity with the sequence of the parent gene. Alternately, analogous sequences have an alignment of between 70 to 100% of the genes found in the parent gene (e.g., *Cellulomonas* strain 69B4 protease) region and/or have at least between 5-10 genes found in the region aligned with the genes in the chromosome containing the parent gene (e.g., the *Cellulomonas* strain 69B4 chromosome). In additional embodiments more than one of the above properties applies to the sequence. Analogous sequences are determined by known methods of sequence alignment. A commonly used alignment method is BLAST, although as indicated above and below, there are other methods that also find use in aligning sequences.

One example of a useful algorithm is PILEUP. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (Feng and Doolittle, J. Mol. Evol., 35:351-360 [1987]). The method is similar to that described by Higgins and Sharp (Higgins and Sharp, CABIOS 5:151-153 [1989]). Useful PILEUP parameters including a default gap weight of 3.00, a default gap length weight of 0.10, and weighted end gaps.

Another example of a useful algorithm is the BLAST algorithm, described by Altschul et al., (Altschul et al., J. Mol. Biol., 215:403-410 [1990]; and Karlin et al., Proc. Natl. Acad. Sci., USA, 90:5873-5787 [1993]). A particularly useful BLAST program is the WU-BLAST-2 program (See, Altschul et al., Meth. Enzymol., 266:460-480 [1996]). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Thus, "percent (%) nucleic acid sequence identity" is defined as the percentage of nucleotide residues in a candidate sequence that are identical to the nucleotide residues of the starting sequence (i.e., the sequence of interest). A preferred method utilizes the BLASTN module of WU-BLAST-2 set to the default parameters, with overlap span and overlap fraction set to 1 and 0.125, respectively.

As used herein, the term "hybridization" refers to the process by which a strand of nucleic acid joins with a complementary strand through base pairing, as known in the art.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° C. below the Tm; "intermediate stringency" at about 10-20° C. below the Tm of the probe; and "low stringency" at about 20-25° C. below the Tm. Functionally, maximum stringency conditions may be used to identify sequences having strict identity or near-strict identity with the hybridization probe; while an intermediate or low stringency hybridization can be used to identify or detect polynucleotide sequence homologs.

Moderate and high stringency hybridization conditions are well known in the art. An example of high stringency conditions includes hybridization at about 42° C. in 50% formamide, 5×SSC, 5×Denhardt's solution, 0.5% SDS and 100 μg/ml denatured carrier DNA followed by washing two times in 2×SSC and 0.5% SDS at room temperature and two additional times in 0.1×SSC and 0.5% SDS at 42° C. An example of moderate stringent conditions include an overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/ml denatured sheared salmon sperm DNA, followed by washing the filters in 1×SSC at about 37-50° C. Those of skill in the art know how to adjust the temperature, ionic strength, etc. as necessary to accommodate factors such as probe length and the like.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. "Recombination," "recombining," and generating a "recombined" nucleic acid are generally the assembly of two or more nucleic acid fragments wherein the assembly gives rise to a chimeric gene.

In a preferred embodiment, mutant DNA sequences are generated with site saturation mutagenesis in at least one codon. In another preferred embodiment, site saturation mutagenesis is performed for two or more codons. In a further embodiment, mutant DNA sequences have more than 50%, more than 55%, more than 60%, more than 65%, more than 70%, more than 75%, more than 80%, more than 85%, more than 90%, more than 95%, or more than 98% homology with the wild-type sequence. In alternative embodiments, mutant DNA is generated in vivo using any known mutagenic procedure such as, for example, radiation, nitrosoguanidine and the like. The desired DNA sequence is then isolated and used in the methods provided herein.

As used herein, the term "target sequence" refers to a DNA sequence in the host cell that encodes the sequence where it is desired for the incoming sequence to be inserted into the host cell genome. In some embodiments, the target sequence encodes a functional wild-type gene or operon, while in other embodiments the target sequence encodes a functional mutant gene or operon, or a non-functional gene or operon.

As used herein, a "flanking sequence" refers to any sequence that is either upstream or downstream of the sequence being discussed (e.g., for genes A-B-C, gene B is flanked by the A and C gene sequences). In a preferred embodiment, the incoming sequence is flanked by a homology box on each side. In another embodiment, the incoming sequence and the homology boxes comprise a unit that is flanked by stuffer sequence on each side. In some embodiments, a flanking sequence is present on only a single side (either 3' or 5'), but in preferred embodiments, it is on each side of the sequence being flanked. In some embodiments, a flanking sequence is present on only a single side (either 3' or 5'), while in preferred embodiments, it is present on each side of the sequence being flanked.

As used herein, the term "stuffer sequence" refers to any extra DNA that flanks homology boxes (typically vector sequences). However, the term encompasses any non-homologous DNA sequence. Not to be limited by any theory, a stuffer sequence provides a noncritical target for a cell to initiate DNA uptake.

As used herein, the terms "amplification" and "gene amplification" refer to a process by which specific DNA sequences are disproportionately replicated such that the amplified gene becomes present in a higher copy number than was initially present in the genome. In some embodiments, selection of cells by growth in the presence of a drug (e.g., an inhibitor of an inhibitable enzyme) results in the amplification of either the endogenous gene encoding the gene product required for growth in the presence of the drug or by amplification of exogenous (i.e., input) sequences encoding this gene product, or both.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "co-amplification" refers to the introduction into a single cell of an amplifiable marker in conjunction with other gene sequences (i.e., comprising one or more non-selectable genes such as those contained within an expression vector) and the application of appropriate selective pressure such that the cell amplifies both the amplifiable marker and the other, non-selectable gene sequences. The amplifiable marker may be physically linked to the other gene sequences or alternatively two separate pieces of DNA, one containing the amplifiable marker and the other containing the non-selectable marker, may be introduced into the same cell.

As used herein, the terms "amplifiable marker," "amplifiable gene," and "amplification vector" refer to a gene or a vector encoding a gene, which permits the amplification of that gene under appropriate growth conditions.

"Template specificity" is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (See e.g., Kacian et al., Proc. Natl. Acad. Sci. USA 69:3038 [1972]) and other nucleic acids are not replicated by this amplification enzyme. Similarly, in the case of T7 RNA polymerase, this amplification enzyme has a stringent specificity for its own promoters (See, Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (See, Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences.

As used herein, the term "amplifiable nucleic acid" refers to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template, which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the methods of U.S. Pat. Nos. 4,683,195 4,683,202, and 4,965,188, hereby incorporated by reference, which include methods for increasing the concentration of a segment of a target sequence in a mixture of genomic DNA without cloning or purification, as known to those of skill in the art. Because the desired amplified segments of the target sequence become the predominant sequences (in terms of concentration) in the mixture, they are said to be "PCR amplified".

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "RT-PCR" refers to the replication and amplification of RNA sequences. In this method, reverse transcription is coupled to PCR, most often using a one enzyme procedure in which a thermostable polymerase is employed, as described in U.S. Pat. No. 5,322,770, herein incorporated by reference. In RT-PCR, the RNA template is converted to cDNA due to the reverse transcriptase activity of the polymerase, and then amplified using the polymerizing activity of the polymerase (i.e., as in other PCR methods).

As used herein, the terms "restriction endonucleases" and "restriction enzymes" refer to bacterial enzymes, each of which cut double-stranded DNA at or near a specific nucleotide sequence.

A "restriction site" refers to a nucleotide sequence recognized and cleaved by a given restriction endonuclease and is frequently the site for insertion of DNA fragments. In certain embodiments of the invention restriction sites are engineered into the selective marker and into 5' and 3' ends of the DNA construct.

As used herein, the term "chromosomal integration" refers to the process whereby an incoming sequence is introduced into the chromosome of a host cell. The homologous regions of the transforming DNA align with homologous regions of the chromosome. Subsequently, the sequence between the homology boxes is replaced by the incoming sequence in a double crossover (i.e., homologous recombination). In some embodiments of the present invention, homologous sections of an inactivating chromosomal segment of a DNA construct align with the flanking homologous regions of the indigenous chromosomal region of the *Bacillus* chromosome. Subsequently, the indigenous chromosomal region is deleted by the DNA construct in a double crossover (i.e., homologous recombination).

"Homologous recombination" means the exchange of DNA fragments between two DNA molecules or paired chromosomes at the site of identical or nearly identical nucleotide sequences. In a preferred embodiment, chromosomal integration is homologous recombination.

"Homologous sequences" as used herein means a nucleic acid or polypeptide sequence having 100%, 99%, 98%, 97%, 96%, 95%, 94%, 93%, 92%, 91%, 90%, 88%, 85%, 80%, 75%, or 70% sequence identity to another nucleic acid or polypeptide sequence when optimally aligned for comparison. In some embodiments, homologous sequences have between 85% and 100% sequence identity, while in other embodiments there is between 90% and 100% sequence identity, and in more preferred embodiments, there is 95% and 100% sequence identity.

As used herein "amino acid" refers to peptide or protein sequences or portions thereof. The terms "protein," "peptide," and "polypeptide" are used interchangeably.

As used herein, "protein of interest" and "polypeptide of interest" refer to a protein/polypeptide that is desired and/or being assessed. In some embodiments, the "protein of interest" is a "parent protein" (i.e., the starting protein). In some embodiments, the parent protein is a wild-type enzyme that is used as a starting point for protein engineering/design. In some embodiments, the protein of interest is expressed intracellularly, while in other embodiments, it is a secreted polypeptide. In particularly preferred embodiments, these enzymes include the serine proteases and metalloproteases described herein. In some embodiments, the protein of interest is a secreted polypeptide fused to a signal peptide (i.e., an amino-terminal extension on a protein to be secreted). Nearly all secreted proteins use an amino-terminal protein extension, which plays a crucial role in the targeting to and translocation of precursor proteins across the membrane. This extension is proteolytically removed by a signal peptidase during or immediately following membrane transfer.

As used herein, the term "heterologous protein" refers to a protein or polypeptide that does not naturally occur in the host cell. Examples of heterologous proteins include enzymes such as hydrolases including proteases. In some embodiments, the gene encoding the proteins are naturally occurring genes, while in other embodiments, mutated and/or synthetic genes are used.

As used herein, "homologous protein" refers to a protein or polypeptide native or naturally occurring in a cell. In preferred embodiments, the cell is a Gram-positive cell, while in particularly preferred embodiments, the cell is a *Bacillus* host cell. In alternative embodiments, the homologous protein is a native protein produced by other organisms, including but not limited to *E. coli, Cellulomonas, Bacillus, Streptomyces, Trichoderma*, and *Aspergillus*. The invention encompasses host cells producing the homologous protein via recombinant DNA technology.

As used herein, proteins are defined as having a common "fold" if they have the same major secondary structures in the same arrangement and with the same topological connections. Different proteins with the same fold often have peripheral elements of secondary structure and turn regions that differ in size and conformation. In some cases, these differing peripheral regions may comprise half the structure. Proteins placed together in the same fold category do not necessarily have a common evolutionary origin (e.g., structural similarities arising from the physics and chemistry of proteins favoring certain packing arrangements and chain topologies).

As used herein, "test protein fold" refers to proteins whose performance index is to be improved on in an assay of interest.

As used herein, the terms "binding" and "partitioning" refer to the amount of enzyme bound to a substrate, or of protein adsorbed onto a surface, regardless of attaining equilibrium in the thermodynamic sense or of being reversibly or irreversibly adsorbed in the kinetic sense.

As used herein, an "operon region" comprises a group of contiguous genes that are transcribed as a single transcription unit from a common promoter, and are thereby subject to co-regulation. In some embodiments, the operon includes a regulator gene. In most preferred embodiments, operons that are highly expressed as measured by RNA levels, but have an unknown or unnecessary function are used.

As used herein, an "antimicrobial region" is a region containing at least one gene that encodes an antimicrobial protein.

A polynucleotide is said to "encode" an RNA or a polypeptide if, in its native state or when manipulated by methods known to those of skill in the art, it can be transcribed and/or translated to produce the RNA, the polypeptide or a fragment thereof. The anti-sense strand of such a nucleic acid is also said to encode the sequences.

As is known in the art, a DNA can be transcribed by an RNA polymerase to produce RNA, but an RNA can be reverse transcribed by reverse transcriptase to produce a DNA. Thus a DNA can encode a RNA and vice versa.

The term "regulatory segment" or "regulatory sequence" or "expression control sequence" refers to a polynucleotide sequence of DNA that is operatively linked with a polynucleotide sequence of DNA that encodes the amino acid sequence of a polypeptide chain to effect the expression of the encoded amino acid sequence. The regulatory sequence can inhibit, repress, or promote the expression of the operably linked polynucleotide sequence encoding the amino acid.

"Host strain" or "host cell" refers to a suitable host for an expression vector comprising DNA according to the present invention.

An enzyme is "overexpressed" in a host cell if the enzyme is expressed in the cell at a higher level that the level at which it is expressed in a corresponding wild-type cell.

The terms "protein" and "polypeptide" are used interchangeability herein. The 3-letter code for amino acids as defined in conformity with the IUPAC-IUB Joint Commission on Biochemical Nomenclature (JCBN) is used through out this disclosure. It is also understood that a polypeptide may be coded for by more than one nucleotide sequence due to the degeneracy of the genetic code.

A "prosequence" is an amino acid sequence between the signal sequence and mature protease that is necessary for the secretion of the protease. Cleavage of the pro sequence will result in a mature active protease.

The term "signal sequence" or "signal peptide" refers to any sequence of nucleotides and/or amino acids that participate in the secretion of the mature or precursor forms of the protein. This definition of signal sequence is a functional one, meant to include all those amino acid sequences encoded by the N-terminal portion of the protein gene, which participate in the effectuation of the secretion of protein. They are often, but not universally, bound to the N-terminal portion of a protein or to the N-terminal portion of a precursor protein. The signal sequence may be endogenous or exogenous. The signal sequence may be that normally associated with the protein (e.g., protease), or may be from a gene encoding another secreted protein. One exemplary exogenous signal sequence comprises the first seven amino acid residues of the signal sequence from *B. subtilis* subtilisin fused to the remainder of the signal sequence of the subtilisin from *B. lentus* (ATCC 21536).

The term "hybrid signal sequence" refers to signal sequences in which part of sequence is obtained from the expression host fused to the signal sequence of the gene to be expressed. In some embodiments, synthetic sequences are utilized.

The term "substantially the same signal activity" refers to the signal activity, as indicated by substantially the same secretion of the protease into the fermentation medium, for example a fermentation medium protease level being at least 50%, at least 60%, at least 70%, at least 80%, at least 90%, at least 95%, at least 98% of the secreted protease levels in the fermentation medium as provided by the signal sequence of SEQ ID NO:9.

The term "mature" form of a protein or peptide refers to the final functional form of the protein or peptide. To exemplify, a mature form of the ASP protease of the present invention at least includes the amino acid sequence of SEQ ID NO:8, while a mature form of the NprE protease of the present invention at least includes the amino acid sequence of SEQ ID NO:3.

The term "precursor" form of a protein or peptide refers to a mature form of the protein having a prosequence operably linked to the amino or carbonyl terminus of the protein. The precursor may also have a "signal" sequence operably linked, to the amino terminus of the prosequence. The precursor may also have additional polynucleotides that are involved in post-translational activity (e.g., polynucleotides cleaved therefrom to leave the mature form of a protein or peptide).

"Naturally occurring enzyme" and "naturally occurring protein" refer to an enzyme or protein having the unmodified amino acid sequence identical to that found in nature. Naturally occurring enzymes include native enzymes, those enzymes naturally expressed or found in the particular microorganism.

The terms "derived from" and "obtained from" refer to not only an enzyme (e.g., protease) produced or producible by a strain of the organism in question, but also an enzyme encoded by a DNA sequence isolated from such strain and produced in a host organism containing such DNA sequence. Additionally, the term refers to a enzyme that is encoded by a DNA sequence of synthetic and/or cDNA origin and which has the identifying characteristics of the enzyme in question.

A "derivative" within the scope of this definition generally retains the characteristic proteolytic activity observed in the wild-type, native or parent form to the extent that the derivative is useful for similar purposes as the wild-type, native or parent form. Functional enzyme derivatives encompass naturally occurring, synthetically or recombinantly produced peptides or peptide fragments having the general characteristics of the parent enzyme.

The term "functional derivative" refers to a derivative of a nucleic acid having the functional characteristics of a nucleic acid encoding an enzyme. Functional derivatives of a nucleic acid, which encode enzymes provided herein encompass naturally occurring, synthetically or recombinantly produced nucleic acids or fragments. Wild type nucleic acid encoding enzymes according to the present invention include naturally occurring alleles and homologues based on the degeneracy of the genetic code known in the art.

The term "identical" in the context of two nucleic acids or polypeptide sequences refers to the residues in the two sequences that are the same when aligned for maximum correspondence, as measured using one of the following sequence comparison or analysis algorithms.

The term "optimal alignment" refers to the alignment giving the highest percent identity score.

"Percent sequence identity," "percent amino acid sequence identity," "percent gene sequence identity," and/or "percent nucleic acid/polynucleotide sequence identity," with respect to two amino acid, polynucleotide and/or gene sequences (as appropriate), refer to the percentage of residues that are identical in the two sequences when the sequences are optimally aligned. Thus, 80% amino acid sequence identity means that 80% of the amino acids in two optimally aligned polypeptide sequences are identical.

The phrase "substantially identical" in the context of two nucleic acids or polypeptides thus refers to a polynucleotide or polypeptide that comprising at least 70% sequence identity, preferably at least 75%, preferably at least 80%, preferably at least 85%, preferably at least 90%, preferably at least 95%, preferably at least 97%, preferably at least 98% and preferably at least 99% sequence identity as compared to a reference sequence using the programs or algorithms (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

The term "isolated" or "purified" refers to a material that is removed from its original environment (e.g., the natural environment if it is naturally occurring). For example, the material is said to be "purified" when it is present in a particular composition in a higher or lower concentration than exists in a naturally occurring or wild type organism or in combination with components not normally present upon expression from a naturally occurring or wild type organism. For example, a naturally-occurring polynucleotide or polypeptide present in a living animal is not isolated, but the same polynucleotide or polypeptide, separated from some or all of the coexisting materials in the natural system, is isolated. In some embodiments, such polynucleotides are part of a vector, and/or such polynucleotides or polypeptides are part of a composition, and still be isolated in that such vector or composition is not part of its natural environment. In some preferred embodiments, a nucleic acid or protein is said to be purified, for example, if it gives rise to essentially one band in an electrophoretic gel or blot.

The term "isolated," when used in reference to a DNA sequence, refers to a DNA sequence that has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (See e.g., Dynan and Tijan, Nature 316:774-78, 1985). The term "an isolated DNA sequence" is alternatively referred to as "a cloned DNA sequence".

The term "isolated," when used in reference to a protein, refers to a protein that is found in a condition other than its native environment. In a preferred form, the isolated protein is substantially free of other proteins, particularly other homologous proteins. An isolated protein is more than 10% pure, preferably more than 20% pure, and even more preferably more than 30% pure, as determined by SDS-PAGE.

Further aspects of the invention encompass the protein in a highly purified form (i.e., more than 40% pure, more than 60% pure, more than 80% pure, more than 90% pure, more than 95% pure, more than 97% pure, and even more than 99% pure), as determined by SDS-PAGE.

As used herein, the term, "combinatorial mutagenesis" refers to methods in which libraries of variants of a starting sequence are generated. In these libraries, the variants contain one or several mutations chosen from a predefined set of mutations. In addition, the methods provide means to introduce random mutations, which were not members of the predefined set of mutations. In some embodiments, the methods include those set forth in U.S. application Ser. No. 09/699,250, filed Oct. 26, 2000, hereby incorporated by reference. In alternative embodiments, combinatorial mutagenesis methods encompass commercially available kits (e.g., QUIKCHANGE® Multisite, Stratagene, La Jolla, Calif.).

As used herein, the term "library of mutants" refers to a population of cells which are identical in most of their genome but include different homologues of one or more genes. Such libraries can be used, for example, to identify genes or operons with improved traits.

As used herein, the term "starting gene" refers to a gene of interest that encodes a protein of interest that is to be improved and/or changed using the present invention.

As used herein, the term "variant" refers to a protein that has been derived from a precursor protein (e.g., "parent" protein) by addition, substitution, or deletion of one or more amino acids. In some embodiments, the variant comprises at least one modification that comprises a change in charge, as compared to the precursor protein. In some preferred embodiments, the precursor protein is parent protein that is a wild-type protein.

As used herein, the terms "multiple sequence alignment" and "MSA" refer to the sequences of multiple homologs of a starting gene that are aligned using an algorithm (e.g., Clustal W).

As used herein, the terms "consensus sequence" and "canonical sequence" refer to an archetypical amino acid sequence against which all variants of a particular protein or sequence of interest are compared. The terms also refer to a sequence that sets forth the nucleotides that are most often present in a DNA sequence of interest. For each position of a gene, the consensus sequence gives the amino acid that is most abundant in that position in the MSA.

As used herein, the term "consensus mutation" refers to a difference in the sequence of a starting gene and a consensus sequence. Consensus mutations are identified by comparing the sequences of the starting gene and the consensus sequence obtained from a MSA. In some embodiments, consensus mutations are introduced into the starting gene such that it becomes more similar to the consensus sequence. Consensus mutations also include amino acid changes that change an amino acid in a starting gene to an amino acid that is more frequently found in an MSA at that position relative to the frequency of that amino acid in the starting gene. Thus, the term consensus mutation comprises all single amino acid changes that replace an amino acid of the starting gene with an amino acid that is more abundant than the amino acid in the MSA.

As used herein, the term "initial hit" refers to a variant that was identified by screening a combinatorial consensus mutagenesis library. In preferred embodiments, initial hits have improved performance characteristics, as compared to the starting gene.

As used herein, the term "improved hit" refers to a variant that was identified by screening an enhanced combinatorial consensus mutagenesis library.

As used herein, the terms "improving mutation" and "performance-enhancing mutation" refer to a mutation that leads to improved performance when it is introduced into the starting gene. In some preferred embodiments, these mutations are identified by sequencing hits identified during the screening step of the method. In most embodiments, mutations that are more frequently found in hits are likely to be improving mutations, as compared to an unscreened combinatorial consensus mutagenesis library.

As used herein, the term "enhanced combinatorial consensus mutagenesis library" refers to a CCM library that is designed and constructed based on screening and/or sequencing results from an earlier round of CCM mutagenesis and screening. In some embodiments, the enhanced CCM library is based on the sequence of an initial hit resulting from an earlier round of CCM. In additional embodiments, the enhanced CCM is designed such that mutations that were frequently observed in initial hits from earlier rounds of mutagenesis and screening are favored. In some preferred embodiments, this is accomplished by omitting primers that encode performance-reducing mutations or by increasing the concentration of primers that encode performance-enhancing mutations relative to other primers that were used in earlier CCM libraries.

As used herein, the term "performance-reducing mutations" refer to mutations in the combinatorial consensus mutagenesis library that are less frequently found in hits resulting from screening as compared to an unscreened combinatorial consensus mutagenesis library. In preferred embodiments, the screening process removes and/or reduces the abundance of variants that contain "performance-reducing mutations."

As used herein, the term "functional assay" refers to an assay that provides an indication of a protein's activity. In particularly preferred embodiments, the term refers to assay systems in which a protein is analyzed for its ability to function in its usual capacity. For example, in the case of enzymes, a functional assay involves determining the effectiveness of the enzyme in catalyzing a reaction.

As used herein, the term "target property" refers to the property of the starting gene that is to be altered. It is not intended that the present invention be limited to any particular target property. However, in some preferred embodiments, the target property is the stability of a gene product (e.g., resistance to denaturation, proteolysis or other degradative factors), while in other embodiments, the level of production in a production host is altered. Indeed, it is contemplated that any property of a starting gene will find use in the present invention.

The term "property" or grammatical equivalents thereof in the context of a nucleic acid, as used herein, refer to any characteristic or attribute of a nucleic acid that can be selected or detected. These properties include, but are not limited to, a property affecting binding to a polypeptide, a property conferred on a cell comprising a particular nucleic acid, a property affecting gene transcription (e.g., promoter strength, promoter recognition, promoter regulation, enhancer function), a property affecting RNA processing (e.g., RNA splicing, RNA stability, RNA conformation, and post-transcriptional modification), a property affecting translation (e.g., level, regulation, binding of mRNA to ribosomal proteins, post-translational modification). For example, a binding site for a transcription factor, polymerase, regulatory factor, etc., of a nucleic acid may be altered to produce desired characteristics or to identify undesirable characteristics.

The term “property” or grammatical equivalents thereof in the context of a polypeptide, as used herein, refer to any characteristic or attribute of a polypeptide that can be selected or detected. These properties include, but are not limited to oxidative stability, substrate specificity, catalytic activity, thermal stability, alkaline stability, pH activity profile, resistance to proteolytic degradation, $K_M$, $k_{cat}$, $k_{cat}/k_M$ ratio, protein folding, inducing an immune response, ability to bind to a ligand, ability to bind to a receptor, ability to be secreted, ability to be displayed on the surface of a cell, ability to oligomerize, ability to signal, ability to stimulate cell proliferation, ability to inhibit cell proliferation, ability to induce apoptosis, ability to be modified by phosphorylation or glycosylation, ability to treat disease.

As used herein, the term “screening” has its usual meaning in the art and is, in general a multi-step process. In the first step, a mutant nucleic acid or variant polypeptide therefrom is provided. In the second step, a property of the mutant nucleic acid or variant polypeptide is determined. In the third step, the determined property is compared to a property of the corresponding parent nucleic acid, to the property of the corresponding naturally occurring polypeptide or to the property of the starting material (e.g., the initial sequence) for the generation of the mutant nucleic acid.

It will be apparent to the skilled artisan that the screening procedure for obtaining a nucleic acid or protein with an altered property depends upon the property of the starting material the modification of which the generation of the mutant nucleic acid is intended to facilitate. The skilled artisan will therefore appreciate that the invention is not limited to any specific property to be screened for and that the following description of properties lists illustrative examples only. Methods for screening for any particular property are generally described in the art. For example, one can measure binding, pH, specificity, etc., before and after mutation, wherein a change indicates an alteration. Preferably, the screens are performed in a high-throughput manner, including multiple samples being screened simultaneously, including, but not limited to assays utilizing chips, phage display, and multiple substrates and/or indicators.

As used herein, in some embodiments, screens encompass selection steps in which variants of interest are enriched from a population of variants. Examples of these embodiments include the selection of variants that confer a growth advantage to the host organism, as well as phage display or any other method of display, where variants can be captured from a population of variants based on their binding or catalytic properties. In a preferred embodiment, a library of variants is exposed to stress (heat, protease, denaturation) and subsequently variants that are still intact are identified in a screen or enriched by selection. It is intended that the term encompass any suitable means for selection. Indeed, it is not intended that the present invention be limited to any particular method of screening.

As used herein, the term “targeted randomization” refers to a process that produces a plurality of sequences where one or several positions have been randomized. In some embodiments, randomization is complete (i.e., all four nucleotides, A, T, G, and C can occur at a randomized position. In alternative embodiments, randomization of a nucleotide is limited to a subset of the four nucleotides. Targeted randomization can be applied to one or several codons of a sequence, coding for one or several proteins of interest. When expressed, the resulting libraries produce protein populations in which one or more amino acid positions can contain a mixture of all 20 amino acids or a subset of amino acids, as determined by the randomization scheme of the randomized codon. In some embodiments, the individual members of a population resulting from targeted randomization differ in the number of amino acids, due to targeted or random insertion or deletion of codons. In further embodiments, synthetic amino acids are included in the protein populations produced. In some preferred embodiments, the majority of members of a population resulting from targeted randomization show greater sequence homology to the consensus sequence than the starting gene. In some embodiments, the sequence encodes one or more proteins of interest. In alternative embodiments, the proteins have differing biological functions. In some further preferred embodiments, the incoming sequence comprises at least one selectable marker.

The terms “modified sequence” and “modified genes” are used interchangeably herein to refer to a sequence that includes a deletion, insertion or interruption of naturally occurring nucleic acid sequence. In some preferred embodiments, the expression product of the modified sequence is a truncated protein (e.g., if the modification is a deletion or interruption of the sequence). In some particularly preferred embodiments, the truncated protein retains biological activity. In alternative embodiments, the expression product of the modified sequence is an elongated protein (e.g., modifications comprising an insertion into the nucleic acid sequence). In some embodiments, an insertion leads to a truncated protein (e.g., when the insertion results in the formation of a stop codon). Thus, an insertion may result in either a truncated protein or an elongated protein as an expression product.

As used herein, the terms “mutant sequence” and “mutant gene” are used interchangeably and refer to a sequence that has an alteration in at least one codon occurring in a host cell’s wild-type sequence. The expression product of the mutant sequence is a protein with an altered amino acid sequence relative to the wild-type. The expression product may have an altered functional capacity (e.g., enhanced enzymatic activity).

The terms “mutagenic primer” or “mutagenic oligonucleotide” (used interchangeably herein) are intended to refer to oligonucleotide compositions which correspond to a portion of the template sequence and which are capable of hybridizing thereto. With respect to mutagenic primers, the primer will not precisely match the template nucleic acid, the mismatch or mismatches in the primer being used to introduce the desired mutation into the nucleic acid library. As used herein, “non-mutagenic primer” or “non-mutagenic oligonucleotide” refers to oligonucleotide compositions that match precisely to the template nucleic acid. In one embodiment of the invention, only mutagenic primers are used. In another preferred embodiment of the invention, the primers are designed so that for at least one region at which a mutagenic primer has been included, there is also non-mutagenic primer included in the oligonucleotide mixture. By adding a mixture of mutagenic primers and non-mutagenic primers corresponding to at least one of the mutagenic primers, it is possible to produce a resulting nucleic acid library in which a variety of combinatorial mutational patterns are presented. For example, if it is desired that some of the members of the mutant nucleic acid library retain their parent sequence at certain positions while other members are mutant at such sites, the non-mutagenic primers provide the ability to obtain a specific level of non-mutant members within the nucleic acid library for a given residue. The methods of the invention employ mutagenic and non-mutagenic oligonucleotides which are generally between 10-50 bases in length, more preferably about 15-45 bases in length. However, it may be necessary to use primers that are either shorter than 10 bases or longer than 50 bases to obtain the mutagenesis result desired. With respect to corresponding mutagenic and non-mutagenic primers, it is not necessary that the corresponding oligonucleotides be of identical length, but only that there is overlap in the region corresponding to the mutation to be added.

In some embodiments, primers are added in a pre-defined ratio. For example, if it is desired that the resulting library have a significant level of a certain specific mutation and a lesser amount of a different mutation at the same or different site, by adjusting the amount of primer added, it is possible to produce the desired biased library. Alternatively, by adding lesser or greater amounts of non-mutagenic primers, it is possible to adjust the frequency with which the corresponding mutation(s) are produced in the mutant nucleic acid library.

As used herein, the phrase "contiguous mutations" refers to mutations that are presented within the same oligonucleotide primer. For example, contiguous mutations may be adjacent or nearby each other, however, they will be introduced into the resulting mutant template nucleic acids by the same primer.

As used herein, the phrase "discontiguous mutations" refers to mutations that are presented in separate oligonucleotide primers. For example, discontiguous mutations will be introduced into the resulting mutant template nucleic acids by separately prepared oligonucleotide primers.

The terms "wild-type sequence," "wild-type nucleic acid sequence," and "wild-type gene" are used interchangeably herein, to refer to a sequence that is native or naturally occurring in a host cell. In some embodiments, the wild-type sequence refers to a sequence of interest that is the starting point of a protein-engineering project. The wild-type sequence may encode either a homologous or heterologous protein. A homologous protein is one the host cell would produce without intervention. A heterologous protein is one that the host cell would not produce but for the intervention.

The term "oxidation stable" refers to proteases of the present invention that retain a specified amount of enzymatic activity over a given period of time under conditions prevailing during the proteolytic, hydrolyzing, cleaning or other process of the invention, for example while exposed to or contacted with bleaching agents or oxidizing agents. In some embodiments, the proteases retain at least about 50%, about 60%, about 70%, about 75%, about 80%, about 85%, about 90%, about 92%, about 95%, about 96%, about 97%, about 98%, or about 99% proteolytic activity after contact with a bleaching or oxidizing agent over a given time period, for example, at least 1 minute, 3 minutes, 5 minutes, 8 minutes, 12 minutes, 16 minutes, 20 minutes, etc.

The term "chelator stable" refers to proteases of the present invention that retain a specified amount of enzymatic activity over a given period of time under conditions prevailing during the proteolytic, hydrolyzing, cleaning or other process of the invention, for example while exposed to or contacted with chelating agents. In some embodiments, the proteases retain at least about 50%, about 60%, about 70%, about 75%, about 80%, about 85%, about 90%, about 92%, about 95%, about 96%, about 97%, about 98%. or about 99% proteolytic activity after contact with a chelating agent over a given time period, for example, at least 10 minutes, 20 minutes, 40 minutes, 60 minutes, 100 minutes, etc.

The terms "thermally stable" and "thermostable" refer to enzymes of the present invention that retain a specified amount of enzymatic activity after exposure to identified temperatures over a given period of time under conditions prevailing during the enzymatic, hydrolyzing, cleaning or other process of the invention, for example while exposed altered temperatures. Altered temperatures include increased or decreased temperatures. In some embodiments, the proteases retain at least about 50%, about 60%, about 70%, about 75%, about 80%, about 85%, about 90%, about 92%, about 95%, about 96%, about 97%, about 98%, or about 99% proteolytic activity after exposure to altered temperatures over a given time period, for example, at least 60 minutes, 120 minutes, 180 minutes, 240 minutes, 300 minutes, etc.

The terms "thermally activated" and "thermal activity" refer to enzymes of the present invention that gain a specified amount of enzymatic activity at identified temperatures over a given period of time under conditions prevailing during the enzymatic, hydrolyzing, cleaning or other process of the invention, for example while exposed altered temperatures. Altered temperatures include increased or decreased temperatures. In some embodiments, the proteases gain at least about 10%, about 20%, about 30%, about 40%, about 50%, about 60%, about 70%, about 75%, about 80%, about 85%, about 90%, about 92%, about 95%, about 96%, about 97%, about 98%, or about 99% or more enzymatic activity at identified temperatures over a given time period, for example, at least 10 minutes, 20 minutes, 30 minutes, 60 minutes, 120 minutes, 180 minutes, 240 minutes, 300 minutes, etc.

As used herein, the term "chemical stability" refers to the stability of a protein (e.g., an enzyme) towards chemicals that adversely affect its activity. In some embodiments, such chemicals include, but are not limited to hydrogen peroxide, peracids, anionic detergents, cationic detergents, non-ionic detergents, chelants, etc. However, it is not intended that the present invention be limited to any particular chemical stability level nor range of chemical stability. In particular, the terms "detergent stable" and "LAS stable" refer to proteases of the present invention that retain a specified amount of enzymatic activity after exposure to a detergent composition over a given period of time under conditions prevailing during the proteolytic, hydrolyzing, cleaning or other process of the invention. In some embodiments, the proteases retain at least about 50%, about 60%, about 70%, about 75%, about 80%, about 85%, about 90%, about 92%, about 95%, about 96%, about 97%, about 98%, or about 99% proteolytic activity after exposure to detergent over a given time period, for example, at least 60 minutes, 120 minutes, 180 minutes, 240 minutes, 300 minutes, etc.

As used herein, the term "wash stability" refers to the stability of a protein (e.g., an enzyme) under conditions prevailing during the enzymatic, hydrolyzing, cleaning or other process of the invention. However, it is not intended that the present invention be limited to any particular wash stability level. In particular, the terms "wash stable" and "wash conditions stability" refer to proteases of the present invention that retain a specified amount of enzymatic activity over a given period of time under conditions prevailing during the enzymatic hydrolyzing, cleaning or other process of the invention. In some embodiments, the proteases retain at least about 50%, about 60%, about 70%, about 75%, about 80%, about 85%, about 90%, about 92%, about 95%, about 96%, about 97%, about 98%, or about 99% proteolytic activity after exposure to detergent over a given time period, for example, at least 5 minutes, 10 minutes, 30 minutes, 60 minutes, 120 minutes, 180 minutes, 240 minutes, 300 minutes, etc.

The term "enhanced stability" or "diminished stability" in the context of an oxidation, chelator, thermal and/or pH stable enzyme refers to a higher or lower retained enzymatic activity respectively over time as compared to wild-type enzymes.

The term "enhanced stability" or "diminished stability" in the context of an oxidation, chelator, thermal and/or pH stable enzyme refers to a higher or lower retained enzymatic activity respectively over time as compared to wild-type enzymes.

The term "enhanced stability" in the context of an oxidation, chelator, thermal and/or pH stable protease refers to a higher retained proteolytic activity over time as compared to other serine proteases (e.g., subtilisin proteases) and/or wild-type enzymes.

The term "diminished stability" in the context of an oxidation, chelator, thermal and/or pH stable protease refers to a lower retained proteolytic activity over time as compared to other serine proteases (e.g., subtilisin proteases) and/or wild-type enzymes.

As used herein, the terms "benefit" and "favorable outcome" refer to the consequence of improving a protein in order to make it more suitable for animal, human and industrial applications. In some embodiments, the favorable outcome is directly related to protein use in the final intended application, such as cleaning performance of detergent proteases, while in other embodiments, it provides a benefit involved in its production. Examples of favorable outcomes include, but are not limited to improvements in: substrate binding, enzyme inhibition, reaction rates, detergent stability, thermal stability, thermal activity, conformational stability, stability towards proteolysis and/or autolysis, expression levels, solubility, recoverability, pH activity profile, emulsifiability, foamability, and wetting.

As used herein, the terms "exothermic" and "endothermic" are used according to their customary meanings in the art. In some of the assay systems described herein, a remaining activity fraction less than unity indicates the variant is less active at higher temperatures (e.g., "exothermic") and hence is more suitable for performance at cold temperatures. Conversely, a remaining activity fraction larger than unity indicates the variant is more active at higher temperatures (e.g., "endothermic"), and hence is more suitable for performance at higher temperatures.

As used herein, the term "physical property" refers to any parameter suitable for describing the physico-chemical characteristics of a protein. As used herein, "physical property of interest" and "property of interest" are used interchangeably to refer to physical properties of proteins that are being investigated and/or modified. The term "protein" in the general sense encompasses enzymes, polypeptides, and polyelectrolytes. Examples of physical properties include, but are not limited to net surface charge and charge distribution on the protein surface, net hydrophobicity and hydrophobic residue distribution on the protein surface, surface charge density, surface hydrophobicity density, total count of surface ionizable groups, surface tension, protein size and its distribution in solution, melting temperature, heat capacity, and second virial coefficient.

As used herein, the term "cleaning composition" includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, car or carpet shampoos, bathroom cleaners; hair shampoos and hair-rinses; shower gels and foam baths and metal cleaners; as well as cleaning auxiliaries such as bleach additives and "stain-stick" or pre-treat types.

As used herein, the terms "detergent composition" and "detergent formulation" are used in reference to mixtures which are intended for use in a wash medium for the cleaning of soiled objects. In some preferred embodiments, the term is used in reference to laundering fabrics and/or garments (e.g., "laundry detergents"). In alternative embodiments, the term refers to other detergents, such as those used to clean dishes, cutlery, etc. (e.g., "dishwashing detergents"). It is not intended that the present invention be limited to any particular detergent formulation or composition. Indeed, it is intended that the term encompasses detergents that contain surfactants, transferase(s), hydrolytic enzymes, oxido reductases, builders, bleaching agents, bleach activators, bluing agents and fluorescent dyes, caking inhibitors, masking agents, enzyme activators, antioxidants, and solubilizers.

As used herein, the term "reference buffer" refers to a buffer of known pH and ionic strength that is used for measurements of a property of interest (e.g., zeta potential).

As used herein, the term "improved variant" refers to an enzyme variant that exhibits a performance index that is greater than 1.0, relative to a wild-type or other parent molecule, as indicated by context.

As used herein, the term "substrate stain-specific enzyme variant" refers to an enzyme that preferentially hydrolyzes a particular stain in the presence of other stains.

As used herein, the term "assay of interest" refers to any testing method used to determine a particular property of interest for an enzyme. In some embodiments, multiple assays of interest are used.

As used herein, "enhanced performance" in a detergent is defined as increasing cleaning of stains (e.g., grass, tea, wine, blood, dingy, food, etc.), as determined by usual evaluation after a standard wash cycle. In particular embodiments, the enzyme variants of the present invention provide enhanced performance in the removal of colored stains and soils. In further embodiments, the enzymes of the present invention provide enhanced performance in the removal and/or decolorization of stains.

As used herein the term "hard surface cleaning composition," refers to detergent compositions for cleaning hard surfaces such as floors, walls, tile, bath and kitchen fixtures, and the like. Such compositions are provided in any form, including but not limited to solids, liquids, emulsions, etc.

As used herein, "dishwashing composition" refers to all forms for compositions for cleaning dishes, including but not limited to granular and liquid forms.

As used herein, "fabric cleaning composition" refers to all forms of detergent compositions for cleaning fabrics, including but not limited to, granular, liquid and bar forms.

As used herein, "textile" refers to woven fabrics, as well as staple fibers and filaments suitable for conversion to or use as yarns, woven, knit, and non-woven fabrics. The term encompasses yarns made from natural, as well as synthetic (e.g., manufactured) fibers.

As used herein, "textile materials" is a general term for fibers, yarn intermediates, yarn, fabrics, and products made from fabrics (e.g., garments and other articles).

As used herein, "fabric" encompasses any textile material. Thus, it is intended that the term encompass garments, as well as fabrics, yarns, fibers, non-woven materials, natural materials, synthetic materials, and any other textile material.

As used herein, the term "compatible," means that the cleaning composition materials do not reduce the enzymatic activity of the enzymes of the present invention to such an extent that the enzymes is not effective as desired during normal use situations. Specific cleaning composition materials are exemplified in detail hereinafter.

As used herein, "effective amount of enzyme" refers to the quantity of enzyme necessary to achieve the enzymatic activity required in the specific application (e.g., personal care product, cleaning composition, etc.). Such effective amounts are readily ascertained by one of ordinary skill in the art and are based on many factors, such as the particular enzyme variant used, the cleaning application, the specific composition of the cleaning composition, and whether a liquid or dry (e.g., granular, bar) composition is required, and the like.

As used herein, "non-fabric cleaning compositions" encompass hard surface cleaning compositions, dishwashing compositions, personal care cleaning compositions (e.g., oral cleaning compositions, denture cleaning compositions, personal cleansing compositions, etc.), and compositions suitable for use in the pulp and paper industry.

Unless otherwise noted, all component or composition levels are in reference to the active level of that component or composition, and are exclusive of impurities, for example, residual solvents or by-products, which may be present in commercially available sources.

Enzyme components weights are based on total active protein. All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The term "cleaning activity" refers to the cleaning performance achieved by the enzyme under conditions prevailing during the enzymatic, hydrolyzing, cleaning or other process of the invention. In some embodiments, cleaning performance is determined by the application of various cleaning assays concerning enzyme sensitive stains, for example grass, blood, milk, or egg protein as determined by various chromatographic, spectrophotometric or other quantitative methodologies after subjection of the stains to standard wash conditions. Exemplary assays include, but are not limited to those described in WO 99/34011, and U.S. Pat. No. 6,605,458 (both of which are herein incorporated by reference), as well as those methods included in the Examples.

The term "cleaning effective amount" of an enzyme refers to the quantity of protease described hereinbefore that achieves a desired level of enzymatic activity in a specific cleaning composition. Such effective amounts are readily ascertained by one of ordinary skill in the art and are based on many factors, such as the particular enzyme used, the cleaning application, the specific composition of the cleaning composition, and whether a liquid or dry (e.g., granular, bar) composition is required, etc.

The term "cleaning adjunct materials" as used herein, means any liquid, solid or gaseous material selected for the particular type of cleaning composition desired and the form of the product (e.g., liquid, granule, powder, bar, paste, spray, tablet, gel; or foam composition), which materials are also preferably compatible with the protease enzyme used in the composition. In some embodiments, granular compositions are in "compact" form, while in other embodiments, the liquid compositions are in a "concentrated" form.

The terms "enhanced performance" and "favorable property" in the context of cleaning activity refer to an increased or greater cleaning activity of certain enzyme sensitive stains such as blood, milk, ink, egg, grass, tea, wine, etc., as determined by usual evaluation after a standard wash cycle and/or multiple wash cycles as compared to the parent enzyme. In particular embodiments, the protease variants of the present invention provide enhanced performance in the removal of colored stains.

The terms "diminished performance" and "unfavorable property" in the context of cleaning activity refer to a decreased or lesser cleaning activity of certain enzyme sensitive stains such as blood, milk, ink, egg, grass, tea, wine, etc., as determined by usual evaluation after a standard wash cycle as compared to the parent enzyme.

The terms "comparative performance" and "acceptable property" in the context of cleaning activity refers to at least about 60%, at least about 70%, at least about 80%, at least about 90%, or at least about 95% of the cleaning activity of a comparative enzyme (e.g., commercially available proteases). Cleaning performance can be determined by comparing the proteases of the present invention with other proteases in various cleaning assays concerning enzyme sensitive stains such as blood, milk and/or ink (BMI) as determined by usual spectrophotometric or analytical methodologies after standard wash cycle conditions.

As used herein, a "low detergent concentration" system includes detergents where less than about 800 ppm of detergent components are present in the wash water. Japanese detergents are typically considered low detergent concentration systems, as they have usually have approximately 667 ppm of detergent components present in the wash water.

As used herein, a "medium detergent concentration" systems includes detergents wherein between about 800 ppm and about 2000 ppm of detergent components are present in the wash water. North American detergents are generally considered to be medium detergent concentration systems as they have usually approximately 975 ppm of detergent components present in the wash water. Brazilian detergents typically have approximately 1500 ppm of detergent components present in the wash water.

As used herein, "high detergent concentration" systems includes detergents wherein greater than about 2000 ppm of detergent components are present in the wash water. European detergents are generally considered to be high detergent concentration systems as they have approximately 3000-8000 ppm of detergent components in the wash water.

As used herein, "fabric cleaning compositions" include hand and machine laundry detergent compositions including laundry additive compositions and compositions suitable for use in the soaking and/or pretreatment of stained fabrics (e.g., clothes, linens, and other textile materials).

As used herein, "non-fabric cleaning compositions" include non-textile (i.e., fabric) surface cleaning compositions, including but not limited to dishwashing detergent compositions, oral cleaning compositions, denture cleaning compositions, and personal cleansing compositions.

The "compact" form of the cleaning compositions herein is best reflected by density and, in terms of composition, by the amount of inorganic filler salt. Inorganic filler salts are conventional ingredients of detergent compositions in powder form. In conventional detergent compositions, the filler salts are present in substantial amounts, typically 17-35% by weight of the total composition. In contrast, in compact compositions, the filler salt is present in amounts not exceeding 15% of the total composition. In some embodiments, the filler salt is present in amounts that do not exceed 10%, or more preferably, 5%, by weight of the composition. In some embodiments, the inorganic filler salts are selected from the alkali and alkaline-earth-metal salts of sulfates and chlorides. A preferred filler salt is sodium sulfate.

DETAILED DESCRIPTION OF THE INVENTION

The present invention provides efficient methods for obtaining a protein with one or more beneficial attributes in industrial, consumer or pharmaceutical applications. In some preferred embodiments, the present invention provides methods for producing superior enzymes for a given application through screening an abbreviated set of candidate enzymes.

Most strategies currently utilized for improving protein performance in industrial, consumer or pharmaceutical applications have focused on amino acid substitutions at or near an enzyme's active site, in order to increase catalytic efficiency. However, during the development of the present invention, it was determined that mutations elsewhere on the enzyme surface dramatically increase enzyme performance beyond what is possible through catalytic efficiency improvements. Basically, the reaction rate governing conversion of substrates to products mediated by enzymes is only partially controlled by the rate of the chemical catalytic conversion step alone. Enzymes and substrates interact as colloids prior to their association as an enzyme-substrate ES complex, as well as during dissociation from the enzyme-product EP complex that is formed after chemical conversion. Even if the reaction step proceeds at a fast rate, enzyme approach towards substrate can be extremely slow (e.g., diffusion-limited), as in the case of same-sign colloids experiencing electrostatic repulsive forces. Likewise, release of enzyme from the enzyme-product EP complex can be extremely slow (e.g., diffusion-limited), as in the case of colloids experiencing attractive short-range hydrophobic and dispersive forces. Both conditions increase the enzyme transit time from substrate to product and become rate-step limiting compared to chemical conversion. While it is possible to envisage that oppositely-charged colloids would actually accelerate the formation of ES complexes (e.g., above the diffusion limit), subsequent dissociation of the EP complex would be painfully slow (assuming that no charges are created nor lost) and the overall reaction rate would decrease. Therefore, the asymmetry of the pair-wise interaction potential is exploited in order to ensure minimal transit times for both the ES and EP complexes. This is particularly important in industrial biotechnology, since it is desirable to convert all of the substrate to product in the shortest amount of time possible under often enzyme-limited conditions. Historically, protein engineers have focused on specific enzyme-substrate interactions of the chemical conversion step and have failed to recognize the contribution of both short- and long-range non-specific interactions, arising from intermolecular colloidal and surface forces, which govern the association and dissociation steps. An objective of the present invention is to optimize intermolecular forces to the point where the chemical conversion step becomes rate-limiting. Once chemical conversion step becomes rate limiting, it can be improved through changes in the enzyme active site. This objective is applicable whether the substrate is a small peptide in solution or an insoluble macroscopic substrate. Nonetheless, knowledge of the mechanism(s) involved is not necessary in order to make and use the present invention. Nor is it intended that the present invention be limited to any particular mechanism.

As an example, in liquid laundry applications, a charge optimum for performance between an enzyme and a charged substrate stain was observed. Without being bound by theory, when enzyme and substrate stains have strongly opposite sign charges, little performance is detected, likely due to tight unproductive binding. Conversely, when their charges are strongly same sign matched, little performance is detected, likely due to increased repulsion. For a given enzyme fold this charge optimum for performance is adequately described in terms of net charge relative to the parent enzyme. When comparing performance across different enzyme folds, however, a common scale must be employed. Exemplary common scales include but are not limited to enzyme charge experimentally determined by zeta potential, electrophoretic, hydrogen-ion titration measurements, or even calculated using public (e.g., SwissProt) or commercial software (e.g., DelPhi, MOE). As described herein, for a given substrate stain and detergent formulation, optimal enzymes from different folds exhibit a comparable net charge. This finding provides the basis for methods of rapidly identifying top-performing enzymes for a given application in any reaction medium.

The location of the performance optimum is largely influenced by medium utilized (e.g., detergent formulation, pH, ionic strength, etc), as well as the net charge and charge distribution of amino acid residues of the enzyme of interest. Thus, an optimal enzyme is contemplated to exist for different formulations of varying pH, ionic strength, surfactant type and ratio, builders and chelators, all of which affect electrostatic phenomena. The use of enzyme blends, in which each member of the blend possesses a different charge optimum, is contemplated for the production of formulations suitable for a wide range of conditions (e.g., proteases in detergent formulations sold in different geographies or locales having differences in water hardness). The use of enzyme blends, in which each member of the blend excels in the cleaning of a different stain, is also contemplated for the production of formulations suitable for cleaning a wide variety of stains. Additionally, the use of enzyme blends, in which each member of the blend possesses a different charge optimum, is contemplated in cases where the enzyme substrate itself undergoes charge changes during enzyme reaction Although described herein in relationship to proteases and blood, milk and ink stains, the methods of the present invention are suitable for optimizing any enzyme-substrate interaction in any reaction medium. In particular, the methods of the present invention are contemplated for use in improving properties of other proteases and enzyme classes (e.g., amylases, cellulases, oxidases, lipases, cutinases, pectinases, mannanases, etc.). Additionally, the methods of the present invention are contemplated to be suitable for use in improving properties of enzymes and other proteins in other formulations (e.g., buffers).

In some embodiments, the methods of the present invention find use in improving cellulases. Cellulases react with cellulosic substrates to provide a variety of benefits in many industrial applications. These include but are not limited to stone washing effects on textiles, stain cleaning from fabrics in laundry, depilling and pill prevention of cotton and cotton/synthetic fiber blends, and break down of biomass to fermentable sugars. The performance of cellulases in all of these applications can be improved by optimizing their surface charge and/or hydrophobicity as described herein for proteases, to obtain optimal performance under given application conditions. In particular, one of the main problems associated with use of cellulases in textile and fabric care applications is that the cellulase treatment weakens the fabric. Since fabric is a charged surface, using the methods of the present invention to optimize the charge of the enzyme surface finds use in preventing cellulase penetration into the fibers. Enzyme variants having an optimal charge can still polish the surface by reacting on the fiber surface, but cannot penetrate the surface. Thus, the present invention provides methods to obtain cellulases having good fabric care performance with lower fabric strength loss. In some additional embodiments, the improved cellulases provided by the present invention find use in biomass and other applications.

In addition, the methods of the present invention find use in improving amylases used in starch hydrolysis useful in various commercial and industrial applications.

Polyesterases and cutinases are used to modify surfaces of polyesters. This reaction finds use in providing fabric care benefits for polyester and polyester/cotton blends. One of the main drawbacks of the known enzymes is that they bind very tightly to fabric. This results in poor performance of the enzyme in a variety of fabric care applications. The present invention provides means to improve the performance of polyesterases and cutinases by modifying the surface charge and/or hydrophobicity of these enzymes.

Lipases are used in laundry applications for cleaning oily stains. Generally, these stains are very hydrophobic. The present invention provides means to improve the performance of lipases by optimizing the surface charge and/or hydrophobicity of these enzymes. Another negative of lipase performance is the malodor generation resulting from lipase binding to the fabric and or stain. Likewise, the present invention finds use in minimizing malodor generation by optimizing the surface charge and/or hydrophobicity of the lipase(s) to reduce the binding of the enzyme to the fabric.

Cleaning compositions normally require formulations that contain a protease along with non protease enzymes. Proteases often degrade other enzymes, as well as themselves (i.e., through autolysis). Currently, this is solved by the addition of compounds that inhibit proteases. The present invention finds use in increasing the resistance of enzymes to proteolysis by determining physical property optimum of a given enzyme with protease resistance.

Briefly the methods of the present invention involve one or more of the steps detailed below: (I) Assay Probe Proteins Spanning a Physical Property Range; (II) Determine Physical Property Optimum for a Given Favorable Outcome; and (III) Provide Variant Proteins Having The Physical Property Optimum.

I. Assay Probe Proteins

In some embodiments, this step involves the testing of multiple probe proteins (i.e., "probe protein folds") spanning the range of a physical property of interest (i.e., a "property of interest") in an appropriate assay. In some embodiments, the probe proteins include a limited set of proteins and/or variants thereof. In some exemplary embodiments, this step involves testing multiple serine proteases and/or metalloproteases (e.g., two different protein folds) for one or more benefits. For instance charge-ladder variants of two proteases, ASP (a serine protease) and NprE (a neutral metalloprotease) were provided. The protease charge-ladder variants of ASP as described herein, span a relative net charge change range of −4 to +4 as compared to the parent ASP (e.g., R14I) or −5 to +3 compared to the wild type ASP. In some embodiments, the probe protein set also includes commercially available proteins, which serve as benchmarks for the intended application (e.g., subtilisin used in detergent formulations).

II. Determine Physical Property Optimum

In some preferred embodiments, this step involves the identification of a physical property optimum or range thereof for a favorable outcome. In some exemplary embodiments, the cleaning performance of protease charge-ladder variants was measured. When comparing benefits obtained with proteins having different folds, a common physical property scale is employed (e.g., protein charge reported as zeta potential). In contrast, when comparing benefits obtained with proteins having the same fold, a relative scale can be employed (e.g., net charge differential relative to wild-type or parent protein). In some particularly preferred embodiments, probe proteins spanning a wide physical property range are employed, in order to increase the likelihood of defining an optimum for that physical property. Once the optimum value or optimum range for a benefit of interest has been established by assaying the probe proteins, it is possible to predict both the general direction and magnitude of change likely to be required for converting an inferior performer (e.g., lying outside of the optimal range) to a superior performer (e.g., within the optimal range).

Usage of more than one probe protein series is contemplated to permit the identification of different physical property optima for a benefit of interest. For instance in some embodiments, both charge-ladders and hydrophobicity-ladders for a detergent protease are tested for cleaning performance in a blood, milk, ink assay. Conversely the same physical property is contemplated to exhibit different optima for different benefits. For instance, there exists an optimal protease charge for cleaning performance for NprE, which is distinct from the optimal protease charge for detergent stability.

In some embodiments, charge-related physical properties are compared across different protein folds in terms of measured zeta potential, net charge, charge density, and/or surface count of ionizable groups. In general, any method of determining protein charge from titration or electrophoretic measurements is suitable for comparing different protein folds. In some alternative embodiments, comparing different protein folds is done by calculation of one or more of the above quantities based upon protein primary, secondary and/or tertiary sequence information when available. Typical bioinformatics tools employed for such purposes include isoelectric point calculators using the Henderson-Hesselbach equation (e.g., European Molecular Biology Laboratory) or Poisson-Boltzmann electrostatic solvers (e.g., DelPhi, MOE).

In some embodiments, hydrophobicity-related physical properties are compared across different protein folds in terms of measured protein partitioning between its native aqueous environment and a hydrophobic phase. Examples include but are not limited to surface tension at the air-water or heptane-water interfaces, as well as contact angle and wetting measurements between aqueous and solid substrate-containing phases. In general, any method suitable for characterizing the partitioning of a protein between two phases is suitable for use in the present invention, including optical (e.g., ellipsometry, surface plasmon resonance, interferometry, and/or reflectivity), acoustic (e.g., quartz-crystal microbalance), fluorescence, spectroscopy (e.g., attenuated total reflection infrared) or concentration (e.g., enzyme activity) determinations. In some embodiments, the overall hydrophobic contribution is calculated using one or more of the many amino-acid hydrophobicity scales available in the literature and known to those in the art, that take into account protein primary, secondary and/or tertiary structure information.

Charge and hydrophobicity scales are not independent from each other since charged residues add hydrophilic character. Thus, rather than simply choosing one scale over another, some embodiments of the present invention employ multiple different scales (e.g., theoretical or experimentally determined) for identifying physical property dependencies. References for 23 of the most commonly used hydrophobicity scales include: hydrophobicity (Rao and Argos) calculates membrane buried helix parameter. (Rao and Argos, Biochim. Biophys. Acta 869:197-214 [1986]); hydrophobicity (Black and Mould) calculates hydrophobicity of physiological L-alpha amino acids (Black and, Mould, Anal. Biochem., 193:72-82 [1991]); hydrophobicity (Bull and Breese) calculates hydrophobicity (free energy of transfer to surface in kcal/mole)(Bull and Breese, Arch. Biochem. Biophys. 161:665-670 [1974]); hydrophobicity (Chothia) calculates proportion of residues 95% buried (in 12 proteins) (Chothia, J. Mol. Biol., 105:1-14 [1976]); hydrophobicity (Kyte and Doolittle) calculates hydropathicity (Kyte and Doolittle, J. Mol. Biol., 157:105-132 [1982]); hydrophobicity (Eisenberg et al.) calculates normalized consensus hydrophobicity scale (Eisenberg et al., J. Mol. Biol. 179:125-142 [1984]); hydrophobicity, (Fauchere and Pliska) calculates hydrophobicity scale (pi-r) (Fauchere and Pliska, Eur. J. Med. Chem., 18:369-375 [1983]); hydrophobicity (Guy) calculates hydrophobicity scale based on free energy of transfer (kcal/mole) (Guy, Biophys J., 47:61-70 [1985]); hydrophobicity (Janin) calculates free energy of transfer from inside to outside of a globular protein (Janin, Nature 277:491-492 [1979]); hydrophobicity (Abraham and Leo) calculates hydrophobicity (delta G1/2cal) (Abraham and Leo, Proteins: Structure, Function and Genetics 2:130-152 [1987]); hydrophobicity (Manavalan et al.) calculates average surrounding hydrophobicity (Manavalan et al., Nature 275:673-674 [1978]); Hydrophobicity (Miyazawa et al.) calculates hydrophobicity scale (contact energy derived from 3D data) (Miyazawa et al., Macromolecules 18:534-552 [1985]); hydrophobicity (Aboderin) calculates mobilities of amino acids on chromatography paper (RF) (Aboderin, Int. J. Biochem., 2:537-544 [1971]); hydrophobicity HPLC (Parker et al.) calculates hydrophilicity scale derived from HPLC peptide retention times (Parker et al., Biochem., 25:5425-5431 [1986]); Hphob. HPLC pH3.4 calculates hydrophobicity indices at ph 3.4 determined by HPLC (Cowan and Whittaker, Peptide Res., 3:75-80 [1990]); Hphob. HPLC pH7.5 calculates hydrophobicity indices at ph 7.5 determined by HPLC (Cowan and Whittaker, Peptide Res., 3:75-80 [1990]); hydrophobicity (Rose et al.)(AA) calculates the mean fractional area loss (f) [average area buried/standard state area] (Rose et al., Science 229:834-838 [1985)); and hydrophobicity (Roseman) calculates hydrophobicity scale (pi-r) (Roseman, J. Mol. Biol., 200:513-522 [1988)).

In some embodiments, solubility-related physical properties are compared across different protein folds in terms of both charge and hydrophobicity scales previously described. In general, any thermodynamic or kinetic quantity characterizing protein-protein versus protein-solvent interactions is suitable for use with the methods of the present invention. For instance second virial coefficient (See, Wilson, Acta Crystallographica, D50:361-365 [1994]), chi parameter, osmotic pressure, and activity or fugacity coefficients reflecting deviations from ideal $4^{th}$ Ed. mixing behavior find use (See e.g., Reid et al., "The Properties of Gases and Liquids", McGraw-Hill, [1987]).

In some embodiments, size-related physical properties are compared across different protein folds using any experimental means suitable for determining protein or polymer dimensions. In additional embodiments, size is inferred from molecular weight using commonly available correlations between protein or polymer conformation (coil, globular, branched), their molecular weight and hydrodynamic or gyration radius. Suitable techniques for size or molecular weight determination include, but are not limited to static and dynamic light scattering, gel electrophoresis, mass spectroscopy and chromatography. In further embodiments, size is readily estimated from knowledge of the experimentally determined protein crystal structures or structural homology models.

Protein melting temperatures ($T_m$) are typically determined through monitoring of a physical reporter property across a temperature scan. Suitable methods include, but are not limited to differential scanning calorimetry, circular dichroism, dynamic light scattering, and UV-visible spectroscopy.

III. Provide Variant Proteins Having the Physical Property Optimum

Once an optimum value or range has been determined in the previous step, a plurality of candidate proteins are provided which are constrained for the physical property of interest. Suitable methods for providing candidate proteins include, but are not limited to the production of artificial enzymes variants by recombinant techniques, as well as the purification of natural enzyme variants (e.g., homologues) by chromatography, the in vitro synthesis of glycosylation or phosphorylation enzyme variants or the in vitro production of enzyme conjugates. Another way to alter the hydrophobicity of a protein via glycosylation is to generate new glycosylation sites on the surface of the enzyme. These variants will be glycosylated in vivo during expression.

The use of ASP and NprE charge ladder probe proteins revealed that the benefit or favorable outcome from varying a physical property is well described by the same standard normal distribution. In some embodiments, a set of probe proteins is used to determine the mean and width of this distribution for a given application. Next, this distribution is used as a reference to determine the direction and magnitude of improvement needed to obtain additional enzyme variants from the same or different fold, that have the desired benefit when tested under the same conditions.

For instance, the optimum expression levels of both ASP and NprE charge ladder variants in *Bacillus subtilis* under the same growth conditions follows the same standard distribution and occurs at zeta potentials of −8.84 mV for each enzyme. For instance, the optimum cleaning performance of ASP charge ladder variants of a blood, milk, ink stains in a buffer matching North American detergent pH and conductivity follows a standard normal distribution with optimum cleaning at zeta potentials of −9.68 mV, essentially equal to that of the substrate stain −8.97 mV. Further, ASP and NprE proteases meeting this charge requirement are provided using protein engineering, chemical modification through covalent or non-covalent linkages, natural isolate selection and post-translational modifications (e.g., glycosylation).

EXPERIMENTAL

The following Examples are provided in order to demonstrate and further illustrate certain preferred embodiments and aspects of the present invention and are not to be construed as limiting the scope thereof.

In the experimental disclosure which follows, the following abbreviations apply: ° C. (degrees Centigrade); rpm (revolutions per minute); $H_2O$ (water); HCl (hydrochloric acid); aa and AA (amino acid); bp (base pair); kb (kilobase pair); kD (kilodaltons); gm (grams); μg and ug (micrograms); mg (milligrams); ng (nanograms); μl and ul (microliters); ml (milliliters); mm (millimeters); nm (nanometers); μm and um (micrometer); M (molar); mM (millimolar); μM and uM (micromolar); U (units); V (volts); MW (molecular weight); sec (seconds); min(s) (minute/minutes); hr(s) (hour/hours); $MgCl_2$ (magnesium chloride); NaCl (sodium chloride); $OD_{280}$ (optical density of 280 nm); $OD_{405}$ (optical density of 405 nm); $OD_{600}$ (optical density at 600 nm); PAGE (polyacrylamide gel electrophoresis); EtOH (ethanol); PBS (phosphate buffered saline [150 mM NaCl, 10 mM sodium phosphate buffer, pH 7.2]); LAS (lauryl sodium sulfonate); SDS (sodium dodecyl sulfate); Tris (tris(hydroxymethyl)aminomethane); TAED (N,N,N'N'-tetraacetylethylenediamine); BES (polyesstersulfone); MES (2-morpholinoethanesulfonic acid, monohydrate; f.w. 195.24; Sigma #M-3671); $CaCl_2$ (calcium chloride, anhydrous; f.w. 110.99; Sigma #C-4901); DMF (N,N-dimethylformamide, f.w. 73.09, d=0.95); Abz-AGLA-Nba (2-Aminobenzoyl-L-alanylglycyl-L-leucyl-L-alamino-4-nitrobenzylamide, f.w. 583.65; Bachem #H-6675, VWR catalog #100040-598); SBG1% ("Super Broth with Glucose"; 6 g Soytone [Difco], 3 g yeast extract, 6 g NaCl, 6 g glucose); the pH was adjusted to 7.1 with NaOH prior to sterilization using methods known in the art; w/v (weight to volume); v/v (volume to volume); Npr and npr (neutral metalloprotease); SEQUEST® (SEQUEST database search program, University of Washington); Npr and npr (neutral metalloprotease gene); nprE and NprE (*B. amyloliquefaciens* neutral metalloprotease); PMN (purified MULTIFECT® metalloprotease); MS (mass spectroscopy); SRI (Stain Removal Index) and BMI (blood milk ink).

In addition materials were obtained from some of the following institutions: TIGR (The Institute for Genomic Research, Rockville, Md.); AATCC (American Association of Textile and Coloring Chemists); Amersham (Amersham Life Science, Inc. Arlington Heights, Ill.); Corning (Corning International, Corning, N.Y.); ICN (ICN Pharmaceuticals, Inc., Costa Mesa, Calif.); Pierce (Pierce Biotechnology, Rockford, Ill.); Equest (Equest, Warwick International Group, Inc., Flintshire, UK); EMPA (Eidgenossische Material Prufungs and Versuch Anstalt, St. Gallen, Switzerland); CFT (Center for Test Materials, Vlaardingen, The Netherlands); Amicon (Amicon, Inc., Beverly, Mass.); ATCC (American Type Culture Collection, Manassas, Va.); Becton Dickinson (Becton Dickinson Labware, Lincoln Park, N.J.); Perkin-Elmer (Perkin-Elmer, Wellesley, Mass.); Rainin (Rainin Instrument, LLC, Woburn, Mass.); Eppendorf (Eppendorf AG, Hamburg, Germany); Waters (Waters, Inc., Milford, Mass.); Geneart (Geneart GmbH, Regensburg, Germany); Perseptive Biosystems (Perseptive Biosystems, Ramsey, Minn.); Molecular Probes (Molecular Probes, Eugene, Oreg.); BioRad (BioRad, Richmond, Calif.); Clontech (CLONTECH Laboratories, Palo Alto, Calif.); Cargill (Cargill, Inc., Minneapolis, Minn.); Difco (Difco Laboratories, Detroit, Mich.); GIBCO BRL or Gibco BRL (Life Technologies, Inc., Gaithersburg, Md.); New Brunswick (New Brunswick Scientific Company, Inc., Edison, N.J.); Thermoelectron (Thermoelectron Corp., Waltham, Mass.); BMG (BMG Labtech, GmbH, Offenburg, Germany); Greiner (Greiner Bio-One, Kremsmuenster, Austria); Novagen (Novagen, Inc., Madison, Wis.); Novex (Novex, San Diego, Calif.); Finnzymes (Finnzymes OY, Finland) Qiagen (Qiagen, Inc., Valencia, Calif.); Invitrogen (Invitrogen Corp., Carlsbad, Calif.); Sigma (Sigma Chemical Co., St. Louis, Mo.); DuPont Instruments (Asheville, N.Y.); Global Medical Instrumentation or GMI (Global Medical Instrumentation; Ramsey, Minn.); MJ Research (MJ Research, Waltham, Mass.); Infors (Infors AG, Bottmingen, Switzerland); Stratagene (Stratagene Cloning Systems, La Jolla, Calif.); Roche (Hoffmann La Roche, Inc., Nutley, N.J.); Agilent (Agilent Technologies, Palo Alto, Calif.); Merck (Merck & Co., Rahway, N.J.); Ion Beam Analysis Laboratory (Ion Bean Analysis Laboratory, The University of Surrey Ion Beam Centre (Guildford, UK); TOM (Terg-o-Meter); BMI (blood, milk, ink); BaChem (BaChem AG, Bubendorf, Switzerland); Molecular Devices (Molecular Devices, Inc., Sunnyvale, Calif.); Corning (Corning International, Corning, N.Y.); MicroCal (Microcal, Inc., Northhampton, Mass.); Chemical Computing (Chemical Computing Corp., Montreal, Canada); NCBI (National Center for Biotechnology Information); Beckman (Beckman-Coulter, Fullerton, Calif.); SeitzSchenk (SeitzSchenk Filtersystems GmbH, Bad Kreuznach, Germany); Pall (Pall Corp., East Hills, N.Y.); and Malvern Instruments (Malvern Instruments, Inc., Worcestershire, UK).

Example 1

Assays

The following assays were used in the Examples described below. Any deviations from the protocols provided below are indicated in the Examples. In these experiments, a spectrophotometer was used to measure the absorbance of the products formed after the completion of the reactions.

A. Protein Content Determination

BCA (Bicinchoninic Acid) Assay

In these assays, BCA (Pierce) assay was used to determine the protein concentration in protease samples on microtiter plate (MTP) scale. In this assay system, the chemical and reagent solutions used were: BCA protein assay reagent, and Pierce dilution buffer (50 mM MES, pH 6.5, 2 mM $CaCl_2$, 0.005% TWEEN®-80). The equipment used was a SpectraMAX (type 340; Molecular Devices) MTP reader. The MTPs were obtained from Costar (type 9017).

In the test, 200 μl BCA Reagent was pipetted into each well, followed by 20 μl diluted protein. After thorough mixing, the MTPs were incubated for 30 minutes at 37° C. Air bubbles were removed, and the optical density (OD) of the solution within the wells was read at 562 nm. To determine the protein concentration, the background reading was subtracted form the sample readings. The $OD_{562}$ was plotted for protein standards (purified protease), to produce a standard curve. The protein concentration of the samples was interpolated from the standard curve.

Bradford Assay

In these assays, the Bradford dye reagent (Quick Start) assay was used to determine the protein concentration in protease samples on MTP scale. In this assay system, the chemical and reagent solutions used were: Quick Start Bradford Dye Reagent (BIO-RAD Catalog No. 500-0205), Dilution buffer (10 mM NaCl, 0.1 mM CaCl2, 0.005% TWEEN®-80). The equipment used was a Biomek FX Robot (Beckman) and a SpectraMAX (type 340) MTP reader. The MTPs were from Costar (type 9017).

In the test, 200 μl Bradford dye reagent was pipetted into each well, followed by 15 μl dilution buffer. Finally 10 μl of filtered culture broth were added to the wells. After thorough mixing, the MTPs were incubated for at least 10 minutes at room temperature. Air bubbles were blown away and the ODs of the wells were read at 595 nm. To determine the protein concentration, the background reading (i.e., from un-inoculated wells) was subtracted form the sample readings. The obtained $OD_{595}$ values provide a relative measure of the protein content in the samples.

B. Enzyme Performance Assays

The detergents used in this assay did not contain enzymes or the enzymes present in commercial detergents had been destroyed through heat deactivation as described elsewhere in this document. The equipment used included an Eppendorf Thermomixer and a SpectraMAX (type 340) MTP reader. The MTPs were obtained from Costar (type 9017).

Detergent Preparation (AATCC HDL; US Conditions)

Milli-Q water was adjusted to 6 gpg water hardness (Ca/Mg=3/1), and 1.5 g/l AATCC 2003 standard reference liquid detergent without brightener was added. The detergent solution was vigorously stirred for at least 15 minutes. Then, 5 mM HEPES (free acid) was added and the pH adjusted to 8.0.

BMI Microswatch Assay

Microswatches containing blood milk and ink (BMI) of 0.25 inch circular diameter were obtained from CFT Vlaardingen. Before cutting of the swatches, the fabric (EMPA 116) was washed with water. One microswatch was vertically placed in each well of a 96-well microtiter plate in order to expose the whole surface area (i.e., not flat on the bottom of the well). The desired detergent solution was prepared as described herein. After equilibrating the Thermomixer at 25° C., 190 μl of detergent solution was added to each well of the MTP, containing microswatches. To this mixture, 10 μl of the diluted enzyme solution was added so that the final enzyme concentration was 1 μg/ml (determined from BCA assay). The MTP was sealed with tape and placed in the incubator for 30 minutes, with agitation at 1400 rpm. Following incubation under the appropriate conditions, 100 μl of the solution from each well was transferred into a fresh MTP. The new MTP containing 100 μl of solution/well was read at 405 nm using a MTP SpectraMax reader. Blank controls, as well as a control containing two microswatches and detergent but no enzyme were also included.

Baked Egg Microcleaning Assay 96-well baked egg yolk substrate plates were prepared from chicken egg yolks. Chicken egg yolks were separated from the whites, released from the membrane sac, and diluted 20% (vol/weight) with Milli-Q water. The diluted yolk was stirred for 15 min at room temperature using a magnetic stirrer. Five μL was carefully pipetted into the center of each well of a 96-well V-bottom plate (Costar #3894) using an 8-channel pipette. The plates were baked at 90° C. for 1 hour and cooled at room temperature. The baked egg yolk substrate plates were stored at room temperature and used within one week of preparation. Automatic dish detergents were prepared as described elsewhere in this document and pre-heated to 50° C. A 190 pt aliquot of detergent was added to each well of the 96-well plate using an 8-channel pipette. Ten μL of diluted enzyme was added to each well using a 96-channel pipetting device. The plate was carefully sealed with an adhesive foil sealer and incubated at 50° C. with shaking for 30 min. 120 μL of the reaction mixture was transferred to a new 96-well flat-bottom plate, and the absorbance/light scattering was determined at 405 nm. The absorbance/light scattering at 405 nm is proportional to egg yolk removal.

Egg Yolk Microswatch Assay

Automatic dish detergents were prepared as described elsewhere in this document. The equipment used included a New Brunswick Innova 4230 shaker/incubator and a SpectraMAX (type 340) MTP reader. The MTPs were obtained from Costar (type 9017). Aged egg yolk with pigment swatches (CS-38) were obtained from Center for Test Materials (Vlaardingen, Netherlands). Before cutting 0.25-inch circular microswatches, the fabric was washed with water. One microswatch was placed in each well of a 96-well microtiter plate. The test detergent was equilibrated at 50° C. 190 μl of detergent solution was added to each well of the MTP, containing microswatches. To this mixture, 10 μl of the diluted enzyme solution was added. The MTP was sealed with adhesive foil and placed in the incubator for 30 minutes, with agitation. Following incubation, 100 μl of the solution from each well was transferred into a fresh MTP. This MTP was read at 405 nm using a SpectraMax MTP reader. Blank controls, as well as controls containing microswatches and detergent but no enzyme were also included.

Rice Starch Microswatch Assay

The rice starch assay is a test of amylase performance. Detergents were prepared as described elsewhere in this document. The equipment used included a New Brunswick Innova 4230 shaker/incubator and a SpectraMAX (type 340) MTP reader. The MTPs were obtained from Corning (type 3641). Aged rice starch with orange pigment swatches (CS-28) were obtained from Center for Test Materials (Vlaardingen, Netherlands). Before cutting 0.25-inch circular microswatches, the fabric was washed with water. Two microswatches were placed in each well of a 96-well microtiter plate. The test detergent was equilibrated at 20° C. (North America) or 40° C. (Western Europe). 190 μl of detergent solution was added to each well of the MTP, containing microswatches. To this mixture, 10 μl of the diluted enzyme solution was added. The MTP was sealed with adhesive foil and placed in the incubator for 1 hour with agitation at 750 rpm at the desired test temperature (typically 20° C. or 40° C.). Following incubation, 150 μl of the solution from each well was transferred into a fresh MTP. This MTP was read at 488 nm using a SpectraMax MTP reader to quantify cleaning. Blank controls, as well as controls containing microswatches and detergent but no enzyme were also included.

Calculation of Enzyme Performance

The obtained absorbance value was corrected for the blank value (i.e., obtained after incubation of microswatches in the absence of enzyme). The resulting absorbance was a measure for the hydrolytic activity.

C. suc-AAPF-pNA Hydrolysis Assay for Testing Protease Activity

In this assay system, the reagent solutions used were: 100 mM Tris/HCl, pH 8.6, 0.005% TWEEN®-80 (Tris); 100 mM Tris/HCl, pH 8.6, 10 mM $CaCl_2$ and 0.005% TWEEN®-80 (Tris/Ca); and 160 mM suc-AAPF-pNA in DMSO (suc-AAPF-pNA stock solution) (Sigma: S-7388). To prepare suc-AAPF-pNA working solution, 1 ml AAPF stock was added to 100 ml Tris/Ca buffer and mixed well for at least 10 seconds. The assay was performed by adding 10 μl of diluted protease solution to each well, followed by the addition (quickly) of 190 μl 1 mg/ml AAPF-working solution. The solutions were mixed for 5 sec., and the rate of absorbance change was determined at 410 nm in an MTP reader, at 25° C.

D. Dimethylcasein Hydrolysis Assay for Testing Protease Activity

In this assay system, the chemicals and solutions used were:

Dimethylcasein (DMC): Sigma C-9801; TWEEN®-80: Sigma P-8074; PIPES buffer (free acid): Sigma P-1851-15.1 g is dissolved in about 960 ml water, pH adjusted to 7.0 with 4N NaOH, 1 ml 5% TWEEN®-80 is added and the volume brought up to 1000 ml. The final concentration of PIPES and TWEEN®-80 is 50 mM and 0.005% respectively;

Picrylsulfonic acid (TNBS): Sigma P-2297 (5% solution in water);

Reagent A: 45.4 g $Na_2B_4O_7$.10H2O (Merck 6308) and 15 ml of 4N NaOH are dissolved together to a final volume of 1000 ml (by heating if needed); and Reagent B: 35.2 g $NaH_2PO_4.1H_2O$ (Merck 6346) and 0.6 g $Na_2SO_3$ (Merck 6657) are dissolved together to a final volume of 1000 ml.

To prepare the substrate, 4 g DMC were dissolved in 400 ml PIPES buffer. The filtered culture supernatants were diluted with PIPES buffer; the final concentration of the controls in the growth plate was 20 ppm. Then, 10 μl of each diluted supernatant were added to 200 μl substrate in the wells of a MTP. The MTP plate was covered with tape, shaken for a few seconds and placed in an oven at 37° C. for 2 hours without agitation. About 15 minutes before removal of the 1st plate from the oven, the TNBS reagent was prepared by mixing 1 ml TNBS solution per 50 ml of reagent A. MTPs were filled with 60 μl TNBS reagent A per well. The incubated plates were shaken for a few seconds, after which 10 μl were transferred to the MTPs with TNBS reagent A. The plates were covered with tape and shaken for 20 minutes in a bench shaker (BMG Thermostar) at room temperature and 500 rpm. Finally, 200 μl reagent B were added to the wells, mixed for 1 minute on a shaker, and the absorbance at 405 nm was determined using an MTP-reader.

The obtained absorbance value was corrected for the blank value (substrate without enzyme). The resulting absorbance is a measure for the hydrolytic activity. The (arbitrary) specific activity of a sample was calculated by dividing the absorbance and the determined protein concentration.

E. Amylase Concentration Determination by Antibody Titration

As described herein, alpha-amylase concentration and specific activity was determined by titration with an inhibitory polyclonal antibody. Polyclonal antibodies raised to *Bacillus stearothermophilus* alpha-amylase (AmyS) were found to be strongly inhibitory of AmyS and the alpha-amylase from *Bacillus* sp. TS23 (e.g., the binding is tight enough to produce a linear titration of activity loss). Therefore, this antibody can be used to measure enzyme concentration, which in turn is used to calculate specific activity. Briefly, the amount of enzyme inhibition produced by several known concentrations of antibody is measured. From this information, the concentration of antibody required for complete inhibition is extrapolated, which is equivalent to the enzyme concentration in the sample. Alpha-amylase activity and inhibition was measured using the fluorogenic BODIPY-starch assay. The buffer was 50 mM MOPS, pH 7.0, containing 0.005% Tween-80.

A polyclonal antibody directed against purified AmyS was raised in a rabbit and purified by standard methods. An empirical "apparent concentration" value of an antibody stock solution was determined by measuring the inhibition of a sample of AmyS of known specific activity. Then the antibody sample was used to determine the concentration and specific activity of AmyS and TS23t variants. These values were used to create normalized 96-well enzyme stock plates, where all of the variants were diluted to a common concentration.

F. Protease Concentration Determination by Eglin C Inhibition

As described herein, subtilisin and ASP protease concentration and specific activity was determined by titration with eglin c. Eglin c from the leech *Hirudo medicinalis* is a tight-binding protein inhibitor of subtilisin and ASP protease (Heinz et al., Biochemistry, 31(37): 8755-66 [1992]). Eglin C can therefore be used to measure enzyme concentration, which in turn permits specific activity to be calculated. Briefly, one measures the amount of enzyme inhibition produced by several known concentrations of eglin c. From this information, the concentration of eglin c required for complete inhibition is calculated. This is equivalent to the enzyme concentration in the sample.

Protease activity was measured using the chromogenic suc-AAPF-pNA assay described above. The gene for eglin c was synthesized and expressed in *E. coli* by standard methods. Its properties and inhibitory potency were the same as eglin c purchased from Sigma. The concentration of an eglin c stock solution was determined by measuring the inhibition of a sample of *Bacillus lentus* subtilisin of known specific activity. Then the calibrated eglin c sample was used to determine the concentration and specific activity of subtilisin and ASP protease variants. These values were used to create normalized 96-well enzyme stock plates, where all of the variants were diluted to a common concentration.

G. Native Protein Gel Electrophoresis

Electrophoretic mobility of variant protein samples was measured using the PhastGel system (GE Healthcare) on pre-cast native polyacrylamide gels (PhastGel Homogeneous) at either 7.5% or 12.5% concentration. Buffer strips (PhastGel Native) were used and consisted of pH 8.8 in 0.88 M L-Alanine, 0.25 M Tris buffer. Typical run conditions consisted of 400 V for 12.75 minutes with an anode-to-cathode distance of 3.7 cm.

Alternatively, electrophoretic mobility of variant protein samples was measured on 1 mm thick 0.5-1.5% agarose gels at various pH values (i.e. 5.8, 8.0 and 10.0) through a choice of a suitable buffer system. The electrophoresis is carried out under non-denaturing conditions. The Cathode-Anode length was 13.9 cm. A sample of 1-2 μg protein was mixed with 5% glycerol +0.05% bromophenol blue and loaded on each lane. Gels were run typically for 1 hour at 100V.

In either case gels were stained with Louiseville blue dye dissolved in 10% acetic acid and destained with 10% methanol and 10% acidic acid in water. It is possible to load between 12 and 20 protein variants simultaneously depending on native gel system used. As a consequence the electrophoretic mobility of a protein variant can be immediately assessed relative to charge ladder standards loaded on the same gel.

H. Detergent Heat Inactivation

Heat inactivation of commercial detergent formulas serves to destroy the enzymatic activity of any protein components while retaining the properties of non-enzymatic components. Thus this method was suitable for preparing commercially purchased detergents for use in testing the enzyme variants of the present invention. For North American (NA) and Western European (WE) heavy duty liquid laundry (HDL) detergents, heat inactivation was performed by placing pre-weighed liquid detergent (in a glass bottle) in a water bath at 95° C. for 2 hours. The incubation time for heat inactivation of North American (NA) and Japanese (JPN) heavy duty granular laundry (HDG) detergent was 8 hours and that for Western European (WE) HDG detergent was 5 hours. The incubation time for heat inactivation of NA and WE auto dish washing (ADW) detergents was 8 hours. The detergents were purchased from local supermarket stores. Both un-heated and heated detergents were assayed within 5 minutes of dissolving the detergent to accurately determine percentage deactivated. Enzyme activity was tested by the suc-AAPF-pNA assay.

For testing of enzyme activity in heat-inactivated detergents, working solutions of detergents were made from the heat inactivated stocks. Appropriate amounts of water hardness (6 gpg or 12 gpg) and buffer were added to the detergent solutions to match the desired conditions (Table 1-1). The solutions were mixed by vortexing or inverting the bottles.

TABLE 1-1

| Laundry and Dish Washing Conditions | | | | | | | |
|---|---|---|---|---|---|---|---|
| Region | Form | Dose | Detergent* | Buffer | Gpg | pH | T (° C.) |
| Laundry (heavy duty liquid and granular) | | | | | | | |
| NA | HDL | 0.78 g/l | P&G TIDE ® 2X | 5 mM HEPES | 6 | 8.0 | 20 |
| WE | HDL | 5.0 g/L | Henkel Persil | 5 mM HEPES | 12 | 8.2 | 40 |
| WE | HDG | 8.0 g/L | P&G Ariel | 2 mM $Na_2CO_3$ | 12 | 10.5 | 40 |
| JPN | HDG | 0.7 g/L | P&G TIDE ® | 2 mM $Na_2CO_3$ | 6 | 10.0 | 20 |
| NA | HDG | 1.0 g/L | P&G TIDE ® | 2 mM $Na_2CO_3$ | 6 | 10.0 | 20 |
| Automatic Dish Washing | | | | | | | |
| WE | ADW | 3.0 g/L | RB Calgonit | 2 mM $Na_2CO_3$ | 21 | 10.0 | 40 |
| NA | ADW | 3.0 g/L | P&G Cascade | 2 mM $Na_2CO_3$ | 9 | 10.0 | 40 |

*Abbreviations: Procter & Gamble (P&G); and Reckitt Benckiser (RB).

I. Bodipy-Starch Assay for Determination of Amylase Activity

The Bodipy-starch assay was performed using the EnzChek® Ultra Amylase Assay Kit (E33651, Invitrogen). A 1 mg/mL stock solution of the DQ starch substrate was prepared by dissolving the contents of the vial containing the lyophilized substrate in 100 μL of 50 mM sodium acetate buffer at pH 4.0. The vial was vortexed for about 20 seconds and left at room temperature, in the dark, with occasional mixing until dissolved. 900 μL of assay buffer (50 mM sodium acetate with 2.6 mM $CaCl_2$ pH 5.8) was added and the vial vortexed for about 20 seconds. The substrate solution was stored at room temperature, in the dark, until ready to use or at 4° C. For the assay, a 100 μg/mL of working solution of the DQ substrate was prepared from the 1 mg/mL substrate solution in the assay buffer. 190 μL of 100 μg/mL substrate solution was added to each well in a 96-well flat-bottom microtiter plate. 10 μL of the enzyme samples were added to the wells, mix for 30 seconds using a thermomixer at 800 rpms. A blank sample that contains buffer and substrate only (no-enzyme blank) was included in the assay. The rate of change of fluorescence intensity was measured (excitation: 485 nm, emission: 520 nm) in a fluorescence microtiter plate reader at 25° C. for 5 minutes.

J. Corn Flour Hydrolysis for Determination of Amylase Activity

Starch Hydrolysis of Corn Flour Substrate Assay for Enymatic Activity. Organic corn flour (Azure Farms, lot no. 03227) was evenly spread into Greiner 96-well microplate, polypropylene, black, flat bottom chimney wells, (Cat. No. 655209), using a solids dispensing device (V&P Scientific). 85 μL of 20 mM sodium acetate pH 5.6 were added to each well and mixed. A foil seal was applied to the top of the plate and the plate pre-incubated at 70° C. in the Thermomixer for 20-30 minutes. Enzyme samples were diluted in Agilent polypropylene plate (5042-1385) in 20 mM sodium acetate buffer. 11 μL of diluted enzyme samples were added to the substrate plate and the plate sealed firmly with another foil. Plates were then transferred to Labnet VorTemp 56 Incubator/Shaker with metal blocks, (Cat. No. S2056A) pre-heated to 95° C. and the shake speed set to 500 rpm. The incubation was continued for 30 minutes. At the end of the incubation, the plates were rapidly cooled in an ice bucket and the starch hydrolysis reaction was stopped by addition of 100 μL of 0.1N H2SO4 to each well. The plate was mixed briefly and the starch hydrolysis reaction products were either analyzed by the PAHBAH assay or HPLC.

Colorimetric detection of Soluble Sugar Concentrations from Enzymatic Hydrolysis of Corn Flour Substrate. Aliquots of 80 μL of 0.5 N NaOH were added to all wells of an empty PCR plate followed by 20 μL of PAHBAH reagent (5% w/v p-hydroxybenzoic acid hydrazide (PAHBAH, Sigma #H9882, dissolved in 0.5 N HCl) and mixed (PAHBAH reaction plate). 10 μL of the starch hydrolysis reaction supernatants were added to the PAHBAH reaction plate. All plates were sealed and placed in the thermocycler (MJ Research Tetrad), programmed for 2 minutes at 95° C., and then cooled to 20° C. Samples of 80 μL of the developed PAHBAH reaction mixtures were transferred to a read plate and absorbance was measured at 405 nm in a spectrophotometer.

HPLC Determination of Soluble Sugar Concentrations from Enzymatic Hydrolysis of Corn Flour Substrate. Soluble sugar standards (DP1-DP7) obtained from Sigma (St. Louis, Mo.) were all diluted in Milli-Q water to 100 mg/mL and used for converting peak area for the sugars to actual sugar concentrations. The quenched plate from the starch hydrolysis assay was spun in a Beckman Coulter Allegra 6R Centrifuge for 5 minutes at 3000 rpm 25° C. The supernatant was pipetted from the spun plate and transferred to a Multiscreen-HV filter plate (Catalog No. MAHVN4550). The filter plate was spun over an Agilent HPLC plate in the Hettich Rotanta centrifuge for 10 minutes at 6000 rpm 25° C. 50 μl of 0.01N sulfuric acid mobile phase (0.1N sulfuric acid diluted 10× with Milli-Q water) was transferred to each well of another clean Agilent HPLC plate. The filtered plate was briefly mixed and 50 μL of the filtrate was transferred the corresponding wells in the plate with 50 μL per well of mobile phase. Diluted sugar standards were added to empty wells in the plate to be included in the calibration. The contents were mixed briefly on a platform shaker and the plate covered with a Nalgene Pre-slit Well Cap. The HPLC column (Bio-Rad Aminex HPX-87H column Cat No. 125-0140) was prepared ahead of time with 2 L of mobile phase running at a constant flow rate of 0.6 mL/minute. All samples in the plate were run with 20 μL injection volume and analyzed using AMINEXH.M and RID (refractive index) as the detector. After the run was completed, the flow rate in the HPLC was dropped down to 0.05 mL/min.

K. Determination of Starch Viscosity Reduction by Amylase

In this assay, viscosity reduction of corn starch substrate solution was measured in a viscometer. The corn starch substrate slurry was made up fresh in batch mode with 30% corn flour dry solids in distilled water and adjusted to pH 5.8 using sulfuric acid. For each run, 50 grams of the slurry (15 grams dry solids) was weighed out and pre-incubated for 10 minutes to warm up to 70° C. Upon amylase addition, the temperature was immediately ramped up from 70° C. to 85° C. with a rotation speed of 75 rpm. Once the temperature of the slurry and amylase mixture reached 85° C., the temperature was held constant and viscosity was monitored for an additional 30 minutes.

L. Measurement of Enzyme Binding to Macromolecular Substrates

Binding assays were done to determine substrate binding of: Protease (ASP) charge ladder variants (charge change=−5 to +3 relative to wild-type ASP) to lignin and cellulose, and Amylase (AmyS) charge ladder variants (charge change=−12 to +12 relative to wild-type AmyS) to corn stover and bagasse. Substrates used included: lignin (recovered from complete saccharification of bagasse), 87.5% liquid, bagasse (sugarcane bagasse from Brazil, dilute-acid pre-treated by National Renewable Energy Laboratory, washed and buffered at pH 5), PASC (phosphoric acid swollen cellulose; pure, amorphous cellulose, diluted in 50 mM Sodium Acetate, pH 5), AFEX (ammonia fiber expansion corn stover), and PCS (dilute sulfuric acid pre-treated corn stover, washed and adjusted to pH 5). All substrates were brought to the desired percentage solids prior to use.

Protease Binding

ASP Protease charge ladder variants (charge change=−5 to +3 relative to wild-type ASP) were purified and diluted to 0.5 mg/ml-1.5 mg/ml. Approximately, 2.4% lignin, 0.5% PASC, and 1% bagasse solutions were prepared in borate buffer (40 mM, pH8.5, 0.016% Tween20). 200 μl of each was added into 96-ell filter plates. Control wells received buffer solution. 10 μl of 0.276 g/ml Tween-20 was added into each well, so that the final concentration of Tween-20 was 1.38%. Control wells received 10 μl of water. For lignin and bagasse binding assay, the ASP charge ladder variants were diluted to 200 ppm and 10 μl of diluted enzyme was added into each well. For PASC binding assay, the ASP ladder was diluted to 40 ppm and 10 μl diluted enzyme was added into each well. After the addition of enzymes, each well was mixed using pipet tips. The plates were sealed and incubated at room temperature with shaking. After 1 hour of incubation, the filtrate was collected in 96-well plates. Enzyme activity in filtrate was measured by suc-AAPF-pNA assay after diluting the filtrate 1:20. Percent protein bound was calculated as ratio of activity in filtrate in samples incubated with substrate to that in control wells.

Amylase Binding

Amylase charge ladder variants were purified and diluted to 200 ppm for testing. A 1% cellulose bagasse solution was prepared in borate buffer (40 mM, pH8.5, 0.016% Tween80). 150 μl of the bagasse solution was added into each well in a microtiter filtration plate. 150 μl of borate buffer was added into a set of separate wells, which served as controls. 10 μl of amylase charge ladder variants was added into the filtration plate, each condition was in duplicates. The plate was incubated at room temperature for 2 hours. The filtrate was collected and amylase activity in the supernatant was measured by BODIPY-starch assay.

Protease Binding to Microswatches

Protease variants were incubated with or without BMI microswatches under standard wash conditions for 30 min. The amount of free enzyme was measured by the suc-AAPF-pNA assay. The fraction of enzyme bound to the microswatches was calculated as follows: Fraction bound=(Activity of enzyme in absence of swatch−Activity of enzyme in presence of swatch)/(Activity of enzyme in absence of swatch)

Alpha-Amylase Binding to Microswatches

Amylase variants were incubated with or without CS-28 rice starch microswatches under standard wash conditions for 30 min. The amount of free enzyme was measured by the BODIPY-starch assay. The fraction of enzyme bound to the microswatches was calculated as follows: Fraction bound=

(Activity of enzyme in absence of swatch −Activity of enzyme in presence of swatch)/(Activity of enzyme in absence of swatch)

Example 2

Protease Production in *B. subtilis*

In this Example, experiments conducted to produce various proteases in *B. subtilis* are described. In particular, the methods used in the transformation of *B. subtilis* with expression vectors for NprE, ASP, GG36, and FNA re provided. Transformation was performed as known in the art (See e.g., WO 02/14490).

NprE Protease Production

The methods used in the transformation of plasmid pUB-nprE into *B. subtilis* are provided. The DNA sequence (nprE leader, nprE pro and nprE mature DNA sequence from *B. amyloliquefaciens*) provided below, encodes the NprE precursor protein:

(SEQ ID NO: 1)

gtgggtttaggtaagaaattgtctgttgctgtcgccgcttcctttatgag
tttaaccatcagtctgccgggtgttcaggccgctgagaatcctcagctta
aagaaaacctgacgaattttgtaccgaagcattctttggtgcaatcagaa
ttgccttctgtcagtgacaaagctatcaagcaatacttgaaacaaaacgg
caaagtctttaaaggcaatccttctgaaagattgaagctgattgaccaaa
cgaccgatgatctcggctacaagcacttccgttatgtgcctgtcgtaaac
ggtgtgcctgtgaaagactctcaagtcattattcacgtcgataaatccaa
caacgtctatgcgattaacggtgaattaaacaacgatgtttccgccaaaa
cggcaaacagcaaaaaattatctgcaaatcaggcgctggatcatgcttat
aaagcgatcggcaaatcacctgaagccgtttctaacggaaccgttgcaaa
caaaaacaaagccgagctgaaagcagcagccacaaaagacggcaaatacc
gcctcgcctatgatgtaaccatccgctacatcgaaccggaacctgcaaac
tgggaagtaaccgttgatgcggaaacaggaaaaatcctgaaaaagcaaaa
caaagtggagcatgccgccacaaccggaacaggtacgactcttaaggaa
aaacggtctcattaaatatttcttctgaaagcggcaaatatgtgctgcgc
gatctttctaaacctaccggaacacaaattattacgtacgatctgcaaaa
ccgcgagtataacctgccgggcacactcgtatccagcaccacaaaccagt
ttacaacttcttctcagcgcgctgccgttgatgcgcattacaacctcggc
aaagtgtatgattatttctatcagaagtttaatcgcaacagctacgacaa
taaaggcggcaagatcgtatcctccgttcattacggcagcagatacaata
acgcagcctggatcggcgaccaaatgatttacggtgacggcgacggttca
ttcttctcacctctttccggttcaatggacgtaaccgctcatgaaatgac
acatggcgttacacaggaaacagccaacctgaactacgaaaatcagccgg
gcgctttaaacgaatccttctctgatgtattcgggtacttcaacgatact
gaggactgggatatcggtgaagatattacggtcagccagccggctctccg
cagcttatccaatccgacaaaatacggacagcctgataatttcaaaaatt
acaaaaaccttccgaacactgatgccggcgactacggcggcgtgcataca

-continued aacagcggaatcccgaacaaagccgcttacaatacgattacaaaaatcgg cgtgaacaaagcggagcagatttactatcgtgctctgacggtatacctca ctccgtcatcaacttttaaagatgcaaaagccgctttgattcaatctgcg cgggacctttacggctctcaagatgctgcaagcgtagaagctgcctggaa tgcagtcggattgtaa.

In the above sequence, bold indicates the DNA that encodes the mature NprE protease, standard font indicates the leader sequence (nprE leader), and underlined indicates the pro sequences (nprE pro). The amino acid sequence (NprE leader, NprE pro and NprE mature DNA sequence) provided below corresponds to the full length NprE precursor protein. In this NprE sequence, underlined indicates the pro sequence and bold indicates the mature NprE protease:

(SEQ ID NO: 2)

MGLGKKLSVAVAASFMSLTISLPGVQAAENPOLKENLTNFVPKHSLVQSE

LPSVSDKAIKQYLKQNGKVFKGNPSERLKLIDQTTDDLGYKHFRYVPVVN

GVPVKDSQVIIHVDKSNNVYAINGELNNDVSAKTANSKKLSANOALDHAY

KAIGKSPEAVSNGTVANKNKAELKAAATKDGKYRLAYDVTIRYIEPEPAN

WEVTVDAETGKILKKQNKVEHAATTGTGTTLKGKTVSLNISSESGKYVLR

DLSKPTGTQIITYDLQNREYNLPGTLVSSTTNQFTTSSQRAAVDAHYNLG

KVYDYFYQKFNRNSYDNKGGKIVSSVHYGSRYNNAAWIGDQMIYGDGDGS

FFSPLSGSMDVTAHEMTHGVTQETANLNYENQPGALNESFSDVFGYFNDT

EDWDIGEDITVSQPALRSLSNPTKYGQPDNFKNYKNLPNTDAGDYGGVHT

NSGIPNKAAYNTITKIGVNKAEQIYYRALTVYLTPSSTFKDAKAALIQSA

RDLYGSQDAASVEAAWNAVGL.

The mature NprE sequence was used as the basis for making the variant libraries:

(SEQ ID NO: 3)

AATTGTGTTLKGKTVSLNISSESGKYVLRDLSKPTGTQIITYDLQNREYN

LPGTLVSSTTNQFTTSSQRAAVDAHYNLGKVYDYFYQKFNRNSYDNKGGK

IVSSVHYGSRYNNAAWIGDQMIYGDGDGSFFSPLSGSMDVTAHEMTHGVT

QETANLNYENQPGALNESFSDVFGYFNDTEDWDICEDITVSQPALRSLSN

PTKYGQPDNFKNYKNLPNTDAGDYGGVHTNSGIPNKAAYNTITKIGVNKA

EQIYYRALTVYLTPSSTFKDAKAALIQSARDLYGSQDAASVEAAWNAVG

L.

The pUBnprE expression vector was constructed by amplifying the nprE gene from the chromosomal DNA of *B. amyloliquefaciens* by PCR using two specific primers:

Oligo AB1740:

(SEQ ID NO: 4)

CTGCAGGAATTCAGATCTTAACATTTTTCCCCTATCATTTTTCCCG;

and

Oligo AB1741:

(SEQ ID NO: 5)

GGATCCAAGCTTCCCGGGAAAAGACATATATGATCATGGTGAAGCC.

PCR was performed on a thermocycler with Phusion High Fidelity DNA polymerase (Finnzymes). The PCR mixture contained 10 μl 5× buffer (Finnzymes Phusion), 1 μl 10 mM dNTP's, 1.5 μl DMSO, 1 μl of each primer, 1 μl Finnzymes Phusion DNA polymerase, 1 μl chromosomal DNA solution 50 ng/μl, 34.5 μl MilliQ water. The following PCR protocol was used: 1) 30 sec at 98° C.; 2) 10 sec at 98° C.; 3) 20 sec at 55° C.; 4) 1 min at 72° C.; 5) 25 cycles of steps 2 to 4; and 5) 5 min at 72° C.

This resulted in a 1.9 kb DNA fragment, which was digested using BglII and BclI DNA restriction enzymes. The multicopy *Bacillus* vector pUB110 (See e.g., Gryczan, J Bacteriol, 134:318-329 [1978]) was digested with BamHI. The PCR fragment×BglII×BclI was then ligated in the pUB 110×BamHI vector to form pUBnprE expression vector.

pUBnprE was transformed to a *B. subtilis* (ΔaprE, ΔnprE, oppA, ΔspoIIE, degUHy32, ΔamyE::(xylR,pxylA-comK) strain. Transformation into *B. subtilis* was performed as described in WO 02/14490, incorporated herein by reference. Selective growth of *B. subtilis* transformants harboring the pUBnprE vector was performed in shake flasks containing 25 ml MBD medium (a MOPS based defined medium), with 20 mg/L neomycin. MBD medium was made essentially as known in the art (See, Neidhardt et al., J Bacteriol, 119: 736-747 [1974]), except that $NH_4Cl_2$, $FeSO_4$, and $CaCl_2$ were left out of the base medium, 3 mM $K_2HPO_4$ was used, and the base medium was supplemented with 60 mM urea, 75 g/L glucose, and 1% soytone. Also, the micronutrients were made up as a 100× stock containing in one liter, 400 mg $FeSO_4.7H_2O$, 100 mg $MnSO_4.H_2O$, 100 mg $ZnSO_4.7H_2O$, 50 mg $CuCl_2.2H_2O$, 100 mg $CoCl_2.6H_2O$, 100 mg $NaMoO_4.2H_2O$, 100 mg $Na_2B_4O_7.10H_2O$, 10 ml of 1M $CaCl_2$, and 10 ml of 0.5 M sodium citrate. The culture was incubated for three days at 37° C. in an incubator/shaker (Infors). This culture resulted in the production of secreted NprE protease with proteolytic activity as demonstrated by protease assays. Gel analysis was performed using NuPage Novex 10%-Bis-Tris gels (Invitrogen, Catalog No. NP0301BOX). To prepare samples for analysis, 2 volumes of supernatant were mixed with 1 volume 1M HCl, 1 volume 4×LDS sample buffer (Invitrogen, Catalog No. NP0007), and 1% PMSF (20 mg/ml) and subsequently heated for 10 minutes at 70° C. Then, 25 μL of each sample were loaded onto the gel, together with 10 μL of SeeBlue plus 2 pre-stained protein standards (Invitrogen, Catalog No. LC5925). The results clearly demonstrated that the nprE cloning strategy described in this example is suitable for production of active NprE in *B. subtilis*.

ASP Protease Production

The methods used for transformation of plasmid pHPLT-ASP-C1-2 into *B. subtilis* are provided. To optimize ASP expression in *B. subtilis*, a synthetic DNA sequence was produced by DNA2.0 for utilization in these expression experiments. The DNA sequence (synthetic ASP DNA sequence) provided below, with codon usage adapted for *Bacillus* species, encodes the wild type ASP precursor protein:

(SEQ ID NO: 6)

atgacaccacgaactgtcacaagagctctggctgtggcaacagcagctgc tacactcttggctgggggtatggcagcacaagctaacgaaccggctcctc caggatctgcatcagcccctccacgattagctgaaaaacttgaccctgac ttacttgaagcaatggaacgcgatctggggttagatgcagaggaagcagc tgcaacgttagcttttcagcatgacgcagctgaaacgggagaggctcttg -continued ctgaggaactcgacgaagatttcgcgggcacgtgggttgaagatgatgtg ctgtatgttgcaaccactgatgaagatgctgttgaagaagtcgaaggcga aggagcaactgctgtgactgttgagcattctcttgctgatttagaggcgt ggaagacggttttggatgctgcgctggagggtcatgatgatgtgcctacg tggtacgtcgacgtgcctacgaattcggtagtcgttgctgtaaaggcagg agcgcaggatgtagctgcaggacttgtggaaggcgctgatgtgccatcag atgcggtcacttttgtagaaacggacgaaacgcctagaacgatgttcgac gtaattggaggcaacgcatatactattggcggccggtctagatgttctat cggattcgcagtaaacggtggcttcattactgccggtcactgcggaagaa caggagccactactgccaatccgactggcacatttgcaggtagctcgttt ccgggaaatgattatgcattcgtccgaacaggggcaggagtaaatttgct tgcccaagtcaataactactcgggcggcagagtccaagtagcaggacata cggccgcaccagttggatctgctgtatgccgctcaggtagcactacaggt tggcattgcggaactatcacggcgctgaattcgtctgtcacgtatccaga gggaacagtccgaggacttatccgcacgacggtttgtgccgaaccaggtg atagcggaggtagccttttagcgggaaatcaagcccaaggtgtcacgtca ggtggttctggaaattgtcggacgggggggaacaacattctttcaaccagt caacccgattttgcaggcttacggcctgagaatgattacgactgactctg gaagttcccctgctccagcacctacatcatgtacaggctacgcaagaacg ttcacaggaaccctcgcagcaggaagagcagcagctcaaccgaacggtag ctatgttcaggtcaaccggagcggtacacattccgtctgtctcaatggac ctagcggtgcggactttgatttgtatgtgcagcgatggaatggcagtagc tgggtaacgtcgctcaatcgacatcgccgggaagcaatgaaaccattacg taccgcggaaatgctggatattatcgctacgtggttaacgctgcgtcagg atcaggagcttacacaatgggactcaccctcccctga.

In the above sequence, bold indicates the DNA that encodes the mature ASP protease, standard font indicates the leader sequence (ASP leader), and the underline indicates the N-terminal and C-terminal prosequences. The amino acid sequence provided below corresponds to the full length ASP precursor protein, with underlines indicating the pro sequences and bold indicating the mature ASP protease.

(SEQ ID NO: 7)

MTPRTVTRALAVATAAATLLAGGMAAQANEPAPPGSASAPPRLAEKLDPD

LLEAMERDLGLDAEEAAATLAFQHDAAETGEALAEELDEDFAGTWVEDDV

LYVATTDEDAVEEVEGEGATAVTVEHSLADLEAWKTVLDAALEGHDDVPT

WYVDVPTNSVVVAVKAGAQDVAAGLVEGADVPSDAVTFVETDETPRTMFD

VIGGNAVTIGGRSRCSIGFAVNGGFITAGHCGRTGATTANPTGTFAGSSF

PGNDYAFVRTGAGVNLLAQVNNYSGGRVQVAGHTAAPVGSAVCRSGSTTG

WHCGTITALNSSVTYPEGTVRGLIRTTVCAEPGDSGGSLLAGNQAQGVTS

GGSGNCRTGGTTFFQPVNPILQAYGLRMITTDSGSSPAPAPTSCTGYART

FTGTLAAGRAAAQPNGSYVQVNRSGTHSVCLNGPSGADFDLYVQRWNGSS

WVTVAQSTSPGSNETITYRGNAGYYRYVVNAASGSGAYTMGLTLP.

The mature ASP sequence was used as the basis for making the variant libraries described herein:

(SEQ ID NO: 8)

FDVIGGNAYTIGGRSRCSIGFAVNGGFITAGHCGRTGATTANPTGTFAGS

SFPGNDYAFVRTGAGVNLLAQVNNYSGGRVQVAGHTAAPVGSAVCRSGST

TGWHCGTITALNSSVTYPEGTVRGLIRTTVCAEPGDSGGSLLAGNQAQGV

TSGGSGNCRTGGTTFFQPVNPILQAYGLRMITTDSGSSP.

Asp expression cassettes were constructed in the pXX-KpnI vector and subsequently cloned into the pHPLT vector for expression of ASP in *B. subtilis*. pXX-KpnI is a pUC based vector with the aprE promoter (*B. subtilis*) driving expression, a cat gene, and a duplicate aprE promoter for amplification of the copy number in *B. subtilis*. The bla gene allows selective growth in *E. coli*. The KpnI, introduced in the ribosomal binding site, downstream of the aprE promoter region, together with the HindIII site enables cloning of Asp expression cassettes in pXX-KpnI. pHPLT-EBS2c2, a derivative of pHPLT (Solingen et al., Extremophiles 5:333-341 [2001]), contains the thermostable amylase LAT promoter ($P_{LAT}$) of *Bacillus licheniformis*, followed by XbaI and HpaI restriction sites for cloning ASP expression constructs. The Asp expression cassette was cloned in the pXX-KpnI vector containing DNA encoding a hybrid signal peptide (SEQ ID NO:9) constructed of 5 subtilisin AprE N-terminal signal peptide amino acids fused to the 25 Asp C-terminal signal peptide amino acids:

MRSKKRTVTRALAVATAAATLLAGGMAAQA. (SEQ ID NO: 9)

The hybrid ASP signal peptide is encoded by the following DNA sequence:

(SEQ ID NO: 10)

ATGAGAAGCAAGAAGCGAACTGTCACAAGAGCTCTGGCTGTGGCAACAGC

AGCTGCTACACTCTTGGCTGGGGGTATGGCAGCACAAGCT.

The Asp expression cassette cloned in the pXX-KpnI vector was transformed into *E. coli* (Electromax DH10B, Invitrogen, Catalog No. 12033-015). The primers and cloning strategy used are provided below. Subsequently, the expression cassettes were cloned from these vectors and introduced in the pHPLT expression vector for transformation into a *B. subtilis* (ΔaprE, ΔnprE, oppA, ΔspoIIE, degUHy32, ΔamyE::(xylR,pxylA-comK) strain. The primers and cloning strategy for ASP expression cassettes cloning in pHPLT are also provided below.

Primers were obtained from MWG and Invitrogen. Invitrogen Platinum Taq DNA polymerase High Fidelity (Catalog No. 11304-029) was used for PCR amplification (0.2 μM primers, 25 up to 30 cycles) according to Invitrogen's protocol. Ligase reactions of ASP expression cassettes and host vectors were completed using Invitrogen T4 DNA Ligase (Catalog No. 15224-025) by utilizing the protocol recommended for general cloning of cohesive ends.

Expression of the asp gene was investigated in a *B. subtilis* strain (ΔaprE, ΔnprE, oppA, ΔspoIIE, degUHy32, ΔamyE::(xylR,pxylA-comK). The plasmid pHPLT-ASP-C1-2, was transformed into *B. subtilis* (ΔaprE, ΔnprE, oppA, ΔspoIIE, degUHy32, ΔamyE::(xylR,pxylA-comK). Transformation was performed as known in the art (See e.g., WO 02/14490, incorporated herein by reference).

Selective growth of *B. subtilis* (ΔaprE, ΔnprE, oppA, ΔspoIIE, degUHy32, ΔamyE::(xylR,pxylA-comK) transformants harboring the pHPLT-ASP-C1-2 vector was performed in shake flasks containing 25 ml Synthetic Maxatase Medium (SMM), with 0.97 g/l $CaCl_2.6H_2O$ instead of 0.5 g/l $CaCl_2$ (See, U.S. Pat. No. 5,324,653, herein incorporated by reference) with 20 mg/L neomycin. This growth resulted in the production of secreted ASP having proteolytic activity. Gel analysis was performed using NuPage Novex 10% Bis-Tris gels (Invitrogen, Catalog No. NP0301BOX). To prepare samples for analysis, 2 volumes of supernatant were mixed with 1 volume 1M HCl, 1 volume 4×LDS sample buffer (Invitrogen, Catalog No. NP0007), and 1% PMSF (20 mg/ml) and subsequently heated for 10 min at 70° C. Then, 25 μL of each sample was loaded onto the gel, together with 10 μL of SeeBlue plus 2 pre-stained protein standards (Invitrogen, Cat. No. LC5925). The results clearly demonstrated that the asp cloning strategy described in this example is suitable for production of active Asp in *B. subtilis*.

TABLE 2-1

ASP in pXX-KpnI and p2JM103-DNNDPI

| Vector Construct | Primers | DNA Template | Host Vector | Restriction Sites Used for Cloning |
|---|---|---|---|---|
| pXX-ASP-4 | ASP-PreCross-I-FW TCATGCAGGGTACCATGAGAAGCA AGAAGCGAACTGTCACAAGAGCTC TGGCT (SEQ ID NO: 11) ASP-syntc-mature-RV GTGTGCAAGCTTTCAAGGGGAACT TCCAGAGTCAGTC (SEQ ID NO: 12) | ASP synthetic DNA sequence | pXX-KpnI | KpnI × HindIII |

TABLE 2-2

ASP Expression Cassettes in pHPLT

| Vector Construct | Primers | DNA Template | Host Vector | Restriction Sites Used for Cloning |
|---|---|---|---|---|
| pHPLT-ASP-C1-2 | ASP-Cross-1&2-FW TGAGCTGCTAGCAAAAGGAGAGGG TAAAGAATGAGAAGCAAGAAG (SEQ ID NO: 13) pHPLT-ASPmat-RV CATGCATCCCGGGTTAAGGGGAAC TTCCAGAGTCAGTC (SEQ ID NO: 14) | pXX-ASP-4 | PHPLT-EBS2c2 (Xbal × HpaI) | NheI × SmaI |

GG36 Protease Production

In this Example, experiments conducted to produce GG36 (also referred to herein as *B. lentus* subtilisin) in *B. subtilis* are provided. The expression plasmid pAC-GG36ci was assembled using the GG36 codon-improved gene fused at the eighth codon of the aprE signal sequence under the control of the consensus aprE promoter and the BPN' transcriptional terminator. In the sequence provided below, bold and italicized font indicates the consensus aprE promoter, standard font indicates the signal sequence, underlined font indicates the pro sequence, bold font indicates DNA that encodes the GG36 mature protease, and underlined italicized font indicates the BPN' terminator. The coding region of the GG36 mature protease is flanked by KpnI and XhoI restriction sites for cloning purposes:

(SEQ ID NO: 15)

*atctcaaaaaaatgggtctactaaaatattactccatccattataata*

*aattcacagaatagtcttttaagtaagtctactctgaatttttttaa*

*aaggagagggtaaaga*gtgagaagcaaaaaattgtggatcgtcgcgtcga ccgcattgctgatttctgttgcttttagctcatccatcgcatccgctgct gaagaagcaaaagaaaaatattaattggctttaatgagcaggaagctgtc agtgagtttgtagaacaagttgaggcaaatgacgaggtagccattctctc tgaggaagaggaagtcgaaattgaattgcttcatgaatttgaaacgattc ctgttctgtccgttgagttaagcccagaagatgtggacgcgttagagctc gatccagctatttcttatattgaagaggatgcagaagtaactacaatggc gcaatcggtaccatggggaattagcagagtacaagccccagctgcacata

-continued accgtggattgacaggttctggtgtaaaagttgctgtccttgataccggt atttccactcatccagacttaaatattcgtggtggagctagctttgtacc aggggaaccatccactcaagatggcaatggacatggcactcatgttgccg gcacaatcgcggctcttaacaattcaattggtgttcttggcgtagcgcca agcgcagaactatacgctgttaaagtattaggagcaagcggttcaggctc tgtcagctctattgcccaaggattggaatgggcagggaacaatggcatgc acgttgctaatcttagtttaggatctccttcgccaagtgccacacttgag caagctgttaatagcgcgacttctagaggcgttcttgttgtagcggcctc

-continued tggaaattcaggtgcaggctcaatcagctatccggcccgttatgcgaacg ctatggcagtcggagctactgaccaaaacaacaaccgcgccagcttttca cagtatggcgcagggcttgacattgtcgcaccaggtgtaaacgtgcagag cacttacccaggttcaacatatgccagcttaaacggtacatcaatggcta ctcctcatgttgcaggtgcggctgcacttgttaaacaaaagaacccatct tggtccaatgtacaaatccgcaatcatcttaagaatacggcaactagctt aggaagcacaaacttgtatggaagcggacttgtcaatgcagaagctgcaa ctcgttaa*aagcttaactcgagataaaaaaccggccttggccccgccggt*

*tttttat*.

The amino acid sequence of the GG36 precursor protein is provided below. In this sequence, bold indicates the mature GG36 protease:

(SEQ ID NO: 16)

MRSKKLWIVASTALLISVAFSSSIASAAEEAKEKYLIGFNEQEAVSEFVE

QVEANDEVAILSEEEEVEIELLHEFETIPVLSVELSPEDVDALELDPAIS

YIEEDAEVTTMAQSVPWGISRVQAPAAHNRGLTGSGVKVAVLDTGISTHP

DLNIRGGASFVPGEPSTQDGNGHGTHVAGTIAALNNSIGVLGVAPSAELY

AVKVLGASGSGSVSSIAQGLEWAGNNGMHVANLSLGSPSPSATLEQAVNS

ATSRGVLVVAASGNSGAGSISYPARYANAMAVGATDQNNNRASFSQYGAG

LDIVAPGVNVQSTYPGSTYASLNGTSMATPHVAGAAALVKQKNPSWSNVQ

IRNHLKNTATSLGSTNLYGSGLVNAEAATR.

The amino acid sequence of the mature GG36 protease was used as the basis for making the variant libraries described herein:

(SEQ ID NO: 16)

AQSVPWGISRVQAPAAHNRGLTGSGVKVAVLDTGISTHPDLNIRGGASFV

PGEPSTQDGNGHGTHVAGTIAALNNSIGVLGVAPSAELYAVKVLGASGSG

SVSSIAQGLEWAGNNGMHVANLSLGSPSPSATLEQAVNSATSRGVLVVAA

SGNSGAGSISYPARYANAMAVGATDQNNNRASFSQYGAGLDIVAPGVNVQ

STYPGSTYASLNGTSMATPHVAGAAALVKQKNPSWSNVQIRNHLKNTATS

LGSTNLYGSGLVNAEAATR.

Elements of plasmid pAC-GG36ci include: pUB110=DNA fragment from plasmid pUB110 (McKenzie et al., *Plasmid* 15:93-103 [1986]), pBR322=DNA fragment from plasmid pBR322 (Bolivar et al., *Gene* 2:95-113 [1977]), pC194=DNA fragment from plasmid pC194 (Horinouchi et al., J Bacteriol, 150:815-825 [1982]). The plasmid features as follows: On for *B. subtilis*=origin of replication from pUB110, CAT=chloramphenicol resistance gene from pC194, pMB 1 origin=origin of replication from pBR322, bla=beta-lactamase from pBR322, Short aprE promoter=consensus transcriptional promoter, Signal Peptide=signal peptide, Pro Peptide=GG36 pro region, GG36ci Mature Peptide=mature GG36 (replaced by the coding regions for each variant expressed in this study), BPN' Terminator=transcriptional terminator from subtilisin BPN'.

FNA Protease Production

In this Example, experiments conducted to produce FNA (also referred to herein as *B. amyloliquefaciens* subtilisin BPN'-Y217L) in *B. subtilis* are described. The expression plasmid pAC-FNAre was assembled using the FNA gene, fused at the eighth codon of the aprE signal sequence under the control of the consensus aprE promoter and BPN' transcriptional terminator. In the sequence provided below, bold and italicized font indicates the consensus aprE promoter, standard font indicates the signal sequence, underlined font indicates the pro sequence, bold font indicates DNA that encodes the FNA mature protease, and underlined italicized font indicates the BPN' terminator. The coding region of the FNA mature protease contains the KpnI and XhoI restriction sites for cloning purposes:

(SEQ ID NO: 18)

*gaattcatctcaaaaaaatgggtctactaaaatattattccatctatt*

*ataataaattcacagaatagtcttttaagtaagtctactctgaatt*

*tttttaaaaggagagggtaaagagtgagaagcaaaaaatt*gtgagaagcaa aaaattgtggatcagtttgctgtttgctttagcgttaatctttacgatgg cgttcggcagcacatccagcgcgcaggctgcagggaaatcaaacggggaa aagaaatatattgtcgggtttaaacagacaatgagcacgatgagcgccgc taagaagaaagacgtcatttctgaaaaaggcgggaaagtgcaaaagcaat tcaaatatgtagacgcagctagcgctacattaaacgaaaaagctgtaaaa gaattgaaaaaagacccgagcgtcgcttacgttgaagaagatcacgtagc acacgcgtacgcgcagtccgtgccatatggcgtatcacaaattaaagccc ctgctctgcactctcaaggctacaccggttcaaatgttaaagtagcggtt atcgacagcggtatcgattcttctcatccagatcttaaagtagcaggcgg agccagcatggttccttctgaaacaaatcctttccaagacaacaactctc acggaacacacgttgctggtaccgttgcggctcttaataactcaatcggt gtattaggcgttgcgccaagcgcatcactttacgctgtaaaagttctcgg cgccgacggttccggccaatacagctggatcattaacggaatcgagtggg cgatcgcaaacaatatggacgttattaacatgagcctcggcggaccgtcc ggttctgctgctttaaaagcggcagttgataaagccgttgcatccggcgt cgtagtcgttgcggcagccggcaacgaaggcacttccggcagctcaagca cagtgggctaccctggtaaataccctttctgtcattgcagtaggcgctgtc gacagcagcaaccaaagagcatctttctcaagcgtaggacctgagctcga tgtcatggcacctggcgtatctatccaaagcacgcttcctggaaacaaat acggcgcgttgaacggtacatcaatggcatctccgcacgttgccggagcc gcggctttgattctttctaagcacccgaactggacaaacactcaagtccg cagctctctagaaaacaccactacaaaacttggtgattctttctactatg gaaaagggctgatcaatgtacaggcggcagctcagtaa*aactaaaactcg*

*agataaaaaaccggccttggccccgccggtttttat*.

The amino acid sequence of the FNA precursor protein is provided below. In this sequence, bold indicates the mature FNA protease:

(SEQ ID NO: 19)

MRSKKLWISLLFALALIFTMAFGSTSSAQAAGKSNGEKKYIVGFKQTMST

MSAAKKKDVISEKGGKVQKQFKYVDAASATLNEKAVKELKKDPSVAYVEE

-continued

DHVAHAYAQSVPYGVSQIKAPALHSQGYTGSNVKVAVIDSGIDSSHPDLK

VAGGASMVPSETNPFQDNNSHGTHVAGTVAALNNSIGVLGVAPSASLYAV

KVLGADGSGQYSWIINGIEWAIANNMDVINMSLGGPSGSAALKAAVDKAV

ASGVVVVAAAGNEGTSGSSSTVGYPGKYPSVIAVGAVDSSNQRASFSSVG

PELDVMAPGVSIQSTLPGNKYGALNGTSMASPHVAGAAALILSKHPNWTN

TQVRSSLENTTTKLGDSFYYGKGLINVQAAAQ.

The amino acid sequence of the mature FNA protease was used as the basis for making the variant libraries described herein:

(SEQ ID NO: 20)

AQSVPYGVSQIKAPALHSQGYTGSNVKVAVIDSGIDSSHPDLKVAGGASM

VPSETNPFQDNNSHGTHVAGTVAALNNSIGVLGVAPSASLYAVKVLGADG

SGQYSWIINGIEWAIANNMDVINMSLGGPSGSAALKAAVDKAVASGVVVV

AAAGNEGTSGSSSTVGYPGKYPSVIAVGAVDSSNQRASFSSVGPELDVMA

PGVSIQSTLPGNKYGALNGTSMASPHVAGAAALILSKHPNWTNTQVRSSL

ENTTTKLGDSFYYGKGLINVQAAAQ.

Elements of plasmid pAC-FNAre include: pUB 110=DNA fragment from plasmid pUB110 (McKenzie et al., *Plasmid* 15:93-103, [1986]), pBR322=DNA fragment from plasmid pBR322 (Bolivar et al., *Gene* 2:95-113 [1977]), pC194=DNA fragment from plasmid pC194 (Horinouchi et al., J. Bacteriol 150:815-825 [1982]). Plasmid features are as follows: On for *B. subtilis*=origin of replication from pUB 110, CAT=chloramphenicol resistance gene from pC194, pMB1 origin=origin of replication from pBR322, bla=beta-lactamase from pBR322, Short aprE promoter=consensus transcriptional promoter, Signal Peptide=signal peptide, Pro Peptide=FNA pro region, FNA Mature Peptide=mature FNA (replaced by the coding regions for each variant expressed in this study), BPN' Terminator=transcriptional terminator from subtilisin BPN'.

Example 3

Amylase Production in *B. subtilis*

In this Example, experiments conducted to produce *Bacillus stearothermophilus* alpha amylase (also referred to herein as AmyS), a mutant truncated form of AmyS (S242Q having a 29 amino acid deletion, also referred to herein as S242Q), and a truncated form of the alpha-amylase from *Bacillus* sp. TS-23 (also referred to herein as AmyTS-23t), and variants thereof in *B. subtilis* are described. Transformation was performed as known in the art (See e.g., WO 02/14490). Briefly, the gene encoding the parent amylases was cloned into the pHPLT expression vector, which contains the LAT promoter (PLAT), a sequence encoding the LAT signal peptide (preLAT), followed by PstI and HpaI restriction sites for cloning.

The coding region for the LAT signal peptide is shown below:

(SEQ ID NO: 21)

atgaaacaacaaaaacggctttacgcccgattgctgacgctgttatttgc gctcatcttcttgctgcctcattctgcagcttcagca.

The amino acid sequence of the LAT signal peptide is shown below:

MKQQKRLYARLLTLLFALIFLLPHSAASA (SEQ ID NO: 22)

The coding region for the mature AmyS amylase is shown below:

(SEQ ID NO: 23)

gccgcaccgtttaacggtaccatgatgcagtattttgaatggtacttgcc ggatgatggcacgttatggaccaaagtggccaatgaagccaacaactat ccagccttggcatcaccgctctttggctgccgcccgcttacaaaggaaca agccgcagcgacgtagggtacggagtatacgacttgtatgacctcggcga attcaatcaaaaagggaccgtccgcacaaaatatggaacaaaagctcaat atcttcaagccattcaagccgcccacgccgctggaatgcaagtgtacgcc gatgtcgtgttcgaccataaaggcggcgctgacggcacggaatgggtgga cgccgtcgaagtcaatccgtccgaccgcaaccaagaaatctcgggcacct atcaaatccaagcatggacgaaatttgattttcccgggcggggcaacacc tactccagctttaagtggcgctggtaccattttgacggcgttgactggga cgaaagccgaaaattaagccgcatttacaaattccgcggcatcggcaaag cgtgggattgggaagtagacacggaaaacggaaactatgactacttaatg tatgccgaccttgatatggatcatcccgaagtcgtgaccgagctgaaaaa ctgggggaaatggtatgtcaacacaacgaacattgatgggttccggcttg atgccgtcaagcatattaagttcagtttttttcctgattggttgtcgtat gtgcgttctcagactggcaagccgctatttaccgtcggggaatattggag ctatgacatcaacaagttgcacaattacattacgaaaacaaacggaacga tgtctttgtttgatgccccgttacacaacaaattttataccgcttccaaa tcagggggcgcatttgatatgcgcacgttaatgaccaatactctcatgaa agatcaaccgacattggccgtcaccttcgttgataatcatgacaccgaac ccggccaagcgctgcagtcatgggtcgacccatggttcaaaccgttggct tacgcctttattctaactcggcaggaaggatacccgtgcgtcttttatgg tgactattatggcattccacaatataacattccttcgctgaaaagcaaaa tcgatccgctcctcatcgcgcgcagggattatgcttacggaacgcaacat gattatcttgatcactccgacatcatcgggtggacaagggaaggggtcac tgaaaaaccaggatccgggctggccgcactgatcaccgatgggccgggag gaagcaaatggatgtacgttggcaaacaacacgctggaaaagtgttctat gaccttaccggcaaccggagtgacaccgtcaccatcaacagtgatggatg gggggaattcaaagtcaatggcggttcggtttcggtttgggttcctagaa aaacgaccgttctaccatcgctcggccgatcacaacccgaccgtggactg gtgaattcgtccgttggaccgaaccacggttggtggcatggcct The amino acid sequence of the mature AmyS amylase was used as the basis for making the variant libraries described herein:

(SEQ ID NO: 24)

AAPFNGTMMQYFEWYLPDDGTLWTKVANEANNLSSLGITALWLPPAYKGT

SRSDVGYGVYDLYDLGEFNQKGTVRTKYGTKAQVLQAIQAAHAAGMQVYA

-continued

DVVFDHKGGADGTEWVDAVEVNPSDRNQEISGTYQIQAWTKFDFPGRGNT

YSSFKWRWYHFDGVDWDESRKLSRIYKFRGIGKAWDWEVDTENGNYDYLM

YADLDMDHPEVVTELKNWGKWYVNTTNIDGFRLDAVKHIKFSFFPDWLSY

VRSQTGKPLFTVGEYWSYDINKLHNYITKTNGTMSLFDAPLHNKFYTASK

SGGAFDMRTLMTNTLMKDQPTLAVTFVDNHDTEPGQALQSWVDPWFKPLA

YAFILTRQEGYPCVFYGDYYGIPQYNIPSLKSKIDPLLIARRDYAYGTQH

DYLDHSDIIGWTREGVTEKPGSGLAALITDGPGGSKWMYVGKQHAGKVFY

DLTGNRSDTVTINSDGWGEFKVNGGSVSVWVPRKTTVSTIARPITTRPWT

GEFVRWTEPRLVAWP.

The amino acid sequence of the mature truncated S242Q amylase with the substituted amino acid shown in italics was used as the basis for making the variant libraries described herein:

(SEQ ID NO: 25)

AAPFNGTMMQYFEWYLPDDGTLWTKVANEANNLSSLGITALWLPPAYKGT

SRSDVGYGVYDLYDLGEFNQKGTVRTKYGTKAQYLQAIQAAHAAGMQVYA

DVVFDHKGGADGTEWVDAVEVNPSDRNQEISGTYQIQAWTKFDFPGRGNT

YSSFKWRWYHFDGVDWDESRKLSRIYKFRGIGKAWDWEVDTENGNYDYLM

YADLDMDHPEVVTELKNWGKWYVNTTNIDGFRLDAVKHIKFQFFPDWLSY

VRSQTGKPLFTVGEYWSYDINKLHNYITKTNGTMSLFDAPLHNKFYTASK

SGGAFDMRTLMTNTLMKDQPTLAVTFVDNHDTEPGQALQSWVDPWFKPLA

YAFILTRQEGYPCVFYGDYYGIPQYNIPSLKSKIDPLLIARRDYAYGTQH

DYLDHSDIIGWTREGVTEKPGSGLAALITDGPGGSKWMYVGKQHAGKVFY

DLTGNRSDTVTINSDGWGEFKVNGGSVSVWVPRKTT.

The coding region for the mature AmyTS-23t amylase is shown below:

(SEQ ID NO: 26)

aatacggcgccgatcaacgaaacgatgatgcagtattttgaatgggatct gccgaatgatggaacgctgtggacgaaagtcaaaaacgaagcggcgaatc ttagcagcctgggaatcacagcactttggcttccgccggcatataaagga acgagccaaagcgatgtcggctatggcgtctatgatctgtatgacctggg cgaatttaaccaaaaaggcacgatccggacgaaatatggcacgaaaacac agtatatccaagcgatccaggcagcaaaagcagcaggcatgcaagtctat gccgacgtcgtctttaatcataaagcgggagcggatggcacagaatttgt cgatgccgtcgaagttgatccgagcaacagaaaccaagaaacgagcggca cgtatcaaatccaagcgtggacgaaatttgattttccgggcagaggcaat acgtatagcagctttaaatggcgctggtatcattttgacggcacggattg ggatgaaagcagaaaactgaaccggatctataaatttcggagcacgggca aagcatgggattgggaagtcgatacggaaaacggcaactatgactatctg atgtttgccgatctggatatggatcatccggaagtcgtcacggaactgaa aaattggggcacgtggtatgttaatacgacgaacatcgatggctttagac tggatgccgtcaaacatatcaaatatagcttttttccggactggctgacg tatgtcagaaaccagacgggcaaaaacctttttgccgtcggcgaattttg gagctatgacgtcaacaaacttcataactatatcacgaaaacgaacggca gcatgagccttttttgatgccccgcttcataacaacttttatacggcgagc aaaagctcaggctattttgatatgagatatctgctgaacaacacgctgat gaaagatcaaccgagcctggcagtcacactggtcgataaccatgatacac aaccgggccaaagccttcaaagctgggtcgaaccgtggtttaaaccgctg gcgtatgcctttatcctgacgagacaagaagggtatccttgcgtcttttta tggcgactattatggcatcccgaaatataatatcccgggcctgaaaagca aaatcgatccgctgctgatcgccagacgggattatgcctatggcacacag cgggattatatcgaccatcaggacatcatcggctggacaagagaaggcat cgatacgaaaccgaatagcggactggcagcactgattacagatggaccgg gcggaagcaaatggatgtatgtcggcaaaaaacatgccggcaaagtcttt tatgatctgacgggcaacagaagcgatacggtcacgatcaatgctgatgg ctggggagaatttaaagtcaatggcggcagcgtttcaatctgggtcgcca aa.

The amino acid sequence of the mature AmyTS-23t amylase was used as the basis for making the variant libraries described herein:

(SEQ ID NO: 27)

NTAPINETMMQYFEWDLPNDGTLWTKVKNEAANLSSLGITALWLPPAYKG

TSQSDVGVGVYDLYDLGEFNQKGTIRTKYGTKTQYIQAIQAAKAAGMQVY

ADVVFNHKAGADGTEFVDAVEVDPSNRNQETSGTYQIQAWTKFDFPGRGN

TYSSFKWRWYHFDGTDWDESRKLNRIYKFRSTGKAWDWEVDTENGNYDYL

MFADLDMDHPEVVTELKNWGTWYVNTTNIDGFRLDAVKHIKYSFFPDWLT

YVRNQTGKNLFAVGEFWSYDVNKLHNYITKTNGSMSLFDAPLHNNFYTAS

KSSGYFDMRYLLNNTLMKDQPSLAVTLVDNHDTQPGQSLQSWVEPWFKPL

AYAFILTRQEGYPCVFYGDYYGIPKYNIPGLKSKIDPLLIARRDYAYGTQ

RDYIDHQDIIGWTREGIDTKPNSGLAALITDGPGGSKWMYVGKKHAGKVF

YDLTGNRSDTVTINADGWGEFKVNGGSVSIWVAK.

The AmyS gene was amplified as a PstI-HpaI fragment from plasmid pICatH-Ethyl4(ori1) using primers:

Ethyl 4 F:

(SEQ ID NO: 28)

5' CTTCTTGCTG CCTCATTCTG CAGCTTCAGC AGCCGCACCG

TTTAACGGTA CCATG 3';

and

Ethyl 4 R:

(SEQ ID NO: 29)

5' CAGGAAATCCGTCCTCTGTTAACTCAGGTCGTTTTTCTAGGAA

C 3'.

The PCR products were purified using Qiaquik columns from Qiagen, and resuspended in 50 μL of deionized water. 50 μL of the purified DNA was digested with HpaI (Roche) and PstI (Roche) and the resultant DNA resuspended in 30 μL of deionized water. 10-20 ng/μL of the DNA was cloned into plasmid pHPLT using PstI and HpaI cloning sites. The ligation mixtures were directly transformed into competent *B. subtilis* cells (genotype: Δvpr, ΔwprA, Δmpr-ybfJ, ΔnprB). The *B. subtilis* cells have a competency gene (comK) which is placed under a xylose inducible promoter, so xylose was used to induce competency for DNA binding and uptake.

The elements of plasmid pHPLT-AmyS include: pUB110=DNA fragment from plasmid pUB110 (McKenzie et al., Plasmid 15: 93-103 [1986]). Plasmid features include: ori-pUB11032 origin of replication from pUB110, neo=neomycin resistance gene from pUB110, Plat=transcriptional promoter from *B. lichenifonnis* amylase, Pre LAT=signal peptide from *B. lichenifonnis* amylase, AmyS=coding region for truncated AmyS and amylase variants, Terminator=transcriptional terminator from *B. lichenifonnis* amylase.

Example 4

Expression of Enzyme Variants

This Example describes the methods used to express various recombinant enzymes of the transformed *B. subtilis* of the preceding Examples.

Neutral Metalloproteases—600 ml Scale

The recombinant *Bacillus subtilis* was cultivated by conventional batch fermentation in a nutrient medium. One glycerol vial of *B. subtilis* culture containing the *B. amyloliquefaciens* neutral metalloprotease or variant thereof was used to inoculate 600 ml of SBG 1% medium containing 200 mg/L chloramphenicol. The cultures were grown for 36-48 hours at 37° C., after which time, the culture fluid was recovered by centrifugation at 12,000 rpm, as known in the art. This procedure was done in duplicate. The secreted neutral metalloproteases were concentrated approximately 10-fold using an Amicon filter system 8400 with a BES (polyethersulfone) 10 kDa cutoff.

The concentrated supernatant was dialyzed overnight at 4° C. against 25 mM MES buffer, pH 5.4, containing 10 mM NaCl. The dialyzate was then loaded onto a cation-exchange column Poros HS20 (total volume ~83 mL; binding capacity ~4.5 g protein/mL column; waters) as described below. The column was pre-equilibrated with 25 mM MES buffer, pH 5.4, containing 10 mM NaCl. Then, approximately 200-300 mL of sample was loaded onto the column. The bound protein was eluted using a pH gradient from 5.4 to 6.2 over 10-column volumes of MES buffer. Elution of the protein was between pH 5.8 and 6.0, and was assessed using proteolytic activity as described herein and 10% (w/v) NUPAGE® SDS-PAGE (Novex). The neutral protease containing fractions were then pooled. Calcium and zinc chloride salts in the ratio of 3:1 were added prior to the adjustment of the pH to 5.8. The Perceptive Biosystems BIOCAD® Vision (GMI) was used for protein purification. The purified protein, assessed using a 10% (w/v) NUPAGE® SDS-PAGE, was determined to be homogenous, with greater than 95% purity.

Serine Proteases—600 ml Scale

The recombinant *Bacillus subtilis* was cultivated by conventional batch fermentation in a nutrient medium. One glycerol vial of *B. subtilis* culture containing the *C. bogoriensis* serine protease or variant thereof was used to inoculate 600 ml of SBG 1% medium containing 200 mg/L chloramphenicol. The cultures were grown for 36-48 hours at 37° C., after which time, the culture fluid was recovered by centrifugation for 30 min at 12,000 rpm (SORVALL® centrifuge model RCSB) at 10° C., as known in the art. This procedure was done in duplicate. The resulting supernatant was clarified by depth filtration over Seitz EKS (SeitzSchenk). The resulting sterile culture supernatant was further concentrated approximately 10 times by ultra filtration using an ultra filtration cassette with a 10 kDa cut-off (Pall Omega 10 kDa Minisette; Pall). The resulting concentrated crude serine protease samples were frozen and stored at −20° C. until further use.

The cell separated culture broth was dialyzed against 20 mM (2-(4-morpholino)-ethane sulfonic acid (MES), pH 5.4, 1 mM $CaCl_2$ using 8K Molecular Weight Cut Off (MWCO) Spectra-Por7 (Spectrum) dialysis tubing. The dialysis was performed overnight or until the conductivity of the sample was less than or equal to the conductivity of the MES buffer. The dialyzed enzyme sample was purified using a BioCad VISION (Applied Biosystems) with a 10×100 mm (7.845 mL) POROS High Density Sulfo-propyl (HS) 20 (20 micron) cation-exchange column (PerSeptive Biosystems). After loading the enzyme on the previously equilibrated column at 5 mL/min, the column was washed at 40 mL/min with a pH gradient from 25 mM MES, pH 6.2, 1 mM $CaCl_2$ to 25 mM (N-[2-hydroxyethyl]piperazine-N'-[2-ethane]sulfonic acid [$C_8H_{18}N_2O_4S$, CAS #7365-45-9]) (HEPES) pH 8.0, 1 mM $CaCl_2$ in 25 column volumes. Fractions (8 mL) were collected across the run. The pH 8.0 wash step was held for 5 column volumes and then the enzyme was eluted using a gradient (0-100 mM NaCl in the same buffer in 35 column volumes). Protease activity in the fractions was monitored using the suc-AAPF-pNA assay. Protease activity that eluted at 40 mM NaCl was concentrated and buffer exchanged (using a 5K MWCO VIVA Science 20 mL concentrator) into 20 mM MES, pH 5.8, 1 mM $CaCl_2$. This material was used for further characterization of the enzyme.

Serine Proteases—200 μl Scale

*B. subtilis* clones containing ASP expression vectors proteins were replicated with a steel 96-well replicator from glycerol stocks into 96-well culture plates (BD, 353075) containing 200 μl of TSP media+20 μg/ml neomycin, grown overnight at 37° C., 220 rpm in a humidified enclosure. A 15 μl aliquot from the overnight culture was used to inoculate 185 μl defined media +20 μg/ml neomycin in Millipore MultiScreen Filter Plates. The cultivation media was an enriched semi-defined media based on MOPS buffer, with urea as major nitrogen source, glucose as the main carbon source, and supplemented with 1% soytone for robust cell growth. Filter plates were incubated in a humidified enclosure at 37° C., 220 rpm, for 60 hours. Following this incubation, culture broths were filtered through the filter plate and collected. No further purification or concentration was performed. Filtrate stocks were formulated to 40% propylene glycol final concentration for long-term stability and stored in 96-well clear non-binding polystyrene plates (Corning, CLS3641) at 4° C.

Subtilisins—2 ml Scale

*B. subtilis* clones containing FNA or GG36 expression vectors were replicated with a steel 96-well replicator from glycerol stocks into 96-well culture plates (BD, 353075) containing 200 μl of LB media+25 μg/ml chloramphenicol, grown overnight at 37° C., 220 rpm in a humidified enclosure. A 200 μl aliquot from the overnight culture was used to inoculate 2000 μl defined media+25 μg/ml chloramphenicol in 5 ml plastic culture tubes. The cultivation media was an enriched semi-defined media based on MOPS buffer, with urea as major nitrogen source, glucose as the main carbon source, and supplemented with 1% soytone for robust cell growth. Culture tubes were incubated at 37° C., 220 rpm, for 60 hours. Following this incubation, the culture broths were centrifuged at greater than 8000×RCF. The supernatant solution was decanted into 15 ml polypropylene conical tubes for storage. No further purification or concentration was performed. Supernatant stocks were formulated to 40% propylene glycol final concentration for long-term stability and stored at 4° C.

Amylase Expression—2 ml Scale

*B. subtilis* clones containing AmyS, S242Q or AmyTS23t expression vectors were replicated with a steel 96-well replicator from glycerol stocks into 96-well culture plates (BD, 353075) containing 150 µl of LB media+10 µg/ml neomycin, grown overnight at 37° C., 220 rpm in a humidified enclosure. A 100 µl aliquot from the overnight culture was used to inoculate 2000 µl defined media+10 µg/ml neomycin in 5 ml plastic culture tubes. The cultivation media was an enriched semi-defined media based on MOPS buffer, with urea as major nitrogen source, glucose as the main carbon source, and supplemented with 1% soytone and 5 mM calcium for robust cell growth. Culture tubes were incubated at 37° C., 250 rpm, for 72 hours. Following this incubation, the culture broths were centrifuged for 10 minutes at 3000×g. The supernatant solution was decanted into 15 ml polypropylene conical tubes and 80 µL of each sample were aliquoted into 96 well plates for protein quantitation.

Example 5

Production of Enzyme Variants

This Example describes the production of enzyme charge ladders and combinatorial charge libraries.

Enzyme Charge Ladders

Multiple protein variants spanning a range of physical properties of interest are selected from existing libraries or are generated by site-directed mutagenesis techniques as known in the art (See e.g., U.S. patent application Ser. Nos., 10/576,331, 11/581,102, and 11/583,334). This defined set of probe proteins is then assayed in a test of interest.

Exemplary protease charge ladder variants are shown in the following tables and assayed as described herein. In these tables, the charge change is relative to the wild-type enzyme.

TABLE 5-1

ASP Charge Ladder Variants

| ASP Variant | Δ Charge |
|---|---|
| R14I-N112E-T116E-R123F-R159F | −5 |
| R14I-N112E-T116E-R123F | −4 |
| R14I-N112E-T116E | −3 |
| R14I-N112E | −2 |
| R14I | −1 |
| R14I-D184T | 0 |
| R14I-T86K-D184T | +1 |
| R14I-A64K-T86K-D184T | +2 |
| R14I-A64K-Q81K-T86K-D184T | +3 |

TABLE 5-2

NprE Charge Ladder Variants

| NprE Variant | Δ Charge |
|---|---|
| S56D-T60D | −2 |
| T60D | −1 |
| wild type | 0 |
| S23R | +1 |
| S23R-N46K | +2 |
| S23R-N46K-T54R | +3 |
| T14R-S23R-N46K-T54R | +4 |

TABLE 5-3

FNA Charge Ladder Variants

| FNA Variant (BPN' numbering) | Δ Charge |
|---|---|
| S87D-N109D-S188D-S248D | −4 |
| S87D-N109D-S188D | −3 |
| S87D-N109D | −2 |
| N109D | −1 |
| (FNA) | 0 |
| N109R | +1 |
| S87R-N109R | +2 |
| S87R-N109R-S188R | +3 |
| S87R-N109R-S188R-S248R | +4 |

TABLE 5-4

GG36 Charge Ladder Variants

| GG36 Variant (GG36 numbering) | GG36 Variant (BPN' numbering) | Δ Charge |
|---|---|---|
| S85D-Q107D-S182D-N242D | S87D-Q109D-S188D-N248D | −4 |
| S85D-Q107D-S182D | S87D-Q109D-S188D | −3 |
| S85D-Q107D | S87D-Q109D | −2 |
| Q107D | Q109D | −1 |
| (GG36) | (GG36) | 0 |
| Q107R | Q109R | +1 |
| S85R-Q107R | S87R-Q109R | +2 |
| S85R-Q107R-S182R | S87R-Q109R-S188R | +3 |
| S85R-Q107R-S182R-N242R | S87R-Q109R-S188R-N248R | +4 |

Exemplary amylase charge ladder variants are shown in the following tables and assayed as described herein. In these tables, the charge change is relative to the wild-type enzyme.

The sequence of the AmyS gene was provided to Gene Oracle (Mountain View, Calif.) for the synthesis of the 28 charge ladder variants shown in Table 5-5. Gene Oracle synthesized and cloned the AmyS variants into vector pGov4 and transformed them into *E. coli*. DNA isolated from minipreps, as well as an agar stab were supplied for each variant.

The variants were PCR amplified and cloned into the pHPLT *B. subtilis* expression vector. The variants were amplified as a PstI-HindIII fragment from plasmid pGov4 using primers:

```
AmySprimer F
                                        (SEQ ID NO: 30)
5'-CTCATCTTCTTGCTGCCTCATTCTGCAGCTTC-3';
and

AmySprimer R
                                        (SEQ ID NO: 31)
5'-TTATCCTTTACCTTGTCTCCAAGC-3'.
```

The PCR products were purified using Qiagen Qiaquik columns, and resuspended in 50 µL of milliQ water. 50 µL of the purified DNA was digested with HindIII (Roche) and PstI (Roche) and the resultant DNA resuspended in 30 µL of deionized water. 10-20 ng/4 of the DNA was cloned into plasmid pHPLT using PstI and HpaI cloning sites. The ligation mixtures were directly transformed into competent *B. subtilis* cells (genotype: amyE::xylRPxylAcomK-phleo). These *B. subtilis* cells have a competency gene (comK) which is placed under a xylose inducible promoter, so xylose was used to induce competency for DNA binding and uptake.

TABLE 5-5

| Number | AmyS Variant | Δ Charge |
|---|---|---|
| | a. First AmyS Charge Ladder | |
| 1-6 | R308Q R483Q K171Q K383Q K447Q K471Q N28D N224D N271D N281D Q86E Q89E | −12 |
| 1-5 | R308Q R483Q K171Q K383Q K447Q N28D N224D N271D N281D Q86E | −10 |
| 1-4 | R308Q R483Q K171Q K383Q N28D N224D N271D N281D | −8 |
| 1-3 | R308Q R483Q K171Q N28D N224D N271D | −6 |
| 1-2 | R308Q R483Q N28D N224D | −4 |
| 1-1 | R308Q N28D | −2 |
| AmyS | Parent | 0 |
| 2-1 | D318N N28R | +2 |
| 2-2 | D318N D306N N28R N224R | +4 |
| 2-3 | D318N D306N D19N N28R N224R N271R | +6 |
| 2-4 | D318N D306N D19N D393N N28R N224R N271R N281R | +8 |
| 2-5 | D318N D306N D19N D393N D458N N28R N224R N271R N281R Q86R | +10 |
| 2-6 | D318N D306N D19N D393N D458N E29Q N28R N224R N271R N281R Q86R Q89R | +12 |
| | b. Second AmyS Charge Ladder | |
| 3-7 | Q97R Q319R Q358E Q443E N28D N224D N271D N281D Q86E Q89E R308Q R483Q K171Q K383Q K447Q K471Q | −12 |
| 3-6 | Q97R Q319R Q358E Q443E N28D N224D N271D N281D Q86E R308Q R483Q K171Q K383Q K447Q | −10 |
| 3-5 | Q97R Q319R Q358E Q443E N28D N224D N271D N281D R308Q R483Q K171Q K383Q | −8 |
| 3-4 | Q97R Q319R Q358E Q443E N28D N224D N271D R308Q R483Q K171Q | −6 |
| 3-3 | Q97R Q319R Q358E Q443E N28D N224D R308Q R483Q | −4 |
| 3-2 | Q97R Q319R Q358E Q443E N28D | −2 |
| 3-1 | Q97R Q319R Q358E Q443E | 0 |
| 4-1 | Q97R Q319R Q358E Q443E N28K D318N | +2 |
| 4-2 | Q97R Q319R Q358E Q443E N28K N224K D318N D306N | +4 |
| 4-3 | Q97R Q319R Q358E Q443E N28K N224K N271K D318N D306N D19N | +6 |
| 4-4 | Q97R Q319R Q358E Q443E N28K N224K N271K N281K D318N D306N D19N D393N | +8 |
| 4-5 | Q97R Q319R Q358E Q443E N28K N224K N271K N281K Q86R D318N D306N D19N D393N D458N | +10 |
| 4-6 | Q97R Q319R Q358E Q443E N28K N224K N271K N281K Q86R Q89R D318N D306N D19N D393N D458N E29Q | +12 |
| 5-1 | Q97R Q319R Q358E Q443E N28D R308Q S242E | −3 |
| 5-2 | Q97R Q319R Q358E Q443E N28D N224D R308Q S242E | −4 |
| 5-3 | Q97R Q319R Q358E Q443E N28D N224D R308Q S242Q | −3 |

TABLE 5-6

| AmyS-S242Q Charge Ladder | |
|---|---|
| AmyS-S242Q Variant | Δ Charge |
| Q97E-Q319E-Q358E-Q443E | −4 |
| Q97E-Q319E-Q358E | −3 |
| Q97E-Q319E | −2 |
| Q97E | −1 |
| Q97R-Q319E | 0 |
| Parent AmyS-S242Q | 0 |
| Q97R | +1 |
| Q97R-Q319R | +2 |
| Q97R-Q319R-Q358R | +3 |
| Q97R-Q319R-Q358R-Q443R | +4 |

Enzyme Combinatorial Charge Libraries

Generation of *B. lentus* Subtilisin (=GG36) Combinatorial Charge Libraries

The pAC-GG36ci plasmid containing the codon-improved GG36 gene was sent to DNA 2.0 Inc. (Menlo Park, Calif.) for the generation of combinatorial charge libraries (CCL). They were also provided with the *Bacillus subtilis* strain (genotype: ΔaprE, ΔnprE, ΔspoIIE, amyE::xylRPxylAcomK-phleo) for transformations. In addition a request was made to DNA2.0 Inc. for the generation of positional libraries at each of the four sites in GG36 protease that are shown in Table 5-7. Variants were supplied as glycerol stocks in 96-well plates.

The GG36 CCL was designed by identifying four well-distributed, surface-exposed, uncharged polar amino-acid residues outside the active site. These residues are Ser-85, Gln-107, Ser-182, and Asn-242 (residues 87, 109, 188, and 248 in BPN' numbering). An 81-member combinatorial library (G-1 to G-81) was created by making all combinations of three possibilities at each site: wild-type, arginine, or aspartic acid.

TABLE 5-7

| GG36 CCL Variants | | | | | |
|---|---|---|---|---|---|
| Variant # | S 85 | Q 107 | S 182 | N 242 | □ Charge |
| G-01 | — | — | — | — | 0 |
| G-02 | — | — | — | D | −1 |
| G-03 | — | — | — | R | +1 |
| G-04 | — | — | D | — | −1 |
| G-05 | — | — | D | D | −2 |
| G-06 | — | — | D | R | 0 |
| G-07 | — | — | R | — | +1 |
| G-08 | — | — | R | D | 0 |
| G-09 | — | — | R | R | +2 |
| G-10 | — | D | — | — | −1 |

TABLE 5-7-continued

| GG36 CCL Variants | | | | | |
|---|---|---|---|---|---|
| Variant # | S 85 | Q 107 | S 182 | N 242 | □ Charge |
| G-11 | — | D | — | D | −2 |
| G-12 | — | D | — | R | 0 |
| G-13 | — | D | D | — | −2 |
| G-14 | — | D | D | D | −3 |
| G-15 | — | D | D | R | −1 |
| G-16 | — | D | R | — | 0 |
| G-17 | — | D | R | D | −1 |
| G-18 | — | D | R | R | +1 |
| G-19 | — | R | — | — | +1 |
| G-20 | — | R | — | D | 0 |
| G-21 | — | R | — | R | +2 |
| G-22 | — | R | D | — | 0 |
| G-23 | — | R | D | D | −1 |
| G-24 | — | R | D | R | +1 |
| G-25 | — | R | R | — | +2 |
| G-26 | — | R | R | D | +1 |
| G-27 | — | R | R | R | +3 |
| G-28 | D | — | — | — | −1 |
| G-29 | D | — | — | D | −2 |
| G-30 | D | — | — | R | 0 |
| G-31 | D | — | D | — | −2 |
| G-32 | D | — | D | D | −3 |
| G-33 | D | — | D | R | −1 |
| G-34 | D | — | R | — | 0 |
| G-35 | D | — | R | D | −1 |
| G-36 | D | — | R | R | +1 |
| G-37 | D | D | — | — | −2 |
| G-38 | D | D | — | D | −3 |
| G-39 | D | D | — | R | −1 |
| G-40 | D | D | D | — | −3 |
| G-41 | D | D | D | D | −4 |
| G-42 | D | D | D | R | −2 |
| G-43 | D | D | R | — | −1 |
| G-44 | D | D | R | D | −2 |
| G-45 | D | D | R | R | 0 |
| G-46 | D | R | — | — | 0 |
| G-47 | D | R | — | D | −1 |
| G-48 | D | R | — | R | +1 |
| G-49 | D | R | D | — | −1 |
| G-50 | D | R | D | D | −2 |
| G-51 | D | R | D | R | 0 |
| G-52 | D | R | R | — | +1 |
| G-53 | D | R | R | D | 0 |
| G-54 | D | R | R | R | +2 |
| G-55 | R | — | — | — | +1 |
| G-56 | R | — | — | D | 0 |
| G-57 | R | — | — | R | +2 |
| G-58 | R | — | D | — | 0 |
| G-59 | R | — | D | D | −1 |
| G-60 | R | — | D | R | +1 |
| G-61 | R | — | R | — | +2 |
| G-62 | R | — | R | D | +1 |
| G-63 | R | — | R | R | +3 |
| G-64 | R | D | — | — | 0 |
| G-65 | R | D | — | D | −1 |
| G-66 | R | D | — | R | +1 |
| G-67 | R | D | D | — | −1 |
| G-68 | R | D | D | D | −2 |
| G-69 | R | D | D | R | 0 |
| G-70 | R | D | R | — | +1 |
| G-71 | R | D | R | D | 0 |
| G-72 | R | D | R | R | +2 |
| G-73 | R | R | — | — | +2 |
| G-74 | R | R | — | D | +1 |
| G-75 | R | R | — | R | +3 |
| G-76 | R | R | D | — | +1 |
| G-77 | R | R | D | D | 0 |
| G-78 | R | R | D | R | +2 |
| G-79 | R | R | R | — | +3 |
| G-80 | R | R | R | D | +2 |
| G-81 | R | R | R | R | +4 |

Generation of *B. amyloliquefaciens* Subtilisin BPN'-Y217L (=FNA) CCL

The pAC-FNAre plasmid containing the FNA gene was sent to DNA 2.0 Inc. (Menlo Park, Calif.) for the generation of CCL. They were also provided with the *Bacillus subtilis* strain (genotype: ΔaprE, ΔnprE, ΔspoIIE, amyE::xylRPxylAcomK-phleo) for transformations. A request was made to DNA 2.0 Inc. for the generation of positional libraries at each of the four FNA protease sites that are shown in Table 5-8. Variants were supplied as glycerol stocks in 96-well plates.

The subtilisin BPN'-Y217L combinatorial charge library was designed by identifying four well-distributed, surface-exposed, uncharged polar amino-acid residues outside the active site. These residues are Ser-87, Asn-109, Ser-188, and Ser-248. An 81-member combinatorial library (F-1 to F-81) was created by making all combinations of three possibilities at each site: wild-type, arginine, or aspartic acid.

TABLE 5-8

| FNA CCL Variants | | | | | |
|---|---|---|---|---|---|
| Variant # | S 87 | N 109 | S 188 | S 248 | Δ Charge |
| F-01 | — | — | — | — | 0 |
| F-02 | — | — | — | D | −1 |
| F-03 | — | — | — | R | +1 |
| F-04 | — | — | D | — | −1 |
| F-05 | — | — | D | D | −2 |
| F-06 | — | — | D | R | 0 |
| F-07 | — | — | R | — | +1 |
| F-08 | — | — | R | D | 0 |
| F-09 | — | — | R | R | +2 |
| F-10 | — | D | — | — | −1 |
| F-11 | — | D | — | D | −2 |
| F-12 | — | D | — | R | 0 |
| F-13 | — | D | D | — | −2 |
| F-14 | — | D | D | D | −3 |
| F-15 | — | D | D | R | −1 |
| F-16 | — | D | R | — | 0 |
| F-17 | — | D | R | D | −1 |
| F-18 | — | D | R | R | +1 |
| F-19 | — | R | — | — | +1 |
| F-20 | — | R | — | D | 0 |
| F-21 | — | R | — | R | +2 |
| F-22 | — | R | D | — | 0 |
| F-23 | — | R | D | D | −1 |
| F-24 | — | R | D | R | +1 |
| F-25 | — | R | R | — | +2 |
| F-26 | — | R | R | D | +1 |
| F-27 | — | R | R | R | +3 |
| F-28 | D | — | — | — | −1 |
| F-29 | D | — | — | D | −2 |
| F-30 | D | — | — | R | 0 |
| F-31 | D | — | D | — | −2 |
| F-32 | D | — | D | D | −3 |
| F-33 | D | — | D | R | −1 |
| F-34 | D | — | R | — | 0 |
| F-35 | D | — | R | D | −1 |
| F-36 | D | — | R | R | +1 |
| F-37 | D | D | — | — | −2 |
| F-38 | D | D | — | D | −3 |
| F-39 | D | D | — | R | −1 |
| F-40 | D | D | D | — | −3 |
| F-41 | D | D | D | D | −4 |
| F-42 | D | D | D | R | −2 |
| F-43 | D | D | R | — | −1 |
| F-44 | D | D | R | D | −2 |
| F-45 | D | D | R | R | 0 |
| F-46 | D | R | — | — | 0 |
| F-47 | D | R | — | D | −1 |
| F-48 | D | R | — | R | +1 |
| F-49 | D | R | D | — | −1 |
| F-50 | D | R | D | D | −2 |
| F-51 | D | R | D | R | 0 |
| F-52 | D | R | R | — | +1 |
| F-53 | D | R | R | D | 0 |

TABLE 5-8-continued

| FNA CCL Variants | | | | | |
|---|---|---|---|---|---|
| Variant # | S 87 | N 109 | S 188 | S 248 | Δ Charge |
| F-54 | D | R | R | R | +2 |
| F-55 | R | — | — | — | +1 |
| F-56 | R | — | — | D | 0 |
| F-57 | R | — | — | R | +2 |
| F-58 | R | — | D | — | 0 |
| F-59 | R | — | D | D | −1 |
| F-60 | R | — | D | R | +1 |
| F-61 | R | — | R | — | +2 |
| F-62 | R | — | R | D | +1 |
| F-63 | R | — | R | R | +3 |
| F-64 | R | D | — | — | 0 |
| F-65 | R | D | — | D | −1 |
| F-66 | R | D | — | R | +1 |
| F-67 | R | D | D | — | −1 |
| F-68 | R | D | D | D | −2 |
| F-69 | R | D | D | R | 0 |
| F-70 | R | D | R | — | +1 |
| F-71 | R | D | R | D | 0 |
| F-72 | R | D | R | R | +2 |
| F-73 | R | R | — | — | +2 |
| F-74 | R | R | — | D | +1 |
| F-75 | R | R | — | R | +3 |
| F-76 | R | R | D | — | +1 |
| F-77 | R | R | D | D | 0 |
| F-78 | R | R | D | R | +2 |
| F-79 | R | R | R | — | +3 |
| F-80 | R | R | R | D | +2 |
| F-81 | R | R | R | R | +4 |

Generation of *B. stearothermophilus* AmyS-S242Q CCL

The AmyS-S242Q plasmid DNA was isolated from a transformed *B. subtilis* strain (gentotype: ΔaprE, ΔnprE, amyE::xylRPxylAcomK-phleo) and sent to DNA2.0 Inc. as the template for CCL construction. A request was made to DNA2.0 Inc. (Mountain View, Calif.) for the generation of positional libraries at each of the four sites in AmyS-S242Q (S242Q) amylase that are shown in Table 5-9. Variants were supplied as glycerol stocks in 96-well plates.

The AmyS S242Q combinatorial charge library was designed by identifying the following four residues: Gln-97, Gln 319, Gln 358, and Gln 443. A four site, 81-member CCL was created by making all combinations of three possibilities at each site: wild-type, arginine, or aspartic acid.

TABLE 5-9

| S242Q CCL Variants | | | | | |
|---|---|---|---|---|---|
| Variant # | Q97 | Q319 | Q358 | Q443 | Δ Charge |
| 1 | Q97E | Q319E | Q358E | Q443E | −4 |
| 2 | Q97E | Q319E | Q358E | Q443R | −2 |
| 3 | Q97E | Q319E | Q358E | — | −3 |
| 4 | Q97E | Q319E | Q358R | Q443E | −2 |
| 5 | Q97E | Q319E | Q358R | Q443R | 0 |
| 6 | Q97E | Q319E | Q358R | — | −1 |
| 7 | Q97E | Q319E | — | Q443E | −3 |
| 8 | Q97E | Q319E | — | Q443R | −1 |
| 9 | Q97E | Q319E | — | — | −2 |
| 10 | Q97E | Q319R | Q358E | Q443E | −2 |
| 11 | Q97E | Q319R | Q358E | Q443R | 0 |
| 12 | Q97E | Q319R | Q358E | — | −1 |
| 13 | Q97E | Q319R | Q358R | Q443E | 0 |
| 14 | Q97E | Q319R | Q358R | Q443R | +2 |
| 15 | Q97E | Q319R | Q358R | — | +1 |
| 16 | Q97E | Q319R | — | Q443E | −1 |
| 17 | Q97E | Q319R | — | Q443R | +1 |
| 18 | Q97E | Q319R | — | — | 0 |
| 19 | Q97E | — | Q358E | Q443E | −3 |
| 20 | Q97E | — | Q358E | Q443R | −1 |
| 21 | Q97E | — | Q358E | — | −2 |

TABLE 5-9-continued

| S242Q CCL Variants | | | | | |
|---|---|---|---|---|---|
| Variant # | Q97 | Q319 | Q358 | Q443 | Δ Charge |
| 22 | Q97E | — | Q358R | Q443E | −1 |
| 23 | Q97E | — | Q358R | Q443R | +1 |
| 24 | Q97E | — | Q358R | — | 0 |
| 25 | Q97E | — | — | Q443E | −2 |
| 26 | Q97E | — | — | Q443R | 0 |
| 27 | Q97E | — | — | — | −1 |
| 28 | Q97R | Q319E | Q358E | Q443E | −2 |
| 29 | Q97R | Q319E | Q358E | Q443R | 0 |
| 30 | Q97R | Q319E | Q358E | — | −1 |
| 31 | Q97R | Q319E | Q358R | Q443E | 0 |
| 32 | Q97R | Q319E | Q358R | Q443R | +2 |
| 33 | Q97R | Q319E | Q358R | — | +1 |
| 34 | Q97R | Q319E | — | Q443E | −1 |
| 35 | Q97R | Q319E | — | Q443R | +1 |
| 36 | Q97R | Q319E | — | — | 0 |
| 37 | Q97R | Q319R | Q358E | Q443E | 0 |
| 38 | Q97R | Q319R | Q358E | Q443R | +2 |
| 39 | Q97R | Q319R | Q358E | — | +1 |
| 40 | Q97R | Q319R | Q358R | Q443E | +2 |
| 41 | Q97R | Q319R | Q358R | Q443R | +4 |
| 42 | Q97R | Q319R | Q358R | — | +3 |
| 43 | Q97R | Q319R | — | Q443E | +1 |
| 44 | Q97R | Q319R | — | Q443R | +3 |
| 45 | Q97R | Q319R | — | — | +2 |
| 46 | Q97R | — | Q358E | Q443E | −1 |
| 47 | Q97R | — | Q358E | Q443R | +1 |
| 48 | Q97R | — | Q358E | — | 0 |
| 49 | Q97R | — | Q358R | Q443E | +1 |
| 50 | Q97R | — | Q358R | Q443R | +3 |
| 51 | Q97R | — | Q358R | — | +2 |
| 52 | Q97R | — | — | Q443E | 0 |
| 53 | Q97R | — | — | Q443R | +2 |
| 54 | Q97R | — | — | — | +1 |
| 55 | — | Q319E | Q358E | Q443E | −3 |
| 56 | — | Q319E | Q358E | Q443R | −1 |
| 57 | — | Q319E | Q358E | — | −2 |
| 58 | — | Q319E | Q358R | Q443E | −1 |
| 59 | — | Q319E | Q358R | Q443R | +1 |
| 60 | — | Q319E | Q358R | — | 0 |
| 61 | — | Q319E | — | Q443E | −2 |
| 62 | — | Q319E | — | Q443R | 0 |
| 63 | — | Q319E | — | — | −1 |
| 64 | — | Q319R | Q358E | Q443E | −1 |
| 65 | — | Q319R | Q358E | Q443R | +1 |
| 66 | — | Q319R | Q358E | — | 0 |
| 67 | — | Q319R | Q358R | Q443E | +1 |
| 68 | — | Q319R | Q358R | Q443R | +3 |
| 69 | — | Q319R | Q358R | — | +2 |
| 70 | — | Q319R | — | Q443E | 0 |
| 71 | — | Q319R | — | Q443R | +2 |
| 72 | — | Q319R | — | — | +1 |
| 73 | — | — | Q358E | Q443E | −2 |
| 74 | — | — | Q358E | Q443R | 0 |
| 75 | — | — | Q358E | — | −1 |
| 76 | — | — | Q358R | Q443E | 0 |
| 77 | — | — | Q358R | Q443R | +2 |
| 78 | — | — | Q358R | — | +1 |
| 79 | — | — | — | Q443E | −1 |
| 80 | — | — | — | Q443R | +1 |
| 81 (parent) | Q97 | Q319 | Q358 | Q443 | 0 |

Generation of *Bacillus* sp. AmyTS23t CCL

AmyTS23t is a truncated form of *Bacillus* sp. TS-23 alpha amylase. Expression of AmyTS23t in a multiple protease deleted *B. subtilis* strain (degU$_{Hy}$32, oppA, ΔspoII3501, amyE::xylRPxylAcomK-ermC, ΔaprE, ΔnprE, Δepr, ΔispA, Δbpr, Δvpr, ΔwprA, Δmpr-ybfJ, ΔnprB) has been described (See, e.g., US2005/0202535A1). The AmyTS23t plasmid DNA isolated from transformed *B. subtilis* cells was sent to DNA2.0 Inc. (Menlo Park, Calif.) as the template for CCL construction. DNA 2.0 was requested to prepare a parent construct for the CCL by introducing the following seven mutations into AmyTS23t, which was consequently termed AmyTS23t-7mut (also designated as TS23t' in this document): Q98R, M201L, S243Q R309A, Q320R, Q359E, and K444E. Variants were supplied as glycerol stocks in 96-well plates. Subsequently a request was made to DNA2.0 Inc. for the generation of positional libraries at each of the four sites in AmyTS23t-7mut amylase that are shown in Table 5-10.

The AmyTS23t combinatorial charge library was designed by identifying the following four residues in AmyTS23t-7mut: Gln 87, Asn 225, Asn 272, and Asn 282. A four site, 81-member CCL was created by making all combinations of three possibilities at each site: wild-type, arginine, or aspartic acid.

TABLE 5-10

| AmyTS23t CCL Variants | | | | | |
|---|---|---|---|---|---|
| Variant # | Q87 | N225 | N272 | N282 | Δ Charge |
| Parent 1 | — | — | — | — | 0 |
| 2 | Q87E | N225E | N272E | N282E | −4 |
| 3 | Q87E | N225E | N272E | N282R | −2 |
| 4 | Q87E | N225E | N272E | — | −3 |
| 5 | Q87E | N225E | N272R | N282E | −2 |
| 6 | Q87E | N225E | N272R | N282R | 0 |
| 7 | Q87E | N225E | N272R | — | −1 |
| 8 | Q87E | N225E | — | N282E | −3 |
| 9 | Q87E | N225E | — | N282R | −1 |
| 10 | Q87E | N225E | — | — | −2 |
| 11 | Q87E | N225R | N272E | N282E | −2 |
| 12 | Q87E | N225R | N272E | N282R | 0 |
| 13 | Q87E | N225R | N272E | — | −1 |
| 14 | Q87E | N225R | N272R | N282E | 0 |
| 15 | Q87E | N225R | N272R | N282R | +2 |
| 16 | Q87E | N225R | N272R | — | +1 |
| 17 | Q87E | N225R | — | N282E | −1 |
| 18 | Q87E | N225R | — | N282R | +1 |
| 19 | Q87E | N225R | — | — | 0 |
| 20 | Q87E | — | N272E | N282E | −3 |
| 21 | Q87E | — | N272E | N282R | −1 |
| 22 | Q87E | — | N272E | — | −2 |
| 23 | Q87E | — | N272R | N282E | −1 |
| 24 | Q87E | — | N272R | N282R | +1 |
| 25 | Q87E | — | N272R | — | 0 |
| 26 | Q87E | — | — | N282E | −2 |
| 27 | Q87E | — | — | N282R | 0 |
| 28 | Q87E | — | — | — | −1 |
| 29 | Q87R | N225E | N272E | N282E | −2 |
| 30 | Q87R | N225E | N272E | N282R | 0 |
| 31 | Q87R | N225E | N272E | — | −1 |
| 32 | Q87R | N225E | N272R | N282E | 0 |
| 33 | Q87R | N225E | N272R | N282R | +2 |
| 34 | Q87R | N225E | N272R | — | +1 |
| 35 | Q87R | N225E | — | N282E | −1 |
| 36 | Q87R | N225E | — | N282R | +1 |
| 37 | Q87R | N225E | — | — | 0 |
| 38 | Q87R | N225R | N272E | N282E | 0 |
| 39 | Q87R | N225R | N272E | N282R | +2 |
| 40 | Q87R | N225R | N272E | — | +1 |
| 41 | Q87R | N225R | N272R | N282E | +2 |
| 42 | Q87R | N225R | N272R | N282R | +4 |
| 43 | Q87R | N225R | N272R | — | +3 |
| 44 | Q87R | N225R | — | N282E | +1 |
| 45 | Q87R | N225R | — | N282R | +3 |
| 46 | Q87R | N225R | — | — | +2 |
| 47 | Q87R | — | N272E | N282E | −1 |
| 48 | Q87R | — | N272E | N282R | +1 |
| 49 | Q87R | — | N272E | — | 0 |
| 50 | Q87R | — | N272R | N282E | +1 |
| 51 | Q87R | — | N272R | N282R | +3 |
| 52 | Q87R | — | N272R | — | +2 |
| 53 | Q87R | — | — | N282E | 0 |
| 54 | Q87R | — | — | N282R | +2 |
| 55 | Q87R | — | — | — | +1 |
| 56 | — | N225E | N272E | N282E | −3 |
| 57 | — | N225E | N272E | N282R | −1 |
| 58 | — | N225E | N272E | — | −2 |
| 59 | — | N225E | N272R | N282E | −1 |
| 60 | — | N225E | N272R | N282R | +1 |

TABLE 5-10-continued

| AmyTS23t CCL Variants | | | | | |
|---|---|---|---|---|---|
| Variant # | Q87 | N225 | N272 | N282 | Δ Charge |
| 61 | — | N225E | N272R | — | 0 |
| 62 | — | N225E | — | N282E | −2 |
| 63 | — | N225E | — | N282R | 0 |
| 64 | — | N225E | — | — | −1 |
| 65 | — | N225R | N272E | N282E | −1 |
| 66 | — | N225R | N272E | N282R | +1 |
| 67 | — | N225R | N272E | — | 0 |
| 68 | — | N225R | N272R | N282E | +1 |
| 69 | — | N225R | N272R | N282R | +3 |
| 70 | — | N225R | N272R | — | +2 |
| 71 | — | N225R | — | N282E | 0 |
| 72 | — | N225R | — | N282R | +2 |
| 73 | — | N225R | — | — | +1 |
| 74 | — | — | N272E | N282E | −2 |
| 75 | — | — | N272E | N282R | 0 |
| 76 | — | — | N272E | — | −1 |
| 77 | — | — | N272R | N282E | 0 |
| 78 | — | — | N272R | N282R | +2 |
| 79 | — | — | N272R | — | +1 |
| 80 | — | — | — | N282E | −1 |
| 81 | — | — | — | N282R | +1 |

Example 6

Enzyme Performance

This Example describes the testing of ASP variants in a BMI (blood, milk, ink) microswatch assay at 1.0 μg/ml in AATCC HDL detergent or 5 mM HEPES buffer under varying ionic strength. Also described is the testing of FNA and GG36 variants in BMI microswatch and baked egg assays in detergents representing various market geographies (e.g., differing pH, T, and/or water hardness), in both laundry and automatic dishwashing applications. This Example further describes the testing of alpha-amylase variants in cleaning applications, as well as in starch liquefaction. The methods provided in Example 1 were used (See, "Enzyme Performance Assays" and "Corn Four Hydrolysis").

Figure 1:
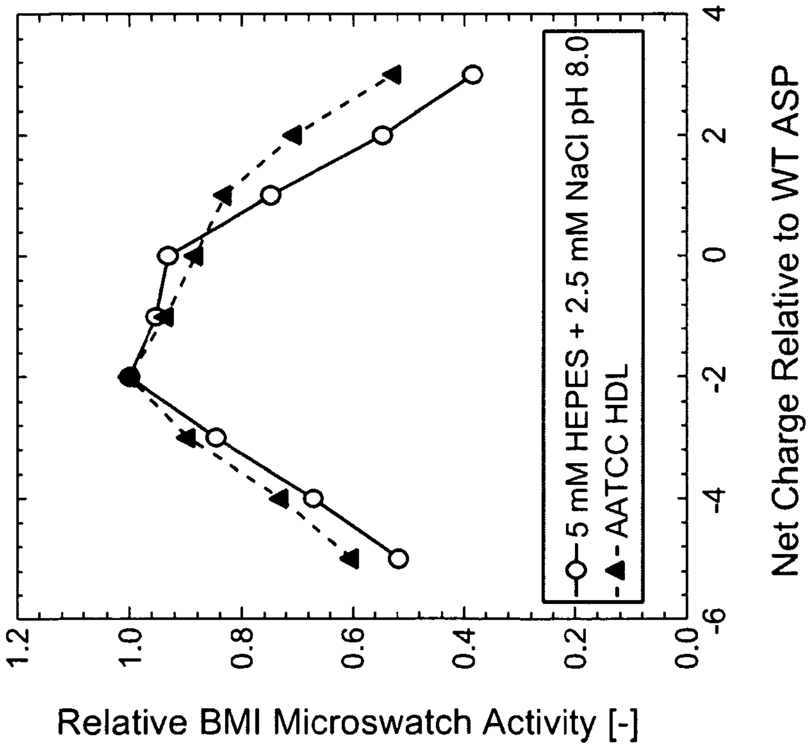
FIG. 1 depicts relative blood, milk, ink (BMI) microswatch activity (normalized with respect to best performer) of ASP variants as a function of net charge change relative to wild type ASP as measured in AATCC liquid detergent (filled triangles) and a buffer (unfilled circles) of matching pH and conductivity (5 mM HEPES pH 8.0, 2.5 mM NaCl).

As shown in FIG. 1, there is an optimal net charge change for cleaning performance for ASP in AATCC HDL detergent. Performance is measured in terms of relative cleaning performance observed in a BMI microswatch activity assay. A value of around 1.0 indicates top. cleaning performance in this assay. As evidenced from the figure, accumulation of extreme negative (−5) or positive (+3) charges relative to the wild-type results in poor cleaning performance. There is a distinct charge optimum for cleaning performance centered at −2 relative to wild-type ASP. This is an example of optimizing a protein physical property (e.g., net charge) for improving a given outcome or benefit (e.g., cleaning performance in a liquid laundry detergent). The charge optimum identified with this limited set of probe proteins coincides with the optimum charge observed when measuring the entire ASP charge combinatorial library as shown in FIG. 2. The use of probe proteins is therefore predictive of the behavior of the entire library.

Figure 3:
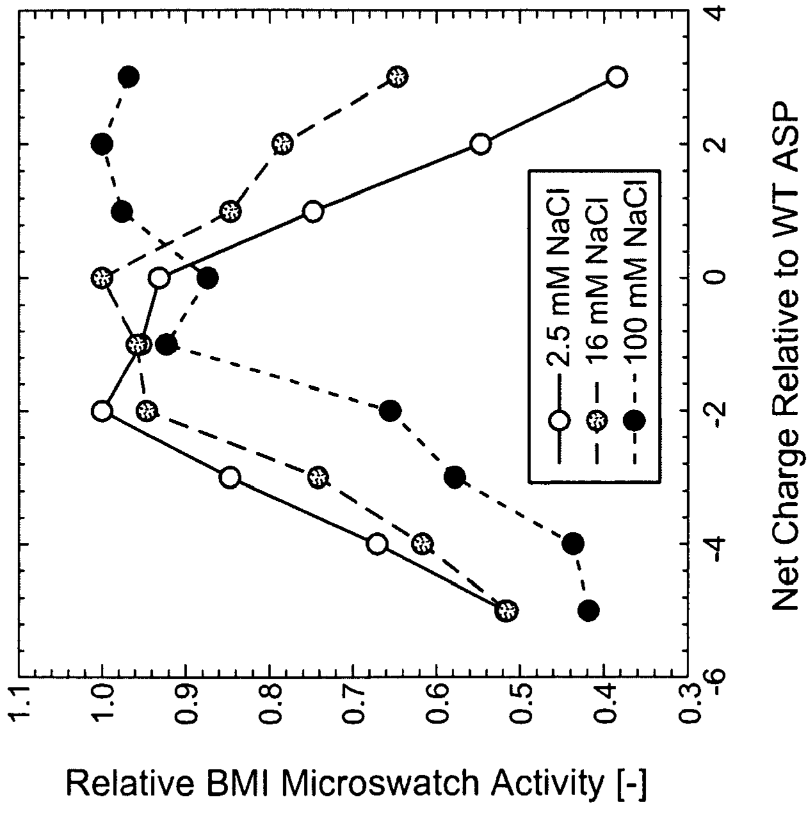
FIG. 3 depicts relative BMI microswatch activity (normalized with respect to best performer) of ASP variants as a function of charge change relative to wild-type ASP as measured in 5 mM HEPES pH 8.0 with varying NaCl concentration: 2.5 mM (unfilled circles), 16 mM (gray circles) and 100 mM (black circles).

According to the Debye-Hückel theory (Israelachivili, Intermolecular and Surface Forces, Second Edition: With Applications to Colloidal and Biological Systems, Academic Press $2^{nd}$ Ed. [1992]), electrostatic interactions are governed primarily by the strength of double-layer forces between interacting species at constant potential or constant charge (enzymes, substrates, fabric, and detergent), their size, and the dielectric constant of the surrounding medium. In order to characterize the electrostatic behavior of particles in a complex medium, such as a detergent formulation, their interaction in a reduced environment possessing the same Debye screening length is sufficient. This was accomplished by choosing a buffer of matching pH and conductivity to that of the detergent under wash conditions. As indicated in FIG. 1, screening of the ASP charge ladder in this buffer correctly predicted the charge optimum at −2 observed in with the AATCC detergent (filled circles). FIG. 3 depicts relative BMI stain removal as a function of charge change relative to wild-type ASP, in 5 mM HEPES buffer at pH 8.0 with varying amounts of indifferent electrolyte, in this case NaCl. Addition of 2.5 mM NaCl to this buffer matches the pH and conductivity of typical North American wash conditions. Addition of a higher concentration of NaCl is representative of Japanese and European wash conditions, typically higher in ionic strength due to both increased water hardness and detergent concentrations. Thus, the ASP charge optimum is a function of the solution environment (e.g., detergent formulation).

There are two features that become immediately apparent. First, usage of a model system consisting of a limited number of probe proteins for a given physical property (e.g., charge ladder ASP variants) in a reduced buffer environment of matching pH and conductivity is predictive of the behavior of a large ASP library screened under detergent conditions. Indeed, the charge optimum shown in FIG. 1 measured in buffer containing 2.5 mM NaCl (unfilled circles) is identical to the optimum observed for this ASP charge-ladder screened in AATCC detergent under North American wash conditions. Second, the location of the charge optimum is a strong function of ionic strength. With further addition of NaCl shifting the charge optimum towards variants with a positive charge relative to wild type ASP. In short, the usage of charge ladder protein probes allows rapid prediction of the performance of different enzyme variants across formulations representative of diverse geographical markets.

Figure 4A:
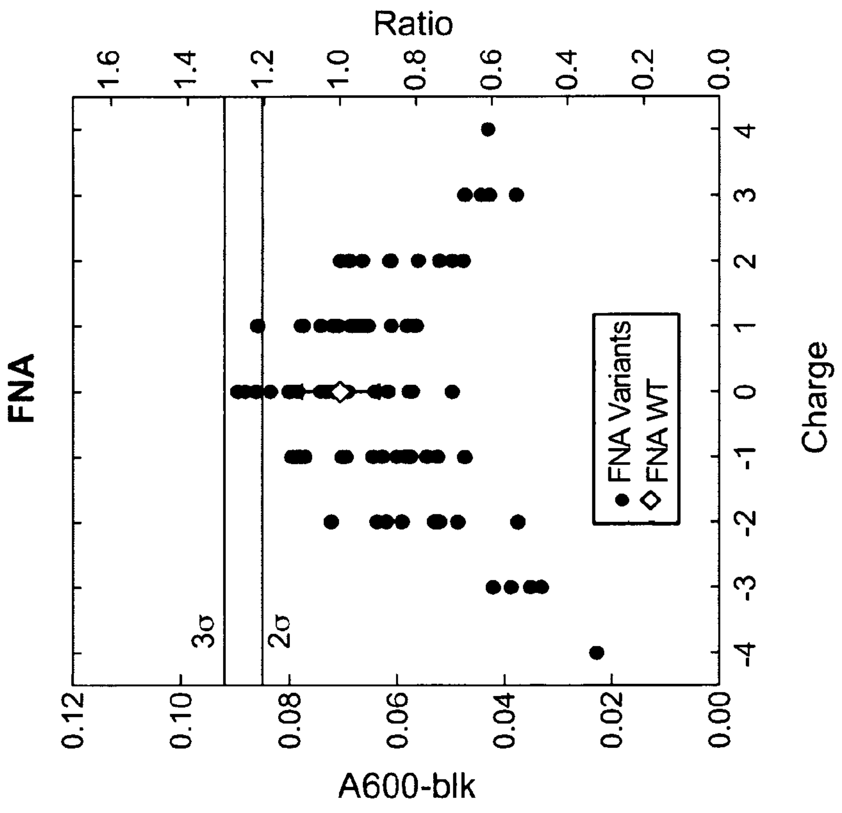
FIG. 4 depicts relative blood, milk, ink (BMI) microswatch activity (normalized with respect to parent molecule) of FNA (panel A) and GG36 (panel B) charge combinatorial library variants (filled symbols) as a function of net charge change relative to parent FNA or wild type GG36 (unfilled symbols) as measured in North American liquid laundry conditions.
Figure 4B:
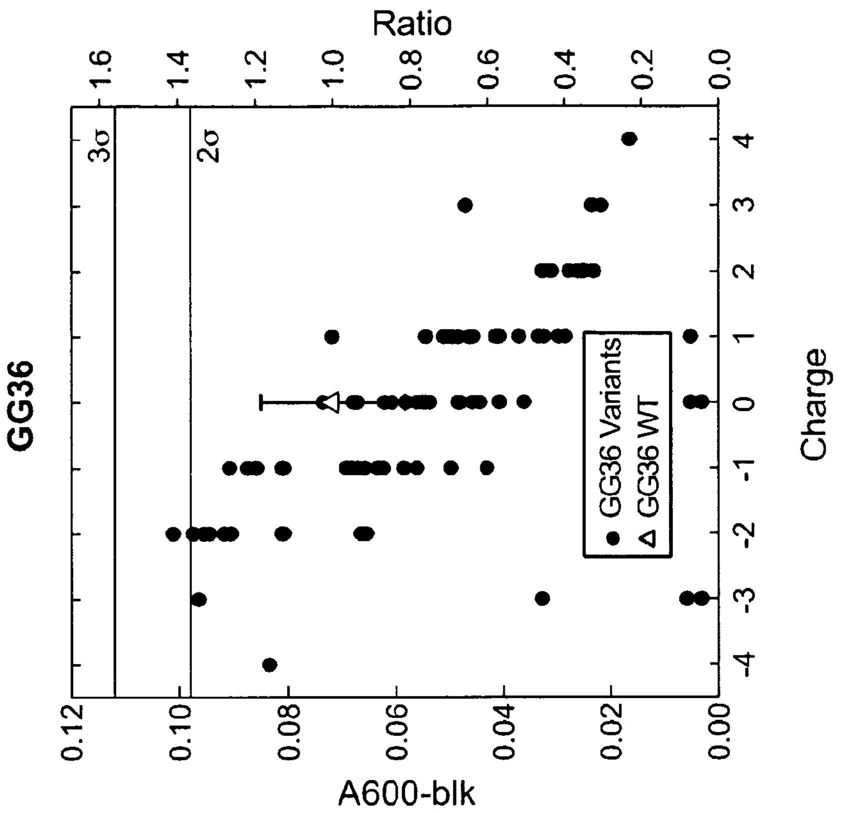
Figure 5A:
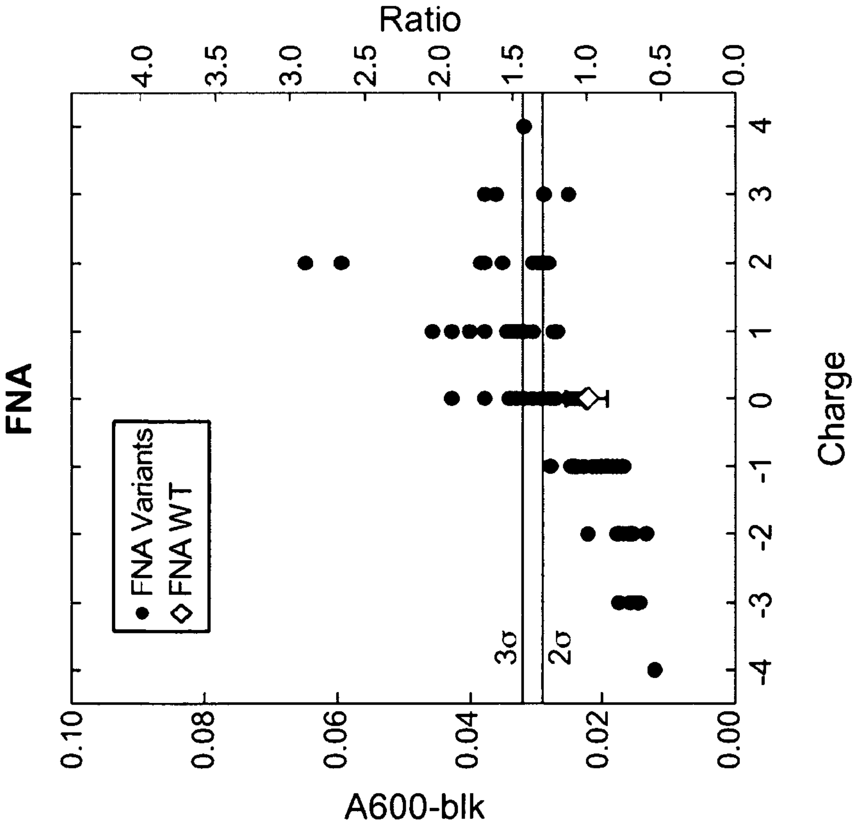
FIG. 5 depicts relative blood, milk, ink (BMI) microswatch activity (normalized with respect to parent molecule) of FNA (panel A) and GG36 (panel B) charge combinatorial library variants (filled symbols) as a function of net charge change relative to parent FNA or wild type GG36 (unfilled symbols) as measured in Western European liquid laundry conditions.
Figure 5B:
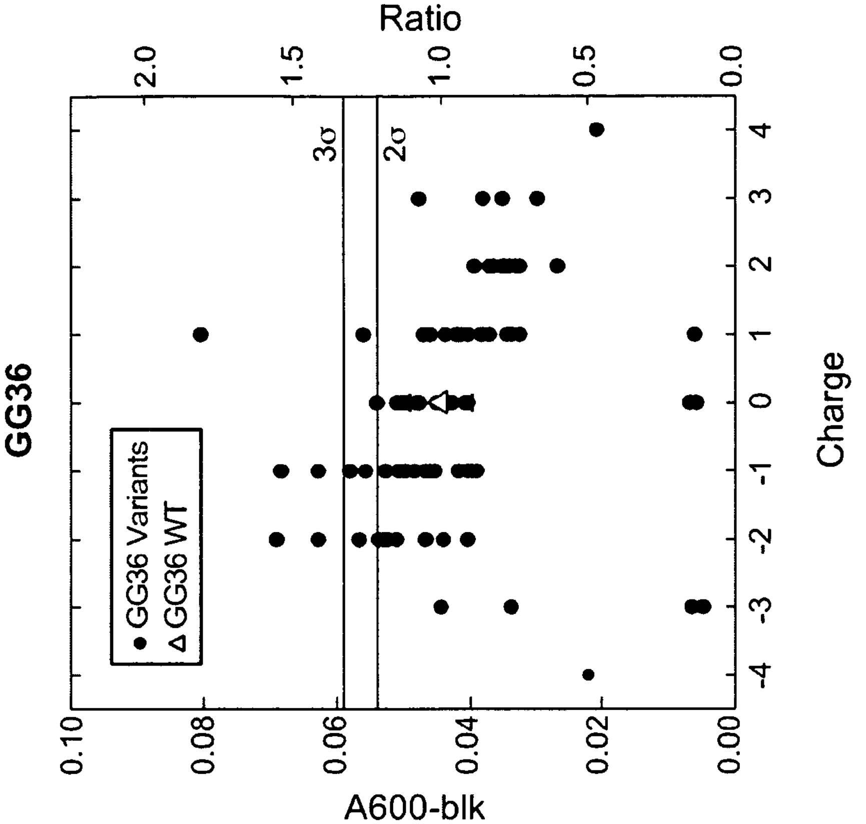
Figure 6B:
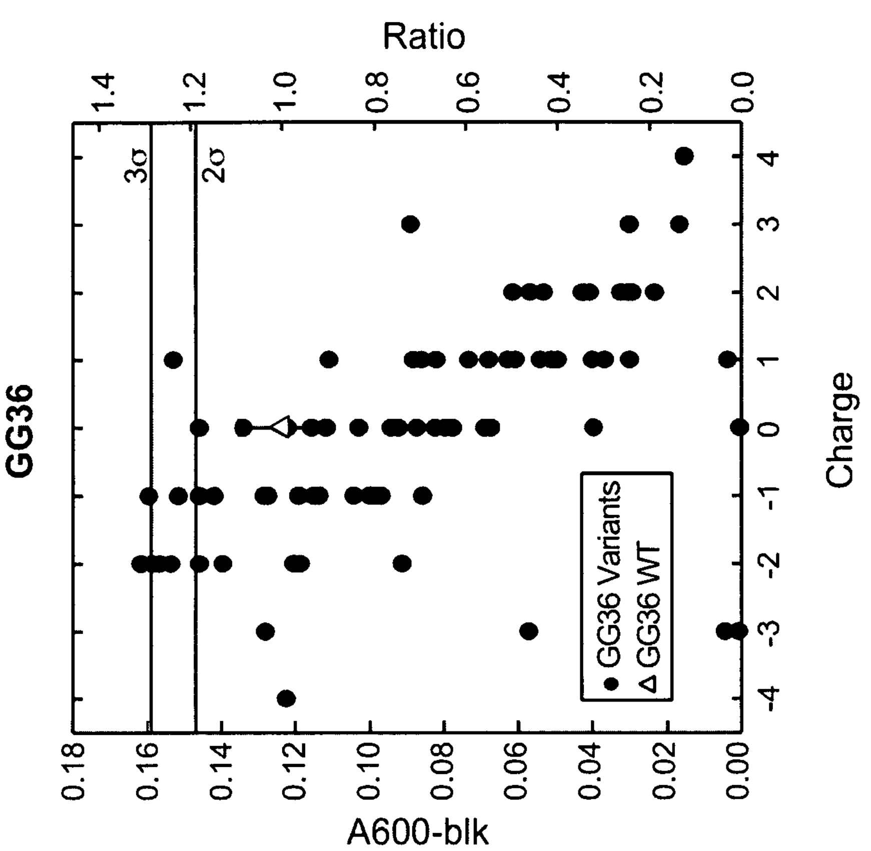
FIG. 6 depicts relative blood, milk, ink (BMI) microswatch activity (normalized with respect to parent molecule) of FNA (panel A) and GG36 (panel B) charge combinatorial library variants (filled symbols) as a function of net charge change relative to parent FNA or wild type GG36 (unfilled symbols) as measured in Japanese laundry powder conditions.
Figure 6A:
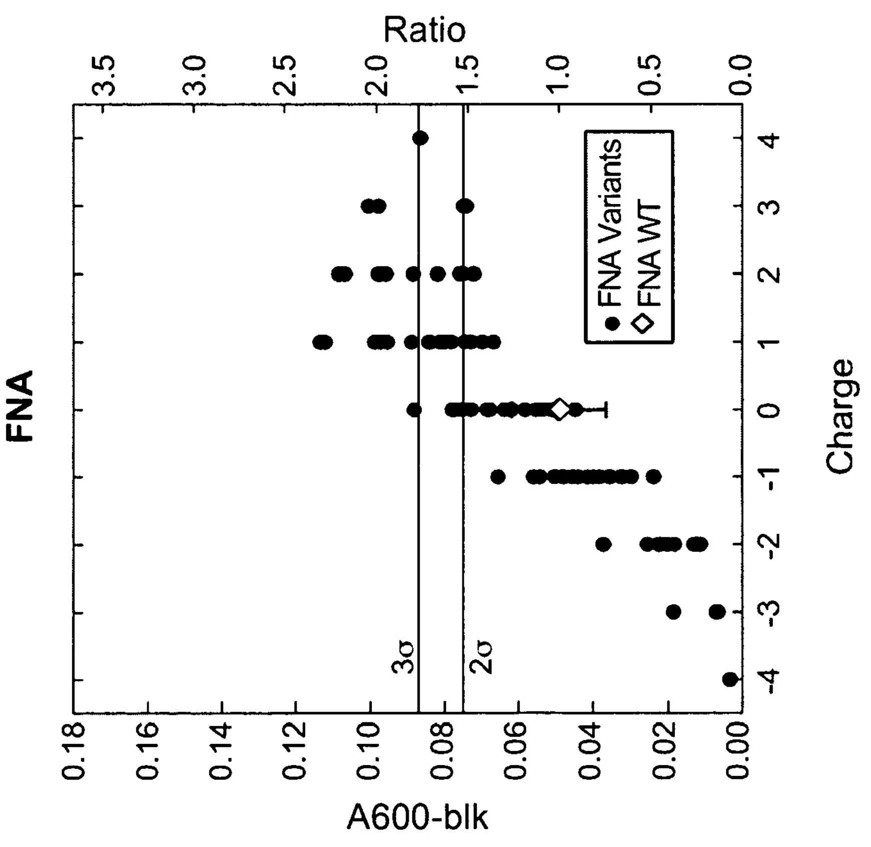
Figure 7B:
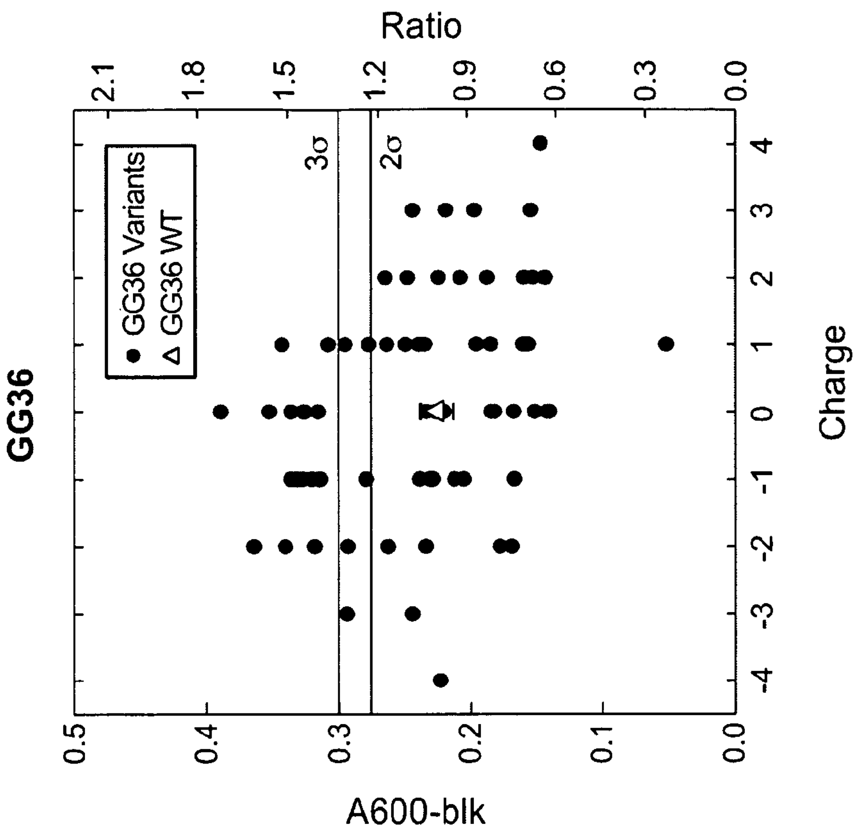
FIG. 7 depicts relative baked egg microswatch activity (normalized with respect to parent molecule) of FNA (panel A) and GG36 (panel B) charge combinatorial library variants (filled symbols) as a function of net charge change relative to parent FNA or wild type GG36 (unfilled symbols) as measured in Western Europe automatic dish washing conditions.
Figure 7A:
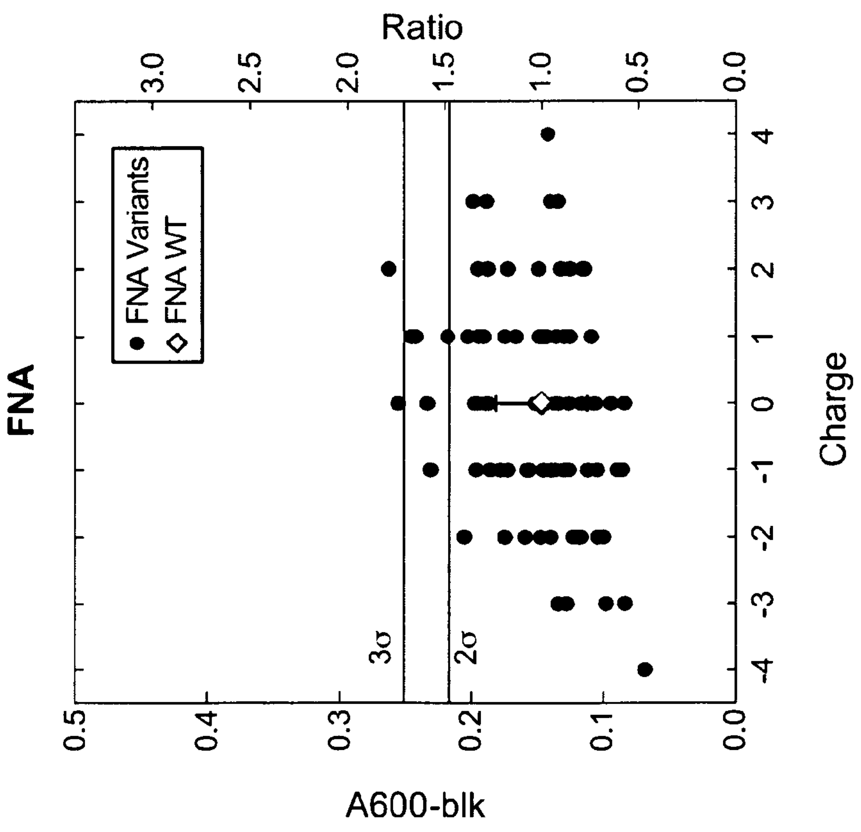

The above observations hold for other serine proteases such as the subtilisins FNA and GG36. For instance FIGS. 4A and 4B shows an optimum charge for FNA and GG36 respectively, in cleaning performance under North American laundry conditions using TIDE 2× detergent. The left Y-axes shows microswatch cleaning performance, where a higher number indicates superior BMI stain removal. The right Y-axes shows the performance index defined as cleaning performance of variants (filled symbols) relative to the parent molecule (unfilled symbols). The horizontal lines indicate a performance index at either 2 or 3 standard deviations above the noise of the assay. The FNA charge combinatorial library (CCL) exhibits a charge optimum at zero charge changes with respect to the parent FNA while the GG36 CCL exhibits an optimum at negative two charges relative to the GG36 parent.

FIGS. 5A, 5B, 6A, 6B, 7A and 7B demonstrate that the location of the charge optimum is a function of the solution environment determined by detergent formulation, pH, temperature and ionic strength due to water hardness and detergent concentration. For instance the charge optimum for FNA CCL shifts dramatically from zero under North American laundry conditions to more positive charges under Western European and Japanese conditions. Moreover the charge optimum is observed for both liquid and granular (powder) laundry detergent formulations. Similarly, a charge optimum was observed for both FNA and GG36 CCL in automatic dish washing (ADW) detergent against (e.g., Reckitt Benckiser Calgonit 40° C., 12 gpg, pH 10) baked egg as the enzyme substrate.

As demonstrated during development of the present invention, the cleaning performance of protease charge variants (e.g., ASP, GG36, FNA, etc) in different detergents is largely dominated by the working solution pH and conductivity. Final conductivity is a measure of ionic strength and is due to water hardness, detergent concentration and composition. For instance, there is a correlation between cleaning performance of GG36 and FNA variants against baked egg stains under European and North American ADW detergent when carried out at pH 10.6 and conductivity of 3.0 mS/cm. In particular, cleaning performance of charge variants is well correlated provided pH and conductivity are the same. This finding makes it possible to screen enzyme performance using a given detergent, for extrapolation of those results to another detergent of matching pH and conductivity. Likewise it is possible to screen enzyme performance in a buffer of matching pH and conductivity, for extrapolation of those results to a detergent exhibiting similar working pH and conductivity.

Figure 9:
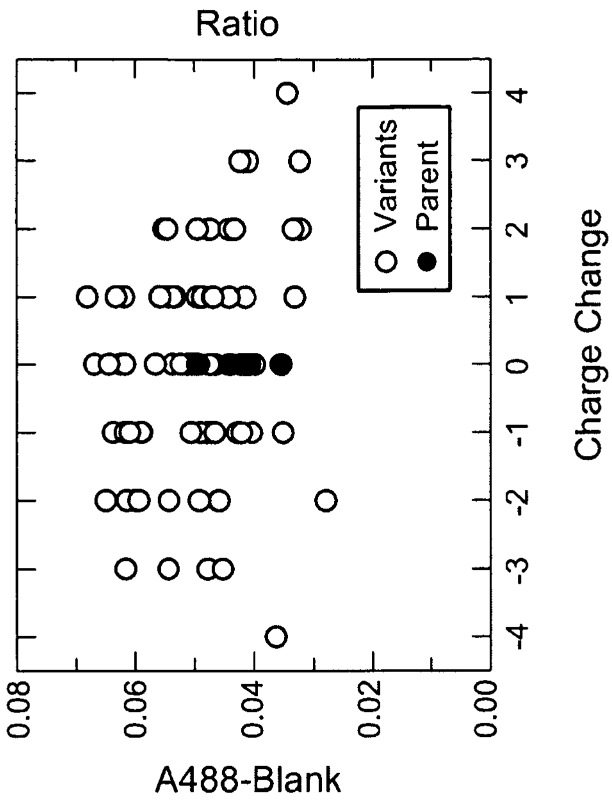
FIG. 9 depicts rice starch microswatch activity (normalized with respect to parent) of TS23t charge combinatorial library variants (unfilled symbols) as a function of net charge change relative to parent (filled symbols) as measured in Western European laundry conditions.
Figure 8:
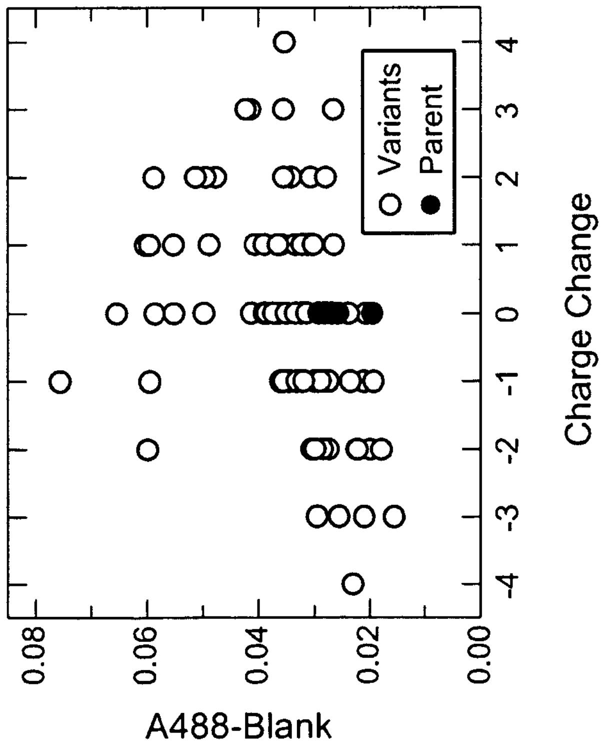
FIG. 8 depicts rice starch microswatch activity (normalized with respect to parent) of S242Q charge combinatorial library variants (unfilled symbols) as a function of net charge change relative to parent (filled symbols) as measured in North American laundry conditions.
Figure 10:
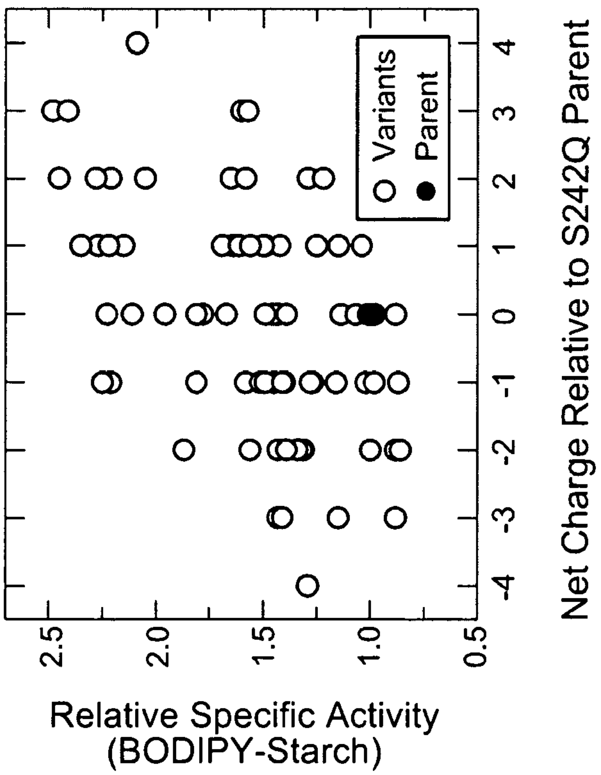
FIG. 10 depicts relative specific BODIPY starch hydrolysis activity (normalized with respect to parent) of S242Q charge combinatorial library variants (unfilled symbols) as a function of net charge change relative to parent (filled symbols).

Likewise there is a charge optimum for cleaning performance of amylase charge variants (e.g., AmyS-S242Q, and AmyTS23t, etc.) in cleaning applications, which is a strong function of the working solution pH and conductivity. Specifically, as determined during development of the present invention, positive charge change variants of S242Q are superior for the cleaning of rice starch microswatches under North American laundry conditions (e.g., TIDE 2×) as indicated in FIG. 8, while negative charge change variants of AmyTS23t are superior for the cleaning of rice starch microswatches under Western European laundry conditions, as indicated in FIG. 9. Furthermore, these observations hold true for amylase used in starch hydrolysis reactions. As shown in FIG. 10, positive S242Q variants exhibit higher specific activity for hydrolysis of BODIPY starch substrates.

Figure 11:
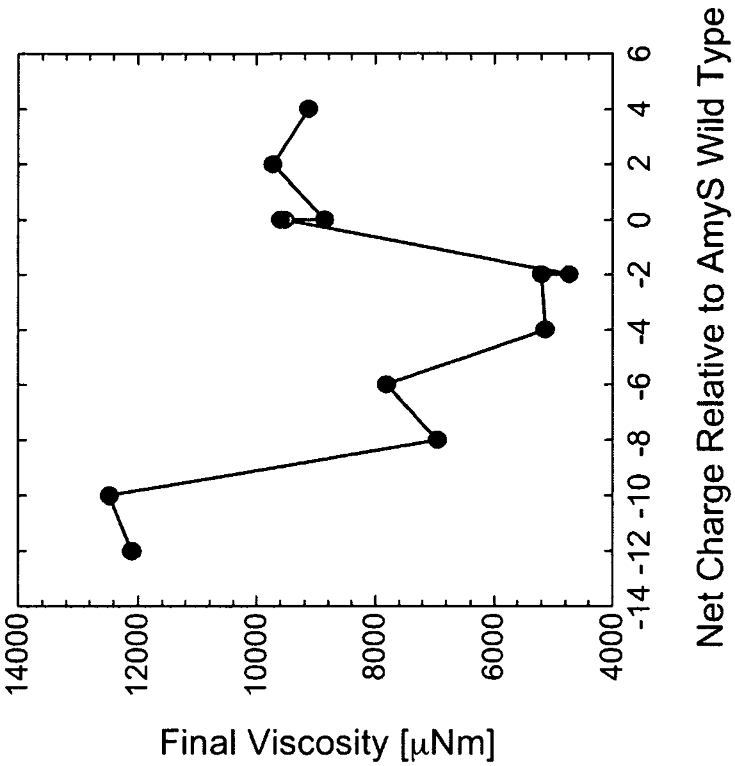
FIG. 11 depicts final viscosity of first AmyS charge ladder as a function of net charge change relative to wild type AmyS.

Starch liquefaction by the AmyS charge ladder variants was determined by monitoring the final viscosity following liquefaction of corn starch. A low viscosity value is indicative of breakdown of starch polysaccharides. As shown in FIG. 11, a charge optimum (e.g., −4 to −2) was observed for liquefaction. AmyS variants that were too negative (e.g., −12 to −10) exhibited very high final viscosities, and variants that were too positive (e.g., +6 or greater) exhibited even higher final viscosities (e.g., beyond limits of lab instrumentation due to torque overload).

Example 7

Zeta Potential Determinations

This Example describes determining the zeta potential of an enzyme and a substrate. The presence of a charge on the surface of a particle influences the distribution of ions in the surrounding interfacial region. The result is an increased concentration of counter ions of opposite charge to that of the particle near the particle surface. As one moves away from the particle surface, the heterogeneous distribution of ions will eventually become homogeneous. The distance at which a homogenous distribution is obtained is called the Debye length ($1/\kappa$) or screening distance, and is dependent upon the ionic strength as shown in the expression below, where $\in_0$ is the permittivity of free space ($8.854\times10^{-12}$ F $m^{-1}$), $\in_r$ is the permittivity of the liquid, k is the Boltzmann constant ($1.38\times10^{-23}$ J $K^{-1}$), T is the temperature in Kelvin, e is the electronic charge ($1.6022\times10^{-19}$ C), I is the molar ionic strength, and NA is Avogadro's constant ($6.022\times10^{23}$ $mol^{-1}$).

$$\text{Debye length} = \frac{1}{k} = \sqrt{\frac{e_0 e_r kT}{NAe^2 2I}} \quad (0.1)$$

The molar ionic strength can be calculated from the following equation, where $C_i$ is the ionic species concentration and $Z_i$ is the valency.

$$I = \frac{1}{2}\text{å}c_i z_i^2 \quad (0.2)$$

For water at 298 K, the Debye length expression reduces to the following form.

$$k^{-1}=0.304(I^{-0.5}) \quad (0.3)$$

The liquid layer surrounding the particle exists as two parts; an inner region (Stern layer) where the ions are strongly bound and an outer (diffuse) region where they are less firmly associated. Within the diffuse layer there is a boundary inside which the ions and particles form a stable entity. When a particle moves, ions within this boundary move with it. Those ions beyond the boundary do not travel with the particle. The electric potential at this boundary, also called the surface of hydrodynamic shear, is defined as the zeta potential.

In electrophoretic light scattering, the zeta potential z is calculated from the measured electrophoretic mobility u using the Henry equation shown below, where ∈ is the dielectric constant, h is the solution viscosity, κ is the inverse Debye length, α is the particle radius, and ƒ(κα) is the Henry function.

$$u = \frac{2ez}{3h} f(ka) \quad (0.4)$$

The units of κ are reciprocal length, with 1/κ being the "thickness" of the electrical double layer (Debye length). The parameter α refers to the radius of the particle, and therefore, κα is the ratio of the particle radius to the electrical double layer thickness. The Henry function, ƒ(κα) depends on particle shape, but is known for a sphere. In the expression above it ranges from ƒ(0)=1 (Hückel limit) to ƒ(¥)=1.5 (Smoluchowski limit). For small particles such as proteins in a low dielectric (or low ionic strength) medium, the Hückel limit of ƒ(κα)=1 is the more appropriate model.

Zeta potentials of proteins were measured with the Zetasizer NS (Malvern Instruments, UK) according to the principle outlined above. Zeta potentials of BMI-stained fabrics were measured with the SurPass (Anton-Paar, Austria) using the streaming potential implementation of the above principle. From the definition of surface charge, usually expressed in Coulombs:

$$q_S=4pe_oe_r\alpha(1+k\alpha)z \quad (0.5)$$

This can also be expressed as a net charge z multiplied by the elementary charge e 1.6*10−19C:

$$q_S=ze \quad (0.6)$$

Therefore the expected change in zeta potential due to a net charge increment is given by:

$$\frac{Dz}{Dz} = \frac{e}{4pe_oe_ra(1+ka)} \quad (0.7)$$

It is also possible to measure zeta potentials using a native gel technique (Sparks et al., Journal of Lipid Research, 33: 123-130 [1992]) as described in Example 1. Electrophoretic mobility measured with native gels is usually less than in solution due to retardation caused by the gel matrix. Zeta potentials calculated this way are usually lower compared to solution-based methods. We therefore refer to them as apparent zeta potentials when obtained via the native gel technique.

Figure 12:
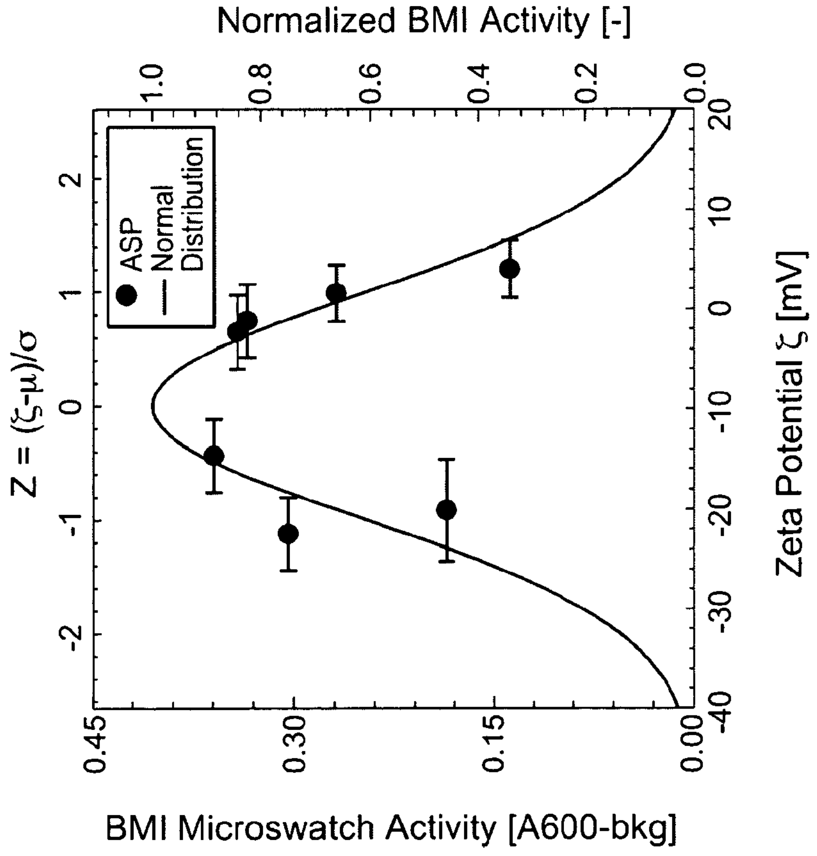
FIG. 12 depicts in the primary axis BMI microswatch activity of ASP variants versus zeta potential as measured in buffer (5 mM HEPES pH 8.0, 2.5 mM NaCl). The secondary axis indicates BMI microswatch activity of ASP variants (normalized by peak value of normal distribution fit, solid line) versus z-score. The zeta potential of the substrate stain is equal to −8.97 mV.

The effective charge in a given formulation is enumerated as its zeta potential. The use of zeta potential as a common charge scale allows comparison of enzyme variants having different folds (e.g., serine proteases, metalloproteases, etc.), as well as interactions with different substrates (e.g., BMI microswatch) under the conditions of interest (e.g., AATCC HDL detergent). Although zeta potential is preferred for comparing different protein folds, electrophoretic mobilities or measured charges also provide an absolute scale and are adequate for comparisons. FIG. 12 shows the BMI performance (left Y axis) as a function of zeta potential (bottom X axis) for a serine protease ASP (black circles). The ASP charge ladder variants span a range of 8 charges relative to the wild type ASP. As described in Example 5, there is a net charge optimum for cleaning performance. FIG. 12 illustrates that BMI performance as a function of enzyme zeta potential is well described by a standard normal distribution, indicated by the solid line, with a mean μ equal to −9.68 mV, standard deviation σ of 11.39 mV and peak value of 0.4056 [A600-background]. This distribution is indicated in standard reduced coordinates by the BMI activity divided by the peak value on the right Y-axis as a function of the Z score on the top X-axis. The Z score is defined as usual as (X−μ)/σ where X in this case is zeta potential.

TABLE 7-1

BMI Microswatch Activity of Proteases

| Performance Level | Z Score | Zeta Potential ζ Window* For BMI Microswatch Activity |
|---|---|---|
| 90% | ±0.46 | −14.92 < ζ < −4.44 |
| 80% | ±0.65 | −17.08 < ζ < −2.28 |
| 70% | ±0.84 | −19.25 < ζ < −0.11 |
| 60% | ±1.00 | −21.07 < ζ < +1.71 |
| 50% | ±1.18 | −23.12 < ζ < +3.76 |

*Mean μ = −9.68 mV, standard deviation σ = 11.39 mV, Zeta potential ζ = Z * σ + μ
Reference buffer: 5 mM HEPES pH 8.0, 2.5 mM NaCl The normal distribution is unique to each substrate stain under given reaction conditions (pH, conductivity, type of salt, detergent chelators, etc.). Different benefits or favorable outcomes follow a normal distribution with a physical property that holds across enzymes from various folds, as is for instance, the case of expression levels and zeta potentials for ASP and NprE charge ladder variants. In a normal distribution the peak value occurs at the mean. Comparison of enzyme and substrate charges on a common zeta potential scale reveals that optimum BMI performance occurs when the mean enzyme zeta potential in this case −9.68 mV, essentially matches the substrate stain zeta potential, in this case −8.97 mV, measured under the same conditions.

Performance levels of standard normal distributions are conveniently described in terms of their z scores as indicated in Table 7-1 (See, Abramowitz and Stegun, Handbook of Mathematical Functions with Formulas, Graphs, and Mathematical Tables, Dover, N.Y., 9th Ed. [1964]). Conversion to zeta potentials is straightforward given knowledge of the mean and standard deviation defining the distribution for a given application. In this example measured cleaning performance for a protein fold is confined to zeta potential values between −40 mV and +20 mV. Variants with a cleaning performance above 80% of their fold optimum (i.e., z=±0.65), are confined to zeta potential values between −17.08 mV and −2.28 mV. Variants with a cleaning performance above 90% of their fold optimum (i.e., z=±0.46), are confined to zeta potential values between −14.92 mV and −4.44 mV.

Different substrate stains (e.g., grass, body soils, tomato) have different zeta potentials under the same formulation and the same substrate stain has different zeta potentials under different formulations (e.g., North American HDL, European powder dishwashing detergent). Regardless, while the substrate stain charge varies, the standard deviation of the normal distribution is expected to remain constant. Knowledge of enzyme and substrate zeta potentials in a given detergent formulation allows rapid identification of the expected performance level for that variant, as well as the direction and magnitude of charge change needed in order to achieve optimal performance levels. Measurement of the substrate zeta potential in the desired reaction medium allows optimization of the enzyme reaction on the particulate substrate in that medium. Any enzyme reaction in any medium can be optimized using a similar process.

In some embodiments, stain-specific enzymes are obtained by optimizing enzyme performance on a specific stain under a given condition. This is achieved by measuring the zeta potential of the stain under the stain removal condition and then altering the enzyme to yield variant(s) having an essentially equivalent zeta potential under the same condition (e.g., zeta-potential corresponding to at least about 80%, about 90%, about 95%, about 97% or about 99% of the optimum performance). In some embodiments, this is accomplished by modifying one or more amino acids on the surface of an enzyme by genetic or chemical modification. In other embodiments, stain-specific enzymes are obtained by screening natural isolates or homologs of a probe enzyme to identify enzymes having a zeta potential within the target range. Although this example is directed to cleaning BMI stains, the methods of the present invention are also suitable for use in optimizing cleaning of other stains such as but not limited to grass, wine or urine. Similarly although this example is directed to serine protease activity, the methods of the present invention are also suitable for use in optimizing activity of other enzymes such as but not limited to proteases, amylases, cellulases, lipases, polyesterases, esterases, cutinases, pectinases, mannanases and oxido reductases.

Example 8

Enzyme-to-Substrate Stain Partition

Figure 13:
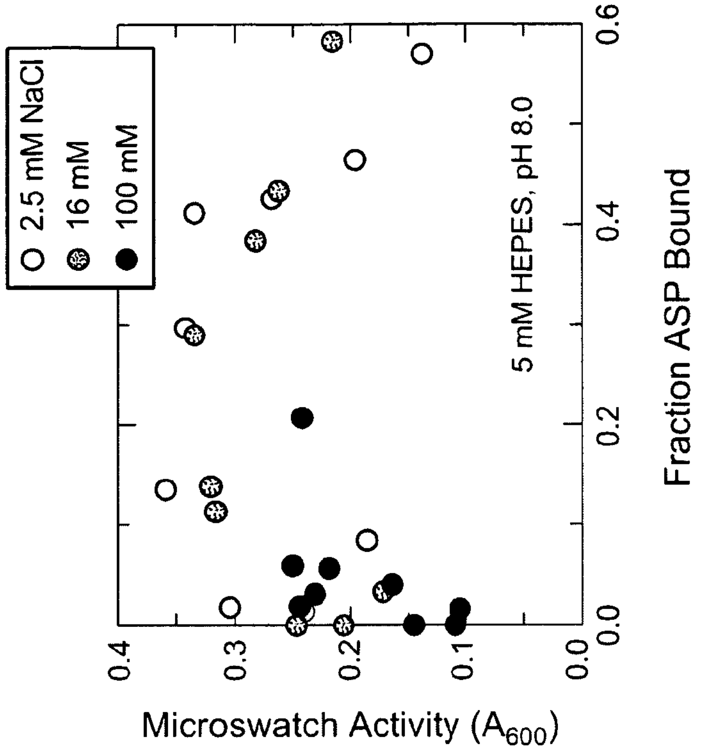
FIG. 13 depicts BMI microswatch activity of ASP variants versus the fraction of ASP bound as measured in 5 mM HEPES pH 8.0 with varying NaCl concentration: 2.5 mM NaCl (unfilled), 16 mM NaCl (gray) and 100 mM NaCl (black).

This Example describes determining the relationship between enzyme charge, substrate stain partitioning and cleaning performance. FIG. 13 and the following tables show cleaning performance of ASP charge ladder probe proteins in 5 mM HEPES pH 8.0 buffer under varying ionic strength, measured as BMI microswatch activity as a function of enzyme partition to the substrate stain measured by depletion. Ionic strength was controlled by addition of varying amounts of indifferent electrolyte: 2.5 mM NaCl (unfilled circles), 16 mM NaCl (gray circles) and 100 mM NaCl (filled circles). BMI cleaning performance of ASP charge ladder probe proteins drops off at both low and high enzyme to substrate stain partition. Optimal partition for cleaning performance occurs between 0.1 and 0.5 fractions of enzyme bound. While low performance with little enzyme-to-substrate partition is expected, the observation of low performance at high enzyme-to-substrate partition is not intuitive.

TABLE 8-1

| 5 mM HEPES pH 8.0 with 2.5 mM NaCl | | |
|---|---|---|
| Net Charge Change Relative to ASP Wild Type | BMI Microswatch Activity [A600-background] | Fraction Bound |
| −5 | 0.1857 | 0.0845 |
| −4 | 0.2407 | 0.0135 |
| −3 | 0.3040 | 0.0178 |
| −2 | 0.3590 | 0.1354 |
| −1 | 0.3420 | 0.2966 |
| 0 | 0.3343 | 0.4120 |
| +1 | 0.2683 | 0.4260 |
| +2 | 0.1963 | 0.4643 |
| +3 | 0.1380 | 0.5704 |

TABLE 8-2

| 5 mM HEPES pH 8.0 with 16 mM NaCl | | |
|---|---|---|
| Net Charge Change Relative to ASP Wild Type | BMI Microswatch Activity [A600-background] | Fraction Bound |
| −5 | 0.1717 | 0.0332 |
| −4 | 0.2057 | 1.0000e−5 |
| −3 | 0.2473 | 1.0000e−5 |
| −2 | 0.3157 | 0.1127 |
| −1 | 0.3197 | 0.1385 |
| 0 | 0.3337 | 0.2900 |
| +1 | 0.2823 | 0.3840 |
| +2 | 0.2617 | 0.4341 |
| +3 | 0.2157 | 0.5830 |

TABLE 8-3

| 5 mM HEPES pH 8.0 with 100 mM NaCl | | |
|---|---|---|
| Net Charge Change Relative to ASP Wild Type | BMI Microswatch Activity [A600-background] | Fraction Bound |
| −5 | 0.1047 | 0.0157 |
| −4 | 0.1093 | 1.0000e−5 |
| −3 | 0.1447 | 1.0000e−5 |
| −2 | 0.1640 | 0.0399 |
| −1 | 0.2310 | 0.0312 |
| 0 | 0.2187 | 0.0558 |
| +1 | 0.2443 | 0.0194 |
| +2 | 0.2503 | 0.0593 |
| +3 | 0.2423 | 0.2067 |

Figure 14:
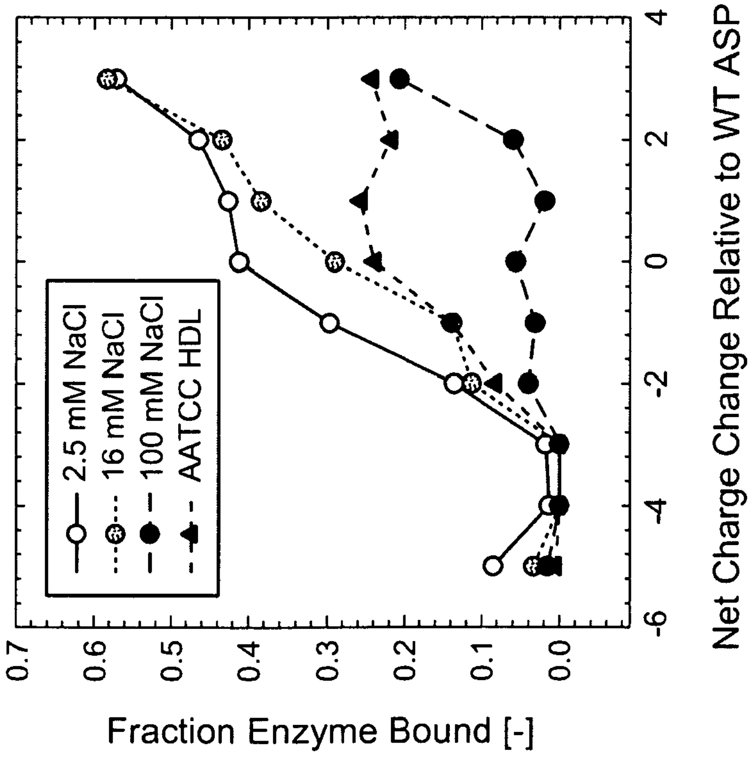
FIG. 14 depicts the fraction of ASP bound as a function of net charge change relative to wild type ASP as measured in AATCC HDL detergent (triangles) or 5 mM HEPES pH 8.0 with varying NaCl concentration: 2.5 mM NaCl (unfilled circles), 16 mM NaCl (gray circles) and 100 mM NaCl (black circles).

FIG. 14 shows the fraction of enzyme bound as a function of charge relative to wild type ASP in 5 mM HEPES pH 8.0 buffer under varying ionic strength (circles) and in AATCC HDL detergent (triangles). As evidenced from this figure, accumulation of extreme negative (−5) charge relative to wild type ASP results in little enzyme partition to the substrate stain and hence poor cleaning performance in low salt conditions. Likewise, as evidenced from this figure, an accumulation of extreme positive (+3) charges relative to wild type ASP results in excess enzyme partition to the substrate stain and hence poor cleaning performance in low salt conditions.

Figure 15:
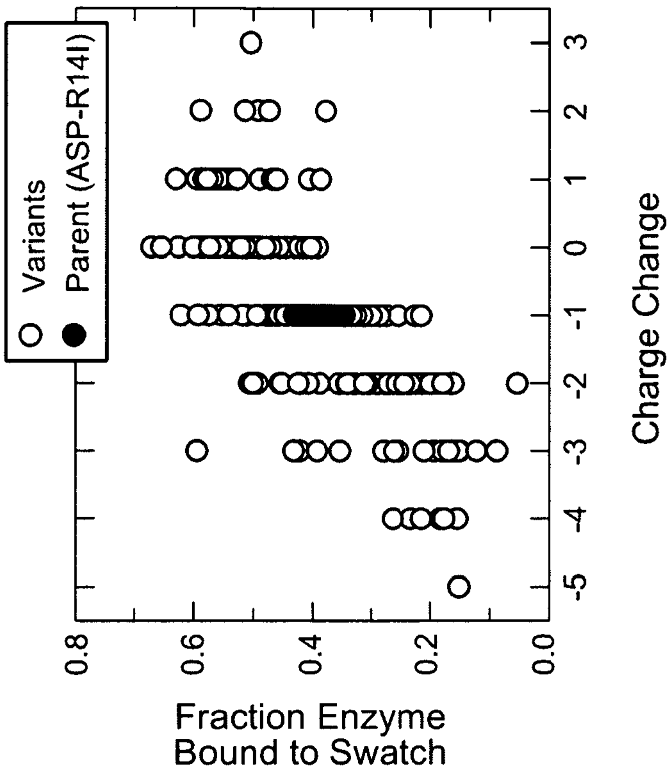
FIG. 15 depicts the fraction bound of ASP charge combinatorial variants (unfilled symbols) as a function of net charge change relative to parent ASP-R14I (filled symbols) as measured in 5 mM HEPES pH 8.0 with 2.5 mM NaCl.

Similarly a plot of the fraction of enzyme bound versus net charge change for the entire ASP charge combinatorial library in 5 mM HEPES pH 8 buffer with 2.5 mM NaCl shown in FIG. 15 resembled the plot obtained for the ASP charge ladder variants. Once again the use of probe proteins (e.g., charge ladder) was representative of the behavior of the entire library. Thus, the use of ASP charge ladder probe proteins allows the rapid identification of optimal charge for enzyme partition to a substrate stain. In this case a net charge range between −2 and +2 relative to wild type ASP corresponds to a fraction bound within 0.1 and 0.5, optimal for cleaning performance in low salt conditions. This is an example of optimizing a protein physical property, in this case net charge/hydrophobicity, for modulating enzyme-substrate binding.

Figure 16:
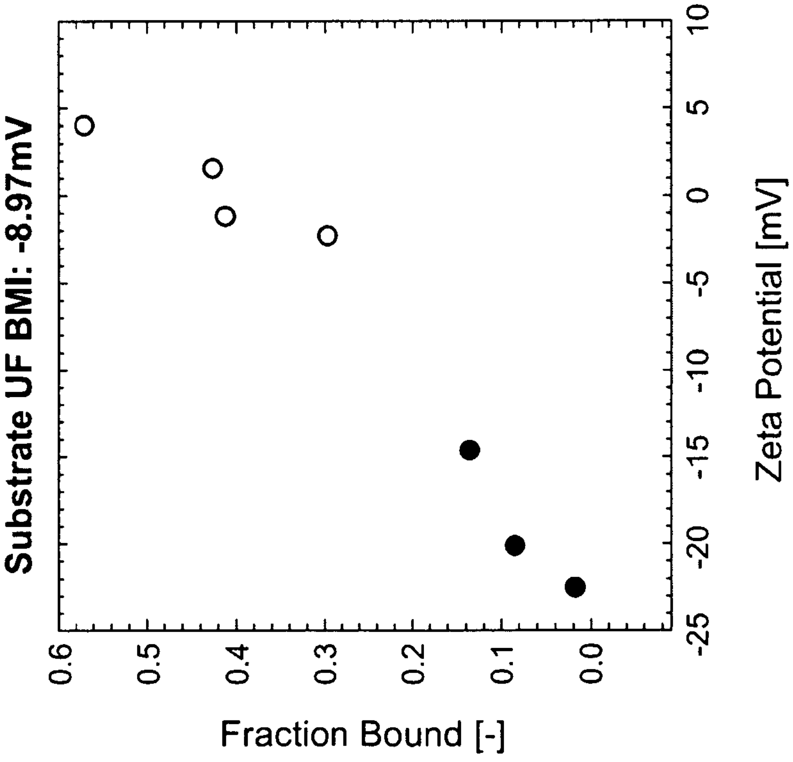
FIG. 16 depicts the fraction of ASP bound as a function of zeta potential measured in 5 mM HEPES pH 8.0 with 2.5 mM NaCl.

FIG. 16 shows the fraction of enzyme bound to the substrate stain as a function of enzyme zeta potential in 5 mM HEPES pH 8.0 buffer with 2.5 mM NaCl. As expected the overall profile is similar to that previously described in FIG. 14, with the same amount of added indifferent electrolyte. The substrate stain zeta potential is equal to −8.97 mV.

Without being bound by theory, negatively charged enzyme variants shown as filled circles (e.g., more negative than −15 mV), are repelled upon approach to the negatively-charged substrate stain, resulting in low partition. Conversely, positively charged variants shown as unfilled circles (e.g., above the point of zero charge), are attracted to the negatively-charged substrate stain resulting in high partition. Thus there is an optimal partition for cleaning performance.

In general for any combination of enzyme, substrate and solution conditions, partition to a substrate stain is confined to a zeta potential window centered at the substrate stain zeta potential value measured under the same conditions, in this case −8.97 mV. The width of the zeta potential window determines the expected fraction bound. For instance a zeta potential window 30-mV wide given by −8.97 mV±15 mV encompasses substrate partition between less than 0.1 (low binders) and greater than 0.5 (high binders). A zeta potential window 20-mV wide given by −8.97 mV±10 mV encompasses substrate partition between more than 0.1 and less than 0.5. A zeta potential window 10-mV wide given by −8.97 mV±5 mV between 0.15 and 0.4 may be considered optimal for cleaning performance for this substrate stain under these conditions.

Different substrate stains (e.g., grass, body soils, tomato, etc.) have different zeta potentials under the same formulation and the same substrate stain has different zeta potentials under different formulations (e.g., North American HDL, European powder dishwashing detergent). Regardless, the zeta potential window encompassing different substrate partition levels is expected to remain constant. Knowledge of enzyme and substrate zeta potentials in a given detergent formulation allows rapid identification of the expected substrate partition level for that variant, as well as the direction and magnitude of charge change needed in order to achieve optimal partitioning. Thus, measurement of the substrate zeta potential in the desired reaction medium allows optimization of the enzyme reaction on the particular substrate in that medium. Any enzyme reaction in any medium can be optimized using a similar process. Conversely knowledge of zeta potential of the supporting fabric matrix (i.e., ballast) finds use to prevent binding. While a BMI stain has a zeta potential of −8.97 mV, the unstained underlying cotton fabric has a zeta potential of −14.43 mV.

Although this example is directed to serine protease partitioning from BMI substrate stains, the methods of the present invention are also suitable for use in optimizing partitioning of other enzymes and substrates. For instance the methods of the present invention are suitable for use in optimizing partitioning of cellulase variants to fabrics or biomass as described in Example 14. In some embodiments, the zeta potential of the fabric to be treated under the application conditions is measured, and cellulase variants are obtained that differ up to +/−30 mV from the zeta potential of the fabric are obtained. These variants are obtained by genetic engineering or chemical modification. Variants are then screened for surface polishing performance and tensile strength loss under application conditions in buffer for textile applications or in detergents for cleaning applications. Thus, cellulase variants with optimal surface polishing performance and minimal tensile strength loss can be efficiently identified using this method. Additionally cellulase variants with optimal binding to plant biopolymer substrates for increased saccharification towards the production of fuel ethanol can be easily identified using this method.

Example 9

Protein Expression

This Example describes determining the relationship between protein charge and protein expression.

Production of ASP Variants on a 14 L Fermentor Scale

A set of fed-batch fermentations on a 14 L scale were carried out to compare the production levels of the ASP protease combinatorial charge library variants (R14I-N112E-T116E-R123F-R159F, R14I-N112E-T116E-R123F, R14I-N112E-T116E, R14I-N112E, R14I, R14I-D184T, R14I-D184T-T86K, R14I-T86K-D184T-A64K and R14I-T86K-D184T-A64K-Q81K), which vary in charge from −5 to +3. Seed cultures were grown by inoculating 2 L unbaffled shake flasks containing 600 mL of culture media (LB broth+1% glucose+20 mg/L neomycin) with 1 mL of *Bacillus subtilis* glycerol stock corresponding to each variant. The cultures were incubated at 37° C., with agitation at 175 rpm in a shaking incubator until $OD_{550}$ reached 0.8-1.5. At that time, the entire seed cultures were transferred aseptically to 14 L fermentors equipped with an integrated controller to monitor: temperature, percent dissolved oxygen (% DO), pH and agitation. Off gases were monitored by in-line mass spectrophotometer. The fermentation media (7 L) that was used consisted of 10% soy meal in a phosphate based buffer containing magnesium sulfate, trace minerals, and additional neomycin at 20 mg/L. The initial fermentation parameters were set to: 37° C. temperature, pH 6.8 (adjusted with ammonium hydroxide during the run), 750 rpm agitation, 40% DO (maintained during run by adjusting air and agitation), 11 slpm airflow, and 1 bar pressure. Antifoam (Mazu DF204) was added on demand to control foaming. A fed batch process of 0.5 to 2.1 g/min of glucose linear feed over 10 hours was programmed (using 60% glucose solution for feed) with a pH rise as trigger. Fermentation sampling occurred every 4 hours, taking 15 mL of whole broth to perform the following measurements: cell density (measure absorbance at 550 nm) on spectrophotometer, ASP variant production, glucose, nitrogen, phosphate and total protein. The total fermentation run times were between 40 and 45 h.

Measurement ASP Variant Titer Using an Aaa-Pna Assay

Samples of the *B. subtilis* cultures obtained during the fermentation were assayed for the production of the variant ASP proteases. The enzymes produced were assayed for activity against the substrate, N-succinyl-Ala-Ala-Ala-p-nitroanilide (AAA-pNA). The assay measured the production of modified protease as the increase in absorbance at 405 nm resulting from the hydrolysis and release of p-nitroaniline (Estell et al., J Biol Chem, 260: 6518-6521 [1985]). Aliquots of the *B. subtilis* clarified supernatants from the fermentor were assayed in buffer containing: 100 mM Tris, 0.01 mM CaCl2, 0.005% Triton X-100, at pH 8.6. A wild type ASP protease standard served to generate a calibration curve for calculation of protein produced in g/L of fermentation broth.

Figure 17:
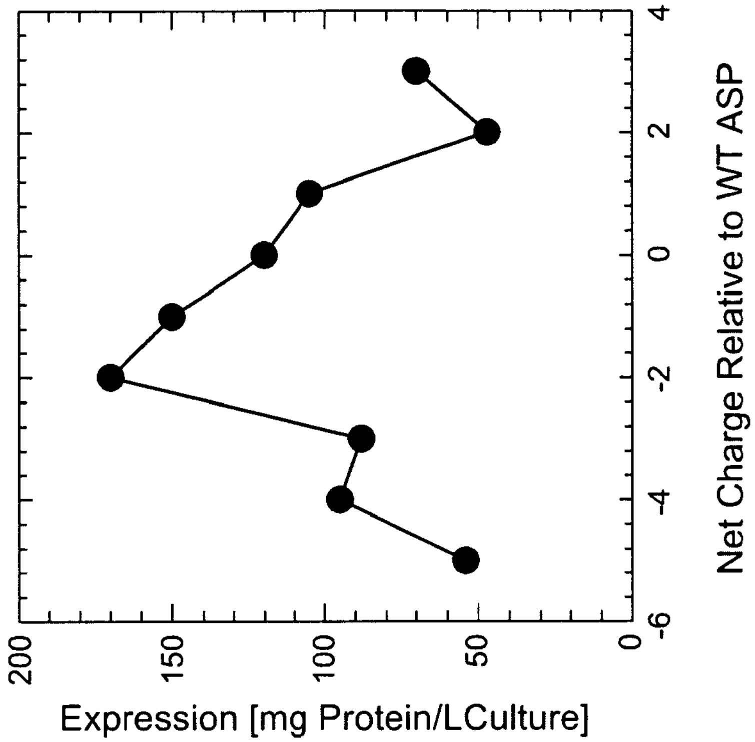
FIG. 17 depicts the expression levels of ASP variants in *Bacillus subtilis* as a function of net charge change relative to wild type ASP.

FIG. 17 depicts expression levels of ASP charge ladder probe proteins in *Bacillus subtilis* as a function of net charge relative to wild type ASP. As evidenced from this figure, accumulation of extreme negative (−5) or positive (+3) charge relative to wild type ASP results in poor expression levels. The use of ASP charge ladder probe proteins allows rapid identification of optimal net charge for improving expression in a given host organism. In this case a net charge range of between −2 and +1 relative to wild type ASP corresponds to optimal expression levels. At the charge optimum itself, observed for ASP (−2) nearly a 4-fold improvement in expression was observed as compared to variants having extreme charge changes. These observations at the shake flask level were confirmed at the 14 L fermentor scale. Table 9-1 shows two measures of expression in the 14 L fermentors, the ASP approximate titer at 40 h, as well as ASP production calculated from the linear portion of the expression curves. Shake flask titers are provided for reference in the last column. All titers have been normalized to ASP-R14I levels. A net charge change range of between −2 and +1 relative to wild type ASP corresponds to optimal expression levels at the fermentor scale. This is another example of optimizing a protein physical property, in this case net charge, for modulating a completely different benefit, in this case recombinant protein expression.

TABLE 9-1

*Bacillus subtilis* Expression of ASP Charge Ladder Variants at 14L Scale*

| Run # | ASP Charge Ladder Variant | ΔCharge | 40 h Titers % R14I | Yield % R14I | Flask Titers % R14I |
|---|---|---|---|---|---|
| 0720 | R14I-N112E-T116E-R123F-R159F | −5 | 7.53 | 8.24 | 36.00 |
| 0716 | R14I-N112E-T116E-R123F | −4 | 9.59 | 13.93 | 63.33 |
| 0719 | R14I-N112E-T116E | −3 | 22.95 | 22.77 | 58.67 |
| 0748 | R14I-N112E | −2 | 104.1 | 110.56 | 113.33 |
| 0746 | R14I | −1 | 100 | 100.00 | 100.00 |
| 0747 | R14I-D184T | 0 | 86.64 | 92.81 | 80.00 |
| 0749 | R14I-D184T-T86K | +1 | 109.93 | 127.27 | 70.00 |
| 0721 | R14I-T86K-D184T-A64K | +2 | 6.84 | 8.61 | 31.33 |
| 0717 | R14I-T86K-D184T-A64K-Q81K | +3 | 55.82 | 72.96 | 46.67 |

*Expression of ASP variants in *Bacillus subtilis* at 14L fermentation scale, and in terms of peak titers and productivity in shake flask scale.

Expression and secretion of a protein in a host cell involves interaction of the expressed protein with a number of host proteins. Optimal interaction of the expressed protein with host cell proteins, especially with the rate limiting interaction, is essential for protein production. This interaction can be optimized by modification of the surface charge/hydrophobicity of the expressed protein (or host cell protein). Nonetheless, knowledge of the mechanism(s) involved is not necessary in order to make and use the present invention.

Figure 18:
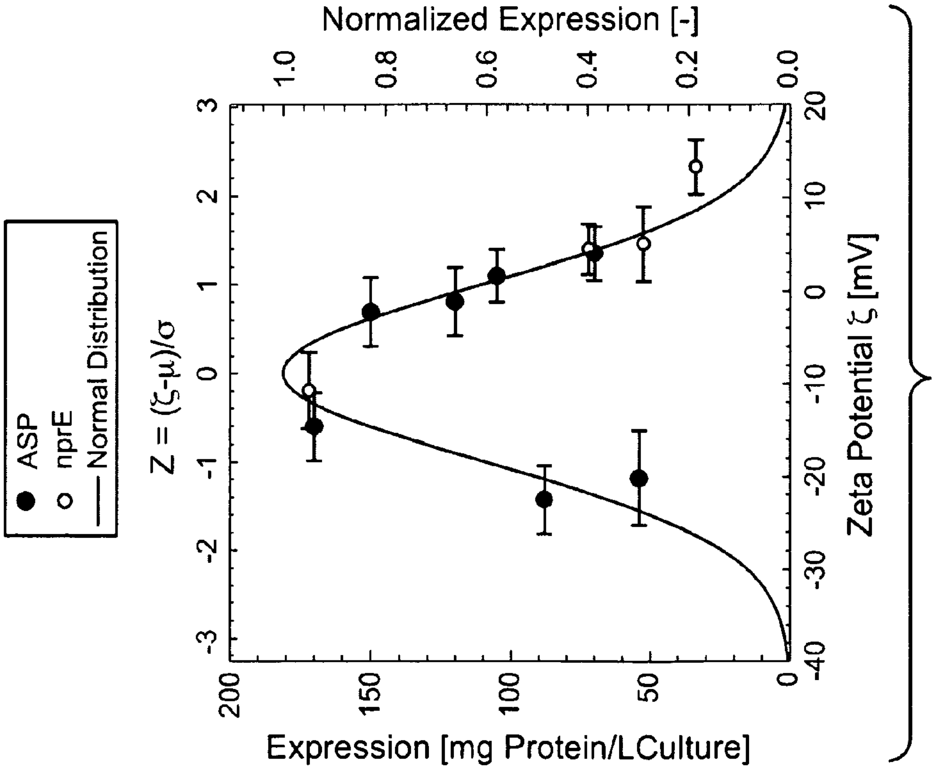
FIG. 18 depicts in the primary axis the expression levels of ASP (filled circles) and NprE (unfilled circles) variants in *Bacillus subtilis* as a function of zeta potential measured in a reference buffer 5 mM HEPES pH 8.0 with 2.5 mM NaCl. The secondary axis indicates the expression levels of ASP variants (normalized by peak value of normal distribution fit, solid line) versus z-score.

FIG. 18 shows the expression levels of two different proteases in *Bacillus subtilis* as a function of zeta potential. Expression of the serine protease ASP is shown in black circles, while expression of the metalloprotease NprE is shown in unfilled triangles. These protease variants span a range of at least 8 charges relative to the wild-type enzymes. As previously described there is a net charge optimum for expression. A common charge scale such as zeta potential in a reference solution such as 5 mM HEPES pH 8.0 with 2.5 mM added NaCl, permits the comparison of expression levels of variants having two vastly different proteins folds. Protein expression is confined to a zeta potential window 40-mV wide, in this case between −40 mV and +20 mV. Just as for BMI performance, the expression levels of ASP and NprE in *Bacillus subtilis* as a function of enzyme zeta potential are well described by a standard normal distribution with a mean $\mu$ equal to −8.92 mV, standard deviation a of 8.95 mV and a peak value of 181 [mg protein per liter of culture] indicated by the solid line. This distribution is indicated in standard reduced coordinates by expression levels divided by the peak value on the right Y-axis as a function of the Z score on the top X-axis. The Z score is defined as usual as $(X-\mu)/\sigma$ where X is in this case zeta potential. This normal distribution is unique to each host organism under given culture conditions (e.g., pH, conductivity, type of salt, minerals, etc.). Optimum expression levels across protein folds occur at the distribution mean equal to −8.92 mV.

The performance levels of standard normal distributions are conveniently described in terms of their z scores as indicated in Table 9-2. Conversion to zeta potential is straightforward given knowledge of the mean and standard deviation defining the distribution for a given application. In this example all measured expression levels is confined to zeta potential values between −40 mV and +20 mV. Variants with expression levels above 80% of their protein fold optimum (i.e., z=±0.65), are confined to zeta potential values between −14.73 mV and −3.11 mV. Variants with expression levels above 90% of their protein fold optimum (i.e., z=±0.46), are confined to zeta potential values between −13.03 mV and −4.80 mV. Other performance levels, z scores and conversion to zeta potential ranges are indicated.

TABLE 9-2

Expression of Proteases in *Bacillus subtilis*

| Performance Level | Z Score | Zeta Potential ζ Window* For Expression |
|---|---|---|
| 90% | ±0.46 | $-13.03 < \zeta < -4.80$ |
| 80% | ±0.65 | $-14.73 < \zeta < -3.11$ |
| 70% | ±0.84 | $-16.43 < \zeta < 1.41$ |
| 60% | ±1.00 | $-17.86 < \zeta < +0.03$ |
| 50% | ±1.18 | $-19.47 < \zeta < +1.63$ |

*Mean $\mu$ = −8.92 mV, standard deviation $\sigma$ = 8.95 mV, Zeta potential $\zeta = Z * \sigma + \mu$
Reference buffer: 5 mM HEPES pH 8.0 with 2.5 mM NaCl Knowledge of zeta potentials for existing proteins expressed in a given production host allows rapid identification of the expected expression levels for proteins having a different protein fold but a comparable zeta potential when measured under the same conditions. In addition knowledge of zeta potentials permits the determination of the direction and magnitude of charge change needed in order to achieve optimal expression levels. The application of this method holds beyond *Bacillus subtilis*, provided expression levels of proteins having different folds are being compared within the same organism (or within an organism having appreciable phylogenetic homology) under the same growth conditions.

By way of illustration, charge optimization of NprE for increased protein expression in *B. subtilis* is described.

Step 1 involves measuring the expression levels of at least one NprE variant, as well as the ASP charge ladder probes cloned in the same host and grown under the same conditions. In this instance, an NprE variant with four positive mutations as compared to wild type NprE (T14R-S23R-N46K-T54R) is expressed in *B. subtilis*. The ASP probe protein series indicates the existence of a charge optimum for expression (FIG. 17). This optimum exists for an ASP variant with 2 negative charges as compared to wild type ASP. To determine the direction and magnitude of charge change for NprE, the ASP probe proteins and parental NprE must be compared on a common charge scale.

Step 2 involves measuring (or calculating) the zeta potential of the ASP charge ladder probe proteins and the NprE variant under the same solution conditions. In this instance, a low ionic reference solution is used to minimize the screening of charge effects. A suitable reference solution is 5 mM HEPES pH 8.0 buffer containing 2.5 mM NaCl.

As previously mentioned, FIG. 18 shows the expression levels of the ASP probe proteins as a function of zeta potential measured in the reference solution. The NprE (+4) variant shown on this graph was found to have a mean zeta potential value of 13.24 mV, corresponding to poor levels of protein expression (e.g., 33.7 mg protein per liter of culture). In order to obtain NprE variants that can be expressed at high levels in

*B. subtilis*, this NprE variant is engineered to be at or near the peak value defined by the normal distribution mean zeta potential μ equal to −8.92 mV. This corresponds to optimal expression levels in this host equal to about 181 mg protein per liter of culture. To achieve this goal, NprE variant(s) that are more negative are obtained (this is the direction of charge change needed). The magnitude of charge change needed is given by: −8.92 mV−(13.28 mV)=−22.2 mV. This is the charge constraint.

Step 3 involves obtaining NprE variants of interest through protein engineering in this Example. Other possibilities for obtaining NprE variants of interest include selection of natural isolates, glycosylation or chemical modification to match the desired zeta potential. Equation (0.7) is used to guide the protein engineering efforts. NprE has a hydrodynamic radius equal to 2.654 nm, measured for instance by light scattering under conditions of high ionic strength to eliminate the contribution of double-layer forces to the hydrodynamic radius. According to equation (0.3) the Debye length $k^{-1}$ is equal to 2.087 nm under the well-defined reference solution conditions of the zeta potential measurements. After introduction of these values in equation (0.7), together with physical constants previously specified, an expected zeta potential change of 3.04 mV for every net charge change is calculated. Therefore in order to close the zeta potential gap for the +4 NprE variant, NprE variants with −22.2/3.04=−7.3 or seven negative charges are engineered. This calculation usually overestimates the number of charges needed, due to uncertainties as to the location of the plane of slip in electrophoretic mobility measurements (See, Hunter in "Zeta Potential in Colloid Science", Academic Press, [1981]). NprE variants having an overall negative charge compared to the parent NprE are designed. For quickly identifying the types of amino acid substitutions for reducing the positive charge of the parent NprE, a charge matrix is provided.

As shown in FIG. 18, an NprE variant T60D having 5 negative charge changes as compared to the parent NprE (T14R-S23R-N46K-T54R) is the closest to the expression optimum of the NprE variants tested. The NprE variant T60D has a zeta potential of −10.72 mV and expression levels equal to 171.9 mg protein per liter of culture. This is a 5-fold improvement compared to values obtained with the parent NprE variant T14R-S23R-N46K-T54R.

Example 10

LAS and Chelant Stability

This Example describes determining the relationship between protein charge and stability in a reaction medium containing one or both of an anionic surfactant and a chelant. For the determination of protease activity of the stressed and unstressed samples, the suc-AAPF-pNA assay was used. For determination of the alpha-amylase activity of the stressed and unstressed samples, the BODIPY-starch assay was used. Residual LAS and EDTA from the stress plates do not affect the suc-AAPF-pNA or BODIPY-starch assays.

LAS Stability

Reagents used included: dodecylbenzenesulfonate, sodium salt (=LAS), Sigma D-2525; TWEEN®-80, Sigma P-8074; TRIS buffer (free acid), Sigma T-1378; 6.35 g is dissolved in about 960 ml water, pH is adjusted to 8.2 with 4N HCl. The final TRIS concentration is 52.5 mM; LAS stock solution: 10.5% LAS solution in MQ water (=10.5 g per 100 ml MQ); TRIS buffer-100 mM/pH 8.6 (100 mM Tris/0.005% TWEEN80); and TRIS-Ca buffer, pH 8.6 (100 mM Tris/10 mM $CaCl_2$/0.005% TWEEN80). Hardware used included: flat bottom MTPs, Costar (#9017); Biomek FX; ASYS Multipipettor; Spectramax MTP Reader; iEMS Incubator/Shaker; Innova 4330 Incubator/Shaker; Biohit multichannel pipette; and BMG Thermostar Shaker.

LAS stability was measured after incubation of the test proteases in the presence of 0.06% LAS (dodecylbenzenesulfonate sodium), by measuring the residual activity in an suc-AAPF-pNA assay. A 0.063% LAS solution was prepared in 52.5 mM Tris buffer pH 8.2. The AAPF working solution was prepared by adding 1 ml of 100 mg/ml AAPF stock solution (in DMSO) to 100 ml (100 mM) TRIS buffer, pH 8.6. To dilute the supernatants, flat-bottomed plates were filled with dilution buffer and an aliquot of the supernatant was added and mixed well. The dilution ratio depended on the concentration of the ASP-controls in the growth plates (suc-AAPF-pNA activity). The desired protein concentration was 80 ppm.

Ten μl of the diluted supernatant were added to 190 μl 0.063% LAS buffer/well. The MTP was covered with tape, shaken for a few seconds and placed in an incubator (Innova 4230) at 25° or 35° C., for 60 minutes at 200 rpm agitation. The initial activity (t=10 minutes) was determined after 10 minutes of incubation by transferring 10 μl of the mixture in each well to a fresh MTP containing 190 μl suc-AAPFpNA working solution. These solutions were mixed well and the suc-AAPF-pNA activity was measured using a MTP Reader (20 readings in 5 minutes and 25° C.).

The final activity (t=60 minutes) was determined by removing another 10 μl of solution from the incubating plate after 60 minutes of incubation. The suc-AAPF-pNA activity was then determined as described above. The calculations were performed as follows:

% Residual Activity=[t−60 value]*100/[t−10value].

Figure 19:
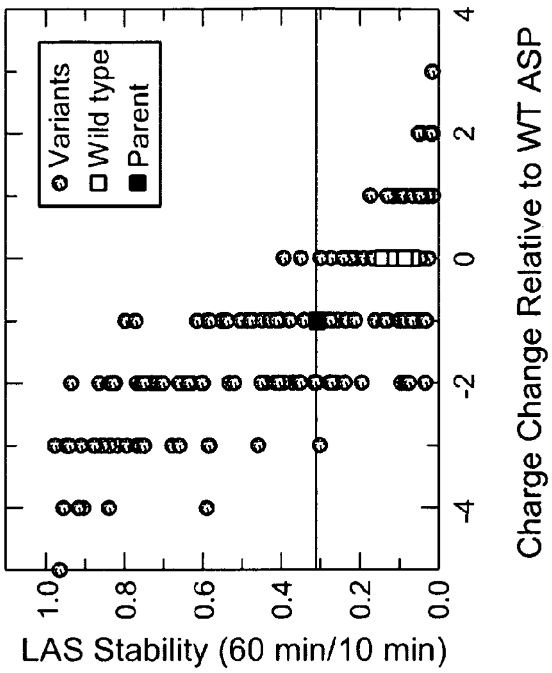
FIG. 19 depicts LAS stability of ASP variants as a function of net charge change relative to wild type ASP.

FIG. 19 depicts LAS stability as a function of net charge change relative to wild type ASP, for a library containing 229 variants. This library was designed and constructed (See e.g., U.S. patent application Ser. Nos. 10/576,331 and 11/583,334) to span several net charges relative to the parent ASP molecule having the mutation R14I. Detergent stability was measured in terms of the ratio of residual activity after incubation in LAS for 60 min over incubation for 10 min only. As evidenced from the figure, accumulation of negative charges (up to −5) relative to wild type ASP, are beneficial for LAS stability. This is an example of optimizing a protein physical property, in this case net charge, for improving protein stability in a complex liquid laundry environment.

LAS/EDTA Stability

Reagents used included: control buffer: 50 mM HEPES, 0.005% Tween-80, pH 8.0; and stress buffer 50 mM HEPES, 0.1% (w/v) LAS (dodecylbenzene-sulfonate, sodium salt, Sigma D-2525), 10 mM EDTA, pH 8.0. Enzyme variants (20 ppm) were diluted 1:20 into 96-well non-binding flat-bottom plate containing either control or stress buffer and mixed. The control plate was incubated at room temperature while the stress plate was immediately placed at 37° C. for 30-60 min (depending on the stability of the enzyme being tested). Following incubation, enzyme activity was measured using suc-AAPF-pNA assay for proteases and BODIPY-starch assay for amylases. The fraction of remaining or residual activity is equal to the reaction rate of the stressed sample divided by the reaction rate of the control sample. The parent enzymes and variants are stable for 60 min in the control buffer.

Figure 20:
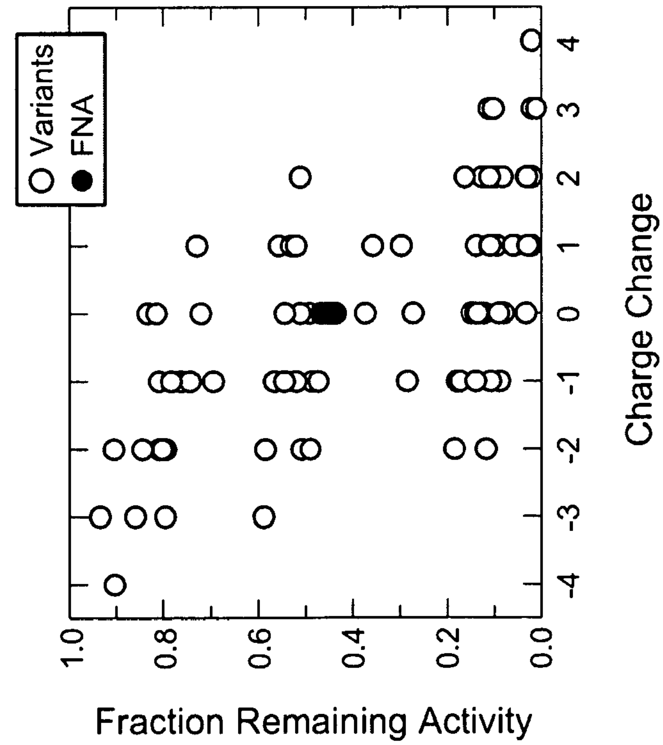
FIG. 20 depicts LAS/EDTA stability of FNA variants as a function of net charge change relative to parent FNA.

FIG. 20 depicts LAS/EDTA stability as a function of net charge change relative to parent FNA, for a library containing 80 variants. This library was designed and constructed according to the methods described in Example 2, to span several net charges relative to the parent FNA molecule. As evidenced from the Figure, accumulation of negative charges (up to −4) relative to parent FNA, are beneficial for combined LAS/chelant stability. This is an example of optimizing a protein physical property, in this case net charge, for improving protein stability in a complex liquid laundry environment.

Figure 21:
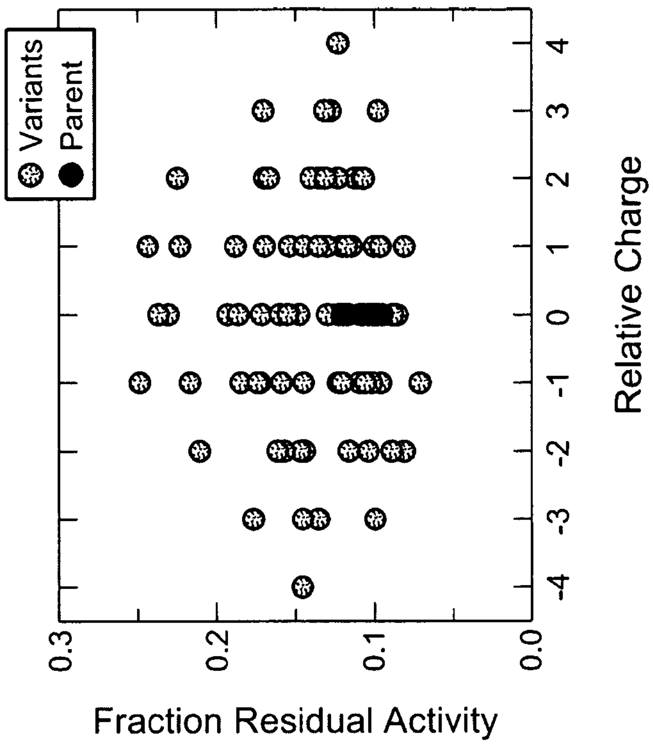
FIG. 21 depicts LAS/EDTA stability of TS23t variants as a function of net charge change relative to parent TS23t-7mut.

For ASP and FNA there is a charge dependence for LAS/EDTA stability. Adding negative charge increases stability. But, even when going one or two charges more positive than the parent, it is possible to find, by our method, an arrangement of charge mutations which confer equal or greater stability than the parent. This approach is also effective in larger enzymes, such as TS23t' shown in FIG. 21 where the detrimental effect of adding positive charges on stability can be compensated by an optimal charge arrangement that increases stability.

Example 11

Thermal Stability

This Example describes determining the relationship between protein charge and thermal stability. Protease assays were based on dimethylcasein (DMC) hydrolysis, before and after heating the buffered culture supernatant. Amylase assays were based on BODIPY starch hydrolysis before and after heating the culture supernatant. The same chemical and reagent solutions for these assays were used as described in Example 1.

Thermal Stability Assay for Proteases

The filtered culture supernatants were diluted to 20 ppm in PIPES buffer (based on the concentration of the controls in the growth plates). First, 10 μl of each diluted enzyme sample was taken to determine the initial activity in the dimethylcasein assay and treated as described below. Then, 50 μl of each diluted supernatant were placed in the empty wells of a MTP. The MTP plate was incubated in an iEMS incubator/shaker HT (Thermo Labsystems) for 90 minutes at 60° C. and 400 rpm. The plates were cooled on ice for 5 minutes. Then, 10 μl of the solution was added to a fresh MTP containing 200 μl dimethylcasein substrate/well to determine the final activity after incubation. This MTP was covered with tape, shaken for a few seconds and placed in an oven at 37° C. for 2 hours without agitation.

Figure 22:
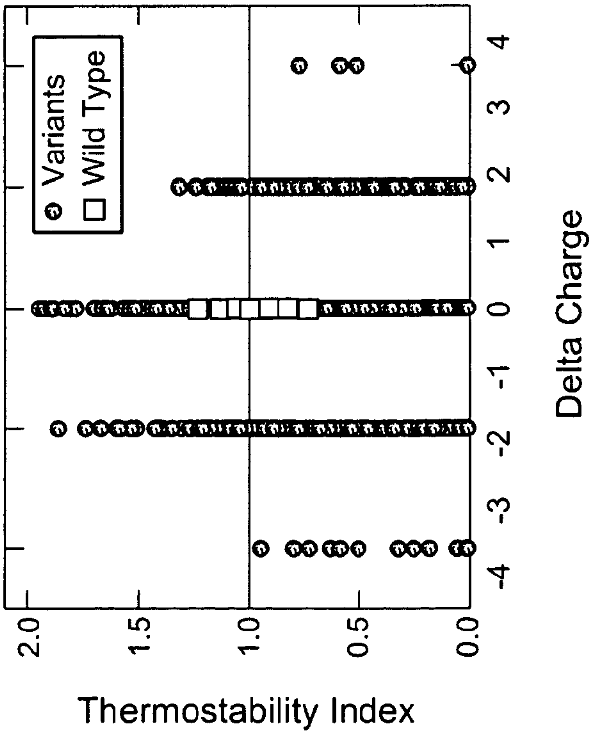
FIG. 22 depicts thermostability of ASP variants as a function of net charge change relative to wild type ASP.

The residual activity of a sample was expressed as the ratio of the final absorbance and the initial absorbance, both corrected for blanks. FIG. 22 shows the thermostability index as a function of net charge change relative to wild type ASP for a SEL library. A higher index indicates a more thermally stable variant. As evidenced from the figure accumulation of extreme negative (−2) or positive (+2) charges relative to the wild type enzyme are detrimental for thermal stability. There is a distinct charge optimum for thermal stability centered at zero net charge changes relative to wild type ASP. This is an example of optimizing a protein physical property, in this case net charge, for improving enzyme thermal stability for a liquid laundry application.

Thermal Stability Assay for Alpha-Amylases

The filtered culture supernatants were serially diluted in 50 mM sodium acetate+2 mM $CaCl_2$ pH 5.8 with 002% Tween. 10 μl of each diluted culture supernatant was assayed to determine the initial amylase activity by the BODIPY starch assay. 50 μA of each diluted culture supernatant was placed in a VWR low profile PCR 96 well plate. 304 of mineral oil was added to each well as a sealant. The plate was incubated in a BioRad DNA engine Peltier Thermal Cycler at 95° C. for 30 or 60 minutes depending on the stability of the parent enzyme. Following incubation, the plate was cooled to 4° C. for 5 min and then kept at room temperature. 10 μl of each sample was added to a fresh plate and assayed to determine the final amylase activity by the BODIPY starch assay as described in Example 1.

Calculation of Thermostability

Figure 23:
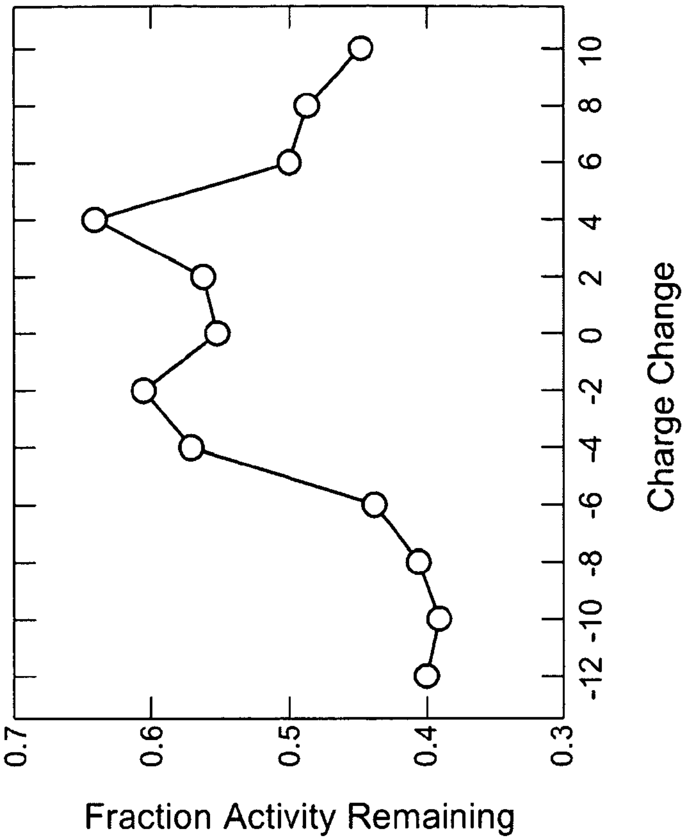
FIG. 23 depicts thermal stability of first AmyS charge ladder as a function of charge change relative to wild type AmyS.

The residual activity of a sample was expressed as the ratio of the final absorbance and the initial absorbance, both corrected for blanks. These observations were also made with amylase charge variants. FIG. 23 shows the residual activity of the first AmyS charge ladder as a function of charge change relative to wild type. Once again accumulation of extreme negative charges (−12) or positive charges (+10) relative to the wild type enzyme are detrimental for thermal stability. This is an example of optimizing a protein physical property, in this case net charge, for improving enzyme thermal stability for a liquid laundry application.

Example 12

Thermal Activity

This Example describes determining the relationship between protein charge and reaction rate dependence upon temperature, where thermal activity is but one manifestation.

Stability Assay During Wash Conditions

This assay is based on the suc-AAPF-pNA hydrolysis assay before and after heating the buffered culture supernatant. The same chemical and reagent solutions were used as described in the suc-AAPF-pNA hydrolysis assay in Example 1.

Method

The filtered culture supernatants were diluted to 400 ppm in 100 mM Tris buffer, pH 8.6 with 0.005 wt % TWEEN 80 (based on the protein concentration (by BCA) of the controls in the growth plates). First, a 20-fold dilution was made for each assay. Then, 10 μL of the diluted sample were added to 190 μL 5 mM HEPES buffer pH 8.0 containing 2.5 mM NaCl. The expected final enzyme concentrations in each well were on the order of 1 ppm. The MTP plate was incubated in an iEMS incubator/shaker HT (Thermo Labsystems) for 30 minutes at 30° C. or 40° C. and 400 rpm. Next, 10 μl of each diluted enzyme sample was taken to determine initial activity with the suc-AAPF-pNA assay and treated as described above at both 7 min and 30 min.

Calculation of Stability During Wash Conditions

The residual activity of the samples were expressed as the ratio of the suc-AAPF-pNA hydrolysis rate at 30 min divided by the suc-AAPF-pNA hydrolysis rate at 7 min, both corrected for blanks.

In some embodiments, it is desirable to engineer enzymes for improved performance at different reaction temperatures. For instance as part of a global energy savings trend there is a desire to develop detergent proteases capable of operating at reduced temperatures, as in the case of cold water washes. For a given enzyme-substrate reaction the total reaction activation barrier is the sum of catalysis (activation energy barrier of chemical conversion) and physics (enthalpy of binding to the substrate and/or product) terms. It is well known that exothermic reactions proceed at a faster rate at lower temperatures, while endothermic reactions proceed at a faster rate at higher temperatures. This phenomenon is well described by the Van't Hoff equation in chemical thermodynamics, relating the change in temperature to the change in the equilibrium constant given the enthalpy change (See, Laidler, "Chemical Kinetics", Harper Collins 3$^{rd}$ Ed. [1987]). It is also described in terms of a partial molar heat capacity or activation energy barrier. While amino acid substitutions away from the active site may not affect the activation barrier for chemical catalysis, they do affect the enthalpy of binding to substrate and/or product. Therefore in order to increase the reaction rate at lower temperatures, the enzyme enthalpy of binding term can be engineered to promote an overall exothermic enthalpy of reaction, irrespective of the enthalpy of reaction associated with the catalytic step only. Conversely, in order to increase the reaction rate at higher temperatures, the enzyme enthalpy of binding term can be engineered to promote an overall endothermic enthalpy of reaction, irrespective of the enthalpy of reaction associated with the catalytic step only. One strategy for accomplishing this is through changing the charge or the hydrophobicity of the enzyme.

Figure 24A:
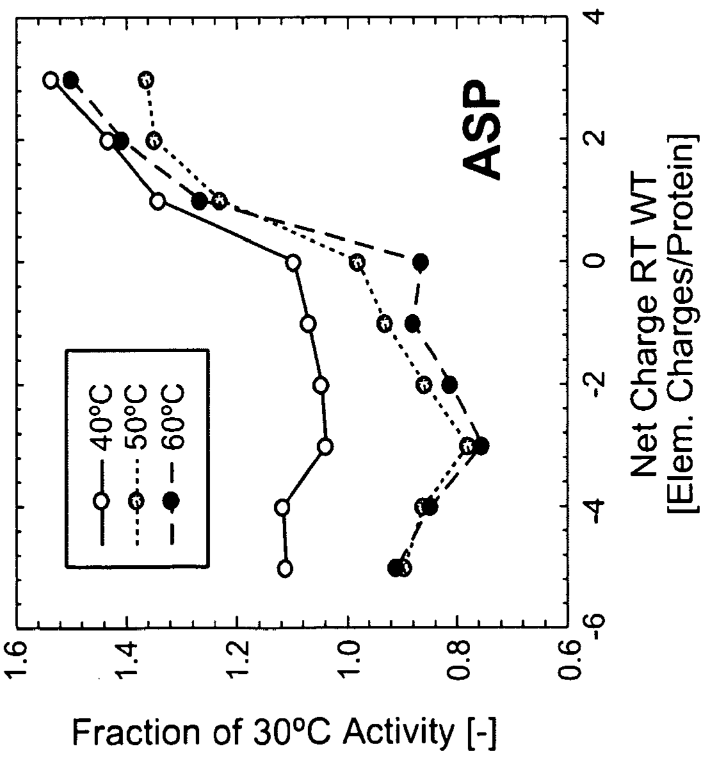
FIG. 24 depicts thermal activity of ASP (panel A) and NprE (panel B) as a function of net charge change relative to wild type ASP and NprE respectively for different temperatures, 40° C., 50° C. and 60° C. Thermal activity is shown as a fraction of 30° C. activity (activity at elevated temperature divided by activity at 30° C.).
Figure 24B:
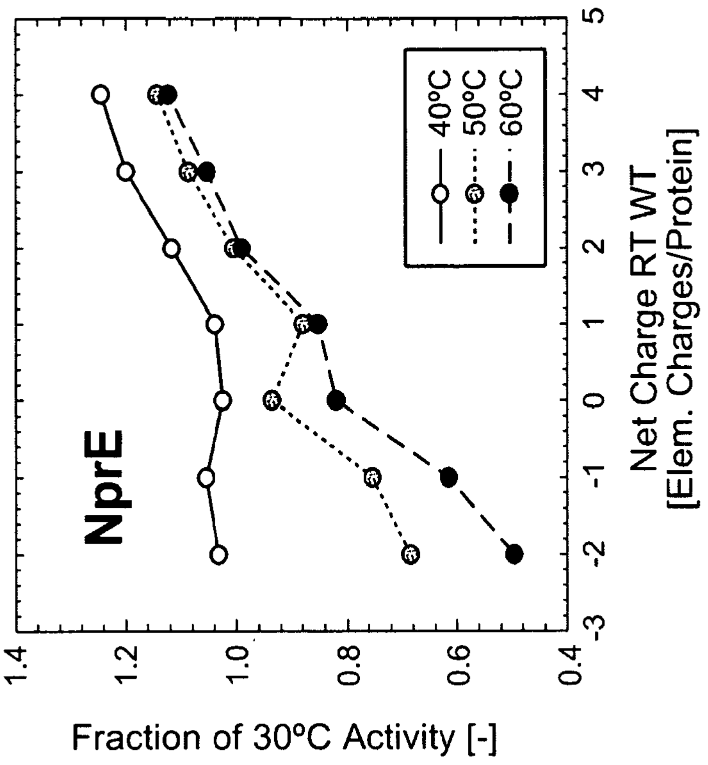
Figure 26:
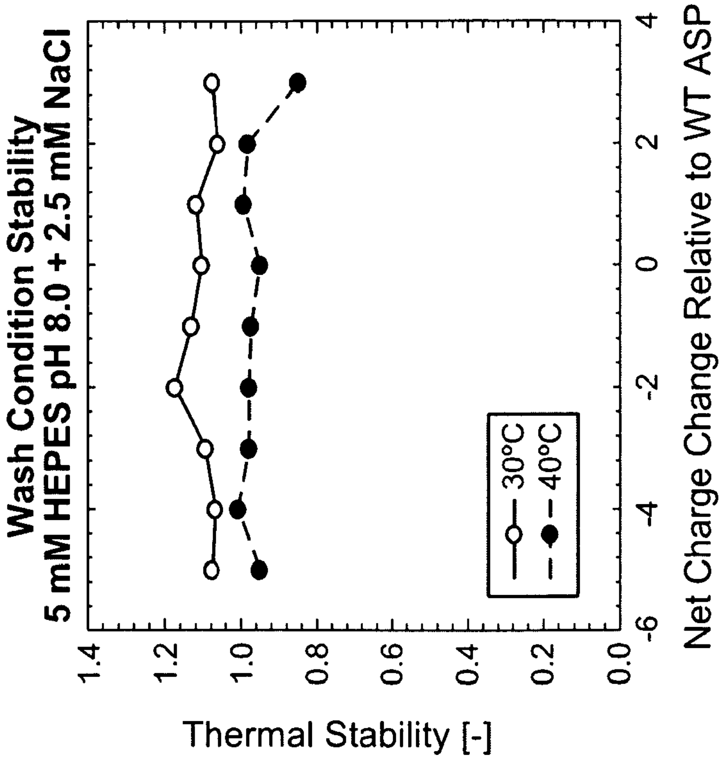
FIG. 26 depicts thermal stability of ASP charge ladder variants at 30° C. (unfilled circles) and 40° C. (filled circles) in 5 mM HEPES pH 8.0 with 2.5 mM NaCl.

FIG. 24 shows the remaining BMI microswatch activity at increasing temperatures as compared to initial cleaning activity at 30° C., as a function of net charge change of ASP and NprE charge ladder protein probes relative to the wild type proteases. A remaining activity fraction less than unity indicates the variant is less active at higher temperatures (e.g., exothermic) and hence is more suitable for performance at cold temperatures. Conversely, a remaining activity fraction larger than unity indicates the variant is more active at higher temperatures (e.g., endothermic), and hence is more suitable for performance at higher temperatures. As shown in this Figure, variants having a more negative charge than the wild type proteases are exothermic, while variants having a more positive charge are endothermic. This information can be applied to efficiently obtain enzymes with superior performance at altered temperatures, provided that stability of the variants is not dramatically impacted. Indeed, FIG. 26 indicates that stability of ASP variants is maintained at both 30° C. and 40° C.

The contribution of the enthalpy of binding to the total enthalpy of reaction is often neglected and improvements in reaction rates are assumed to be solely due to the catalytic step. As a matter of fact, reaction rates are expected to only increase with temperature, provided the enzyme is thermostable, according to some variation of Arrhenius' law (See, Laidler, supra). As shown herein, exothermic ASP and NprE variants (negative with respect to their wild type proteases), being less active at higher temperatures, clearly contradict this assumption. This is an example of optimizing a protein physical property, in this case net charge, for improving enzyme reaction rates at defined temperatures in a liquid laundry application. Thus use of a limited set of ASP or NprE charge ladder probe proteins permits the rapid identification of endothermic and exothermic variants within these protein folds. In particular, when the goal is to identify enzymes for improved cold wash performance, the present invention teaches confining the search to exothermic variants.

Figure 25A:
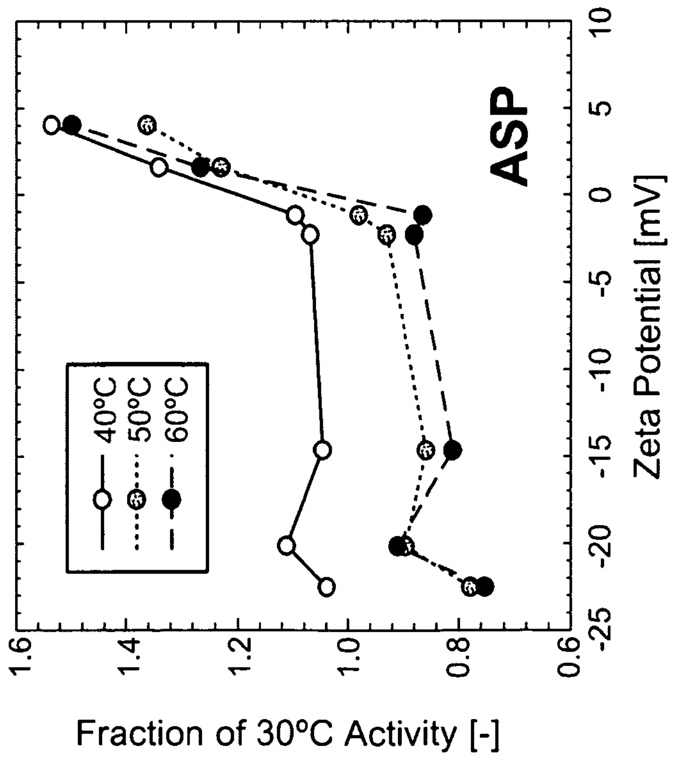
FIG. 25 depicts thermal activity of ASP (panel A) and NprE (panel B) as a function of zeta potential for different temperatures, 40° C., 50° C. and 60° C. Thermal activity is, shown as a fraction of 30° C. activity (activity at elevated temperature divided by activity at 30° C.).
Figure 25B:
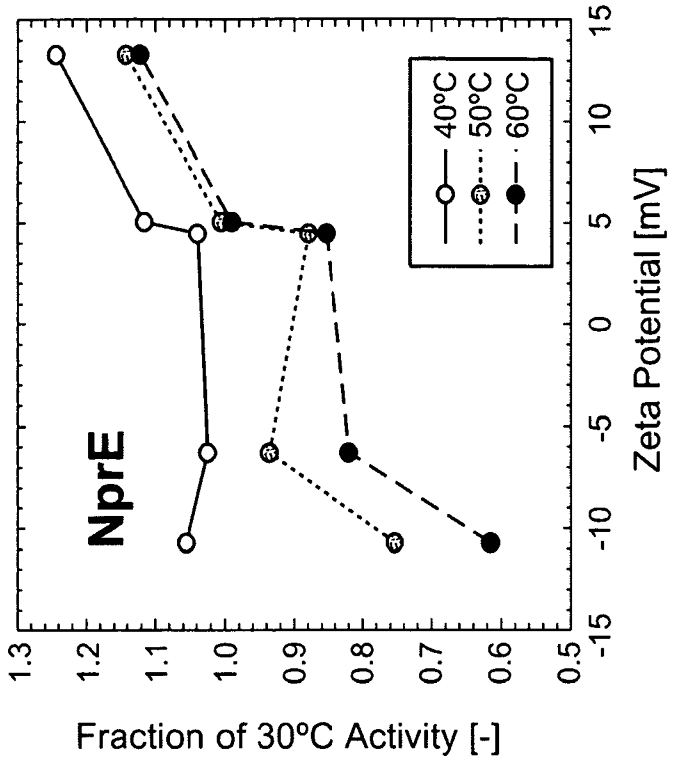

In order to devise a set of criteria for applying these findings across other protein folds, it is necessary to describe charge effects on a common scale. FIG. 25 shows the remaining BMI microswatch activity at increasing temperatures as compared to the initial activity at 30° C. as a function of the zeta potential of ASP and NprE charge ladder protein probes measured under the same conditions (reaction buffer is 5 mM HEPES pH 8.0 containing 2.5 mM NaCl). The value of the zeta potential substrate stain, unfixed BMI, is equal to −8.97 mV when measured under the same conditions. As expected the overall profile of each curve is similar to FIG. 24 with charge expressed as net change relative to the wild-type proteases. In addition knowledge of the zeta potential indicates that under these conditions truly positive variants (above the point of zero charge; e.g., 0 mV) are endothermic, whereas negative variants are exothermic. When searching for enzymes suitable for cold wash applications, either through selection of natural isolates, chemical modifications or protein engineering, the present invention provides guidance in identifying proteins from any protein fold that are constrained to negative zeta potentials under these conditions. In short, the use of probe proteins spanning a physical property of interest (e.g., ASP charge ladders), supplied the criteria for rapid identification of winners (e.g., protein variants having a favorable outcome in a test of interest).

The methods of the present invention can be extrapolated to any enzyme, substrate and reaction medium combination. Specifically, the zeta potential values indicative of exothermic or endothermic behavior are a function of enzyme and substrate charges in a given formulation environment. In this case enzyme variants of opposite sign compared to the substrate are endothermic. This is dramatically indicated by the change in slope at or near 0 mV, the point of zero charge when a protein quickly changes sign. Without being bound by theory, oppositely charged enzymes and substrates (or reaction products) are tightly bound and remain in contact much longer than the chemical catalytic conversion step (e.g., diffusion-limited). This limits the concentration of enzyme available to carry out subsequent reactions. Addition of thermal energy therefore improves enzyme performance since it helps disengage enzymes from the substrate (or product) complex and thus, reduces the amount of unproductive binding. For any given combination of enzyme, substrate and formulation environment, the region of exothermic and endothermic variants is a function of the point of zero charge and of substrate charge. If under the conditions of the application the substrate is negatively charged, endothermic variants are confined to positive zeta potential values or to the right of the point of zero charge. Conversely, if the substrate is positively charged, endothermic variants are confined to negative zeta potential values or to the left of the point of zero charge. In general the product of enzyme and substrate zeta potentials is negative for endothermic variants and positive for exothermic ones.

Thus use of a limited set of ASP or NprE charge ladder probe proteins permits the rapid identification of endothermic and exothermic variants within these protein folds. In particular, when the goal is to identify enzymes for improved cold wash performance, the present invention teaches confining the search to exothermic variants.

This method is applicable to the improvement of proteases for cleaning performance at various temperatures, amylases in starch liquefaction, cellulases in biomass degradation and any enzyme that requires thermal activation at either cold or hot temperatures. Under circumstances where the accumulation of charges is detrimental, for instance towards thermal stability or the efficiency of the catalytic step, use of the methods described in U.S. Application No. 60/933,331 for balancing conflicting properties are useful in order to achieve thermal activation using this approach.

Example 13

Statistical Determination of Amino Acid Properties

Amino acid characteristics such as charge, hydrophobicity, hydrogen bonding, etc. are important properties of proteins. For example, with a charged substrate, surface charge or overall charge of the protein is likely to be important for activity, while hydrophobicity is likely to be important for solubility. It is of interest to have a statistically based test to identify amino acid properties that are important for protein performance. Such a test can indicate the existence of a correlation between amino acid properties and mutant protein performance. For every amino acid property there is a score that numerically reflects the change in property when one amino acid is substituted for another. Several scoring matrices exist or can be constructed to predict changes in properties upon amino acid substitution. Four examples of this are given in the figures. A charge change matrix for approximate charge change at pH 8.6 is provided in FIG. 27. A hydrogen bond scoring matrix is provided in FIG. 28. A Kyte-Doolittle hydropathicity matrix is provided in FIG. 29 (Kyte and Doolittle, supra). Lastly, an Eisenberg hydrophobicity matrix is provided in FIG. 30 (Eisenberg et al., supra).

For any set of variant data, such as the site evaluation library data for ASP protease (WO 2005/052146), the data can be sorted into those variants that are better than an arbitrary cutoff value (such as >100% wt activity, >50% wt activity or >5% wt activity), and those that are worse. An amino acid scoring matrix can be used to give a score value to every amino acid substitution. For convenience, the scores can be used as is (charge scores) or parsed into Quintiles (hydropathicity, hydrophobicity, hydrogen bonding). For example, Kyte-Doolittle hydrophathicity, scores were divided into the −2 quintile (scores <−4), −1 quintile (scores between −4 and −1), 0 quintile (scores between −1 and +1), +1 quintile (scores between 1 and 4) and the +2 quintile (scores greater than 4). A simple count can be made of the number of variants that exceed the cutoff value and have a certain score or range of scores for the amino acid property. From the percentages of mutations that are above and below the cutoff values, and the percentages of amino acid changes that have a given score or range of scores, an expected number of each class may be calculated based on no correlation between amino acid property and performance. This can be compared to the observed number and a ratio of observed to expected is calculated. Ratios significantly greater than 1 are indicative of a positive correlation of the property with performance, and ratios less than 1 are indicative of a negative correlation of the property with performance. A set of ten random shufflings of the amino acid scores is generated and ten observed/expected (o/e) rations are calculated for the random data sets. The results are then averaged and the standard deviations for the randomized data are determined. The actual o/e ratios can be compared to the randomized averages, and determined as significant at the 1, 2, or 3 sigma level based on the randomized standard deviations. The results for ASP, acyl transferase (ACT), and AmyS are shown in Tables 13-1, 13-2, and 13-3 respectively. Observed/expected ratios that are significant at the 1 sigma level are in bold type.

TABLE 13-1

ASP Quintiles for Multiple Properties

| ASP | o/e | ASP | o/e | ASP | o/e | ASP | o/e |
|---|---|---|---|---|---|---|---|
| CAS ΔΔG | | CAS ΔΔG | | CAS ΔΔG | | CAS ΔΔG | |
| Δ CHRG −2 | **2.26** | Δ HB −2 | **1.41** | Δ K-D −2 | **0.65** | Δ E −2 | **0.68** |
| Δ CHRG −1 | **0.82** | Δ HB −1 | **1.04** | Δ K-D −1 | **0.92** | Δ E −1 | **0.85** |
| Δ CHRG 0 | 0.99 | Δ HB 0 | **0.95** | Δ K-D 0 | **1.18** | Δ E 0 | 0.99 |
| Δ CHRG +1 | **1.13** | Δ HB +1 | 1.03 | Δ K-D +1 | 0.99 | Δ E +1 | **1.22** |
| Δ CHRG +2 | **2.30** | Δ HB +2 | 0.68 | Δ K-D +2 | **1.35** | Δ E +2 | **1.36** |
| AAPF ΔΔG | | AAPF ΔΔG | | AAPF ΔΔG | | AAPF ΔΔG Δ | |
| Δ CHRG −2 | **4.19** | Δ HB −2 | **2.10** | Δ K-D −2 | **0.50** | E −2 | **0.35** |
| Δ CHRG −1 | **2.05** | Δ HB −1 | **1.24** | Δ K-D −1 | **0.74** | Δ E −1 | **0.68** |
| Δ CHRG 0 | **0.86** | Δ HB 0 | **0.82** | Δ K-D 0 | 0.97 | Δ E 0 | **0.82** |
| Δ CHRG +1 | **0.49** | Δ HB +1 | 0.73 | Δ K-D +1 | **1.35** | Δ E +1 | **1.44** |
| Δ CHRG +2 | 1.99 | Δ HB +2 | 0.67 | Δ K-D +2 | **1.66** | Δ E +2 | **3.75** |
| KER ΔΔG | | KER ΔΔG | | KER ΔΔG | | KER ΔΔG | |
| Δ CHRG −2 | **4.99** | Δ HB −2 | **1.93** | Δ K-D −2 | **0.52** | Δ E −2 | **0.15** |
| Δ CHRG −1 | **2.55** | Δ HB −1 | **1.18** | Δ K-D −1 | **0.77** | Δ E −1 | **0.75** |
| Δ CHRG 0 | **0.84** | Δ HB 0 | **0.85** | Δ K-D 0 | 1.01 | Δ E 0 | **0.80** |
| Δ CHRG +1 | **0.13** | Δ HB +1 | **0.84** | Δ K-D +1 | **1.45** | Δ E +1 | **1.36** |
| Δ CHRG +2 | **0.00** | Δ HB +2 | 0.61 | Δ K-D +2 | **1.41** | Δ E +2 | **4.08** |
| BMI ΔΔG | | BMI ΔΔG | | BMI ΔΔG | | BMI ΔΔG | |
| Δ CHRG −2 | **3.09** | Δ HB −2 | **2.00** | Δ K-D −2 | **0.60** | Δ E −2 | **0.24** |
| Δ CHRG −1 | **2.22** | Δ HB −1 | **1.22** | Δ K-D −1 | **0.70** | Δ E −1 | **0.76** |
| Δ CHRG 0 | **0.86** | Δ HB 0 | **0.84** | Δ K-D 0 | **1.07** | Δ E 0 | **0.76** |
| Δ CHRG +1 | **0.39** | Δ HB +1 | **0.82** | Δ K-D +1 | **1.30** | Δ E +1 | **1.37** |
| Δ CHRG +2 | 0.92 | Δ HB +2 | 0.57 | Δ K-D +2 | **1.55** | Δ E +2 | **4.00** |
| LAS ΔΔG | | LAS ΔΔG | | LAS ΔΔG | | LAS ΔΔG | |
| Δ CHRG −2 | **5.31** | Δ HB −2 | **2.09** | Δ K-D −2 | **0.33** | Δ E −2 | **0.30** |
| Δ CHRG −1 | **2.41** | Δ HB −1 | **1.21** | Δ K-D −1 | **0.94** | Δ E −1 | **0.71** |
| Δ CHRG 0 | **0.76** | Δ HB 0 | **0.81** | Δ K-D 0 | **0.76** | Δ E 0 | **0.80** |
| Δ CHRG +1 | **0.69** | Δ HB +1 | **0.76** | Δ K-D +1 | **1.62** | Δ E +1 | **1.46** |
| Δ CHRG +2 | 0.84 | Δ HB +2 | 0.72 | Δ K-D +2 | **1.45** | Δ E +2 | **3.36** |
| PRO ΔΔG | | PRO ΔΔG | | PRO ΔΔG | | PRO ΔΔG | |
| Δ CHRG −2 | **0.56** | Δ HB −2 | **0.47** | Δ K-D −2 | **1.11** | Δ E −2 | 1.10 |
| Δ CHRG −1 | **1.07** | Δ HB −1 | **1.08** | Δ K-D −1 | **1.14** | Δ E −1 | **1.13** |
| Δ CHRG 0 | 1.00 | Δ HB 0 | **1.04** | Δ K-D 0 | 1.04 | Δ E 0 | 0.97 |
| Δ CHRG +1 | 0.98 | Δ HB +1 | 1.01 | Δ K-D +1 | **0.91** | Δ E +1 | **0.89** |
| Δ CHRG +2 | **0.00** | Δ HB +2 | 1.24 | Δ K-D +2 | **0.69** | Δ E +2 | **0.47** |
| THER ΔΔG | | THER ΔΔG | | THER ΔΔG | | THER ΔΔG Δ | |
| Δ CHRG −2 | 0.97 | Δ HB −2 | 1.28 | Δ K-D −2 | **0.31** | E −2 | **0.21** |
| Δ CHRG −1 | **1.44** | Δ HB −1 | **1.53** | Δ K-D −1 | 1.04 | Δ E 1 | **0.73** |
| Δ CHRG 0 | 0.99 | Δ HB 0 | **0.81** | Δ K-D 0 | **1.17** | Δ E 0 | 1.00 |
| Δ CHRG +1 | **0.62** | Δ HB +1 | 1.03 | Δ K-D +1 | **1.22** | Δ E +1 | **1.38** |
| Δ CHRG +2 | **0.00** | Δ HB +2 | 0.60 | Δ K-D +2 | **1.30** | Δ E +2 | **1.77** |

TABLE 13-2

| ACT Quintiles for Multiple Properties | | | |
|---|---|---|---|
| ACT | o/e | ACT | o/e |
| PAF ΔΔG | **0.32** | PAF ΔΔG | **0.92** |
| Δ CHRG −2 | | Δ K-D −2 | |
| Δ CHRG −1 | **0.64** | Δ K-D −1 | **0.90** |
| Δ CHRG 0 | **0.97** | Δ K-D 0 | **1.10** |
| Δ CHRG +1 | **1.32** | Δ K-D +1 | **1.08** |
| Δ CHRG +2 | **1.71** | Δ K-D +2 | 1.05 |
| PAD ΔΔG | 1.15 | PAD ΔΔG | **0.73** |
| Δ CHRG −2 | | Δ K-D −2 | |
| Δ CHRG −1 | 1.09 | Δ K-D −1 | 0.97 |
| Δ CHRG 0 | 0.98 | Δ K-D 0 | **1.08** |

TABLE 13-2-continued

| ACT Quintiles for Multiple Properties | | | |
|---|---|---|---|
| ACT | o/e | ACT | o/e |
| Δ CHRG +1 | 0.99 | Δ K-D +1 | **1.11** |
| Δ CHRG +2 | 1.17 | Δ K-D +2 | **1.21** |
| [protein] ΔΔG | 1.01 | [protein] ΔΔG | **0.56** |
| Δ CHRG −2 | | Δ K-D −2 | |
| Δ CHRG −1 | **0.89** | Δ K-D −1 | **1.26** |
| Δ CHRG 0 | **1.21** | Δ K-D 0 | **1.29** |
| Δ CHRG +1 | **0.39** | Δ K-D +1 | 1.05 |
| Δ CHRG +2 | **0.00** | Δ K-D +2 | **0.86** |

TABLE 13-3

| AmyS Quintiles for Multiple Properties | | | | | | | |
|---|---|---|---|---|---|---|---|
| AmyS | o/e | AmyS | o/e | AmyS | o/e | AmyS | o/e |
| CF5 ΔΔG | | CF5 ΔΔG | | CF5 ΔΔG | | CF5 ΔΔG | |
| Δ CHRG −2 | **1.60** | Δ HB −2 | **0.84** | Δ K-D −2 | **1.12** | Δ E −2 | **1.13** |
| Δ CHRG −1 | **1.29** | Δ HB −1 | 0.98 | Δ K-D −1 | **1.19** | Δ E −1 | **1.09** |
| Δ CHRG 0 | **0.97** | Δ HB 0 | 1.02 | Δ K-D 0 | **0.83** | Δ E 0 | **1.05** |
| Δ CHRG +1 | **0.84** | Δ HB +1 | **0.92** | Δ K-D +1 | **1.15** | Δ E +1 | **0.89** |
| Δ CHRG +2 | **0.56** | Δ HB +2 | **1.19** | Δ K-D +2 | **0.77** | Δ E +2 | 1.12 |
| CF10 ΔΔG | | CF10 ΔΔG | | CF10 ΔΔG | | CF10 ΔΔG | |
| Δ CHRG −2 | **1.66** | Δ HB −2 | **0.86** | Δ K-D −2 | **1.10** | Δ E −2 | **1.26** |
| Δ CHRG −1 | **1.18** | Δ HB −1 | 1.00 | Δ K-D −1 | **1.15** | Δ E −1 | 1.04 |
| Δ CHRG 0 | **0.97** | Δ HB 0 | 1.02 | Δ K-D 0 | **0.86** | Δ E 0 | **1.08** |
| Δ CHRG +1 | **0.91** | Δ HB +1 | 0.97 | Δ K-D +1 | **1.12** | Δ E +1 | **0.90** |
| Δ CHRG +2 | 0.77 | Δ HB +2 | **1.12** | Δ K-D +2 | **0.82** | Δ E +2 | 1.16 |
| CF60 ΔΔG | | CF60 ΔΔG | | CF60 ΔΔG | | CF60 ΔΔG | |
| Δ CHRG −2 | **1.46** | Δ HB −2 | 1.00 | Δ K-D −2 | 0.94 | Δ E −2 | 0.98 |
| Δ CHRG −1 | **1.33** | Δ HB −1 | 0.96 | Δ K-D −1 | **1.15** | Δ E −1 | 1.01 |
| Δ CHRG 0 | **0.96** | Δ HB 0 | 1.01 | Δ K-D 0 | **0.79** | Δ E 0 | **1.05** |
| Δ CHRG +1 | **0.84** | Δ HB +1 | 0.95 | Δ K-D +1 | **1.16** | Δ E +1 | **0.94** |
| Δ CHRG +2 | 0.82 | Δ HB +2 | 1.05 | Δ K-D +2 | **0.89** | Δ E +2 | **1.54** |
| pH4 ΔΔG | | pH4 ΔΔG | | pH4 ΔΔG | | pH4 ΔΔG | |
| Δ CHRG −2 | **1.63** | Δ HB −2 | **0.91** | Δ K-D −2 | **1.29** | Δ E −2 | 1.07 |
| Δ CHRG −1 | **1.28** | Δ HB −1 | **0.89** | Δ K-D −1 | **1.19** | Δ E −1 | **1.13** |
| Δ CHRG 0 | **0.96** | Δ HB 0 | 0.97 | Δ K-D 0 | **0.72** | Δ E 0 | 1.01 |
| Δ CHRG +1 | **0.88** | Δ HB +1 | **0.93** | Δ K-D +1 | **1.12** | Δ E +1 | **0.89** |
| Δ CHRG +2 | **0.19** | Δ HB +2 | **1.26** | Δ K-D +2 | **0.86** | Δ E +2 | 0.95 |
| pH5.8 ΔΔG | | pH5.8 ΔΔG | | pH5.8 ΔΔG | | pH5.8 ΔΔG | |
| Δ CHRG −2 | **1.66** | Δ HB −2 | 0.99 | Δ K-D −2 | 1.00 | Δ E −2 | **1.23** |
| Δ CHRG −1 | **1.26** | Δ HB −1 | 0.99 | Δ K-D −1 | **1.17** | Δ E −1 | **1.06** |
| Δ CHRG 0 | **0.95** | Δ HB 0 | **0.95** | Δ K-D 0 | **0.80** | Δ E 0 | 0.99 |
| Δ CHRG +1 | **0.94** | Δ HB +1 | **0.90** | Δ K-D +1 | **1.08** | Δ E +1 | **0.94** |
| Δ CHRG +2 | 0.83 | Δ HB +2 | **1.15** | Δ K-D +2 | **0.92** | Δ E +2 | 1.16 |
| Clean8 ΔΔG | | Clean8 ΔΔG | | Clean8 ΔΔG | | Clean8 ΔΔG | |
| Δ CHRG −2 | **1.34** | Δ HB −2 | **1.07** | Δ K-D −2 | **0.89** | Δ E −2 | **0.88** |
| Δ CHRG −1 | **1.22** | Δ HB −1 | **1.02** | Δ K-D −1 | **1.10** | Δ E −1 | **0.98** |
| Δ CHRG 0 | **0.96** | Δ HB 0 | **0.96** | Δ K-D 0 | **0.83** | Δ E 0 | 1.00 |
| Δ CHRG +1 | **0.94** | Δ HB +1 | **0.90** | Δ K-D +1 | **1.07** | Δ E +1 | 1.01 |
| Δ CHRG +2 | **0.62** | Δ HB +2 | **1.05** | Δ K-D +2 | 1.02 | Δ E +2 | **1.32** |
| Clean10 ΔΔG | | Clean10 ΔΔG | | Clean10 ΔΔG | | Clean10 ΔΔG | |
| Δ CHRG −2 | 1.32 | Δ HB −2 | **0.86** | Δ K-D −2 | 1.03 | Δ E −2 | 0.81 |
| Δ CHRG −1 | **1.43** | Δ HB −1 | **1.36** | Δ K-D −1 | **1.11** | Δ E −1 | 1.03 |
| Δ CHRG 0 | **0.92** | Δ HB 0 | **0.72** | Δ K-D 0 | **0.80** | Δ E 0 | 1.00 |
| Δ CHRG +1 | **0.88** | Δ HB +1 | 1.07 | Δ K-D +1 | **1.16** | Δ E +1 | 0.97 |
| Δ CHRG +2 | 0.74 | Δ HB +2 | 1.11 | Δ K-D +2 | **0.91** | Δ E +2 | **1.48** |
| EXP ΔΔG | | EXP ΔΔG | | EXP ΔΔG | | EXP ΔΔG Δ | |
| Δ CHRG −2 | **0.00** | Δ HB −2 | **0.63** | Δ K-D −2 | **0.65** | E −2 | 0.71 |
| Δ CHRG −1 | **0.35** | Δ HB −1 | 0.91 | Δ K-D −1 | 1.11 | Δ E −1 | **1.29** |
| Δ CHRG 0 | **1.08** | Δ HB 0 | 0.95 | Δ K-D 0 | **1.49** | Δ E 0 | 1.06 |
| Δ CHRG +1 | **1.35** | Δ HB +1 | **1.39** | Δ K-D +1 | **0.77** | Δ E +1 | **0.79** |
| Δ CHRG +2 | **1.64** | Δ HB +2 | **1.16** | Δ K-D +2 | **0.72** | Δ E +2 | **0.20** |

Table 13-1 shows the calculations for ASP variants that are better than wild type (ΔΔG<0) compared to the charge change scores based on the matrix in FIG. 27 (Δ CHRG). There is a strong effect of charge change that is significant at the 3 sigma level for keratin (KER) and AAPF activity, as well as BMI Activity, LAS, thermal (THER) stability, while the effects are not as pronounced for casein (CAS) activity and protein expression ([protein]) in *B. subtilis*. Table 13-1 also shows values for hydrogen bonding (Δ HB), with a score of −2 meaning the loss of hydrogen bonding ability. For this enzyme and these properties, decreased hydrogen bonding is generally preferential. In addition Table 13-1 shows the results for Kyte-Doolittle hydropathicity (Δ K-D) and Eisenberg hydrophobicity scales (Δ E). There are significant hydrophobicity effects for all properties, with the Eisenberg scale showing more pronounced effects.

Table 13-2 shows the effects of charge change (Δ CHRG) and Kyte-Doolittle hydropathicity (Δ K-D) for ACT (See e.g., U.S. patent application Ser. No. 10/581,014) on peracid formation (PAF), peracid degradation (PAD) and protein expression in *E. coli*. Clearly properties of amino acid substitutions such as charge and hydrophobicity can affect expression levels in *B. subtilis* and *E. coli*, as well as basic activity and stability of proteins.

Table 13-3 shows the calculations for AmyS variants that are better than wild type for corn flour hydrolysis at 5, 10, and 60 min (CF5, CF10, CF60), activity on DP7 substrates at pH 4.0 and 5.8 (pH 4, pH 5.8), rice starch cleaning at pH 8.6 and 10 (Clean 8 and Clean 10), and protein expression in *B. subtilis* (EXP). The effect of charge on activity has the opposite direction to the effect of charge on expression. Hydrogen bonding and hydrophobicity also demonstrate statistically relevant effects on these properties. Clearly, properties of amino acid substitutions such as charge and hydrophobicity can affect expression levels in *B. subtilis* and *E. coli*, as well as basic activity and stability of proteins.

TABLE 13-4

| AmyE Quintiles for Multiple Properties | | | | | | | |
|---|---|---|---|---|---|---|---|
| AmyE | o/e | AmyE | o/e | AmyE | o/e | AmyE | o/e |
| CF ΔΔG | 1.34 | CF ΔΔG | **1.14** | CF ΔΔG | **0.83** | CF ΔΔG | **0.69** |
| Δ CHRG −2 | | Δ HB −2 | | Δ K-D −2 | | Δ E −2 | |
| Δ CHRG −1 | 1.01 | Δ HB −1 | **1.07** | Δ K-D −1 | **0.90** | Δ E −1 | **0.87** |
| Δ CHRG 0 | **0.95** | Δ HB 0 | **0.92** | Δ K-D 0 | 1.08 | Δ E 0 | **0.93** |
| Δ CHRG +1 | **1.12** | Δ HB +1 | 1.03 | Δ K-D +1 | **1.05** | Δ E +1 | **1.10** |
| Δ CHRG +2 | 0.84 | Δ HB +2 | **0.77** | Δ K-D +2 | 1.01 | Δ E +2 | **1.79** |
| DP3 ΔΔG | **1.20** | DP3 ΔΔG | 1.00 | DP3 ΔΔG | **1.13** | DP3 ΔΔG | 0.90 |
| Δ CHRG −2 | | Δ HB −2 | | Δ K-D −2 | | Δ E −2 | |
| Δ CHRG −1 | **1.07** | Δ HB −1 | **0.91** | Δ K-D −1 | **0.94** | Δ E −1 | **0.97** |
| Δ CHRG 0 | **1.02** | Δ HB 0 | **1.08** | Δ K-D 0 | 1.04 | Δ E 0 | **1.03** |
| Δ CHRG +1 | **0.88** | Δ HB +1 | 1.04 | Δ K-D +1 | 1.00 | Δ E +1 | 0.99 |
| Δ CHRG +2 | **0.88** | Δ HB +2 | 0.97 | Δ K-D +2 | 0.98 | Δ E +2 | **1.48** |
| DP7 ΔΔG | 0.85 | DP7 ΔΔG | **1.03** | DP7 ΔΔG | 1.04 | DP7 ΔΔG | 0.94 |
| Δ CHRG −2 | | Δ HB −2 | | Δ K-D −2 | | Δ E −2 | |
| Δ CHRG −1 | 1.06 | Δ HB −1 | 1.02 | Δ K-D −1 | **0.90** | Δ E −1 | **0.94** |
| Δ CHRG 0 | 1.01 | Δ HB 0 | 0.98 | Δ K-D 0 | **1.06** | Δ E 0 | 1.00 |
| Δ CHRG +1 | **0.95** | Δ HB +1 | 1.06 | Δ K-D +1 | 1.00 | Δ E +1 | **1.02** |
| Δ CHRG +2 | 0.98 | Δ HB +2 | **0.89** | Δ K-D +2 | 1.01 | Δ E +2 | **1.52** |
| DP3 HS ΔΔG | **2.20** | DP3 HS ΔΔG | **1.10** | DP3 HS ΔΔG | **1.21** | DP3 HS ΔΔG | **1.13** |
| Δ CHRG −2 | | Δ HB −2 | | Δ K-D −2 | | Δ E −2 | |
| Δ CHRG −1 | **1.42** | Δ HB −1 | **0.83** | Δ K-D −1 | 1.00 | Δ E −1 | 1.04 |
| Δ CHRG 0 | **0.90** | Δ HB 0 | 1.00 | Δ K-D 0 | 1.06 | Δ E 0 | **0.92** |
| Δ CHRG +1 | 0.99 | Δ HB +1 | 1.08 | Δ K-D +1 | 1.03 | Δ E +1 | 0.98 |
| Δ CHRG +2 | 1.01 | Δ HB +2 | 0.98 | Δ K-D +2 | **0.86** | Δ E +2 | **2.40** |
| Clean 8 ΔΔG | 0.83 | Clean 8 ΔΔG | **1.05** | Clean 8 ΔΔG | 1.10 | Clean 8 ΔΔG | **1.40** |
| Δ CHRG −2 | | Δ HB −2 | | Δ K-D −2 | | Δ E −2 | |
| Δ CHRG −1 | **0.66** | Δ HB −1 | 1.00 | Δ K-D −1 | 1.02 | Δ E −1 | 1.04 |
| Δ CHRG 0 | **0.92** | Δ HB 0 | 1.01 | Δ K-D 0 | 1.01 | Δ E 0 | **0.92** |
| Δ CHRG +1 | **1.40** | Δ HB +1 | **0.90** | Δ K-D +1 | 0.97 | Δ E +1 | **1.02** |
| Δ CHRG +2 | **1.83** | Δ HB +2 | 1.01 | Δ K-D +2 | 0.97 | Δ E +2 | **0.63** |
| Clean 10 ΔΔG | 0.97 | Clean 10 ΔΔG | **0.95** | Clean 10 ΔΔG | 1.02 | Clean 10 ΔΔG | **1.44** |
| Δ CHRG −2 | | Δ HB −2 | | Δ K-D −2 | | Δ E −2 | |
| Δ CHRG −1 | **0.77** | Δ HB −1 | **0.93** | Δ K-D −1 | **1.19** | Δ E −1 | **1.16** |
| Δ CHRG 0 | **0.94** | Δ HB 0 | 1.01 | Δ K-D 0 | 1.01 | Δ E 0 | **0.87** |
| Δ CHRG +1 | **1.27** | Δ HB +1 | 1.03 | Δ K-D +1 | **0.95** | Δ E +1 | 0.97 |
| Δ CHRG +2 | **1.70** | Δ HB +2 | **1.13** | Δ K-D +2 | **0.88** | Δ E +2 | **0.65** |
| EXP ΔΔG | 1.22 | EXP ΔΔG | **0.86** | EXP ΔΔG | **1.16** | EXP ΔΔG Δ | 1.10 |
| Δ CHRG −2 | | Δ HB −2 | | Δ K-D −2 | | E −2 | |
| Δ CHRG −1 | 1.11 | Δ HB −1 | **1.36** | Δ K-D −1 | 1.08 | Δ E −1 | **1.07** |
| Δ CHRG 0 | 0.97 | Δ HB 0 | **0.72** | Δ K-D 0 | 1.04 | Δ E 0 | 1.00 |
| Δ CHRG +1 | 1.05 | Δ HB +1 | 1.07 | Δ K-D +1 | **0.86** | Δ E +1 | 0.97 |
| Δ CHRG +2 | **0.46** | Δ HB +2 | 1.11 | Δ K-D +2 | 0.99 | Δ E +2 | **0.54** |

Table 13-4 shows the calculations for AmyE variants that are better than wt for corn flour hydrolysis (CF), activity on DP3 and DP7 oligosaccharide substrates (DP3 and DP7), thermal stability (DP3 HS), rice starch microswatch cleaning at pH 8.6 and 10 (Clean 8 and Clean 10), and expression in *B. subtilis* (EXP). Cleaning activity has the strongest charge effect.

Example 14

Optimizing Reactions on Substrates Exhibiting Variable Charge

Cellulose conversion was evaluated by techniques known in the art (See e.g., Baker et al., Appl Biochem Biotechnol, 70-72:395-403 [1998]). A standard cellulosic conversion assay was used in the experiments. In this assay enzyme and buffered substrate were placed in containers and incubated at a temperature over time. The reaction was quenched with enough 100 mM glycine, pH 11, to bring the pH of the reaction mixture to at least pH 10. Once the reaction was quenched, an aliquot of the reaction mixture was filtered through a 0.2 micron membrane to remove solids. The filtered solution was then assayed for soluble sugars by HPLC according to the methods described in Baker et al., supra.

Pretreated Corn Stover (PCS)

Corn stover was pretreated with 2% w/w $H_2SO_4$ as described (Schell et al., J Appl Biochem Biotechnol, 105:69-86 [2003]) and followed by multiple washes with deionized water to obtain a pH of 4.5. Sodium acetate was added to make a final concentration of 50 mM and the solution was titrated to pH 5.0. The cellulose concentration in the reaction mixture was approximately 7%.

PCS aliquots before and after saccharification by a commercial cellulase mixture, Spezyme CP and Indiage 44 L, were dosed into 1.5 mL Eppendorf centrifugation tubes and occupied about one third of the volume. Samples were centrifuged at 6,000 rpm for 5 min, the supernatant exchanged for Milli-Q™ water and the process repeated 5 times. A 100 mg/mL stock solution in MIlli-Q™ water was prepared from the rinsed corn stover. This stock was diluted to 1 mg/mL into a 50 mM sodium acetate buffer pH 5.0 for zeta potential measurements. 1 mL aliquot of each substrate sample was transferred to a clean Malvern Instruments (UK) disposable Zetasizer NS™ cuvette.

Table 14-1 indicates that throughout the course of the saccharification reaction the PCS substrate charge, expressed as zeta potential, nearly became twice as negative. Without being bound by theory, there are many explanations for a net negative charge increase including but not limited to enrichment in lignin, the non-reactive portion of this substrate, as well as non-productive binding or fouling of whole cellulases and other proteins. As seen from the BMI microswatch activity in Example 8 (enzyme-to-substrate partition) there is an optimal enzyme zeta potential for performance (e.g., extent of reaction and reaction rate), which matches the substrate zeta potential under reaction medium conditions. Different biomass pretreatments may dramatically influence initial substrate charge. If the enzyme or the substrate become zeta potential mismatched throughout the course of the reaction, the enzyme-substrate interaction will no longer be optimal. This effect will be dramatic for changes of nearly 10 mV, which are the case for biomass conversion.

Strategies to remedy this situation include but are not limited to supplying an enzyme blend spanning various charges; a fed-batch process approach where enzymes possessing different charges at the new optimum are supplied at different reaction times and/or extents of conversion; control of substrate surface charge through addition of formulation agents, particularly surfactants (ionic and non-ionic) or other proteins; control of substrate surface charge through pH adjustments; ionic strength adjustments throughout the reaction in order to shift the enzyme charge optima; membrane filtration, particularly reverse osmosis and nanofiltration, to control ionic strength throughout the reaction; addition of chelators to control ionic strength through elimination of salts; and control of biomass substrate charge through pretreatment processes.

TABLE 14-1

Zeta Potential Of Acid Pretreated Corn Stover

| PCS Condition | Zeta Potential |
|---|---|
| Initial (before saccarification) | −12.0 ± 7.00 mV |
| After saccharification by Spezyme CP | −22.2 ± 8.67 mV |
| After saccharification by Indiage 44L | −22.7 ± 6.84 mV |

Chemical Modification of a *Trichoderma* sp. Cellulase Preparation

This Example describes the treatment of a commercial *Trichoderma* sp. cellulase preparation LAMINEX BG enzyme complex (Genencor Division, Danisco US, Inc.) with succinic anhydride to acetylate the lysine residues. Acetylation of the lysine residues of the LAMINEX BG enzyme complex alters the net charge of the proteins (e.g., increased negative charge). Other similar chemical modifications can be used to also convert the positive charge of the lysine to a negative charged group (for example with acetoxysuccinic anhydride, maleic anhydride, tartaric anhydride and phthalic anhydride treatment) or even to two negative charges (for example with trimellitic anhydride, cis-aconitic anhydride and 4-nitrophthalic anhydride treatment). Other chemical modifications can be used to remove the positive charges of lysine residues resulting in a noncharged residue (e.g., acetic anhydride, butyric anhydride, isobutyric anhydride, hexanoic anhydride, valeric anhydride, isovaleric anhydride and pivalic anhydride treatment).

Lysine residues on a cellulase preparation were modified using succinic anhydride, using a variation of published methods (Lundblad, Chemical Reagents for Protein Modification, Editor: R. Lundblad, $3^{rd}$ Edition CRC press, 1984). For this reaction, a 236 mg sample of LAMINEX BG enzyme complex was prepared in 1 mL of 500 mM HEPES buffer pH 8. A succinic anhydride (Aldrich) solution was prepared by dissolving the powder in DMSO to a 500 mg/mL final concentration before addition of the enzyme complex. An aliquot of succinic anhydride was added such that a ratio of >1:100 lysine to succinic acid was achieved in the reaction tube. Another reaction tube was set up with DMSO and enzyme only, using similar volumes, to serve as the unmodified protein control. The tubes were vortexed and left at room temp overnight. The following day, a 1:10 volume of 1 M glycine pH 3 was added to each tube to quench the succinic anhydride reaction.

Chemical modification was confirmed by comparing modified and unmodified proteins on native gels. Aliquots from each reaction (chemically-modified and unmodified) were analyzed on gradient 8-25%, native gels run at pH 8.8 at 100 volts (Phast System gels, GE Healthcare). Proteins were visualized after Coomassie blue staining of the gel, to confirm that the modification was successful. Staining revealed shifts in protein band migration, confirming the changes in charge of the various protein components of the cellulase preparation. Modified samples of *Trichoderma* sp. cellulase preparations were more negatively charged than unmodified samples.

To isolate the modified and unmodified (control) proteins, 80 μl aliquots of each sample were desalted using spin desalt columns (Pierce). The absorbance at 280 nm of desalted samples (including the control without modification) was measured using a NanoDrop™ spectrophotometer (Thermo), in duplicates after a 1:10 sample dilution to determine the total protein concentration of the samples.

Evaluation of Lignin Binding

Lignin, a complex biopolymer of phenylpropanoid, is the chief non-carbohydrate constituent of wood that binds to cellulose fibers to harden and strengthen cell walls of plants. Because it is cross-linked to other cell wall components, lignin minimizes the accessibility of cellulose and hemicellulose to cellulose degrading enzymes. Hence, lignin is generally associated with reduced digestibility of all plant biomass (Berlin et al., Appl Biochem Biotechnol, 121-124:163-170 [2005]). In particular the binding of cellulases to lignin reduces the degradation of cellulose by cellulases. Lignin is hydrophobic and apparently negatively charged. Thus the inventors contemplated that the addition of negative charges to cellulases may reduce their binding to lignin.

As described herein a reaction was set up to measure the effect of chemical modification on the ability of a *Trichoderma* sp. cellulase preparation to bind a component of plant polymers, namely lignin. Briefly 50 μL of 1.16% lignin (recovered from complete saccharification of bagasse) prepared in 50 mM sodium acetate buffer at pH 5 was combined with 4 μl of a desalted modified or an unmodified *Trichoderma* sp. cellulase preparation. Microfuge tubes containing the reaction mixture were incubated at room temperature for 1 hour, and then centrifuged at high speed to separate soluble from insoluble materials. Ten μl of the supernatant from each tube was collected. The reaction tubes were re-mixed and incubated for an additional 2 hours after which second 10 μl aliguots of the supernatant from each tube were collected. The supernatant samples were analyzed by SDS-PAGE. Reduction of the band intensity in modified *Trichoderma* sp. cellulase preparations was indicative of a reduction in lignin binding.

Evaluation of Bagasse Binding

Bagasse is the biomass that remains after sugarcane has been crushed to extract its juice. A solution containing 2% cellulose of bagasse (acid treated, 28% solid, 57% glycan) was prepared in 50 mM sodium acetate at pH 5. Samples of unmodified or chemically-modified *Trichoderma* sp. cellulase preparations were diluted ten fold in the same sodium acetate buffer. Aliquots of the diluted enzymes were mixed with either bagasse solution or buffer alone and incubated for 1 hr at room temperature. The supernatant was collected and assayed for activity of a component of cellulase, namely beta-glucosidase.

Beta-glucosidase activity was measured using the chloro-nitro-phenyl-beta-D-glucoside (CNPG) assay. The CNPG assay is a kinetic assay in which β-glucosidase converts CNPG to the colored product 2-chloro-4-nitrophenol (CNP). OD is measured at 405 nm over a period of 10 minutes at 37° C. Rates are obtained as Vmax using the SpectraMax software and then converted to specific activity (μM CNP/sec/mg Protein). Briefly, 200 μl of 50 mM sodium acetate buffer pH 5.0 was added to each well of a 96-well microtiter plate. The plate was covered and placed in an Eppendorf Thermomixer at 37° C. for 15 minutes to allow it to equilibrate to temperature. Five μl of the enzyme samples, serially diluted in 50 mM sodium acetate buffer, pH 5.0 were added to each well after equilibration. A 10 mM CNPG stock solution was diluted 1:5 using 50 mM sodium acetate buffer, pH5.0, then 20 μl of the diluted CNPG solution (2 mM) was added to each well containing enzyme samples. The microtiter plate was transferred to a spectrophotometer (SpectraMAX, type 340; Molecular Devices) set at 37° C. and OD was read at 405 nm for 0-15 min, reading at ≤9 sec interval.

The amount of beta-glucosidase activity of the cellulase enzyme samples that remained unbound to the bagasse substrate was considerably greater in the case of the chemically-modified *Trichoderma* sp. cellulase preparation. In particular as determined by the CNPG assay, less than 50% of the unmodified beta-glucosidase remained unbound (e.g., 50% bound) to the bagasse substrate, while nearly 80% of the modified bglu remained unbound (e.g., 20% bound) to the bagasse substrate. Taken together the modified cellulase binding data indicate that reducing the positive charges on cellulase leads to reduced binding to a more negatively-charged plant polymer substrate. In this case the plant polymer substrate was lignin remaining in acid treated biomass. Acid treated biomass from corn stover, a plant biopolymer of similar chemical composition, was demonstrated to adopt an increasingly more negative charged during the course of saccharification, as determined by measurement of zeta potential (See, Table 14-1).

Saccharification of Acid-Pretreated Bagasse

Saccharification of cellulose present in acid-pretreated bagasse (APB) containing varying amounts of additional lignin was evaluated using chemically-modified and unmodified *Trichoderma* sp. cellulase preparations and assayed by HPLC to monitor release of sugars, DP1 to DP7. In a microtiter plate, 200 μl of 3.5% APB was prepared in 50 mM sodium acetate buffer at pH 5, and adjusted to varying amounts of lignin. Twenty microliters of cellulase enzyme solution (unmodified or modified LAMINEX BG) was added to the wells. The plates were covered with aluminum plate sealers and placed in incubators at 50° C., with shaking, for 24 hrs or 48 hrs. The reaction was terminated by adding 100 μl 100 mM glycine pH 10 to each well. Following thorough mixing, the contents of the microtiter plate wells were filtered through a Millipore 96-well filter plate (0.45 μm, PES). The filtrate was diluted into a plate containing 100 μl 10 mM glycine pH 10 and the amount of soluble sugars (DP1 through DP7) produced measured by HPLC. The Agilent 1100 series HPLC was equipped with a de-ashing/guard column (Biorad Catalog No. 125-0118) and an Aminex lead based carbohydrate column (Aminex Catalog No. HPX-87P). The mobile phase used was water with a 0.6 ml/min flow rate. Soluble sugar standards (DP1-DP7) obtained from Sigma were all diluted in Milli-Q water to 100 mg/mL and used for converting peak area for the individual sugars to actual sugar concentrations. The percent of conversion was calculated by dividing the sugars measured from HPLC by 100% conversion of cellulose to glucose.

Cellulase binding to lignin will decrease its efficiency for degrading cellulose. This is demonstrated as a reduction in cellulose conversion in the presence of increasing amounts of lignin present in the saccharification reactions. This trend persists in the modified cellulase preparations. However, there was a 10% increase in cellulose conversion in the modified cellulase samples as compared to unmodified cellulase samples under the above reaction conditions. This result indicates that increasing negative charge of the cellulase reduces the nonproductive binding of cellulase to lignin. In addition, this example demonstrates that chemical modification is an alternative to mutagenesis for control of enzyme charge.

Chemically-Modified CBH2 Increases Saccharification of APB

Purified *Trichoderma* sp. CBH1, CBH2 variant, EG1, EG2 and beta-glucosidase were chemically modified as described above. The CBH2 variant used in this experiment has multiple substitutions (P98L/M134V/T154A/I2112V/S316P/S413Y with numbers corresponding to the wild type mature CBH2 cellulase) as described in US Pub. No. 2006/0205042. The amino acid sequence of the mature CBH2 variant is as follows:

(SEQ ID NO: 32)
QACSSVWGQCGGQNWSGPTCCASGSTCVYSNDYYSQCLPGAASSSSSTRA

ASTTSRVSPTTSRSSSATPPPGSTTTRVPPVGSGTATYSGNPFVGVTLWA

NAYYASEVSSLAIPSLTGAMATAAAAVAKVPSFVWLDTLDKTPLMEQTLA

DIRAANKNGGNYAGQFVVYDLPDRDCAALASNGEYSIADGGVAKYKNYID

TIRQIVVEYSDVRTLLVIEPDSLANLVTNLGTPKCANAQSAYLECINYAV

TQLNLPNVAMYLDAGHAGWLGWPANQDPAAQLFANVYKNASSPRALRGLA

TNVANYNGWNITSPPPYTQGNAVYNEKLYIHAIGPLLANHGWSNAFFITD

QGRSGKQPTGQQQWGDWCNVIGTGFGIRPSANTGDSLLDSFVWVKPGGEC

DGTSDSSAPRFDYHCALPDALQPAPQAGAWFQAYFVQLLTNANPSFL.

Chemical modifications of CBH1, CBH2 variant, EG1, EG2 and beta-glucosidase were verified by their shifted mobility on the native gel compared to the unmodified proteins. Modified CBH1, CBH2 variant, EG1, EG2 and beta-glucosidase have more negative charges. All the protein concentrations were measured using a NanoDrop™ spectrophotometer (Thermo). A saccharification reaction was set up in a microtiter plate, in each well of a microtiter plate, 150 uL of 7% APB was prepared in 50 mM sodium acetate buffer at pH 5, 20 μl of enzyme mix of 21 μg total protein was added so that the final protein to cellulose ratio in each well was 20 mg/g. Six enzyme mixes were made by adding purified modified or unmodified Bglu, CBH2 variant, EG1, or EG2 to a *T. reesei* background in which the genes encoding cellobiohydrolase I (CBHI, Cel7a), cellobiohydrolase II (CBHII, Cel6a), endoglucanase I (EGI, Cel7b), and endoglucanase II (EGII, Cel5a) have been inactivated (See, US 2007/0128690). In each mix, 72.5% *T. reesei* background, 2.5% Bglu, 15% CBH2 variant, 5% EG1, 5% EG2 were added, the first four mixes have one protein that is not modified, the fifth mix has all the protein not modified, and the sixth mix has all the protein modified. The plate was incubated at 50° C. for 72 hours. The reaction was terminated by adding 100 μl 100 mM glycine pH 10 to each well. Following thorough mixing, the contents of the microtiter plate wells were filtered through a Millipore 96-well filter plate (0.45 μm, PES). The filtrate was diluted into a plate containing 100 μl 10 mM glycine pH 10 and the amount of soluble sugars (DP1 through DP7) produced was measured by HPLC. The Agilent 1100 series HPLC was equipped with a de-ashing/guard column (Biorad Catalog No. 125-0118) and an Aminex lead based carbohydrate column (Aminex Catalog No. HPX-87P). The mobile phase used was water with a 0.6 ml/min flow rate. Soluble sugar standards (DP1-DP7) obtained from Sigma were all diluted in Milli-Q water to 100 mg/mL and used for converting peak area for the individual sugars to actual sugar concentrations. The percent of conversion was calculated by dividing the sugars measured from HPLC by 100% conversion of cellulose to glucose.

As determined during development of the present invention, the sixth enzyme mix (modified EG2, EG1, CBH2 variant and beta-glucosidase) with all protein modified had the greatest cellulose conversion, while the fifth enzyme mix with all protein unmodified has the lowest cellulose conversion. Comparing the first four enzyme mixes, the second enzyme mix with the unmodified CBH2 gave next lowest net cellulose conversion. Thus the modified proteins had demonstrable advantages over unmodified proteins in cellulose conversion.

Preparation of *T. reesei* CBH2 Surface Charge Variants

As determined during development of the present invention, succinylation of surface lysine residues of CBH2 improved performance on APB as described above, and on pretreated corn stover. The charge of modified CBH2 variant was about −17 compared to the unmodified CBH2 variant. With this in mind a CBH2 charge ladder was designed for determination of the optimal surface charge in cellulase performance applications. The coding region of the parent wild type *T. reesei* cbh2 is shown below, with standard font indicating DNA of the signal sequence and bold font indicating the DNA sequence of the mature enzyme:

(SEQ ID NO: 33)
atgattgtcggcattctcaccacgctggctacgctggccacactcgcagc tagtgtgcctctagaggagcggcaagcttgctcaagcgtctggggccaat gtggtggccagaattggtcgggtccgacttgctgtgcttccggaagcaca tgcgtctactccaacgactattactcccagtgtcttcccggcgctgcaag ctcaagctcgtccacgcgcgccgcgtcgacgacttctcgagtatccccca caacatcccggtcgagctccgcgacgcctccacctggttctactactacc agagtacctccagtcggatcgggaaccgctacgtattcaggcaacccttt tgttggggtcactccttgggccaatgcatattacgcctctgaagttagca gcctcgctattcctagcttgactggagccatggccactgctgcagcagct gtcgcaaaggttccctcttttatgtggctggatactcttgacaagacccc tctcatggagcaaaccttggccgacatccgcaccgccaacaagaatggcg gtaactatgccggacagtttgtggtgtatgacttgccggatcgcgattgc gctgcccttgcctcgaatggcgaatactctattgccgatggtggcgtcgc caaatataagaactatatcgacaccattcgtcaaattgtcgtggaatatt ccgatatccggaccctcctggttattgagcctgactctcttgccaacctg gtgaccaacctcggtactccaaagtgtgccaatgctcagtcagcctacct tgagtgcatcaactacgccgtcacacagctgaaccttccaaatgttgcga tgtatttggacgctggccatgcaggatggcttggctggccggcaaaccaa gacccggccgctcagctatttgcaaatgtttacaagaatgcatcgtctcc gagagctcttcgcggattggcaaccaatgtcgccaactacaacgggtgga acattaccagccccccatcgtacacgcaaggcaacgctgtctacaacgag aagctgtacatccacgctattggacctcttcttgccaatcacggctggtc caacgccttcttcatcactgatcaaggtcgatcgggaaagcagcctaccg gacagcaacagtggggagactggtgcaatgtgatcggcaccggatttggt attcgcccatccgcaaacactggggactcgttgctggattcgtttgtctg ggtcaagccaggcggcgagtgtgacggcaccagcgacagcagtgcgccac gatttgactcccactgtgcgctcccagatgccttgcaaccggcgcctcaa gctggtgcttggttccaagcctactttgtgcagcttctcacaaacgcaaa cccatcgttcctgtaa.

The amino acid sequence of the parent wild type *T. reesei* cbh2 precursor protein is shown below:

(SEQ ID NO: 34)

```
MIVGILTTLATLATLAASVPLEERQACSSVWGQCGGQNWSGPTCCASGST
CVYSNDYYSQCLPGAASSSSSTRAASTTSRVSPTTSRSSSATPPPGSTTT
RVPPVGSGTATYSGNPFVGVTPWANAYYASEVSSLAIPSLTGAMATAAAA
VAKVPSFMWLDTLDKTPLMEQTLADIRTANKNGGNYAGQFVVYDLPDRDC
AALASNGEYSIADGGVAKYKNYIDTIRQIVVEYSDIRTLLVIEPDSLANL
VTNLGTPKCANAQSAYLECINYAVTQLNLPNVAMYLDAGHAGWLGWPANQ
DPAAQLFANVYKNASSPRALRGLATNVANYNGWNITSPPSYTQGNAVYNE
KLYIHAIGRLLANHGWSNAFFITDQGRSGKQPTGQQQWGDWCNVIGTGFG
IRPSANTGDSLLDSFVWVKPGGECDGTSDSSAPRFDSHCALPDALQPAAQ
AGAWFQAYFVQLLTNANPSFL.
```

The amino acid sequence of the parent wild type *T. reesei* cbh2 mature protein is shown below:

(SEQ ID NO: 35)

```
QACSSVWGQCGGQNWSGPTCCASGSTCVYSNDYYSQCLPGAASSSSSTRA
ASTTSRVSPTTSRSSSATPPPGSTTTRVPPVGSGTATYSGNPFVGVTPWA
NAYYASEVSSLAIPSLTGAMATAAAAVAKVPSFMWLDTLDKTPLMEQTLA
DIRTANKNGGNYAGQFVVYDLPDRDCAALASNGEYSIADGGVAKYKNYID
TIRQIVVEYSDIRTLLVIEPDSLANLVTNLGTPKCANAQSAYLECINYAV
TQLNLPNVAMYLDAGHAGWLGWPANQDPAAQLFANVYKNASSPRALRGLA
TNVANYNGWNITSPPSYTQGNAVYNEKLYIHAIGRLLANHGWSNAFFITD
QGRSGKQPTGQQQWGDWCNVIGTGFGIRPSANTGDSLLDSFVWVKPGGEC
DGTSDSSAPRFDSHCALPDALQPAAQAGAWFQAYFVQLLTNANPSFL.
```

Residues selected to be mutagenized included non-conserved, exposed lysine, arginine, asparigine, and glutamine residues, which were selected for substitution to introduce negative charges. Succinylated lysines in modified CBH2 were identified by mass spectrometry and selected for mutagenesis to glutamate, resulting in a −2 charge difference per substitution. Other residues were selected for substitution by analysis of CBH2 three-dimensional structure combined with amino acid alignment of homologous CBH2 sequences (See e.g., US Pub. No. US 2006/0205042, FIG. 3 herein incorporated by reference). Surface residues that were highly variable in the CBH2 amino acid sequence alignment were candidates for mutagenesis. However, accumulation of substitutions in close proximity was avoided. Arginine was replaced with glutamine (charge −1), and glutamine and asparagine were substituted with the respective carboxyl variants (charge −1). In addition, aspartate and glutamate residues were selected for substitution to the respective amine residues for completion of the charge ladder (charge +1). Specific CBH2 substitutions are shown in Table 5-1, with all positions shown with the exception of R63 and R77, located in the CBH2 catalytic domain. A net positive charge can be created by either removal of a negatively charged residue or by introduction of a positively charged residue. Likewise a net negative charge can be created by either removal of a positively charged residue or by introduction of a negatively charged residue.

TABLE 14-2

| CBH2 Charge Ladder Substitutions | | | | | |
|---|---|---|---|---|---|
| −2 Lysine | −1 Arginine | −1 Asparagine | −1 Glutamine | +1 Aspartate | +1 Glutamate |
| K157E | R153Q | N382D | Q204E | D189N | E208Q |
| K129E | R294Q | N344D | Q147E | D211N | E244Q |
| K288E | R203Q | N237D | Q239E | D405N | E146Q |
| K194E | R378Q | N339D | Q281E | D277N | |
| K356E | R63Q | N289D | | D151N | |
| K327E | R77Q | N161D | | | |
| | | N285D | | | |
| | | N197D | | | |
| | | N254D | | | |
| | | N247D | | | |

For preparation of a CBH2 charge ladder, ten CBH2 charge variants (C-1 to C-10) were designed spanning a charge range of +8 to −32 as compared to the wild-type CBH2 and shown in Table 14-3.

TABLE 14-3

| CBH2 Charge Ladder Variants | | | | | | | | | | |
|---|---|---|---|---|---|---|---|---|---|---|
| C-1 8 | C-2 4 | CBH2 0 | C-3 −4 | C-4 −8 | C-5 −12 | C-6 −16 | C-7 −20 | C-8 −24 | C-9 −28 | C-10 −32 |
| D189N | D189N | WT | K157E | K157E | K157E | K157E | K157E | K157E | K157E | K157E |
| E208Q | E208Q | | K129E | K129E | K129E | K129E | K129E | K129E | K129E | K129E |
| D211N | D211N | | | K288E | K288E | K288E | K288E | K288E | K288E | K288E |
| D405N | D405N | | | K194E | K194E | K194E | K194E | K194E | K194E | K194E |
| E244Q | | | | | K356E | K356E | K356E | K356E | K356E | K356E |
| D277N | | | | | K327E | K327E | K327E | K327E | K327E | K327E |
| D151N | | | | | | R153Q | R153Q | R153Q | R153Q | R153Q |
| E146Q | | | | | | R294Q | R294Q | R294Q | R294Q | R294Q |
| | | | | | | R203Q | R203Q | R203Q | R203Q | R203Q |
| | | | | | | R378Q | R378Q | R378Q | R378Q | R378Q |
| | | | | | | | N382D | N382D | N382D | N382D |
| | | | | | | | N344D | N344D | N344D | N344D |
| | | | | | | | N237D | N237D | N237D | N237D |
| | | | | | | | N339D | N339D | N339D | N339D |
| | | | | | | | | N289D | N289D | N289D |
| | | | | | | | | N161D | N161D | N161D |
| | | | | | | | | Q204E | Q204E | Q204E |
| | | | | | | | | Q147E | Q147E | Q147E |
| | | | | | | | | | N285D | N285D |
| | | | | | | | | | N197D | N197D |

TABLE 14-3-continued

| CBH2 Charge Ladder Variants | | | | | | | | | | |
|---|---|---|---|---|---|---|---|---|---|---|
| C-1 8 | C-2 4 | CBH2 0 | C-3 −4 | C-4 −8 | C-5 −12 | C-6 −16 | C-7 −20 | C-8 −24 | C-9 −28 | C-10 −32 |
| | | | | | | | | | N254D N247D | N254D N247D Q239E Q281E R63Q R77Q |

The amino acid sequences of the variants were back translated to DNA and codon optimized for expression in *Trichoderma reesei* using GeneDesigner software (DNA2.0). The codon-optimized cbh2 variant genes were synthesized and the DNA of the CBH2 surface charge variants (SCVs) was PCR-amplified from the DNA2.0 constructs using primers:

```
GGHTK22 forward
                                    (SEQ ID NO: 34)
5'-CACCATGATCGTGGGAATTCTTACTACTC-3';
and

GGTHK23 reverse
                                    (SEQ ID NO: 37)
5'-CTACAAAAACGAAGGGTTCGCATT-3'.
```

However in one experiment, site directed mutagenesis was used to introduce K129E and K157E mutations (cbh2 charge variant C3) into the genomic DNA of wild type CBH2. CBH2 cbh2 charge variant C3 was cloned into pTrex3GM and expressed as described herein. The PCR products were purified and cloned into pENTR/TOPO for transformation of *E. coli* TOP10 cells. Plasmid DNA was isolated from single colonies and the correct sequence was verified. CBH2 SCVs were cloned into pTrex3GM, pTTTpyr(pcbhl), and pTTTpyr (pstpl) as shown in Table 14-4.

TABLE 14-4

Expression Clones of CBH2 Surface Charge Variants

| CBH2 Variant | Destination Vectors pTrex3gM | pTTTpyr ($P_{cbh1}$) | pTTTpyr($P_{stp1}$) |
|---|---|---|---|
| C-1 (pTK354a) | 1 | 11 | 21 |
| C-2 (pTK355a) | 2 | 12 | 22 |
| C-3 (pTK356a) | 3 | 13 | 23 |
| C-4 (pTK357a) | 4 | 14 | 24 |
| C-5 (pTK358a) | 5 | 15 | 25 |
| C-8 (pTK361a) | 6 | 16 | 26 |
| C-6 (pTK359a) | (7) | (17) | (27) |
| C-7 (pTK360a) | 8 | 18 | 28 |
| C-9 (pTK362a) | 9 | 19 | 29 |
| C-10 (pTK363b) | 10 | 20 | 30 |

Expression of CBH2 Variants in *T. reesei*

This Example describes methods used for expression of CBH2 surface charge variants (SCV) in *T. reesei*. Briefly, biolistic transformation of *T. reesei* with the pTrex3 μM expression vector containing the cbh2 charge variant C3 (with K129E and K157E mutations) open reading frame was performed using the following protocol. *T. reesei* in which the genes encoding cellobiohydrolase I (CBHI, Cel7a), cellobiohydrolase II (CBHII, Cel6a), endoglucanase I (EGI, Cel7b), and endoglucanase II (EGII, Cel5a) have been inactivated was used. Transformation of the *Trichoderma reesei* strain by the biolistic transformation method was accomplished using a Biolistic® PDS-1000/he Particle Delivery System from Bio-Rad (Hercules, Calif.) following the manufacturer's instructions (See WO 05/001036 and US 2006/0003408). Transformants were transferred to new acetamide selection plates. Stable transformants were inoculated into filter microtiter plates (Millipore), containing 200⊠ l/well of glycine minimal media (6.0 g/L glycine; 4.7 g/L $(NH_4)_2SO_4$; 5.0 g/L $KH_2PO_4$; 1.0 g/L $MgSO_4.7H_2O$; 33.0 g/L PIPPS; p.H. 5.5) with post sterile addition of ~2% glucose/sophorose mixture as the carbon source, 10 ml/L of 100 g/L of $CaCl_2$, 2.5 ml/L of *T. reesei* trace elements (400×): 175 g/L Citric acid anhydrous; 200 g/L $FeSO_4.7H_2O$; 16 g/L $ZnSO_4.7H_2O$; 3.2 g/L $CuSO_4.5H_2O$; 1.4 g/L $MnSO_4.H_2O$; 0.8 g/L $H_3BO_3$. Transformants were grown in liquid culture for 5 days in $O_2$ rich chamber housed in a 28° C. incubator. The supernatant samples from the filter microtiter plate were obtained by using a vacuum manifold. Samples were run on 4-12% NuPAGE gels (Invitrogen) according to the manufactures instructions. The gel was stained with Simply Blue stain (Invitrogen). Expression of additional CHB2 surface charge variants may be accomplished using this method.

Example 15

Modulating of an Enzyme's pH-Activity Profile

This Example describes the use of surface charge mutations to optimize an enzyme's pH-activity profile for a given reaction.

Figure 31:
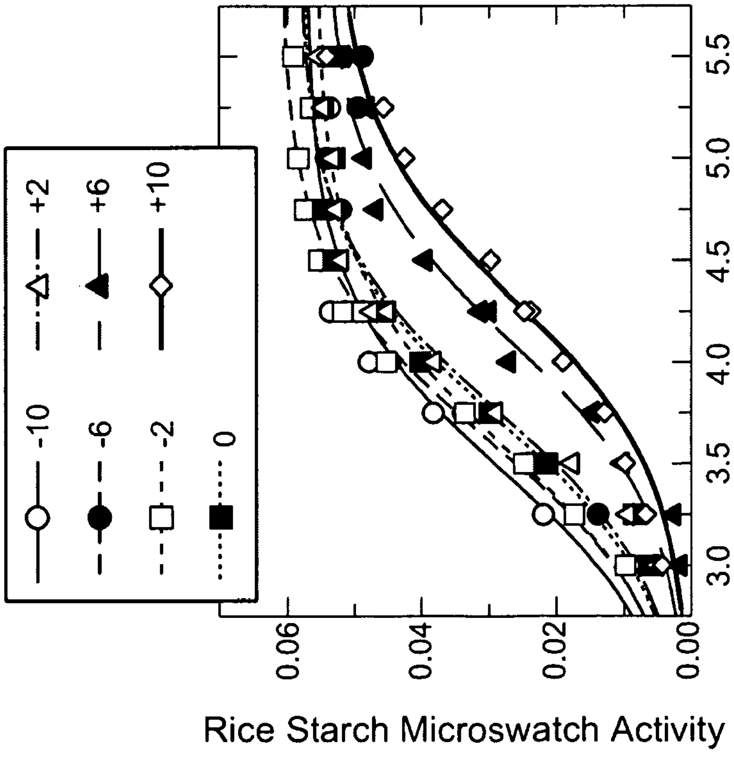
FIG. 31 provides rice starch cleaning activity of the first AmyS charge ladder as a function of pH. pH 3.0-4.25 is 200 mM Na formate+0.01% Tween-80. pH 4.25-5.5 is 200 mM Na acetate+0.01% Tween-80. The data are fit to titration curves, each with a single pKa value.

FIG. 31 shows rice starch microswatch cleaning activity as a function of pH for the first AmyS charge ladder of Example 5. The pH range from 3.0 to 4.25 was in 200 mM Na formate containing 0.01% Tween-80, while the pH range from 4.25 to 5.5 was in 200 mM Na acetate containing 0.01% Tween-80. The data are fit to titration curves, each with a single pKa value.

Figure 32:
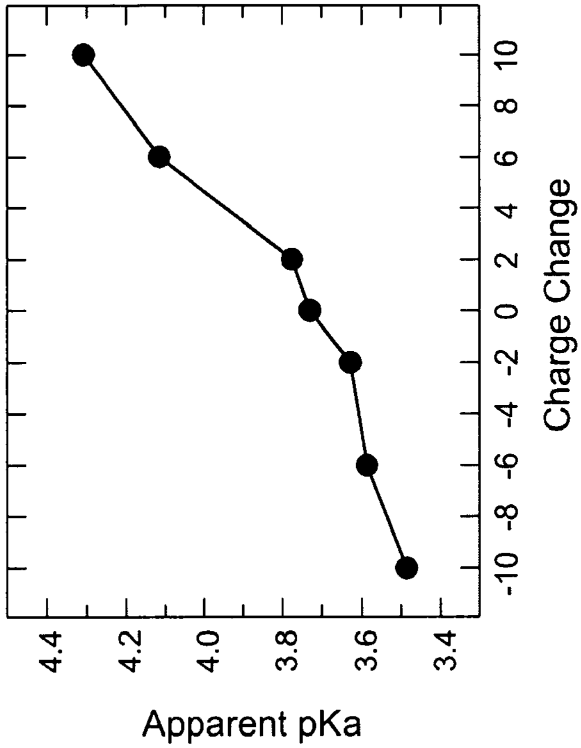
FIG. 32 provides pKa values determined in FIG. 31 plotted against charge change relative to wild type AmyS.

FIG. 32 show an apparent pKa for AmyS catalysis as a function of charge change for the first AmyS charge ladder of Example 5. These data demonstrate that pH-activity profiles for an alpha-amylase can be significantly shifted by surface charge mutations, even in 200 mM buffer. Although this had been reported at very low ionic strength for subtilisin (Russell et al., *J Mol Biol,* 193: 803-13 [1987]) and for D-xylose isomerase (Cha et al., Mol Cell, 8: 374-82 [1998]) this is believed to be the first time this has been accomplished with alpha-amylase, and, surprisingly even at high ionic strength.

All patents and publications mentioned in the specification are indicative of the levels of those skilled in the art to which the invention pertains. Those of skill in the art readily appreciate that the present invention is well adapted to carry out the objects and obtain the ends and advantages mentioned, as well as those inherent therein. The compositions and methods described herein are representative of preferred embodiments, are exemplary, and are not intended as limitations on the scope of the invention. It is readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by herein.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not excised material is specifically recited herein.

What invention claimed is:

1. A method for identifying protein variants having improved cleaning performance, comprising:

a) providing a plurality of candidate protein variants having a zeta potential between −17.08 mV and −2.28 mV, such that the plurality of candidate protein variants is enriched in members having a value of at least 80% of a maximal cleaning performance, wherein said protein of interest is a protease or an amylase;

b) testing said plurality of candidate protein variants and at least one wild type protein for cleaning performance; and c) identifying protein variants having improved cleaning performance, wherein the wild type protein achieves a performance index value of 1.0 in cleaning performance and the protein variants have a value greater than 1.0 for cleaning performance.

2. The method of claim 1, wherein the candidate protein variants have a zeta potential between −14.92 mV and −4.44 mV, such that the plurality of candidate protein variants is enriched in members having a value of at least 90% of the maximal cleaning performance.

3. The method of claim 1, wherein said protein of interest is a protease.

4. The method of claim 3, wherein said protease is a neutral metalloprotease or serine protease.

5. The method of claim 4, wherein said serine protease is a subtilisin.

6. The method of claim 4, wherein said neutral metalloprotease is obtained from a member of the family *Bacillaceae.*

7. The method of claim 4, wherein said serine protease is obtained from a member of the genus *Cellulomonas.*

8. The method of claim 1, wherein said protein of interest is an amylase.

9. The method of claim 1, wherein said zeta potential of said candidate protein variants and said wild type enzyme are determined and compared.

10. The method of claim 1, wherein said wash performance comprises blood, milk, and ink wash performance.

11. The method of claim 10, wherein said candidate protein variants and wild-type protein are tested in a detergent composition.

12. The method of claim 11, wherein said detergent composition is formulated into a powdered or liquid detergent having a pH of between about 5 and about 12.0.

13. The method of claim 11, wherein said wash performance is tested in a cold water liquid detergent having a basic pH.

14. The method of claim 11, wherein said wash performance is tested in a hot water detergent.

* * * * *

SEQUENCE LISTING

```
<160> NUMBER OF SEQ ID NOS: 39

<210> SEQ ID NO 1
<211> LENGTH: 1566
<212> TYPE: DNA
<213> ORGANISM: Bacillus amyloliquefaciens

<400> SEQUENCE: 1

gtgggtttag gtaagaaatt gtctgttgct gtcgccgctt cctttatgag tttaaccatc     60
agtctgccgg gtgttcaggc cgctgagaat cctcagctta aagaaaacct gacgaatttt    120
gtaccgaagc attctttggt gcaatcagaa ttgccttctg tcagtgacaa agctatcaag    180
caatacttga aacaaaacgg caaagtcttt aaaggcaatc cttctgaaag attgaagctg    240
attgaccaaa cgaccgatga tctcggctac aagcacttcc gttatgtgcc tgtcgtaaac    300
ggtgtgcctg tgaaagactc tcaagtcatt attcacgtcg ataaatccaa caacgtctat    360
gcgattaacg gtgaattaaa caacgatgtt tccgccaaaa cggcaaacag caaaaaatta    420
tctgcaaatc aggcgctgga tcatgcttat aaagcgatcg gcaaatcacc tgaagccgtt    480
tctaacggaa ccgttgcaaa caaaaacaaa gccgagctga aagcagcagc cacaaaagac    540
ggcaaatacc gcctcgccta tgatgtaacc atccgctaca tcgaaccgga acctgcaaac    600
tgggaagtaa ccgttgatgc ggaaacagga aaaatcctga aaaagcaaaa caaagtggag    660
catgccgcca caaccggaac aggtacgact cttaaaggaa aaacggtctc attaaatatt    720
tcttctgaaa gcggcaaata tgtgctgcgc gatctttcta aacctaccgg aacacaaatt    780
attacgtacg atctgcaaaa ccgcgagtat aacctgccgg gcacactcgt atccagcacc    840
acaaaccagt ttacaacttc ttctcagcgc gctgccgttg atgcgcatta caacctcggc    900
aaagtgtatg attatttcta tcagaagttt aatcgcaaca gctacgacaa taaaggcggc    960
aagatcgtat cctccgttca ttacggcagc agatacaata acgcagcctg gatcggcgac   1020
caaatgattt acggtgacgg cgacggttca ttcttctcac ctctttccgg ttcaatggac   1080
gtaaccgctc atgaaatgac acatggcgtt acacaggaaa cagccaacct gaactacgaa   1140
aatcagccgg gcgctttaaa cgaatccttc tctgatgtat tcgggtactt caacgatact   1200
gaggactggg atatcggtga agatattacg gtcagccagc cggctctccg cagcttatcc   1260
aatccgacaa aatacggaca gcctgataat ttcaaaaatt acaaaaacct tccgaacact   1320
gatgccggcg actacggcgg cgtgcataca aacagcggaa tcccgaacaa agccgcttac   1380
aatacgatta caaaaatcgg cgtgaacaaa gcggagcaga tttactatcg tgctctgacg   1440
gtatacctca ctccgtcatc aacttttaaa gatgcaaaag ccgctttgat tcaatctgcg   1500
cgggaccttt acggctctca agatgctgca agcgtagaag ctgcctggaa tgcagtcgga   1560
```

ttgtaa 1566

<210> SEQ ID NO 2
<211> LENGTH: 521
<212> TYPE: PRT
<213> ORGANISM: Bacillus amyloliquefaciens

<400> SEQUENCE: 2

```
Met Gly Leu Gly Lys Lys Leu Ser Val Ala Val Ala Ala Ser Phe Met
1               5                   10                  15

Ser Leu Thr Ile Ser Leu Pro Gly Val Gln Ala Ala Glu Asn Pro Gln
            20                  25                  30

Leu Lys Glu Asn Leu Thr Asn Phe Val Pro Lys His Ser Leu Val Gln
        35                  40                  45

Ser Glu Leu Pro Ser Val Ser Asp Lys Ala Ile Lys Gln Tyr Leu Lys
    50                  55                  60

Gln Asn Gly Lys Val Phe Lys Gly Asn Pro Ser Glu Arg Leu Lys Leu
65                  70                  75                  80

Ile Asp Gln Thr Thr Asp Asp Leu Gly Tyr Lys His Phe Arg Tyr Val
                85                  90                  95

Pro Val Val Asn Gly Val Pro Val Lys Asp Ser Gln Val Ile Ile His
            100                 105                 110

Val Asp Lys Ser Asn Asn Val Tyr Ala Ile Asn Gly Glu Leu Asn Asn
        115                 120                 125

Asp Val Ser Ala Lys Thr Ala Asn Ser Lys Lys Leu Ser Ala Asn Gln
    130                 135                 140

Ala Leu Asp His Ala Tyr Lys Ala Ile Gly Lys Ser Pro Glu Ala Val
145                 150                 155                 160

Ser Asn Gly Thr Val Ala Asn Lys Asn Lys Ala Glu Leu Lys Ala Ala
                165                 170                 175

Ala Thr Lys Asp Gly Lys Tyr Arg Leu Ala Tyr Asp Val Thr Ile Arg
            180                 185                 190

Tyr Ile Glu Pro Glu Pro Ala Asn Trp Glu Val Thr Val Asp Ala Glu
        195                 200                 205

Thr Gly Lys Ile Leu Lys Lys Gln Asn Lys Val Glu His Ala Ala Thr
    210                 215                 220

Thr Gly Thr Gly Thr Thr Leu Lys Gly Lys Thr Val Ser Leu Asn Ile
225                 230                 235                 240

Ser Ser Glu Ser Gly Lys Tyr Val Leu Arg Asp Leu Ser Lys Pro Thr
                245                 250                 255

Gly Thr Gln Ile Ile Thr Tyr Asp Leu Gln Asn Arg Glu Tyr Asn Leu
            260                 265                 270

Pro Gly Thr Leu Val Ser Ser Thr Thr Asn Gln Phe Thr Thr Ser Ser
        275                 280                 285

Gln Arg Ala Ala Val Asp Ala His Tyr Asn Leu Gly Lys Val Tyr Asp
    290                 295                 300

Tyr Phe Tyr Gln Lys Phe Asn Arg Asn Ser Tyr Asp Asn Lys Gly Gly
305                 310                 315                 320

Lys Ile Val Ser Ser Val His Tyr Gly Ser Arg Tyr Asn Asn Ala Ala
                325                 330                 335

Trp Ile Gly Asp Gln Met Ile Tyr Gly Asp Gly Asp Gly Ser Phe Phe
            340                 345                 350

Ser Pro Leu Ser Gly Ser Met Asp Val Thr Ala His Glu Met Thr His
        355                 360                 365
```

```
Gly Val Thr Gln Glu Thr Ala Asn Leu Asn Tyr Glu Asn Gln Pro Gly
    370                 375                 380

Ala Leu Asn Glu Ser Phe Ser Asp Val Phe Gly Tyr Phe Asn Asp Thr
385                 390                 395                 400

Glu Asp Trp Asp Ile Gly Glu Asp Ile Thr Val Ser Gln Pro Ala Leu
                405                 410                 415

Arg Ser Leu Ser Asn Pro Thr Lys Tyr Gly Gln Pro Asp Asn Phe Lys
            420                 425                 430

Asn Tyr Lys Asn Leu Pro Asn Thr Asp Ala Gly Asp Tyr Gly Gly Val
        435                 440                 445

His Thr Asn Ser Gly Ile Pro Asn Lys Ala Ala Tyr Asn Thr Ile Thr
    450                 455                 460

Lys Ile Gly Val Asn Lys Ala Glu Gln Ile Tyr Tyr Arg Ala Leu Thr
465                 470                 475                 480

Val Tyr Leu Thr Pro Ser Ser Thr Phe Lys Asp Ala Lys Ala Ala Leu
                485                 490                 495

Ile Gln Ser Ala Arg Asp Leu Tyr Gly Ser Gln Asp Ala Ala Ser Val
            500                 505                 510

Glu Ala Ala Trp Asn Ala Val Gly Leu
        515                 520


<210> SEQ ID NO 3
<211> LENGTH: 300
<212> TYPE: PRT
<213> ORGANISM: Bacillus amyloliquefaciens

<400> SEQUENCE: 3

Ala Ala Thr Thr Gly Thr Gly Thr Thr Leu Lys Gly Lys Thr Val Ser
1               5                   10                  15

Leu Asn Ile Ser Ser Glu Ser Gly Lys Tyr Val Leu Arg Asp Leu Ser
            20                  25                  30

Lys Pro Thr Gly Thr Gln Ile Ile Thr Tyr Asp Leu Gln Asn Arg Glu
        35                  40                  45

Tyr Asn Leu Pro Gly Thr Leu Val Ser Ser Thr Thr Asn Gln Phe Thr
    50                  55                  60

Thr Ser Ser Gln Arg Ala Ala Val Asp Ala His Tyr Asn Leu Gly Lys
65                  70                  75                  80

Val Tyr Asp Tyr Phe Tyr Gln Lys Phe Asn Arg Asn Ser Tyr Asp Asn
                85                  90                  95

Lys Gly Gly Lys Ile Val Ser Ser Val His Tyr Gly Ser Arg Tyr Asn
            100                 105                 110

Asn Ala Ala Trp Ile Gly Asp Gln Met Ile Tyr Gly Asp Gly Asp Gly
        115                 120                 125

Ser Phe Phe Ser Pro Leu Ser Gly Ser Met Asp Val Thr Ala His Glu
    130                 135                 140

Met Thr His Gly Val Thr Gln Glu Thr Ala Asn Leu Asn Tyr Glu Asn
145                 150                 155                 160

Gln Pro Gly Ala Leu Asn Glu Ser Phe Ser Asp Val Phe Gly Tyr Phe
                165                 170                 175

Asn Asp Thr Glu Asp Trp Asp Ile Gly Glu Asp Ile Thr Val Ser Gln
            180                 185                 190

Pro Ala Leu Arg Ser Leu Ser Asn Pro Thr Lys Tyr Gly Gln Pro Asp
        195                 200                 205

Asn Phe Lys Asn Tyr Lys Asn Leu Pro Asn Thr Asp Ala Gly Asp Tyr
```

-continued

```
    210                 215                 220

Gly Gly Val His Thr Asn Ser Gly Ile Pro Asn Lys Ala Ala Tyr Asn
225                 230                 235                 240

Thr Ile Thr Lys Ile Gly Val Asn Lys Ala Glu Gln Ile Tyr Tyr Arg
                245                 250                 255

Ala Leu Thr Val Tyr Leu Thr Pro Ser Ser Thr Phe Lys Asp Ala Lys
            260                 265                 270

Ala Ala Leu Ile Gln Ser Ala Arg Asp Leu Tyr Gly Ser Gln Asp Ala
        275                 280                 285

Ala Ser Val Glu Ala Ala Trp Asn Ala Val Gly Leu
    290                 295                 300


<210> SEQ ID NO 4
<211> LENGTH: 46
<212> TYPE: DNA
<213> ORGANISM: Artificial
<220> FEATURE:
<223> OTHER INFORMATION: synthetic primer

<400> SEQUENCE: 4

ctgcaggaat tcagatctta acatttttcc cctatcattt ttcccg                    46


<210> SEQ ID NO 5
<211> LENGTH: 46
<212> TYPE: DNA
<213> ORGANISM: Artificial
<220> FEATURE:
<223> OTHER INFORMATION: synthetic primer

<400> SEQUENCE: 5

ggatccaagc ttcccgggaa aagacatata tgatcatggt gaagcc                    46


<210> SEQ ID NO 6
<211> LENGTH: 1488
<212> TYPE: DNA
<213> ORGANISM: Artificial
<220> FEATURE:
<223> OTHER INFORMATION: synthetic codon optimized ASP coding sequence

<400> SEQUENCE: 6

atgacaccac gaactgtcac aagagctctg gctgtggcaa cagcagctgc tacactcttg     60

gctgggggta tggcagcaca agctaacgaa ccggctcctc caggatctgc atcagcccct    120

ccacgattag ctgaaaaact tgaccctgac ttacttgaag caatggaacg cgatctgggg    180

ttagatgcag aggaagcagc tgcaacgtta gcttttcagc atgacgcagc tgaaacggga    240

gaggctcttg ctgaggaact cgacgaagat ttcgcgggca cgtgggttga agatgatgtg    300

ctgtatgttg caaccactga tgaagatgct gttgaagaag tcgaaggcga aggagcaact    360

gctgtgactg ttgagcattc tcttgctgat ttagaggcgt ggaagacggt tttggatgct    420

gcgctggagg gtcatgatga tgtgcctacg tggtacgtcg acgtgcctac gaattcggta    480

gtcgttgctg taaaggcagg agcgcaggat gtagctgcag gacttgtgga aggcgctgat    540

gtgccatcag atgcggtcac ttttgtagaa acggacgaaa cgcctagaac gatgttcgac    600

gtaattggag gcaacgcata tactattggc ggccggtcta gatgttctat cggattcgca    660

gtaaacggtg gcttcattac tgccggtcac tgcggaagaa caggagccac tactgccaat    720

ccgactggca catttgcagg tagctcgttt ccgggaaatg attatgcatt cgtccgaaca    780

ggggcaggag taaatttgct tgcccaagtc aataactact cgggcggcag agtccaagta    840
```

-continued

```
gcaggacata cggccgcacc agttggatct gctgtatgcc gctcaggtag cactacaggt    900

tggcattgcg gaactatcac ggcgctgaat tcgtctgtca cgtatccaga gggaacagtc    960

cgaggactta tccgcacgac ggtttgtgcc gaaccaggtg atagcggagg tagcctttta   1020

gcgggaaatc aagcccaagg tgtcacgtca ggtggttctg gaaattgtcg gacgggggga   1080

acaacattct ttcaaccagt caacccgatt ttgcaggctt acggcctgag aatgattacg   1140

actgactctg gaagttcccc tgctccagca cctacatcat gtacaggcta cgcaagaacg   1200

ttcacaggaa ccctcgcagc aggaagagca gcagctcaac cgaacggtag ctatgttcag   1260

gtcaaccgga gcggtacaca ttccgtctgt ctcaatggac ctagcggtgc ggactttgat   1320

ttgtatgtgc agcgatggaa tggcagtagc tgggtaaccg tcgctcaatc gacatcgccg   1380

ggaagcaatg aaaccattac gtaccgcgga aatgctggat attatcgcta cgtggttaac   1440

gctgcgtcag gatcaggagc ttacacaatg ggactcaccc tcccctga                1488


<210> SEQ ID NO 7
<211> LENGTH: 495
<212> TYPE: PRT
<213> ORGANISM: Cellulomonas bogoriensis

<400> SEQUENCE: 7

Met Thr Pro Arg Thr Val Thr Arg Ala Leu Ala Val Ala Thr Ala Ala
1               5                   10                  15

Ala Thr Leu Leu Ala Gly Gly Met Ala Ala Gln Ala Asn Glu Pro Ala
            20                  25                  30

Pro Pro Gly Ser Ala Ser Ala Pro Pro Arg Leu Ala Glu Lys Leu Asp
        35                  40                  45

Pro Asp Leu Leu Glu Ala Met Glu Arg Asp Leu Gly Leu Asp Ala Glu
    50                  55                  60

Glu Ala Ala Ala Thr Leu Ala Phe Gln His Asp Ala Ala Glu Thr Gly
65                  70                  75                  80

Glu Ala Leu Ala Glu Glu Leu Asp Glu Asp Phe Ala Gly Thr Trp Val
                85                  90                  95

Glu Asp Asp Val Leu Tyr Val Ala Thr Thr Asp Glu Asp Ala Val Glu
            100                 105                 110

Glu Val Glu Gly Glu Gly Ala Thr Ala Val Thr Val Glu His Ser Leu
        115                 120                 125

Ala Asp Leu Glu Ala Trp Lys Thr Val Leu Asp Ala Ala Leu Glu Gly
    130                 135                 140

His Asp Asp Val Pro Thr Trp Tyr Val Asp Val Pro Thr Asn Ser Val
145                 150                 155                 160

Val Val Ala Val Lys Ala Gly Ala Gln Asp Val Ala Ala Gly Leu Val
                165                 170                 175

Glu Gly Ala Asp Val Pro Ser Asp Ala Val Thr Phe Val Glu Thr Asp
            180                 185                 190

Glu Thr Pro Arg Thr Met Phe Asp Val Ile Gly Gly Asn Ala Tyr Thr
        195                 200                 205

Ile Gly Gly Arg Ser Arg Cys Ser Ile Gly Phe Ala Val Asn Gly Gly
    210                 215                 220

Phe Ile Thr Ala Gly His Cys Gly Arg Thr Gly Ala Thr Thr Ala Asn
225                 230                 235                 240

Pro Thr Gly Thr Phe Ala Gly Ser Ser Phe Pro Gly Asn Asp Tyr Ala
                245                 250                 255

Phe Val Arg Thr Gly Ala Gly Val Asn Leu Leu Ala Gln Val Asn Asn
```

```
            260                 265                 270

Tyr Ser Gly Gly Arg Val Gln Val Ala Gly His Thr Ala Ala Pro Val
        275                 280                 285

Gly Ser Ala Val Cys Arg Ser Gly Ser Thr Thr Gly Trp His Cys Gly
    290                 295                 300

Thr Ile Thr Ala Leu Asn Ser Ser Val Thr Tyr Pro Glu Gly Thr Val
305                 310                 315                 320

Arg Gly Leu Ile Arg Thr Thr Val Cys Ala Glu Pro Gly Asp Ser Gly
                325                 330                 335

Gly Ser Leu Leu Ala Gly Asn Gln Ala Gln Gly Val Thr Ser Gly Gly
            340                 345                 350

Ser Gly Asn Cys Arg Thr Gly Gly Thr Thr Phe Phe Gln Pro Val Asn
        355                 360                 365

Pro Ile Leu Gln Ala Tyr Gly Leu Arg Met Ile Thr Thr Asp Ser Gly
    370                 375                 380

Ser Ser Pro Ala Pro Ala Pro Thr Ser Cys Thr Gly Tyr Ala Arg Thr
385                 390                 395                 400

Phe Thr Gly Thr Leu Ala Ala Gly Arg Ala Ala Ala Gln Pro Asn Gly
                405                 410                 415

Ser Tyr Val Gln Val Asn Arg Ser Gly Thr His Ser Val Cys Leu Asn
            420                 425                 430

Gly Pro Ser Gly Ala Asp Phe Asp Leu Tyr Val Gln Arg Trp Asn Gly
        435                 440                 445

Ser Ser Trp Val Thr Val Ala Gln Ser Thr Ser Pro Gly Ser Asn Glu
    450                 455                 460

Thr Ile Thr Tyr Arg Gly Asn Ala Gly Tyr Tyr Arg Tyr Val Val Asn
465                 470                 475                 480

Ala Ala Ser Gly Ser Gly Ala Tyr Thr Met Gly Leu Thr Leu Pro
                485                 490                 495


<210> SEQ ID NO 8
<211> LENGTH: 189
<212> TYPE: PRT
<213> ORGANISM: Cellulomonas bogoriensis

<400> SEQUENCE: 8

Phe Asp Val Ile Gly Gly Asn Ala Tyr Thr Ile Gly Gly Arg Ser Arg
1               5                   10                  15

Cys Ser Ile Gly Phe Ala Val Asn Gly Gly Phe Ile Thr Ala Gly His
            20                  25                  30

Cys Gly Arg Thr Gly Ala Thr Thr Ala Asn Pro Thr Gly Thr Phe Ala
        35                  40                  45

Gly Ser Ser Phe Pro Gly Asn Asp Tyr Ala Phe Val Arg Thr Gly Ala
    50                  55                  60

Gly Val Asn Leu Leu Ala Gln Val Asn Asn Tyr Ser Gly Gly Arg Val
65                  70                  75                  80

Gln Val Ala Gly His Thr Ala Ala Pro Val Gly Ser Ala Val Cys Arg
                85                  90                  95

Ser Gly Ser Thr Thr Gly Trp His Cys Gly Thr Ile Thr Ala Leu Asn
            100                 105                 110

Ser Ser Val Thr Tyr Pro Glu Gly Thr Val Arg Gly Leu Ile Arg Thr
        115                 120                 125

Thr Val Cys Ala Glu Pro Gly Asp Ser Gly Gly Ser Leu Leu Ala Gly
    130                 135                 140
```

```
Asn Gln Ala Gln Gly Val Thr Ser Gly Gly Ser Gly Asn Cys Arg Thr
145                 150                 155                 160

Gly Gly Thr Thr Phe Phe Gln Pro Val Asn Pro Ile Leu Gln Ala Tyr
                165                 170                 175

Gly Leu Arg Met Ile Thr Thr Asp Ser Gly Ser Ser Pro
            180                 185

<210> SEQ ID NO 9
<211> LENGTH: 30
<212> TYPE: PRT
<213> ORGANISM: Artificial
<220> FEATURE:
<223> OTHER INFORMATION: synthetic hybrid signal sequence

<400> SEQUENCE: 9

Met Arg Ser Lys Lys Arg Thr Val Thr Arg Ala Leu Ala Val Ala Thr
1               5                   10                  15

Ala Ala Ala Thr Leu Leu Ala Gly Gly Met Ala Ala Gln Ala
            20                  25                  30

<210> SEQ ID NO 10
<211> LENGTH: 90
<212> TYPE: DNA
<213> ORGANISM: Artificial
<220> FEATURE:
<223> OTHER INFORMATION: synthetic hybrid signal coding sequence

<400> SEQUENCE: 10

atgagaagca agaagcgaac tgtcacaaga gctctggctg tggcaacagc agctgctaca      60

ctcttggctg ggggtatggc agcacaagct                                      90

<210> SEQ ID NO 11
<211> LENGTH: 53
<212> TYPE: DNA
<213> ORGANISM: Artificial
<220> FEATURE:
<223> OTHER INFORMATION: synthetic primer

<400> SEQUENCE: 11

tcatgcaggg taccatgaga agcaagaagc gaactgtcac aagagctctg gct            53

<210> SEQ ID NO 12
<211> LENGTH: 37
<212> TYPE: DNA
<213> ORGANISM: Artificial
<220> FEATURE:
<223> OTHER INFORMATION: synthetic primer

<400> SEQUENCE: 12

gtgtgcaagc tttcaagggg aacttccaga gtcagtc                              37

<210> SEQ ID NO 13
<211> LENGTH: 45
<212> TYPE: DNA
<213> ORGANISM: Artificial
<220> FEATURE:
<223> OTHER INFORMATION: synthetic primer

<400> SEQUENCE: 13

tgagctgcta gcaaaaggag agggtaaaga atgagaagca agaag                     45

<210> SEQ ID NO 14
<211> LENGTH: 38
<212> TYPE: DNA
```

<213> ORGANISM: Artificial
<220> FEATURE:
<223> OTHER INFORMATION: synthetic primer

<400> SEQUENCE: 14
catgcatccc gggttaaggg gaacttccag agtcagtc 38

<210> SEQ ID NO 15
<211> LENGTH: 1303
<212> TYPE: DNA
<213> ORGANISM: Artificial
<220> FEATURE:
<223> OTHER INFORMATION: synthetic coding sequence

<400> SEQUENCE: 15
atctcaaaaa aatgggtcta ctaaaatatt actccatcta ttataataaa ttcacagaat 60
agtcttttaa gtaagtctac tctgaatttt tttaaaagga gagggtaaag agtgagaagc 120
aaaaaattgt ggatcgtcgc gtcgaccgca ttgctgattt ctgttgcttt tagctcatcc 180
atcgcatccg ctgctgaaga agcaaaagaa aaatatttaa ttggctttaa tgagcaggaa 240
gctgtcagtg agtttgtaga acaagttgag gcaaatgacg aggtagccat tctctctgag 300
gaagaggaag tcgaaattga attgcttcat gaatttgaaa cgattcctgt tctgtccgtt 360
gagttaagcc cagaagatgt ggacgcgtta gagctcgatc cagctatttc ttatattgaa 420
gaggatgcag aagtaactac aatggcgcaa tcggtaccat ggggaattag cagagtacaa 480
gccccagctg cacataaccg tggattgaca ggttctggtg taaaagttgc tgtccttgat 540
accggtattt ccactcatcc agacttaaat attcgtggtg gagctagctt tgtaccaggg 600
gaaccatcca ctcaagatgg caatggacat ggcactcatg ttgccggcac aatcgcggct 660
cttaacaatt caattggtgt tcttggcgta gcgccaagcg cagaactata cgctgttaaa 720
gtattaggag caagcggttc aggctctgtc agctctattg cccaaggatt ggaatgggca 780
gggaacaatg gcatgcacgt tgctaatctt agtttaggat ctccttcgcc aagtgccaca 840
cttgagcaag ctgttaatag cgcgacttct agaggcgttc ttgttgtagc ggcctctgga 900
aattcaggtg caggctcaat cagctatccg gcccgttatg cgaacgctat ggcagtcgga 960
gctactgacc aaaacaacaa ccgcgccagc ttttcacagt atggcgcagg gcttgacatt 1020
gtcgcaccag gtgtaaacgt gcagagcact tacccaggtt caacatatgc cagcttaaac 1080
ggtacatcaa tggctactcc tcatgttgca ggtgcggctg cacttgttaa acaaaagaac 1140
ccatcttggt ccaatgtaca aatccgcaat catcttaaga atacggcaac tagcttagga 1200
agcacaaact tgtatggaag cggacttgtc aatgcagaag ctgcaactcg ttaaaagctt 1260
aactcgagat aaaaaaccgg ccttggcccc gccggttttt tat 1303

<210> SEQ ID NO 16
<211> LENGTH: 380
<212> TYPE: PRT
<213> ORGANISM: Artificial
<220> FEATURE:
<223> OTHER INFORMATION: synthetic GG36 sequence

<400> SEQUENCE: 16

Met Arg Ser Lys Lys Leu Trp Ile Val Ala Ser Thr Ala Leu Leu Ile
1 5 10 15

Ser Val Ala Phe Ser Ser Ser Ile Ala Ser Ala Ala Glu Glu Ala Lys
20 25 30

Glu Lys Tyr Leu Ile Gly Phe Asn Glu Gln Glu Ala Val Ser Glu Phe

```
        35                  40                  45

Val Glu Gln Val Glu Ala Asn Asp Glu Val Ala Ile Leu Ser Glu Glu
    50                  55                  60

Glu Glu Val Glu Ile Glu Leu Leu His Glu Phe Glu Thr Ile Pro Val
65                  70                  75                  80

Leu Ser Val Glu Leu Ser Pro Glu Asp Val Asp Ala Leu Glu Leu Asp
                85                  90                  95

Pro Ala Ile Ser Tyr Ile Glu Glu Asp Ala Glu Val Thr Thr Met Ala
            100                 105                 110

Gln Ser Val Pro Trp Gly Ile Ser Arg Val Gln Ala Pro Ala Ala His
        115                 120                 125

Asn Arg Gly Leu Thr Gly Ser Gly Val Lys Val Ala Val Leu Asp Thr
    130                 135                 140

Gly Ile Ser Thr His Pro Asp Leu Asn Ile Arg Gly Gly Ala Ser Phe
145                 150                 155                 160

Val Pro Gly Glu Pro Ser Thr Gln Asp Gly Asn Gly His Gly Thr His
                165                 170                 175

Val Ala Gly Thr Ile Ala Ala Leu Asn Asn Ser Ile Gly Val Leu Gly
            180                 185                 190

Val Ala Pro Ser Ala Glu Leu Tyr Ala Val Lys Val Leu Gly Ala Ser
        195                 200                 205

Gly Ser Gly Ser Val Ser Ser Ile Ala Gln Gly Leu Glu Trp Ala Gly
    210                 215                 220

Asn Asn Gly Met His Val Ala Asn Leu Ser Leu Gly Ser Pro Ser Pro
225                 230                 235                 240

Ser Ala Thr Leu Glu Gln Ala Val Asn Ser Ala Thr Ser Arg Gly Val
                245                 250                 255

Leu Val Val Ala Ala Ser Gly Asn Ser Gly Ala Gly Ser Ile Ser Tyr
            260                 265                 270

Pro Ala Arg Tyr Ala Asn Ala Met Ala Val Gly Ala Thr Asp Gln Asn
        275                 280                 285

Asn Asn Arg Ala Ser Phe Ser Gln Tyr Gly Ala Gly Leu Asp Ile Val
    290                 295                 300

Ala Pro Gly Val Asn Val Gln Ser Thr Tyr Pro Gly Ser Thr Tyr Ala
305                 310                 315                 320

Ser Leu Asn Gly Thr Ser Met Ala Thr Pro His Val Ala Gly Ala Ala
                325                 330                 335

Ala Leu Val Lys Gln Lys Asn Pro Ser Trp Ser Asn Val Gln Ile Arg
            340                 345                 350

Asn His Leu Lys Asn Thr Ala Thr Ser Leu Gly Ser Thr Asn Leu Tyr
        355                 360                 365

Gly Ser Gly Leu Val Asn Ala Glu Ala Ala Thr Arg
    370                 375                 380


<210> SEQ ID NO 17
<211> LENGTH: 269
<212> TYPE: PRT
<213> ORGANISM: Artificial
<220> FEATURE:
<223> OTHER INFORMATION: synthetic GG36 sequence

<400> SEQUENCE: 17

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
```

```
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 18
<211> LENGTH: 1326
<212> TYPE: DNA
<213> ORGANISM: Artificial
<220> FEATURE:
<223> OTHER INFORMATION: synthetic coding sequence

<400> SEQUENCE: 18

```
gaattcatct caaaaaaatg ggtctactaa aatattattc catctattat aataaattca     60

cagaatagtc ttttaagtaa gtctactctg aatttttta aaaggagagg gtaaagagtg    120

agaagcaaaa aattgtgaga agcaaaaaat tgtggatcag tttgctgttt gctttagcgt    180

taatctttac gatggcgttc ggcagcacat ccagcgcgca ggctgcaggg aaatcaaacg    240

gggaaaagaa atatattgtc gggtttaaac agacaatgag cacgatgagc gccgctaaga    300

agaaagacgt catttctgaa aaaggcggga aagtgcaaaa gcaattcaaa tatgtagacg    360

cagctagcgc tacattaaac gaaaaagctg taaaagaatt gaaaaaagac ccgagcgtcg    420

cttacgttga agaagatcac gtagcacacg cgtacgcgca gtccgtgcca tatggcgtat    480

cacaaattaa agcccctgct ctgcactctc aaggctacac cggttcaaat gttaaagtag    540

cggttatcga cagcggtatc gattcttctc atccagatct taaagtagca ggcggagcca    600

gcatggttcc ttctgaaaca aatcctttcc aagacaacaa ctctcacgga acacacgttg    660
```

```
ctggtaccgt tgcggctctt aataactcaa tcggtgtatt aggcgttgcg ccaagcgcat    720

cactttacgc tgtaaaagtt ctcggcgccg acggttccgg ccaatacagc tggatcatta    780

acggaatcga gtgggcgatc gcaaacaata tggacgttat taacatgagc ctcggcggac    840

cgtccggttc tgctgcttta aaagcggcag ttgataaagc cgttgcatcc ggcgtcgtag    900

tcgttgcggc agccggcaac gaaggcactt ccggcagctc aagcacagtg ggctaccctg    960

gtaaataccc ttctgtcatt gcagtaggcg ctgtcgacag cagcaaccaa agagcatctt   1020

tctcaagcgt aggacctgag ctcgatgtca tggcacctgg cgtatctatc caaagcacgc   1080

ttcctggaaa caaatacggc gcgttgaacg gtacatcaat ggcatctccg cacgttgccg   1140

gagccgcggc tttgattctt tctaagcacc cgaactggac aaacactcaa gtccgcagct   1200

ctctagaaaa caccactaca aaacttggtg attctttcta ctatggaaaa gggctgatca   1260

atgtacaggc ggcagctcag taaaactcga gataaaaaac cggccttggc cccgccggtt   1320

ttttat                                                              1326
```

```
<210> SEQ ID NO 19
<211> LENGTH: 382
<212> TYPE: PRT
<213> ORGANISM: Artificial
<220> FEATURE:
<223> OTHER INFORMATION: synthetic FNA sequence

<400> SEQUENCE: 19

Met Arg Ser Lys Lys Leu Trp Ile Ser Leu Leu Phe Ala Leu Ala Leu
1               5                   10                  15

Ile Phe Thr Met Ala Phe Gly Ser Thr Ser Ser Ala Gln Ala Ala Gly
            20                  25                  30

Lys Ser Asn Gly Glu Lys Lys Tyr Ile Val Gly Phe Lys Gln Thr Met
        35                  40                  45

Ser Thr Met Ser Ala Ala Lys Lys Lys Asp Val Ile Ser Glu Lys Gly
    50                  55                  60

Gly Lys Val Gln Lys Gln Phe Lys Tyr Val Asp Ala Ala Ser Ala Thr
65                  70                  75                  80

Leu Asn Glu Lys Ala Val Lys Glu Leu Lys Lys Asp Pro Ser Val Ala
                85                  90                  95

Tyr Val Glu Glu Asp His Val Ala His Ala Tyr Ala Gln Ser Val Pro
            100                 105                 110

Tyr Gly Val Ser Gln Ile Lys Ala Pro Ala Leu His Ser Gln Gly Tyr
        115                 120                 125

Thr Gly Ser Asn Val Lys Val Ala Val Ile Asp Ser Gly Ile Asp Ser
    130                 135                 140

Ser His Pro Asp Leu Lys Val Ala Gly Gly Ala Ser Met Val Pro Ser
145                 150                 155                 160

Glu Thr Asn Pro Phe Gln Asp Asn Asn Ser His Gly Thr His Val Ala
                165                 170                 175

Gly Thr Val Ala Ala Leu Asn Asn Ser Ile Gly Val Leu Gly Val Ala
            180                 185                 190

Pro Ser Ala Ser Leu Tyr Ala Val Lys Val Leu Gly Ala Asp Gly Ser
        195                 200                 205

Gly Gln Tyr Ser Trp Ile Ile Asn Gly Ile Glu Trp Ala Ile Ala Asn
    210                 215                 220

Asn Met Asp Val Ile Asn Met Ser Leu Gly Gly Pro Ser Gly Ser Ala
225                 230                 235                 240
```

```
Ala Leu Lys Ala Ala Val Asp Lys Ala Val Ala Ser Gly Val Val Val
                245                 250                 255

Val Ala Ala Ala Gly Asn Glu Gly Thr Ser Gly Ser Ser Ser Thr Val
            260                 265                 270

Gly Tyr Pro Gly Lys Tyr Pro Ser Val Ile Ala Val Gly Ala Val Asp
        275                 280                 285

Ser Ser Asn Gln Arg Ala Ser Phe Ser Ser Val Gly Pro Glu Leu Asp
    290                 295                 300

Val Met Ala Pro Gly Val Ser Ile Gln Ser Thr Leu Pro Gly Asn Lys
305                 310                 315                 320

Tyr Gly Ala Leu Asn Gly Thr Ser Met Ala Ser Pro His Val Ala Gly
                325                 330                 335

Ala Ala Ala Leu Ile Leu Ser Lys His Pro Asn Trp Thr Asn Thr Gln
            340                 345                 350

Val Arg Ser Ser Leu Glu Asn Thr Thr Thr Lys Leu Gly Asp Ser Phe
        355                 360                 365

Tyr Tyr Gly Lys Gly Leu Ile Asn Val Gln Ala Ala Ala Gln
    370                 375                 380


<210> SEQ ID NO 20
<211> LENGTH: 275
<212> TYPE: PRT
<213> ORGANISM: Artificial
<220> FEATURE:
<223> OTHER INFORMATION: synthetic FNA sequence

<400> SEQUENCE: 20

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Leu Asn Gly Thr Ser Met Ala Ser
    210                 215                 220
```

-continued

```
Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275
```

<210> SEQ ID NO 21
<211> LENGTH: 87
<212> TYPE: DNA
<213> ORGANISM: Artificial
<220> FEATURE:
<223> OTHER INFORMATION: synthetic LAT coding region

<400> SEQUENCE: 21

```
atgaaacaac aaaaacggct ttacgcccga ttgctgacgc tgttatttgc gctcatcttc      60

ttgctgcctc attctgcagc ttcagca                                          87
```

<210> SEQ ID NO 22
<211> LENGTH: 29
<212> TYPE: PRT
<213> ORGANISM: Artificial
<220> FEATURE:
<223> OTHER INFORMATION: synthetic LAT signal peptide

<400> SEQUENCE: 22

```
Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ser Ala
            20                  25
```

<210> SEQ ID NO 23
<211> LENGTH: 1545
<212> TYPE: DNA
<213> ORGANISM: Artificial
<220> FEATURE:
<223> OTHER INFORMATION: synthetic amylase

<400> SEQUENCE: 23

```
gccgcaccgt ttaacggtac catgatgcag tattttgaat ggtacttgcc ggatgatggc      60

acgttatgga ccaaagtggc caatgaagcc aacaacttat ccagccttgg catcaccgct     120

ctttggctgc cgcccgctta caaaggaaca agccgcagcg acgtagggta cggagtatac     180

gacttgtatg acctcggcga attcaatcaa aaagggaccg tccgcacaaa atatggaaca     240

aaagctcaat atcttcaagc cattcaagcc gcccacgccg ctggaatgca agtgtacgcc     300

gatgtcgtgt tcgaccataa aggcggcgct gacggcacgg aatgggtgga cgccgtcgaa     360

gtcaatccgt ccgaccgcaa ccaagaaatc tcgggcacct atcaaatcca agcatggacg     420

aaatttgatt ttcccgggcg gggcaacacc tactccagct ttaagtggcg ctggtaccat     480

tttgacggcg ttgactggga cgaaagccga aaattaagcc gcatttacaa attccgcggc     540

atcggcaaag cgtgggattg ggaagtagac acggaaaacg gaaactatga ctacttaatg     600

tatgccgacc ttgatatgga tcatcccgaa gtcgtgaccg agctgaaaaa ctgggggaaa     660

tggtatgtca acacaacgaa cattgatggg ttccggcttg atgccgtcaa gcatattaag     720

ttcagttttt ttcctgattg gttgtcgtat gtgcgttctc agactggcaa gccgctattt     780

accgtcgggg aatattggag ctatgacatc aacaagttgc acaattacat tacgaaaaca     840
```

```
aacggaacga tgtctttgtt tgatgccccg ttacacaaca aattttatac cgcttccaaa     900

tcagggggcg catttgatat gcgcacgtta atgaccaata ctctcatgaa agatcaaccg     960

acattggccg tcaccttcgt tgataatcat gacaccgaac ccggccaagc gctgcagtca    1020

tgggtcgacc catggttcaa accgttggct tacgccttta ttctaactcg gcaggaagga    1080

tacccgtgcg tcttttatgg tgactattat ggcattccac aatataacat tccttcgctg    1140

aaaagcaaaa tcgatccgct cctcatcgcg cgcagggatt atgcttacgg aacgcaacat    1200

gattatcttg atcactccga catcatcggg tggacaaggg aaggggtcac tgaaaaacca    1260

ggatccgggc tggccgcact gatcaccgat gggccgggag gaagcaaatg gatgtacgtt    1320

ggcaaacaac acgctggaaa agtgttctat gaccttaccg gcaaccggag tgacaccgtc    1380

accatcaaca gtgatggatg gggggaattc aaagtcaatg gcggttcggt ttcggtttgg    1440

gttcctagaa aaacgaccgt ttctaccatc gctcggccga tcacaacccg accgtggact    1500

ggtgaattcg tccgttggac cgaaccacgg ttggtggcat ggcct                    1545


<210> SEQ ID NO 24
<211> LENGTH: 515
<212> TYPE: PRT
<213> ORGANISM: Artificial
<220> FEATURE:
<223> OTHER INFORMATION: synthetic amylase

<400> SEQUENCE: 24

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240
```

```
Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515
```

<210> SEQ ID NO 25
<211> LENGTH: 486
<212> TYPE: PRT
<213> ORGANISM: Artificial
<220> FEATURE:
<223> OTHER INFORMATION: synthetic protease

<400> SEQUENCE: 25

```
Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80
```

-continued

```
Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Gln Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr
                485
```

<210> SEQ ID NO 26
<211> LENGTH: 1452
<212> TYPE: DNA
<213> ORGANISM: Artificial
<220> FEATURE:
<223> OTHER INFORMATION: synthetic amylase

<400> SEQUENCE: 26
aatacggcgc cgatcaacga aacgatgatg cagtattttg aatgggatct gccgaatgat 60
ggaacgctgt ggacgaaagt caaaaacgaa gcggcgaatc ttagcagcct gggaatcaca 120
gcactttggc ttccgccggc atataaagga acgagccaaa gcgatgtcgg ctatggcgtc 180
tatgatctgt atgacctggg cgaatttaac caaaaaggca cgatccggac gaaatatggc 240
acgaaaacac agtatatcca agcgatccag gcagcaaaag cagcaggcat gcaagtctat 300
gccgacgtcg tctttaatca taaagcggga gcggatggca cagaatttgt cgatgccgtc 360
gaagttgatc cgagcaacag aaaccaagaa acgagcggca cgtatcaaat ccaagcgtgg 420
acgaaatttg attttccggg cagaggcaat acgtatagca gctttaaatg gcgctggtat 480
cattttgacg gcacggattg ggatgaaagc agaaaactga accggatcta taaatttcgg 540
agcacgggca aagcatggga ttgggaagtc gatacggaaa acggcaacta tgactatctg 600
atgtttgccg atctggatat ggatcatccg gaagtcgtca cggaactgaa aaattggggc 660
acgtggtatg ttaatacgac gaacatcgat ggctttagac tggatgccgt caaacatatc 720
aaatatagct tttttccgga ctggctgacg tatgtcagaa accagacggg caaaaacctt 780
tttgccgtcg gcgaattttg gagctatgac gtcaacaaac ttcataacta tatcacgaaa 840
acgaacggca gcatgagcct ttttgatgcc ccgcttcata acaactttta tacggcgagc 900
aaaagctcag gctattttga tatgagatat ctgctgaaca acacgctgat gaaagatcaa 960
ccgagcctgg cagtcacact ggtcgataac catgatacac aaccgggcca aagccttcaa 1020
agctgggtcg aaccgtggtt taaaccgctg gcgtatgcct ttatcctgac gagacaagaa 1080
gggtatcctt gcgtctttta tggcgactat tatggcatcc cgaaatataa tatcccgggc 1140
ctgaaaagca aaatcgatcc gctgctgatc gccagacggg attatgccta tggcacacag 1200
cgggattata tcgaccatca ggacatcatc ggctggacaa gagaaggcat cgatacgaaa 1260
ccgaatagcg gactggcagc actgattaca gatggaccgg gcggaagcaa atggatgtat 1320
gtcggcaaaa aacatgccgg caaagtcttt tatgatctga cgggcaacag aagcgatacg 1380
gtcacgatca atgctgatgg ctggggagaa tttaaagtca atggcggcag cgtttcaatc 1440
tgggtcgcca aa 1452

<210> SEQ ID NO 27
<211> LENGTH: 484
<212> TYPE: PRT
<213> ORGANISM: Artificial
<220> FEATURE:
<223> OTHER INFORMATION: synthetic amylase

<400> SEQUENCE: 27

Asn Thr Ala Pro Ile Asn Glu Thr Met Met Gln Tyr Phe Glu Trp Asp
1 5 10 15

Leu Pro Asn Asp Gly Thr Leu Trp Thr Lys Val Lys Asn Glu Ala Ala
20 25 30

Asn Leu Ser Ser Leu Gly Ile Thr Ala Leu Trp Leu Pro Pro Ala Tyr
35 40 45

```
Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Thr Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Ser Thr Gly Lys Ala Trp Asp Trp Glu Val Asp Thr
            180                 185                 190

Glu Asn Gly Asn Tyr Asp Tyr Leu Met Phe Ala Asp Leu Asp Met Asp
        195                 200                 205

His Pro Glu Val Val Thr Glu Leu Lys Asn Trp Gly Thr Trp Tyr Val
    210                 215                 220

Asn Thr Thr Asn Ile Asp Gly Phe Arg Leu Asp Ala Val Lys His Ile
225                 230                 235                 240

Lys Tyr Ser Phe Phe Pro Asp Trp Leu Thr Tyr Val Arg Asn Gln Thr
                245                 250                 255

Gly Lys Asn Leu Phe Ala Val Gly Glu Phe Trp Ser Tyr Asp Val Asn
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Thr Ala Ser Lys Ser Ser Gly
    290                 295                 300

Tyr Phe Asp Met Arg Tyr Leu Leu Asn Asn Thr Leu Met Lys Asp Gln
305                 310                 315                 320

Pro Ser Leu Ala Val Thr Leu Val Asp Asn His Asp Thr Gln Pro Gly
                325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
        355                 360                 365

Asp Tyr Tyr Gly Ile Pro Lys Tyr Asn Ile Pro Gly Leu Lys Ser Lys
    370                 375                 380

Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
                405                 410                 415

Ile Asp Thr Lys Pro Asn Ser Gly Leu Ala Ala Leu Ile Thr Asp Gly
            420                 425                 430

Pro Gly Gly Ser Lys Trp Met Tyr Val Gly Lys Lys His Ala Gly Lys
        435                 440                 445

Val Phe Tyr Asp Leu Thr Gly Asn Arg Ser Asp Thr Val Thr Ile Asn
    450                 455                 460

Ala Asp Gly Trp Gly Glu Phe Lys Val Asn Gly Gly Ser Val Ser Ile
```

-continued 465 470 475 480

Trp Val Ala Lys

<210> SEQ ID NO 28
<211> LENGTH: 55
<212> TYPE: DNA
<213> ORGANISM: Artificial
<220> FEATURE:
<223> OTHER INFORMATION: synthetic primer

<400> SEQUENCE: 28
cttcttgctg cctcattctg cagcttcagc agccgcaccg tttaacggta ccatg 55

<210> SEQ ID NO 29
<211> LENGTH: 44
<212> TYPE: DNA
<213> ORGANISM: Artificial
<220> FEATURE:
<223> OTHER INFORMATION: synthetic primer

<400> SEQUENCE: 29
caggaaatcc gtcctctgtt aactcaggtc gtttttctag gaac 44

<210> SEQ ID NO 30
<211> LENGTH: 32
<212> TYPE: DNA
<213> ORGANISM: Artificial
<220> FEATURE:
<223> OTHER INFORMATION: synthetic primer

<400> SEQUENCE: 30
ctcatcttct tgctgcctca ttctgcagct tc 32

<210> SEQ ID NO 31
<211> LENGTH: 24
<212> TYPE: DNA
<213> ORGANISM: Artificial
<220> FEATURE:
<223> OTHER INFORMATION: synthetic primer

<400> SEQUENCE: 31
ttatccttta ccttgtctcc aagc 24

<210> SEQ ID NO 32
<211> LENGTH: 447
<212> TYPE: PRT
<213> ORGANISM: Trichoderma sp.

<400> SEQUENCE: 32

Gln Ala Cys Ser Ser Val Trp Gly Gln Cys Gly Gly Gln Asn Trp Ser
1 5 10 15

Gly Pro Thr Cys Cys Ala Ser Gly Ser Thr Cys Val Tyr Ser Asn Asp
20 25 30

Tyr Tyr Ser Gln Cys Leu Pro Gly Ala Ala Ser Ser Ser Ser Ser Thr
35 40 45

Arg Ala Ala Ser Thr Thr Ser Arg Val Ser Pro Thr Thr Ser Arg Ser
50 55 60

Ser Ser Ala Thr Pro Pro Pro Gly Ser Thr Thr Thr Arg Val Pro Pro
65 70 75 80

Val Gly Ser Gly Thr Ala Thr Tyr Ser Gly Asn Pro Phe Val Gly Val
85 90 95

Thr Leu Trp Ala Asn Ala Tyr Tyr Ala Ser Glu Val Ser Ser Leu Ala

-continued

```
            100                 105                 110

Ile Pro Ser Leu Thr Gly Ala Met Ala Thr Ala Ala Ala Ala Val Ala
        115                 120                 125

Lys Val Pro Ser Phe Val Trp Leu Asp Thr Leu Asp Lys Thr Pro Leu
    130                 135                 140

Met Glu Gln Thr Leu Ala Asp Ile Arg Ala Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Val Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Pro Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Tyr His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445


<210> SEQ ID NO 33
<211> LENGTH: 1416
<212> TYPE: DNA
<213> ORGANISM: Trichoderma reesei

<400> SEQUENCE: 33

atgattgtcg gcattctcac cacgctggct acgctggcca cactcgcagc tagtgtgcct      60

ctagaggagc ggcaagcttg ctcaagcgtc tggggccaat gtggtggcca gaattggtcg     120

ggtccgactt gctgtgcttc cggaagcaca tgcgtctact ccaacgacta ttactcccag     180
```

-continued

```
tgtcttcccg gcgctgcaag ctcaagctcg tccacgcgcg ccgcgtcgac gacttctcga    240

gtatccccca caacatcccg gtcgagctcc gcgacgcctc cacctggttc tactactacc    300

agagtacctc cagtcggatc gggaaccgct acgtattcag gcaacccttt tgttggggtc    360

actccttggg ccaatgcata ttacgcctct gaagttagca gcctcgctat tcctagcttg    420

actggagcca tggccactgc tgcagcagct gtcgcaaagg ttccctcttt tatgtggctg    480

gatactcttg acaagacccc tctcatggag caaaccttgg ccgacatccg caccgccaac    540

aagaatggcg gtaactatgc cggacagttt gtggtgtatg acttgccgga tcgcgattgc    600

gctgcccttg cctcgaatgg cgaatactct attgccgatg gtggcgtcgc caaatataag    660

aactatatcg acaccattcg tcaaattgtc gtggaatatt ccgatatccg gaccctcctg    720

gttattgagc ctgactctct tgccaacctg gtgaccaacc tcggtactcc aaagtgtgcc    780

aatgctcagt cagcctacct tgagtgcatc aactacgccg tcacacagct gaaccttcca    840

aatgttgcga tgtatttgga cgctggccat gcaggatggc ttggctggcc ggcaaaccaa    900

gacccggccg ctcagctatt tgcaaatgtt tacaagaatg catcgtctcc gagagctctt    960

cgcggattgg caaccaatgt cgccaactac aacgggtgga acattaccag ccccccatcg   1020

tacacgcaag gcaacgctgt ctacaacgag aagctgtaca tccacgctat tggacctctt   1080

cttgccaatc acggctggtc caacgccttc ttcatcactg atcaaggtcg atcgggaaag   1140

cagcctaccg gacagcaaca gtggggagac tggtgcaatg tgatcggcac cggatttggt   1200

attcgcccat ccgcaaacac tggggactcg ttgctggatt cgtttgtctg ggtcaagcca   1260

ggcggcgagt gtgacggcac cagcgacagc agtgcgccac gatttgactc ccactgtgcg   1320

ctcccagatg ccttgcaacc ggcgcctcaa gctggtgctt ggttccaagc ctactttgtg   1380

cagcttctca caaacgcaaa cccatcgttc ctgtaa                             1416
```

<210> SEQ ID NO 34
<211> LENGTH: 471
<212> TYPE: PRT
<213> ORGANISM: Trichoderma reesei

<400> SEQUENCE: 34

```
Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60

Ala Ala Ser Ser Ser Ser Ser Thr Arg Ala Ala Ser Thr Thr Ser Arg
65                  70                  75                  80

Val Ser Pro Thr Thr Ser Arg Ser Ser Ser Ala Thr Pro Pro Pro Gly
                85                  90                  95

Ser Thr Thr Thr Arg Val Pro Pro Val Gly Ser Gly Thr Ala Thr Tyr
            100                 105                 110

Ser Gly Asn Pro Phe Val Gly Val Thr Pro Trp Ala Asn Ala Tyr Tyr
        115                 120                 125

Ala Ser Glu Val Ser Ser Leu Ala Ile Pro Ser Leu Thr Gly Ala Met
    130                 135                 140

Ala Thr Ala Ala Ala Ala Val Ala Lys Val Pro Ser Phe Met Trp Leu
145                 150                 155                 160
```

```
Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asp Gly Gly Val Ala Lys Tyr Lys Asn Tyr Ile Asp
    210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
        275                 280                 285

Gly His Ala Gly Trp Leu Gly Trp Pro Ala Asn Gln Asp Pro Ala Ala
    290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350

Tyr Ile His Ala Ile Gly Arg Leu Leu Ala Asn His Gly Trp Ser Asn
        355                 360                 365

Ala Phe Phe Ile Thr Asp Gln Gly Arg Ser Gly Lys Gln Pro Thr Gly
    370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
            420                 425                 430

Pro Arg Phe Asp Ser His Cys Ala Leu Pro Asp Ala Leu Gln Pro Ala
        435                 440                 445

Ala Gln Ala Gly Ala Trp Phe Gln Ala Tyr Phe Val Gln Leu Leu Thr
    450                 455                 460

Asn Ala Asn Pro Ser Phe Leu
465                 470


<210> SEQ ID NO 35
<211> LENGTH: 447
<212> TYPE: PRT
<213> ORGANISM: Trichoderma reesei

<400> SEQUENCE: 35

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
```

```
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Arg Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Ser His Cys Ala
                405                 410                 415

Leu Pro Asp Ala Leu Gln Pro Ala Ala Gln Ala Gly Ala Trp Phe Gln
            420                 425                 430

Ala Tyr Phe Val Gln Leu Leu Thr Asn Ala Asn Pro Ser Phe Leu
        435                 440                 445


<210> SEQ ID NO 36
<211> LENGTH: 29
<212> TYPE: DNA
<213> ORGANISM: Artificial
```

-continued

```
<220> FEATURE:
<223> OTHER INFORMATION: synthetic primer

<400> SEQUENCE: 36

caccatgatc gtgggaattc ttactactc                                        29


<210> SEQ ID NO 37
<211> LENGTH: 24
<212> TYPE: DNA
<213> ORGANISM: Artificial
<220> FEATURE:
<223> OTHER INFORMATION: synthetic primer

<400> SEQUENCE: 37

ctacaaaaac gaagggttcg catt                                             24


<210> SEQ ID NO 38
<211> LENGTH: 4
<212> TYPE: PRT
<213> ORGANISM: Artificial
<220> FEATURE:
<223> OTHER INFORMATION: synthetic reagent

<400> SEQUENCE: 38

Ala Ala Pro Phe
1


<210> SEQ ID NO 39
<211> LENGTH: 4
<212> TYPE: PRT
<213> ORGANISM: Artificial
<220> FEATURE:
<223> OTHER INFORMATION: synthetic reagent

<400> SEQUENCE: 39

Ala Gly Leu Ala
1
```